(12) United States Patent
Yoshida et al.

(10) Patent No.: US 9,920,026 B2
(45) Date of Patent: *Mar. 20, 2018

(54) AMIDE DERIVATIVES, PROCESS FOR PREPARATION THEREOF AND USE THEREOF AS INSECTICIDE

(71) Applicant: MITSUI CHEMICALS, INC., Tokyo (JP)

(72) Inventors: Kei Yoshida, Chiba (JP); Takeo Wakita, Chiba (JP); Hiroyuki Katsuta, Chiba (JP); Akiyoshi Kai, Chiba (JP); Yutaka Chiba, Chiba (JP); Kiyoshi Takahashi, Fukuoka (JP); Hiroko Kato, Aichi (JP); Nobuyuki Kawahara, Chiba (JP); Michikazu Nomura, Chiba (JP); Hidenori Daido, Chiba (JP); Junji Maki, Chiba (JP); Shinichi Banba, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/854,627

(22) Filed: Sep. 15, 2015

(65) Prior Publication Data
US 2016/0002198 A1  Jan. 7, 2016

Related U.S. Application Data

(62) Division of application No. 14/220,673, filed on Mar. 20, 2014, now Pat. No. 9,185,912, which is a division
(Continued)

(30) Foreign Application Priority Data

Jan. 28, 2004 (JP) ................................ 2004-019438
Feb. 24, 2004 (JP) ................................ 2004-048031
Jul. 15, 2004 (JP) ................................ 2004-209002

(51) Int. Cl.
*C07C 237/42* (2006.01)
*C07D 333/38* (2006.01)
(Continued)

(52) U.S. Cl.
CPC .......... *C07D 333/38* (2013.01); *A01N 37/22* (2013.01); *A01N 37/44* (2013.01); *A01N 43/08* (2013.01); *A01N 43/10* (2013.01); *A01N 43/12* (2013.01); *A01N 43/16* (2013.01); *A01N 43/30* (2013.01); *A01N 43/40* (2013.01); *A01N 43/42* (2013.01); *A01N 43/54* (2013.01); *A01N 43/56* (2013.01); *A01N 43/58* (2013.01); *A01N 43/60* (2013.01); *A01N 43/78* (2013.01); *A01N 43/80* (2013.01); *C07C 237/42* (2013.01); *C07C 237/48* (2013.01); *C07C 317/40* (2013.01); *C07C 323/42* (2013.01); *C07C 327/48* (2013.01); *C07D 207/34* (2013.01); *C07D 207/416* (2013.01); *C07D 213/64* (2013.01); *C07D 213/73* (2013.01); *C07D 213/81* (2013.01); *C07D 213/82* (2013.01); *C07D 213/89* (2013.01); *C07D 215/52* (2013.01); *C07D 231/14* (2013.01); *C07D 231/16* (2013.01); *C07D 239/28* (2013.01); *C07D 239/30* (2013.01); *C07D 241/24* (2013.01); *C07D 261/18* (2013.01); *C07D 263/34* (2013.01); *C07D 275/03* (2013.01); *C07D 277/56* (2013.01); *C07D 307/24* (2013.01); *C07D 307/68* (2013.01); *C07D 307/84* (2013.01); *C07D 307/85* (2013.01);
(Continued)

(58) Field of Classification Search
CPC ... C07C 317/40; C07C 327/48; C07C 323/42; C07C 237/42
See application file for complete search history.

(56) References Cited

U.S. PATENT DOCUMENTS

4,284,813 A  8/1981  Takematsu et al.
5,770,736 A  6/1998  Arya et al.
(Continued)

FOREIGN PATENT DOCUMENTS

AU  2004268104  3/2005
EP  1661886  5/2006
(Continued)

OTHER PUBLICATIONS

Elhadi et al, Tetrahedron Lett., 1980, 21(43), 4215-4218.*
Elhadi et al, J. Chem. Soc. Perkin. Trans., 1982, (8), 1727-32.*
European Search Report dated Sep. 25, 2007 for PCT/JP2004/019770.
STN Registry File: RN 389602-58-8; Entered STN: Feb. 5, 2002; Benzoyl Chloride, 3-[(4'-methyl[1,1'-biphenyl]-2-yl) carbonyl] amino]—Reference: 1. Biphenylcarboxylic acid amides as inhibitors of microsomal triglyceride transfer protein, by Priepke, Henning: Hauel, Norbert; Thomas, Leo; Mark, Michael; Dahmann, Georg. From PCT Int. Appl (2002), WO 2002004403 A1 Jan. 17, 2002. language: German, Database: CAPLUS.
(Continued)

*Primary Examiner* — Sudhakar Katakam
*Assistant Examiner* — Jennifer C Sawyer
(74) *Attorney, Agent, or Firm* — Rankin, Hill & Clark LLP

(57) ABSTRACT

A compound represented by Formula (1):

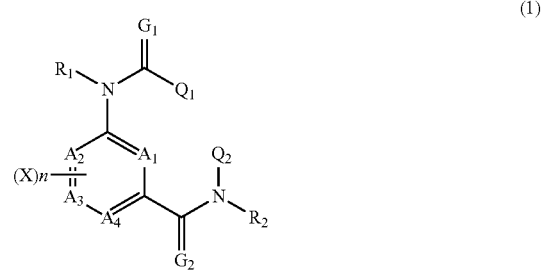

The compound can be used as insecticides.

1 Claim, No Drawings

Related U.S. Application Data of application No. 14/033,005, filed on Sep. 20, 2013, now Pat. No. 8,710,234, which is a division of application No. 13/427,176, filed on Mar. 22, 2012, now Pat. No. 8,563,736, which is a division of application No. 10/587,990, filed as application No. PCT/JP2004/019770 on Dec. 24, 2004, now Pat. No. 8,168,825.

(51) Int. Cl.

| | | |
|---|---|---|
| A01N 37/44 | (2006.01) |
| A01N 43/08 | (2006.01) |
| A01N 43/10 | (2006.01) |
| A01N 43/12 | (2006.01) |
| A01N 43/16 | (2006.01) |
| A01N 43/30 | (2006.01) |
| A01N 43/40 | (2006.01) |
| A01N 43/42 | (2006.01) |
| A01N 43/54 | (2006.01) |
| A01N 43/56 | (2006.01) |
| A01N 43/58 | (2006.01) |
| A01N 43/78 | (2006.01) |
| A01N 43/80 | (2006.01) |
| C07C 317/40 | (2006.01) |
| C07C 323/42 | (2006.01) |
| C07C 327/48 | (2006.01) |
| C07D 207/416 | (2006.01) |
| C07D 213/64 | (2006.01) |
| C07D 213/73 | (2006.01) |
| C07D 213/81 | (2006.01) |
| C07D 213/82 | (2006.01) |
| C07D 213/89 | (2006.01) |
| C07D 215/52 | (2006.01) |
| C07D 231/14 | (2006.01) |
| C07D 231/16 | (2006.01) |
| C07D 239/30 | (2006.01) |
| C07D 241/24 | (2006.01) |
| C07D 263/34 | (2006.01) |
| C07D 275/03 | (2006.01) |
| C07D 277/56 | (2006.01) |
| C07D 307/24 | (2006.01) |
| C07D 307/68 | (2006.01) |
| C07D 307/84 | (2006.01) |
| C07D 309/08 | (2006.01) |
| C07D 309/28 | (2006.01) |
| C07D 317/62 | (2006.01) |
| C07D 333/68 | (2006.01) |
| A01N 37/22 | (2006.01) |
| A01N 43/60 | (2006.01) |
| C07C 237/48 | (2006.01) |
| C07D 207/34 | (2006.01) |
| C07D 239/28 | (2006.01) |
| C07D 261/18 | (2006.01) |
| C07D 307/85 | (2006.01) |
| C07D 317/46 | (2006.01) |

(52) U.S. Cl.
CPC ......... *C07D 309/08* (2013.01); *C07D 309/28* (2013.01); *C07D 317/46* (2013.01); *C07D 317/62* (2013.01); *C07D 333/68* (2013.01)

(56) References Cited

U.S. PATENT DOCUMENTS

| 6,211,242 B1 | 4/2001 | Setoi et al. |
|---|---|---|
| 6,417,188 B1 | 7/2002 | Jonas et al. |
| 6,548,514 B1 | 4/2003 | Brown |
| 6,559,341 B2 | 5/2003 | Tohnishi et al. |
| 6,642,379 B1 | 11/2003 | Furuya et al. |
| 6,747,047 B2 | 6/2004 | Lahm et al. |
| 7,015,237 B2 | 3/2006 | Barvian et al. |
| 8,067,638 B2 | 11/2011 | Kai et al. |
| 9,328,062 B2* | 5/2016 | Fukazawa ............ C07C 237/52 |
| 2002/0032238 A1 | 3/2002 | Priepke et al. |
| 2004/0009982 A1 | 1/2004 | Tohnishi et al. |
| 2004/0248947 A1 | 12/2004 | Bold et al. |

FOREIGN PATENT DOCUMENTS

| GB | 1110099 | 4/1968 |
|---|---|---|
| WO | 00/07980 | 2/2000 |
| WO | 00/55120 | 9/2000 |
| WO | 01/05769 | 1/2001 |
| WO | 01/70671 | 9/2001 |
| WO | 03/011028 | 2/2003 |
| WO | 03/027099 | 4/2003 |
| WO | 2004035545 | 4/2004 |
| WO | 2005021488 | 2/2005 |
| WO | 2006/067445 | 6/2006 |

OTHER PUBLICATIONS

STN Registry File: RN 295349-75-6; Entered STN: Oct. 13, 2000; Benzoyl Chloride, 5-(benzoylamino)-2-methyl—Reference: 1. Preparation of benzamides for treating diseases mediated by cytokines, by Brown, Dearg Sutherland. From PCT Int. Appl (2000) WO 2000055120 A1 Sep. 21, 2000. Language: English, Database: CAPLUS.
STN Registry File: RN 295349-74-5; Entered STN: Oct. 13, 2000; Benzoyl Chloride, 5-[(4-cyanobenzoyl)amino]-2-methyl—Reference: 1. Preparation of benzamides for treating diseases mediated by cytokines, by Brown, Dearg Sutherland. From PCT Int. Appl (2000), WO 2000055120 A1 Sep. 21, 2000. Language: English, Database: CAPLUS.
STN Registry File: RN 258864-29-8; Entered STN: Mar. 10, 2000; Benzoyl Chloride, 4-chloro-3-[(6-quinolinylcarbonyl) amino]—Reference: 1. Preparation of benzamides as cytokokine inhibitors, by Brown, Dearg Sutherland; Brown, George Robert. From PCT Int. Appl (2000) WO 2000007980 A1 Feb. 17, 2000, Language: English, Database: CAPLUS.
STN Registry File: RN 258864-28-7; Entered STN: Mar. 10, 2000; Benzoyl Chloride, 4-chloro-3-[(4-propylbenzoyl) amino]—Reference: 1. Preparation of benzamides as cytokine inhibitors, by Brown, Dearg Sutherland, Brown, George Robert. From PCT Int. Appl (2000) WO 2000007980 A1 Feb. 17, 2000, Language: English, Database: CAPLUS.
STN Registry File: RN 252724-81-5; Entered STN: Jan. 12, 2000; Benzoyl Chloride, 3-[(4-methoxybenzoyl) amino]—Reference: 1. Preparation of arylacylpyridazines as phosphodiesterase IV inhibitors, by Jonas, Rochus; Wolf, Michael; Kluxen, Franz-Werner. From PCT Int. Appl (1999) WO 9965880 A1 Dec. 23, 1999. Language: German, Database: CAPLUS.
STN Registry File: RN 252724-80-4; Entered STN Jan. 12, 2000; Benzoyl Chloride, 3-[(3-chlorobenzoyl)amino]-.
STN Registry File: RN 252724-79-1; Entered STN Jan. 12, 2000; Benzoyl Chloride, 3-[(3-methylbenzoyl)amino]-.
STN Registry File: RN 252724-78-0; Entered STN: Jan. 12, 2000; Benzoyl Chloride, 3-[(3, 4-dimethoxybenzoyl)amino—Reference: 1. Preparation of arylacylpyridazines as phosphodiesterase IV inhibitors, by Jonas, Rochus; Wolf, Michael; Kluxen, Franz-Werner. From PCT Int. Appl (1999) WO 9965880 A1 Dec. 23, 1999. Language: German, Database: CAPLUS.
STN Registry File: RN 209329-83-9; Entered STN: Aug. 2, 1998; Benzoyl Chloride, 3-[(3-pyridinylcarbonyl)amino]-.
STN Registry File: RN 77149-33-8; Entered STN: Nov. 16, 1984; Benzoyl Chloride, 3-[methyl(3-nitrobenzoyl)amine]-.
STN Registry File: RN 76712-94-2; Entered STN; Nov. 16, 1984; Benzoyl Chloride, 3-(benzoylamino)-.
STN Registry File: RN 16360-90-0; Entered STN: Nov. 16, 1984; Benzoyl Chloride, 3-[(3-nitrobenzoyl)amino]-.

(56) References Cited

OTHER PUBLICATIONS

STN Registry File: RN 389602-61-3; Entered STN; Feb. 5, 2002; Benzoyl Chloride, 3[(4'-fluoro(1'-biphenyl]-2-yl)carbonyl]amino)—Reference 1: Biphenyicarboxylic acid amides as inhibitors of microsomal triglycende transfer protein, by Priepke. Henning. et al. From PCT Int. Appl (2007) WO 2002004403 A1 Jan. 17, 2002. Language: German, Database: CAPLUS.

D1: RN 389602-59-9 Registry; ED Entered STN: Feb. 5, 2002; CN Benzol chloride, 3[[[4'-(triflouromethyl) [1.1'-biphenyl]-2-yl]carbonyl)amino]—(CA INDES Name).

Indian Office Action dated Jan. 21, 2009 corresponding to U.S. Appl. No. 10/587,990, filed Jul. 28, 2006.

Elhadl, F.E. et al., "Conformational Behavior of Medium-sized Rings. Part 15 1.9.17-Triaza [2.2.2] metacychlophane-2, 10, 18-trione Derivatives", J. Chem. Soc. Perkin Trans. pp. 1739-32, 1982.

CAS Registry No. 326016-46-0.—Applicant presumes the information was published before Jan. 28, 2004.

Australian Office Action dated Nov. 2, 2010.

Korean Office Action dated Dec. 8, 2008 corresponding to U.S. Appl. No. 10/587,990, filed Jul. 28, 2006.

Smith, et al; March's Advianced Organic Chemistry, pp. 1187-1189, 2001.

International Search Report for PCT/JP2004/019770, dated Apr. 5, 2005.

European Office Action dated Jul. 31, 2012, seven pages.

U.S. Office Action dated Dec. 17, 2010 filed in related U.S. Appl. No. 10/587,990.

U.S. Office Action dated Jan. 29, 2013 filed in related U.S. Appl. No. 13/427,176.

U.S. Office Action dated Aug. 24, 2012 filed in related U.S. Appl. No. 13/427,176.

U.S. Notice of Allowability dated Dec. 5, 2013 filed in related U.S. Appl. No. 14/033,005.

* cited by examiner

AMIDE DERIVATIVES, PROCESS FOR PREPARATION THEREOF AND USE THEREOF AS INSECTICIDE

TECHNICAL FIELD

The present invention relates to a compound represented by Formula (1):

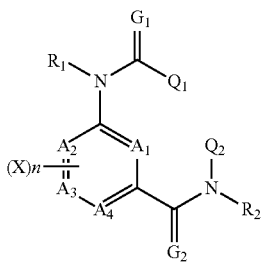

wherein $A_1$, $A_2$, $A_3$ and $A_4$ each represent a carbon atom, a nitrogen atom or an oxidized nitrogen atom;

$R_1$ and $R_2$ each represent a hydrogen atom, an optionally substituted alkyl group or an optionally substituted C1-C4 alkylcarbonyl group;

$G_1$ and $G_2$ each represent an oxygen atom or a sulfur atom;

X, which may be identical or different, represents a hydrogen atom, a halogen atom, a C1-C3 alkyl group or a trifluoromethyl group;

n is an integer of 0 to 4; and $Q_1$ and $Q_2$ each represent an optionally substituted phenyl group, an optionally substituted naphthyl group or an optionally substituted heterocyclic group, an insecticide comprising the compound as the active ingredient, and a process for preparation thereof and use thereof.

BACKGROUND ART

International Publication WO 2000/55120 and U.S. Pat. No. 6,548,514 describe a compound similar to the compound of the present invention for the use as medicament, but they do not describe on the insecticidal activity of the compound. The compound clearly does not fall within the scope of claims of the present invention.

International Publication WO 2000/7980 describes a compound similar to the compound of the present invention for the use as medicament, but it does not describe on the insecticidal activity of the compound. The compound clearly does not fall within the scope of claims of the present invention.

US Patent Laid-Open No. 2002-032238 describes a compound similar to the compound of the present invention for the use as medicament, but it does not describe on the insecticidal activity of the compound. The compound clearly does not fall within the scope of claims of the present invention.

DISCLOSURE OF THE INVENTION

The object of the present invention is to provide a pesticide having a high insecticidal efficacy. Another object of the present invention is to provide a compound represented by Formula (1), a process for preparation of the compound, an insecticide comprising the compound as an active ingredient, and a process for controlling pests by using a combination of the compound with another pesticide and/or a fungicide.

The inventors have conducted intensive studies to solve the above problems and discovered that the compound of the invention is a novel compound unknown in the documents and has remarkably excellent insecticidal effects, thus finding a novel application of the compound as a pesticide. Further, they also discovered that a compound unknown in the documents is a useful intermediate for the preparation of the compound of the present invention. As a result, they have completed the present invention.

The subject of the invention is as follows.

[1] A compound represented by Formula (1):

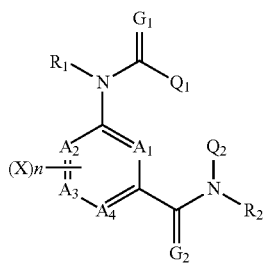

wherein $A_1$, $A_2$, $A_3$ and $A_4$ each represent a carbon atom, a nitrogen atom or an oxidized nitrogen atom;

$R_1$ and $R_2$ each represent a hydrogen atom, an optionally substituted alkyl group or an optionally substituted C1-C4 alkylcarbonyl group;

$G_1$ and $G_2$ each represent an oxygen atom or a sulfur atom;

Xs, which may be identical or different each other, represent a hydrogen atom, a halogen atom, a C1-C3 alkyl group or a trifluoromethyl group;

n is an integer of 0 to 4; and $Q_1$ represents an optionally substituted phenyl group, an optionally substituted naphthyl group or an optionally substituted heterocyclic group;

$Q_2$ represents a phenyl group or heterocyclic group having one or more substituents, at least one of the substituent being any of a C1-C4 haloalkoxy group, a C2-C6 perfluoroalkyl group, a C1-C6 perfluoroalkylthio group, a C1-C6 perfluoroalkylsulfinyl group and a C1-C6 perfluoroalkylsulfonyl group.

[2] The compound as described in [1] represented by Formula (1), wherein $R_1$ and $R_2$ are each a hydrogen atom, a C1-C4 alkyl group or an optionally substituted C1-C4 alkylcarbonyl group;

Xs, which may be identical or different each other, are a hydrogen atom, a halogen atom or a trifluoromethyl group;

$Q_1$ is a phenyl group, or a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group, and a phenyl group; a heterocyclic group (the heterocyclic group herein represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group or a tetrazolyl group), or a substituted heterocyclic group (which means the same as those described above) having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group, and a phenyl group;

$Q_2$ is represented by Formula (2):

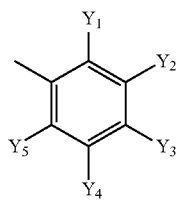

(2)

(wherein $Y_1$ and $Y_5$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group, a C1-C6 perfluoroalkylthio group, a C1-C6 perfluoroalkylsulfinyl group or a C1-C6 perfluoroalkylsulfonyl group; and $Y_2$ and $Y_4$ each represent a hydrogen atom, a halogen atom or a C1-C4 alkyl group);

or by Formula (3):

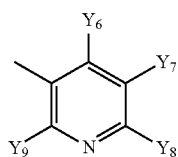

(3)

(wherein $Y_6$ and $Y_9$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C1-C4 haloalkoxy group, a C2-C6 perfluoroalkyl group, a C1-C6 perfluoroalkylthio group, a C1-C6 perfluoroalkylsulfinyl group or a C1-C6 perfluoroalkylsulfonyl group; and $Y_7$ represents a hydrogen atom, a halogen atom or a C1-C4 alkyl group).

[3] The compound as described in [2], represented by Formula (1a), which is Formula (1) with $A_1$, $A_2$, $A_3$ and $A_4$ being all carbon atoms:

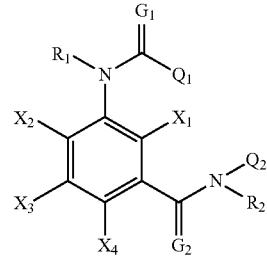

(1a)

wherein $R_1$, $R_2$, $G_1$, $G_2$ and $Q_1$ have the same meanings as those described in [2], and $Q_2$ is represented either by Formula (2):

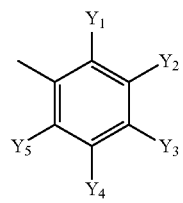

(2)

(wherein $Y_1$ and $Y_5$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C1-C6 perfluoroalkylthio group, a C1-C6 perfluoroalkylsulfinyl group or a C1-C6 perfluoroalkylsulfonyl group; and $Y_2$ and $Y_4$ each represent a hydrogen atom, a halogen atom or a C1-C4 alkyl group);

or by Formula (3):

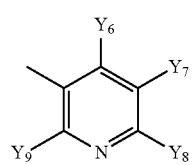

(3)

(wherein $Y_6$ and $Y_9$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C1-C4 haloalkoxy group, a C1-C6 perfluoroalkylthio group, a C1-C6 perfluoroalkylsulfinyl group or a C1-C6 perfluoroalkylsulfonyl group; and $Y_7$ represents a hydrogen atom, a halogen atom or a C1-C4 alkyl group), wherein in Formula (1a), $X_1$ and $X_2$ each represent a hydrogen atom or a fluorine atom; and $X_3$ and $X_4$ represent a hydrogen atom.

[4] The compound as described in [3], represented by Formula (1a), wherein $Q_1$ is a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a pyridyl group; or a substituted pyridyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group.

[5] The compound as described in [1] or [2], represented by Formula (1a), which is Formula (1) with $A_1$, $A_2$, $A_3$ and $A_4$ being all carbon atoms:

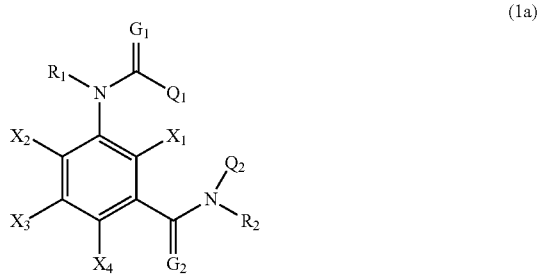

(1a)

wherein $Q_2$ is represented either by Formula (2):

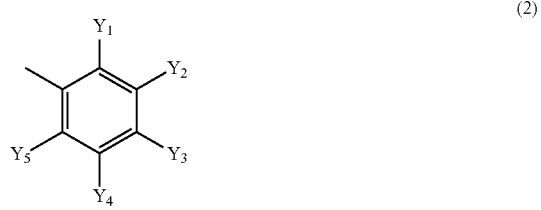

(2)

(wherein $Y_1$ and $Y_5$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group; and $Y_2$ and $Y_4$ each represent a hydrogen atom, a halogen atom or a C1-C4 alkyl group);

or by Formula (3):

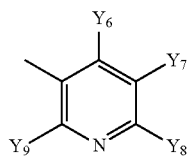

(3)

(wherein $Y_6$ and $Y_9$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C2-C6 perfluoroalkyl group; and $Y_7$ represents a hydrogen atom, a halogen atom or a C1-C4 alkyl group);

$X_1$ and $X_2$ each represent a hydrogen atom or a fluorine atom;

$X_3$ and $X_4$ represent a hydrogen atom;

one of $R_1$ and $R_2$ is a hydrogen atom, the other is a C1-C4 alkyl group or an optionally substituted C1-C4 alkylcarbonyl group, or both of them are independently a C1-C4 alkyl group or an optionally substituted C1-C4 alkylcarbonyl group;

$G_1$ and $G_2$ each represent an oxygen atom or a sulfur atom; and $Q_1$ represents a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a heterocyclic group (the heterocyclic group herein represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group or a tetrazolyl group); or a substituted heterocyclic group (which means the same as those described above) having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group.

[6] The compound as described in [5], represented by Formula (1a), wherein $Q_1$ is a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a pyridyl group; or a substituted pyridyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group.

[7] The compound as described in [1] or [2], wherein $A_1$ is a nitrogen atom or an oxidized nitrogen atom; $A_2$, $A_3$ and $A_4$ are a carbon atom; $R_1$ and $R_2$ are each a hydrogen or a C1-C4 alkyl group; X is a hydrogen atom and a fluorine atom; n is 0 or 1; and $G_1$ and $G_2$ are an oxygen atom.

[8] The compound as described in [7], represented by Formula (1), wherein $Q_1$ is a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a pyridyl group; or a substituted pyridyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group.

[9] A compound represented by Formula (4):

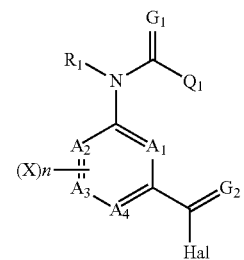

(4)

wherein $A_1$, $A_2$, $A_3$ and $A_4$ each represent a carbon atom, a nitrogen atom or an oxidized nitrogen atom;

$R_1$ represents a hydrogen atom, a C1-C4 alkyl group or a C1-C4 alkylcarbonyl group;

$G_1$ and $G_2$ each represent an oxygen atom or a sulfur atom;

X, which may be identical or different each other, represents a hydrogen atom, a halogen atom, an optionally substituted C1-C3 alkyl group or a trifluoromethyl group;

n represents an integer of 0 to 4;

$Q_1$ represents a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a heterocyclic group (the heterocyclic group herein represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group or a tetrazolyl group); or a substituted heterocyclic group (which means the same as those described above) having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group or a phenyl group; and Hal represents a chlorine atom or a bromine atom.

[10] A process for preparation of the compound represented by Formula (1) as described in [1], wherein the compound represented by Formula (4) as described in [9] is reacted with a compound represented by Formula (5):

$$R_2-\overset{H}{\underset{}{N}}-Q_2 \tag{5}$$

(wherein $R_2$ represents a hydrogen atom, an optionally substituted alkyl group or an optionally substituted C1-C4 alkylcarbonyl group; and $Q_2$ represents an optionally substituted phenyl group, an optionally substituted naphthyl group or an optionally substituted heterocyclic group).

[11] A compound represented by Formula (6):

$$\text{(6)}$$

wherein $A_1$, $A_2$, $A_3$ and $A_4$ each represented by a carbon atom, a nitrogen atom or an oxidized nitrogen atom;

$R_1$ and $R_2$ each represent a hydrogen atom, a C1-C4 alkyl group or a C1-C4 alkylcarbonyl group;

$G_2$ represents an oxygen atom or a sulfur atom;

X, which may be identical or different, represents a hydrogen atom, a halogen atom, an optionally substituted C1-C3 alkyl group or a trifluoromethyl group;

n represents an integer of 0 to 4;

$Q_2$ is represented either by Formula (2):

$$\text{(2)}$$

(wherein $Y_1$ and $Y_5$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_3$ represents a C2-C6 perfluoroalkyl group, a C1-C6 perfluoroalkylthio group, a C1-C6 perfluoroalkylsulfinyl group or a C1-C6 perfluoroalkylsulfonyl group; and $Y_2$ and $Y_4$ each represent a hydrogen atom, a halogen atom or a C1-C4 alkyl group);

or by Formula (3):

$$\text{(3)}$$

(wherein $Y_6$ and $Y_9$, which may be identical or different, each represent a halogen atom, a C1-C4 alkyl group, a C1-C4 haloalkyl group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group or a cyano group; $Y_8$ represents a C1-C4 haloalkoxy group, a C2-C6 perfluoroalkyl group, a C1-C6 perfluoroalkylthio group, a C1-C6 perfluoroalkylsulfinyl group or a C1-C6 perfluoroalkylsulfonyl group; and $Y_7$ represents a hydrogen atom, a halogen atom or a C1-C4 alkyl group).

[12] A process for preparation of the compound represented by Formula (1) as described in [1], wherein the compound represented by Formula (6) as described in [11] is reacted with a compound represented by Formula (7):

$$\text{(7)}$$

(wherein $G_1$ represents an oxygen atom or a sulfur atom; $Q_1$ represents a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a heterocyclic group (the heterocyclic group herein represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group or a tetrazolyl group); or a substituted heterocyclic group (which means the same as those described above) having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group or a phenyl group; and L represents a halogen atom or a hydroxyl group).

[13] A compound represented by Formula (8):

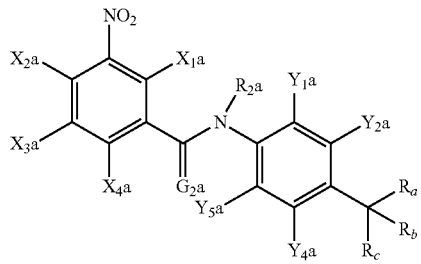

(8)

wherein $X_1a$, $X_2a$, $X_3a$ and $X_4a$ each represent a hydrogen atom, a C1-C3 alkyl group, a trifluoromethyl group, a hydroxyl group, an amino group or a halogen atom;

$R_a$ and $R_b$ each represent a fluorine atom or a C1-C4 perfluoroalkyl group;

$R_c$ represents a hydroxyl group, a group —O—$R_d$ (wherein $R_d$ represents a C1-C3 alkyl group, a C1-C3 haloalkyl group, a C1-C3 alkylsulfonyl, a C1-C3 haloalkylsulfonyl group, an arylsulfonyl group, a C1-C4 alkylcarbonyl group or a C1-C4 haloalkylcarbonyl group), a chlorine atom, a bromine atom or an iodine atom;

$R_2a$ represents a hydrogen atom, a C1-C3 alkyl group, a C1-C3 haloalkyl group, a C1-C3 alkoxy group, a C1-C3 haloalkoxy group, a C1-C4 alkylthio group, a C1-C4 haloalkylthio group, a C1-C4 alkylcarbonyl group or a C1-C4 haloalkylcarbonyl group;

$Y_1a$ and $Y_5a$ each represent a C1-C4 alkyl group, a C1-C4 haloalkyl group, a C1-C4 alkylthio group, a C1-C4 haloalkylthio group, a C1-C3 alkylsulfinyl group or a C1-C3 haloalkylsulfinyl group, a C1-C3 alkylsulfonyl group, a C1-C3 haloalkylsulfonyl group, a cyano group, a hydroxyl group or a halogen atom;

$Y_2a$ and $Y_4a$ each represent a hydrogen atom, a C1-C4 alkyl group or a halogen atom; and $G_2a$ represents an oxygen atom or a sulfur atom.

[14] A process for preparation of the compound represented by Formula (8) as described in [13], wherein a compound represented by Formula (9):

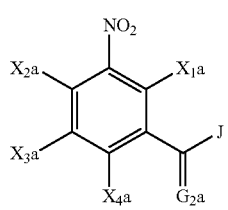

(9)

(wherein J represents a halogen atom or a hydroxyl group; and $X_1a$, $X_2a$, $X_3a$, $X_4a$ and $G_2a$ have the same meanings as those described in [13]), is reacted with a compound represented by Formula (10):

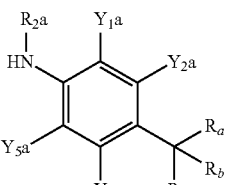

(10)

(wherein $R_a$, $R_b$, $R_c$, $Y_1a$, $Y_2a$, $Y_4a$, $Y_5a$ and $R_2a$ have the same meanings as those described in [13]).

[15] A process for preparation of a compound represented by Formula (8b):

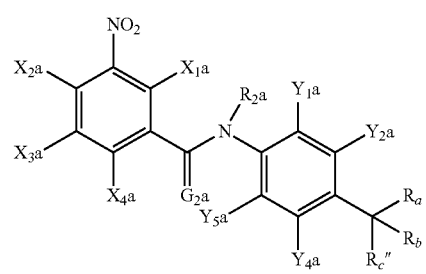

(8b)

(wherein $X_1a$, $X_2a$, $X_3a$, $X_4a$, $G_2a$, $R_2a$, $Y_1a$, $Y_2a$, $Y_4a$, $Y_5a$, $R_a$ and $R_b$ have the same meanings as those described in [13]; and $R_c''$ represents a chlorine atom, a bromine atom or an iodide atom);

wherein a compound represented by Formula (8a):

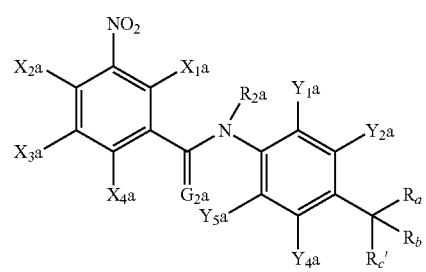

(8a)

(wherein $X_1a$, $X_2a$, $X_3a$, $X_4a$, $G_2a$, $R_2a$, $Y_1a$, $Y_2a$, $Y_4a$, $Y_5a$, $R_a$ and $R_b$ have the same meanings as those described in [13]; and $R_c'$ represents a hydroxyl group or a group —O—$R_d$ (wherein $R_d$ represents a C1-C3 alkyl group, a C1-C3 haloalkyl group, a C1-C3 alkylsulfonyl group, a C1-C3 haloalkylsulfonyl group, an arylsulfonyl group, a C1-C4 alkylcarbonyl group or a C1-C4 haloalkylcarbonyl group)), is reacted with a suitable halogenating agent.

[16] A compound represented by Formula (11):

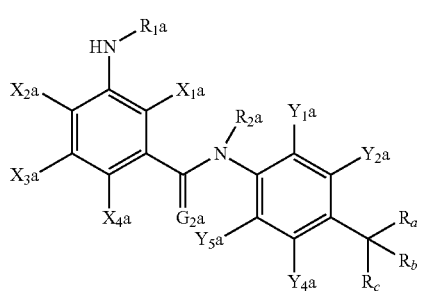

(11)

wherein $X_1a$, $X_2a$, $X_3a$ and $X_4a$ each represent a hydrogen atom, a C1-C3 alkyl group, a trifluoromethyl group, a hydroxyl group, an amino group or a halogen atom;

$R_a$ and $R_b$ each represent a fluorine atom or a C1-C4 perfluoroalkyl group;

$R_c$ represents a hydroxyl group, a group —O—$R_d$ (wherein $R_d$ represents a C1-C3 alkyl group, a C1-C3 haloalkyl group, a C1-C3 alkylsulfonyl group, a C1-C3 haloalkylsulfonyl group, an arylsulfonyl group, a C1-C4 alkylcarbonyl group or a C1-C4 haloalkylcarbonyl group), a chlorine atom, a bromine atom or an iodine atom;

$R_1a$ and $R_2a$ each represent a hydrogen atom, a C1-C3 alkyl group, a C1-C3 haloalkyl group, a C1-C3 alkoxy group, a C1-C3 haloalkoxy group, a C1-C4 alkylthio group, a C1-C4 haloalkylthio group, a C1-C4 alkylcarbonyl group or a C1-C4 haloalkylcarbonyl group;

$Y_1a$ and $Y_5a$ each represent a C1-C4 alkyl group, a C1-C4 haloalkyl group, a C1-C4 alkylthio group, a C1-C4 haloalkylthio group, a C1-C3 alkylsulfinyl group, a C1-C3 haloalkylsulfinyl group, a C1-C3 alkylsulfonyl group, a C1-C3 haloalkylsulfonyl group, a cyano group, a hydroxyl group or a halogen atom;

$Y_2a$ and $Y_4a$ each represent a hydrogen atom, a C1-C4 alkyl group or a halogen atom; and $G_2a$ represents an oxygen atom or a sulfur atom.

[17] A process for preparation of the compound represented by Formula (11) as described in [16]:

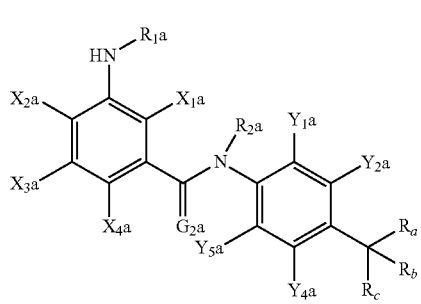

(11)

(wherein $X_1a$, $X_2a$, $X_3a$, $X_4a$, $R_a$, $R_b$, $R_c$, $R_1a$, $R_2a$, $Y_1a$, $Y_2a$, $Y_4a$, $Y_5a$ and $G_2a$ have the same meanings as those described in [16]), wherein the compound represented by Formula (8) as described in [13] is reacted in the presence of a suitable reducing agent.

[18] A process for preparation of a compound represented by Formula (12):

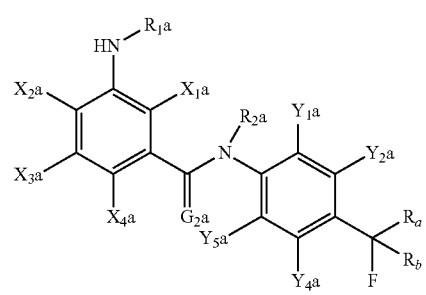

(12)

wherein $X_1a$, $X_2a$, $X_3a$ and $X_4a$ each represent a hydrogen atom, a C1-C3 alkyl group, a trifluoromethyl group, a hydroxyl group, an amino group or a halogen atom;

$R_a$ and $R_b$ each represent a fluorine atom or a C1-C4 perfluoroalkyl group;

$R_1a$ and $R_2a$ each represent a hydrogen atom, a C1-C3 alkyl group, a C1-C3 haloalkyl group, a C1-C3 alkoxy group, a C1-C3 haloalkoxy group, a C1-C4 alkylthio group, a C1-C4 haloalkylthio group, a C1-C4 alkylcarbonyl group or a C1-C4 haloalkylcarbonyl group;

$Y_1a$ and $Y_5a$ each represent a C1-C4 alkyl group, a C1-C4 haloalkyl group, a C1-C4 alkylthio group, a C1-C4 haloalkylthio group, a C1-C3 alkylsulfinyl group, a C1-C3 haloalkylsulfinyl group, a C1-C3 alkylsulfonyl group, a C1-C3 haloalkylsulfonyl group, a cyano group, a hydroxyl group or a halogen atom;

$Y_2a$ and $Y_4a$ each represent a hydrogen atom, a C1-C4 alkyl group or a halogen atom; and $G_2a$ represents an oxygen atom or a sulfur atom.

[19] A process for preparation of a compound represented by Formula (11b):

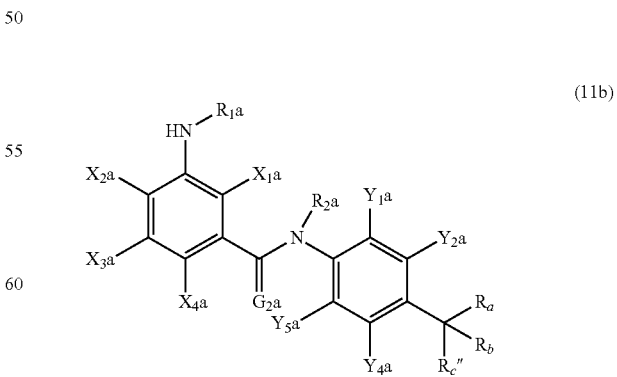

(11b)

(wherein $X_1a$, $X_2a$, $X_3a$, $X_4a$, $G_2a$, $R_1a$, $R_2a$, $Y_1a$, $Y_2a$, $Y_4a$, $Y_5a$, $R_a$ and $R_b$ have the same meanings as those described in [18]; and $R_c''$ represents a chlorine atom, a bromine atom or an iodine atom);

wherein a compound represented by Formula (11a):

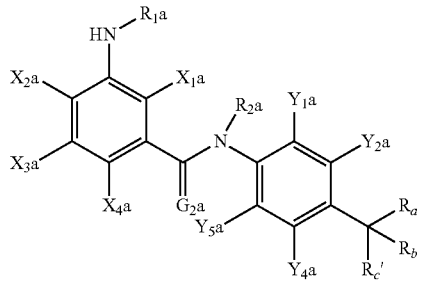

(11a)

(wherein $X_1a$, $X_2a$, $X_3a$, $X_4a$, $G_2a$, $R_1a$, $R_2a$, $Y_1a$, $Y_2a$, $Y_4a$, $Y_5a$, $R_a$ and $R_b$ have the same meanings as those described in [18]; and $R_c'$ represents a hydroxyl group or a group —O—$R_d$ (wherein $R_d$ represents a C1-C3 alkyl group, a C1-C3 haloalkyl group, a C1-C3 alkylsulfonyl group, a C1-C3 haloalkylsulfonyl group, an arylsulfonyl group, a C1-C4 alkylcarbonyl group or a C1-C4 haloalkylcarbonyl group)), is reacted with a suitable halogenating agent.

[20] A compound represented by Formula (13):

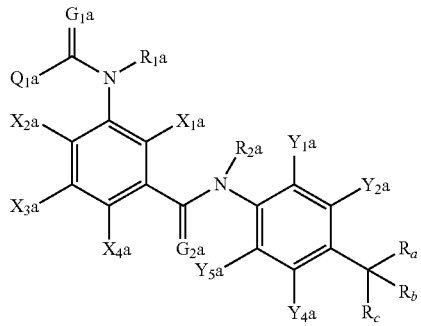

(13)

wherein $X_1a$, $X_2a$, $X_3a$ and $X_4a$ each represent a hydrogen atom, a c1-C3 alkyl group, a trifluoromethyl group, a hydroxyl group, an amino group or a halogen atom;

$R_a$ and $R_b$ each represent a fluorine atom or a C1-C4 perfluoroalkyl group;

$R_c$ represents a hydroxyl group, a group —O—$R_d$ (wherein $R_d$ represents a C1-C3 alkyl group, a C1-C3 haloalkyl group, a C1-C3 alkylsulfonyl group, a C1-C3 haloalkylsulfonyl group, an arylsulfonyl group, a C1-C4 alkylcarbonyl group or a C1-C4 haloalkylcarbonyl group), a chlorine atom, a bromine atom or an iodine atom;

$R_1a$ and $R_2a$ each represent a hydrogen atom, a C1-C3 alkyl group, a C1-C3 haloalkyl group, a C1-C3 alkoxy group, a C1-C3 haloalkoxy group, a C1-C4 alkylthio group, a C1-C4 haloalkylthio group, a C1-C4 alkylcarbonyl group or a C1-C4 haloalkylcarbonyl group;

$Y_1a$ and $Y_5a$ each represent a C1-C4 alkyl group, a C1-C4 haloalkyl group, a C1-C4 alkylthio group, a C1-C4 haloalkylthio group, a C1-C3 alkylsulfinyl group, a C1-C3 haloalkylsulfinyl group, a C1-C3 alkylsulfonyl group, a C1-C3 haloalkylsulfonyl group, a cyano group, a hydroxyl group or a halogen atom;

$Y_2a$ and $Y_4a$ each represent a hydrogen atom, a C1-C4 alkyl group or a halogen atom;

$G_1a$ and $G_2a$ each represent an oxygen atom or a sulfur atom;

$Q_1a$ represents a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a heterocyclic group (the heterocyclic group herein represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group or a tetrazolyl group); or a substituted heterocyclic group (which means the same as those described above) having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group.

[21] A process for preparation of the compound represented by Formula (13) as described in [20], wherein the compound represented by Formula (11) as described in [16] is reacted with a compound represented by Formula (14):

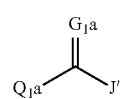

(14)

(wherein J' represents a halogen atom or a hydroxyl group; and $Q_1a$ and $G_1a$ have the same meanings as those described in [20]);

or a compound represented by Formula (15):

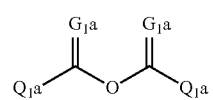

(15)

(wherein $Q_1a$ and $G_1a$ have the same meanings as those described in [20]).

[22] A process for preparation of the compound represented by Formula (13) as described in [20], wherein a compound represented by Formula (16):

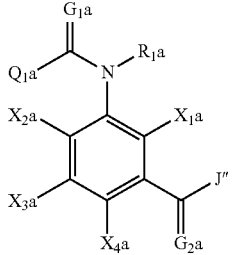

(16)

(wherein J″ represents a halogen atom or a hydroxyl group; and $X_1a$, $X_2a$, $X_3a$, $X_4a$, $G_1a$, $G_2a$, $R_1a$ and $Q_1a$ have the same meanings as those described in [20]),
is reacted with the compound represented by Formula (10) as described in [14].

[23] A process for preparation of a compound represented by Formula (17):

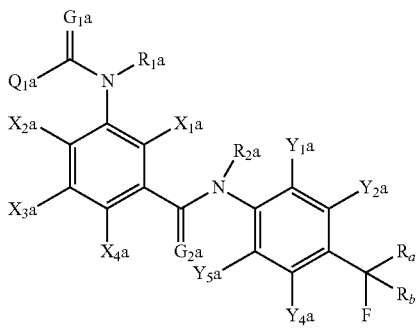

(17)

(wherein $X_1a$, $X_2a$, $X_3a$, $X_4a$, $R_a$, $R_b$, $R_1a$, $R_2a$, $Y_1a$, $Y_2a$, $Y_4a$, $Y_5a$, $G_1a$, $G_2a$ and $Q_1a$ have the same meanings as those described in [20]),
wherein the compound represented by Formula (13) as described in [20] is reacted with a suitable fluorinating agent.

[24] A process for preparation of a compound represented by Formula (13b):

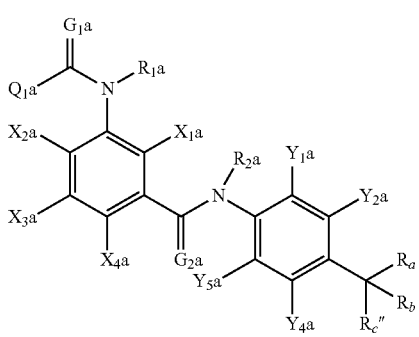

(13b)

(wherein $X_1a$, $X_2a$, $X_3a$, $X_4a$, $R_a$, $R_b$, $R_1a$, $R_2a$, $Y_1a$, $Y_2a$, $Y_4a$, $Y_5a$, $G_1a$, $G_2a$ and $Q_1a$ have the same meanings as those described in [20]; and $R_c''$ represents a chlorine atom, a bromine atom or an iodine atom),
wherein a compound represented by Formula (13a):

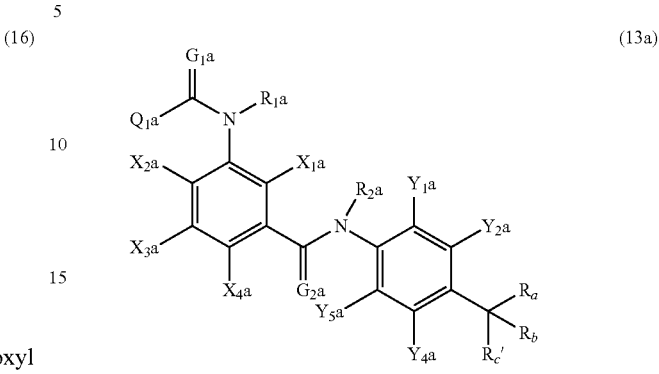

(13a)

(wherein $X_1a$, $X_2a$, $X_3a$, $X_4a$, $R_a$, $R_b$, $R_1a$, $R_2a$, $Y_1a$, $Y_2a$, $Y_4a$, $Y_5a$, $G_1a$, $G_2a$ and $Q_1a$ have the same meanings as those described in [20]; and $R_c'$ represents a hydroxyl group or a group —O—$R_d$ (wherein $R_d$ represents a C1-C3 alkyl group, a C1-C3 haloalkyl group, a C1-C3 alkylsulfonyl group, a C1-C3 haloalkylsulfonyl group, an arylsulfonyl group, a C1-C4 alkylcarbonyl group or a C1-C4 haloalkylcarbonyl group)),
is reacted with a suitable halogenating agent.

[25] An insecticide containing the compound as described in [1] to [8] as the active ingredient.

[26] A horticultural or agricultural insecticide containing the compound as described in [1] to [8] as an active ingredient.

[27] A method of using formulation in treating crops for cultivation or the soil to be treated with an effective amount of the compound as described in [1] to [8], in order to protect the crops from harmful organisms.

[28] A composition in which the compound as described in [1] to [8] is mixed with a suitable inert carrier, and optionally with an auxiliary agent.

[29] A mixture in which the compound as described in [1] to [8] is combined with at least one other insecticide and/or fungicide.

The compound of the present invention exhibits an excellent controlling effect as a pesticide at low doses, and also exhibits an excellent controlling effect when used in combination with a pesticide, an acaricide, a nematocide, a fungicide, a herbicide, a plant growth controlling agent, a biocide or the like.

BEST MODE FOR CARRYING OUT THE INVENTION

The terms used in the formulae described in the present invention, such as Formula (1) have the meanings as described below, respectively.

A "halogen atom" represents a fluorine atom, a chlorine atom, a bromine atom or an iodine atom.

The expression "$C_a$-$C_b$ (wherein, a and b represent an integer of 1 or more)" means such that, for example, "C1-C3" means having 1 to 3 carbon atoms, "C2-C6" means having 2 to 6 carbon atoms, and "C1-C4" means having 1 to 4 carbon atoms.

The terms "n-", "i-", "s-" and "t-" mean normal-, iso-, secondary- and tertiary-, respectively.

The term "optionally substituted alkyl group" means a straight, branched or cyclic alkyl group substituted with substituents, which may be identical or different, such as a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, a di-C1-C6-alkylamino group, an optionally substituted phenyl group, an optionally substituted phenylcarbonyl group, an optionally substituted phenylamino group and an optionally substituted heterocyclic group.

The term "optionally substituted C1-C4 alkylcarbonyl group" means a straight, branched or cyclic alkylcarbonyl group having 1 to 4 carbon atoms which is substituted with substituents, which may be identical or different, such as a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, a di-C1-C6-alkylamino group, an optionally substituted phenyl group, an optionally substituted phenylcarbonyl group, an optionally substituted phenylamino group and an optionally substituted heterocyclic group.

The term "optionally substituted phenyl group" means a phenyl substituted with substituents, which may be identical or different, such as a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, a di-C1-C6-alkylamino group, an acetylamino group, an optionally substituted phenyl group, an optionally substituted phenylcarbonyl group, an optionally substituted phenylamino group and an optionally substituted heterocyclic group.

The term "optionally substituted naphthyl group" means a naphthyl group substituted with substituents, which may be identical or different, such as a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, a di-C1-C6-alkylamino group, an acetylamino group, an optionally substituted phenyl group, an optionally substituted phenylcarbonyl group, an optionally substituted phenylamino group and an optionally substituted heterocyclic group.

The term "optionally substituted heterocyclic group" means a heterocyclic group substituted with substituents, which may be identical or different, such as a hydrogen atom, a halogen atom, a hydroxyl group, a cyano group, a nitro group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylcarbonyl group, a C1-C6 haloalkylcarbonyl group, a C1-C6 alkoxycarbonyl group, a C1-C6 haloalkoxycarbonyl group, a C1-C6 alkylcarbonyloxy group, a C1-C6 haloalkylcarbonyloxy group, an amino group, a C1-C6 alkylamino group, a di-C1-C6-alkylamino group, an acetylamino group, an optionally substituted phenyl group, an optionally substituted phenylcarbonyl group, an optionally substituted phenylamino group or an optionally substituted heterocyclic group.

Further, the term "C1-C3 alkyl group" represents a straight or branched alkyl group having 1 to 3 carbon atoms, such as methyl, ethyl, n-propyl, i-propyl, cyclopropyl, etc.; the term "C1-C4 alkyl group" represents a straight or branched alkyl group having 1 to 4 carbon atoms such as, for example, n-butyl, s-butyl, i-butyl, t-butyl, etc. in addition to the C1-C3 alkyl group; and the term "C1-C6 alkyl group" represents a straight or branched alkyl group having 1 to 6 carbon atoms, such as n-pentyl, 2-pentyl, 3-pentyl, neopentyl, n-hexyl, 2-hexyl, 4-methyl-2-pentyl, 3-methyl-n-pentyl, etc. in addition to the C1-C4 alkyl group.

The term "C1-C3 haloalkyl group" represents a straight or branched alkyl group having 1 to 3 carbon atoms, substituted with one or more halogen atoms which may be identical or different, such as monofluoromethyl, difluoromethyl, trifluoromethyl, monochloromethyl, dichloromethyl, trichloromethyl, monobromomethyl, dibromomethyl, tribromomethyl, 1-fluoroethyl, 2-fluoroethyl, 2,2-difluoroethyl, 2,2,2-trifluoroethyl, 1-chloroethyl, 2-chloroethyl, 2,2-dichloroethyl, 2,2,2-trichloroethyl, 1-bromoethyl, 2-bromoethyl, 2,2-dibromoethyl, 2,2,2-tribromoehtyl, 2-iodoethyl, pentafluoroethyl, 3-fluoro-n-propyl, 3-chloro-n-propyl, 3-bromo-n-propyl, 1,3-difluoro-2-propyl, 1,3-dichloro-2-propyl, 1,1,1-trifluoro-2-propyl, 1-chloro-3-fluoro-2-propyl, 1,1,1,3,3,3-hexafluoro-2-propyl, 1,1,1,3,3,3-hexafluoro-2-chloro-2-propyl, 2,2,3,3,3-pentafluoro-n-propyl, heptafluoro-i-propyl or heptafluoro-n-propyl. The term "C1-C4 haloalkyl group" represents a straight or branched alkyl group having 1 to 4 carbon atoms and being substituted with one or more halogen atoms which may be identical or different, such as 4-fluoro-n-butyl, nonafluoro-n-butyl and nonafluoro-2-butyl in addition to the "C1-C3 haloalkyl group".

The term "C2-C4 alkenyl group" represents an alkenyl group having 2 to 4 carbon atoms and a double bond in the carbon chain, such as vinyl, allyl, 2-butenyl or 3-butenyl. The Term "C2-C4 haloalkenyl group" represents a straight or branched alkenyl group having 2 to 4 carbon atoms and a double bond in the carbon chain, and being substituted with one or more halogen atoms which may be identical or different, such as 3,3-diflouro-2-propenyl, 3,3-dichloro-2-propenyl, 3,3-dibromo-2-propenyl, 2,3-dibromo-2-propenyl, 4,4-difluoro-3-butenyl and 3,4,4-tribromo-3-butenyl.

The term "C2-C4 alkynyl group" represents a straight or branched alkynyl group having 2 to 4 carbon atoms and a triple bond in the carbon chain, such as propargyl, 1-butyn-3-yl and 1-butyn-3-methyl-3-yl. The term "C2-C4 haloalkynyl group" represents a straight or branched alkenyl group having 2 to 4 carbon atoms and a triple bond in the carbon chain, and being substituted with one or more halogen atoms which may be identical or different.

The term "C3-C6 cycloalkyl group" represents a cycloalkyl group having a ring structure of 3 to 6 carbon atoms, such as cyclopropyl, cyclobutyl, cyclopentyl, 2-methylcyclopentyl, 3-methylcyclopentyl and cyclohexyl. The term "C3-C6 halocycloalkyl group" represents a cycloalkyl group having a ring structure of 3 to 6 carbon atoms and being substituted with one more halogen atoms which may be identical or different, such as 2,2,3,3-tetrafluorocylcobutyl, 2-chlorocyclohexyl and 4-chlorocyclohexyl.

The term "C1-C3 alkoxy group" represents a straight or branched alkoxy group having 1 to 3 carbon atoms, such as methoxy, ethoxy, n-propyloxy and isopropyloxy. The term "C1-C3 haloalkoxy group" represents a straight or branched haloalkoxy group having 1 to 3 carbon atoms, substituted with one or more halogen atoms which may be identical or different, such as trifluoromethoxy, 1,1,1,3,3,3-hexafluoro-2-propyloxy, 2,2,2-trifluoroethoxy, 2-chloroethoxy and 3-fluoro-n-propyloxy. The term "C1-C4 haloalkoxy group" represents a straight or branched haloalkoxy group having 1 to 4 carbon atoms and being substituted with one or more halogen atoms which may be identical or different, such as 1,1,1,3,3,4,4,4-octafluoro-2-butyloxy in addition to the "C1-C3 haloalkoxy group".

The term "C1-C3 alkylthio group" represents a straight or branched alkylthio group having 1 to 3 carbon atoms, such as methylthio, ethylthio, n-propylthio, i-propylthio and cyclopropylthio. The term "C1-C4 alkylthio group" represents a straight or branched alkylthio group having 1 to 4 carbon atoms, such as n-butylthio, i-butylthio, s-butylthio, t-butylthio and cyclopropylmethylthio in addition to the "C1-C3 alkylthio group". The term "C1-C3 haloalkylthio group" represents a straight or branched alkylthio group having 1 to 3 carbon atoms, substituted with one or more halogen atoms which may be identical of different, such as trifluoromethylthio, pentafluoroethylthio, 2,2,2-trifluoroethylthio, heptafluoro-n-propylthio and heptafluoro-i-propylthio. The term "C1-C4 haloalkylthio group" represents a straight or branched alkylthio group having 1 to 4 carbon atoms and being substituted with one or more halogen atoms which may be identical or different, such as nonafluoro-n-butylthio, nonafluoro-s-butylthio and 4,4,4-trifluoro-n-butylthio in addition to the "C1-C3 haloalkylthio group".

The term "C1-C3 alkylsulfinyl group" represents a straight or branched alkylsulfinyl group having 1 to 3 carbon atoms, such as methylsulfinyl, ethylsulfinyl, n-propylsulfinyl, i-propylsulfinyl or cyclopropylsulfinyl. The term "C1-C3 haloalkylsulfinyl group" represents a straight or branched alkylsulfinyl group having 1 to 3 carbon atoms, substituted with one or more halogen atoms which may be identical or different, such as trifluoromethylsulfinyl, pentafluoroethylsulfinyl, 2,2,2-trifluoroethylsulfinyl, heptafluoro-n-propylsulfinyl and heptafluoro-i-propylsulfinyl.

The term "C1-C3 alkylsulfonyl group" represents a straight or branched alkylsulfonyl group having 1 to 3 carbon atoms, such as methylsulfonyl, ethylsulfonyl, n-propylsulfonyl, i-propylsulfonyl and cyclopropylsulfonyl. The "C1-C3 haloalkylsulfonyl group" represents a straight or branched alkylsulfonyl group having 1 to 3 carbon atoms, substituted with one or more halogen atoms which may be identical or different, such as trifluomethylsulfonyl, pentafluoroethylsulfonyl, 2,2,2-trifluoroethylsulfonyl, heptafluoro-n-propylsulfonyl or heptafluoro-i-propylsulfonyl.

The term "arylsulfonyl group" represents an arylsulfonyl group having an aromatic ring of 6 to 14 carbon atoms, such as phenylsulfonyl, p-toluenesulfonyl, 1-naphthylsulfonyl, 2-naphthylsulfonyl, anthrylsulfonyl, phenanthrylsulfonyl and acenaphthylenylsulfonyl.

The term "C1-C4 alkylamino group" represents a straight, branched or cyclic alkylamino group having 1 to 4 carbon atoms, such as methylamino, ethylamino, n-propylamino, i-propylamino, n-butylamino and cyclopropylamino. The term "di-C1-C4-alkylamino group" represents an amino group substituted with two straight or branched alkyl group having 1 to 4 carbon atoms which may be identical or different, such as dimethylamino, diethylamino and N-ethyl-N-methylamino.

The term "C1-C4 alkylcarbonyl group" represents a straight, branched or cyclic alkylcarbonyl group having 1 to 4 carbon atoms, such as formyl, acetyl, propionyl, isopropylcarbonyl and cyclopropylcarbonyl.

The term "C1-C4 haloalkylcarbonyl group" represents a straight or branched alkylcarbonyl group having 1 to 4 carbon atoms and being substituted with one or more halogen atoms which may be identical or different, such as fluoroacetyl, difluoroacetyl, trifluoroacetyl, chloroacetyl, dichloroacetyl, trichloroacetyl, bromoacetyl, iodoacetyl, 3,3,3-trifluoropropionyl and 2,2,3,3,3-pentafluoropropionyl.

The term "C1-C4 alkylcarbonyloxy group" represents a straight or branched alkylcarbonyloxy group having 1 to 4 carbon atoms, such as acetoxy and propionyloxy.

The term "C1-C4 alkoxycarbonyl group" represents a straight or branched alkoxycarbonyl group having 1 to 4 carbon atoms, such as methoxycarbonyl, ethoxycarbonyl or isopropyloxycarbonyl.

The term "C1-C4 perfluoroalkyl group" represents a straight or branched alkyl group having 1 to 4 carbon atoms and being completely substituted with fluorine atoms, such as trifluoromethyl, pentafluoroethyl, heptafluoro-n-propyl, heptafluoro-i-propyl, nonafluoro-n-butyl, nonafluoro-2-butyl and nonafluoro-i-butyl. The term "C2-C6 perfluoroakyl group" represents a straight or branched alkyl group having 2 to 6 carbon atoms and being completely substituted with fluorine atoms, such as pentafluoroethyl, heptafluoro-n-propyl, heptafluoro-i-propyl, nonafluoro-n-butyl, nonafluoro-2-butyl, nonafluoro-i-butyl, perfluoro-n-pentyl and perfluoro-n-hexyl.

The term "C1-C6 perfluoroalkylthio group" represents a straight or branched alkylthio group having 1 to 6 carbon atoms and being completely substituted with fluorine atoms, such as trifluoromethylthio, pentafluoroethylthio, heptafluoro-n-propylthio, heptafluoro-i-propylthio, nonafluoro-n-butylthio, nonafluoro-2-butylthio, nonafluoro-i-butylthio, perfluoro-n-pentylthio and perfluoro-n-hexylthio.

The term "C1-C6 perfluoroalkylsulfinyl group" represents a straight or branched alkylsulfinyl group having 1 to 6 carbon atoms and being completely substituted with fluorine atoms, such as trifluoromethylsulfinyl, pentafluoroethylsulfinyl, heptafluoro-n-propylsulfinyl, heptafluoro-i-propylsulfinyl, nonafluoro-n-butylsulfinyl, nonafluoro-2-butylsulfinyl, nonafluoro-i-butylsulfinyl, perfluoro-n-pentylsulfinyl and perfluoro-n-hexylsulfinyl.

The term "C1-C6 perfluoroalkylsulfonyl group" represents a straight or branched alkylsulfonyl group having 1 to 6 carbon atoms and being completely substituted with fluorine atoms, such as trifluoromethylsulfonyl, pentafluoroethylsulfonyl, heptafluoro-n-propylsulfonyl, heptafluoro-i-propylsulfonyl, nonafluoro-n-butylsulfonyl, nonafluoro-2-butylsulfonyl, nonafluoro-i-butylsulfonyl, perfluoro-n-pentylsulfonyl and perfluoro-n-hexylsulfonyl.

The compound represented by Formula (1) of the invention may comprise one or a plurality of chiral carbon atoms or chiral centers in the structure, and thus two or more optical isomers may exist. The present invention includes all of the individual optical isomers and mixtures comprising them at any proportions. Furthermore, the compound represented by Formula (1) of the invention may exist in the form of two or more stereoisomers originating from carbon-carbon double bonds in the structure, and the invention includes all of the individual stereoisomers and mixtures comprising them at any proportions.

The substituents or atoms preferred as the substituents for the compounds represented by the above-mentioned formulae such as Formula (1) of the invention will be presented below.

$A_1$, $A_2$, $A_3$ and $A_4$ are preferably such that $A_1$ is a carbon atom, a nitrogen atom or an oxidized nitrogen atom and at the same time $A_2$, $A_3$ and $A_4$ are all carbon atoms, and more preferably such that $A_1$, $A_2$, $A_3$ and $A_4$ are all carbon atoms.

$R_1$ is preferably a hydrogen atom or a C1-C4 alkyl group, and more preferably a hydrogen atom, a methyl group or an ethyl group.

$R_2$ is preferably a hydrogen atom or a C1-C4 alkyl group, and more preferably a hydrogen atom, a methyl group or an ethyl group.

$G_1$ and $G_2$ are each preferably an oxygen atom or a sulfur atom, and more preferably $G_1$ and $G_2$ are both an oxygen atom.

X is preferably a hydrogen atom or a halogen atom, and more preferably a hydrogen atom or a fluorine atom.

n is preferably 0, 1 or 2, and more preferably 0 or 1.

$X_1$ is preferably a hydrogen atom or a halogen atom, and more preferably a hydrogen atom or a fluorine atom.

$X_2$ is preferably a hydrogen atom or a fluorine atom, and more preferably a hydrogen atom.

$X_3$ and $X_4$ are preferably a hydrogen atom.

$Q_1$ is preferably a phenyl group; a phenyl group optionally substituted with one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group and an acetylamino group; a pyridyl group; or a pyridyl group optionally substituted with one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group and an acetylamino group.

More preferably, $Q_1$ is a phenyl group; a phenyl group having 1 to 3 substituents, which may be identical or different, selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group; a pyridyl group; or a pyridyl group having 1 or 2 substituents, which may be identical or different, selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group.

$Q_2$ is preferably a substituted phenyl group represented by Formula (2) or a substituted pyridyl group represented by Formula (3), wherein:

$Y_1$ and $Y_5$ are each preferably a chlorine atom, a bromine atom, an iodine atom, a methyl group, an ethyl group, an n-propyl group, an i-propyl group, an n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group and a cyano group;

$Y_6$ and $Y_9$ are each preferably a chlorine atom, a bromine atom, an iodine atom, a methyl group, an ethyl group, an n-propyl group, an i-propyl group, an n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group and a cyano group;

$Y_2$, $Y_4$ and $Y_7$ are each preferably a hydrogen atom, a halogen atom or a methyl group, and more preferably a hydrogen atom;

$Y_3$ is preferably a pentafluoroethyl group, a heptafluoro-n-propyl group, a heptafluoro-i-propyl group, a nonafluoro-n-butyl group, a nonafluoro-2-butyl group, a nonafluoro-i-butyl group, a trifluoromethylthio group, a pentafluoroethylthio group, a heptafluoro-n-propylthio group, a heptafluoro-i-propylthio group, a nonafluoro-n-butylthio group, a nonafluoro-2-butylthio group, a trifluoromethylsulfinyl group, a pentafluoroethylsulfinyl group, a heptafluoro-n-propylsulfinyl group, a heptafluoro-i-propylsulfinyl group, a nonafluoro-n-butylsulfinyl group, a nonafluoro-2-butylsulfinyl group, a trifluoromethylsulfonyl group, a pentafluoroethylsulfonyl group, a heptafluoro-n-propylsulfonyl group, a heptafluoro-i-propylsulfonyl group, a nonafluoro-n-butylsulfonyl group or anonafluoro-2-butylsulfonyl group;

$Y_8$ is preferably a pentafluoroethyl group, a heptafluoro-n-propyl group, a heptafluoro-i-propyl group, a nonafluoro-n-butyl group, a nonafluoro-2-butyl group, a nonafluoro-i-butyl group, a trifluoromethylthio group, a pentafluoroethylthio group, a heptafluoro-n-propylthio group, a heptafluoro-i-propylthio group, a nonafluoro-n-butylthio group, a nonafluoro-2-butylthio group, a trifluoromethylsulfinyl group, a pentafluoroethylsulfinyl group, a heptafluoro-n-propylsulfinyl group, a heptafluoro-i-propylsulfinyl group, a nonafluoro-n-butylsulfinyl group, a nonafluoro-2-butylsulfinyl group, a trifluoromethylsulfonyl group, a pentafluoroethylsulfonyl group, a heptafluoro-n-propylsulfonyl group, a heptafluoro-i-propylsulfonyl group, a nonafluoro-n-butylsulfonyl group, a nonafluoro-2-butylsulfonyl group, a pentafluoroethoxy group and a 1,1,1,3,3,3-hexafluoro-i-propyloxy group.

L is preferably a chlorine atom, a bromine atom or a hydroxyl group.

$R_1a$ is preferably a hydrogen atom or a C1-C4 alkyl group, and more preferably a hydrogen atom, a methyl group or an ethyl group.

$R_2a$ is preferably a hydrogen atom or a C1-C4 alkyl group, and more preferably a hydrogen atom, a methyl group or an ethyl group.

$G_1a$ and $G_2a$ are each preferably an oxygen atom or a sulfur atom, and more preferably $G_1a$ and $G_2a$ are both an oxygen atom.

$X_1a$ is preferably a hydrogen atom or a halogen atom, and more preferably a hydrogen atom or a fluorine atom.

$X_2a$ is preferably a hydrogen atom or a fluorine atom, and more preferably a hydrogen atom.

$X_3a$ and $X_4a$ are preferably a hydrogen atom.

$Y_1a$ and $Y_5a$ are each preferably a chlorine atom, a bromine atom, an iodine atom, a methyl group, an ethyl group, an n-propyl group, an i-propyl group, an n-butyl group, a 2-butyl group, a trifluoromethyl group, a methylthio group, a methylsulfinyl group, a methylsulfonyl group, a trifluoromethylthio group, a trifluoromethylsulfinyl group, a trifluoromethylsulfonyl group or a cyano group.

$Y_2a$ and $Y_4a$ are each preferably a hydrogen atom, a halogen atom and a methyl group, and more preferably a hydrogen atom.

$Q_1a$ is preferably a phenyl group; a phenyl group optionally substituted with one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group and an acetylamino group; a pyridyl group; or a pyridyl group optionally substituted with one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a c3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group and an acetylamino group.

More preferably, $Q_1a$ is a phenyl group; a phenyl group having 1 to 3 substituents, which may be identical or different, selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group; a pyridyl group; or a pyridyl group having 1 or 2 substituents, which may be identical or different, selected from a fluorine atom, a chlorine atom, a bromine atom, an iodine atom, a methyl group, a trifluoromethyl group, a methoxy group, a trifluoromethoxy group, a methylthio group, a methylsulfinyl group, a methylsulfonyl group, a trifluoromethylthio group, a trifluoromethylsulfinyl group, a trifluoromethylsulfonyl group, a methylamino group, a dimethylamino group, a cyano group and a nitro group.

$R_a$ and $R_b$ are each preferably a fluorine atom, a trifluoromethyl group, a pentafluoroethyl group or a heptafluoro-n-propyl group, and more preferably a fluorine atom, a trifluoromethyl group or a pentafluoroethyl group.

$R_c$ is preferably a hydroxyl group, a chlorine atom, a bromine atom, an iodine atom, a methoxy group, an ethoxy group, a methylsulfonyloxy group, a trifluoromethylsulfonyloxy group, a phenylsulfonyloxy group, a p-toluenesulfonyloxy group, an acetoxy group or a trifluoroacetoxy group, and more preferably a hydroxyl group, a chlorine atom, a bromine atom, a methoxy group, a methylsulfonyloxy group, a trifluoromethylsulfonyloxy group, a phenylsulfonyloxy group or a p-toluenesulfonyloxy group, and even more preferably a hydroxyl group, a chlorine atom or a bromine atom.

$R_c'$ is preferably a hydroxyl group.

$R_c''$ is preferably a chlorine atom or a bromine atom.

J, J' and J″ are each preferably a hydroxyl group, a chlorine atom or a bromine atom, and more preferably a chlorine atom.

Representative processes for preparation of the compound of the invention will be described in the following. Preparation of the compound of the invention is possible by following the procedure, but the preparation route is not limited only to the process for preparation described below.

With regard to the formulae prepared by the following processes for preparation, $X_1$, $X_2$, $X_3$, $X_4$, $Y_1$, $Y_2$, $Y_4$, $Y_5$, $G_1$, $G_2$, $R_1$, $R_2$ and $Q_1$ may correspond to $X_1a$, $X_2a$, $X_3a$, $X_4a$, $Y_1a$, $Y_2a$, $Y_4a$, $Y_5a$, $G_1a$, $G_2a$, $R_1a$, $R_2a$ and $Q_1a$, respectively, and it is also possible vice versa. Further, $Q_2$ has the meaning as described in claim 1 or is represented by Formula (2):

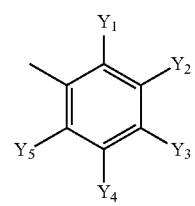

(2)

(wherein $Y_1$, $Y_2$, $Y_3$, $Y_4$ and $Y_5$ have the same meanings as described above), by Formula (3):

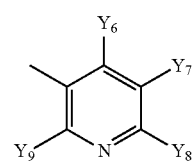

(3)

(wherein $Y_6$, $Y_7$, $Y_8$ and $Y_9$ have the same meanings as described above),
or by Formula (18):

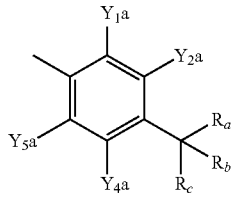

(18)

(wherein $Y_1a$, $Y_2a$, $Y_4a$, $Y_5a$, $R_a$, $R_b$ and $R_c$ have the same meaning as described above).

Preparation Process 1

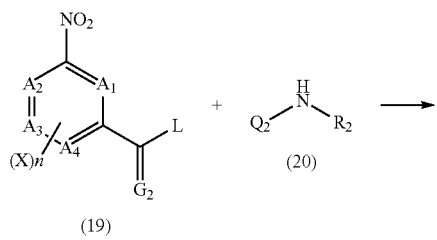

(19)

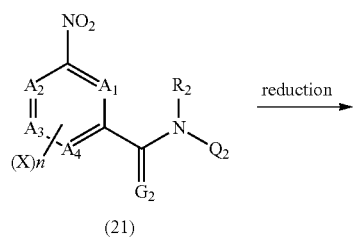

(21)

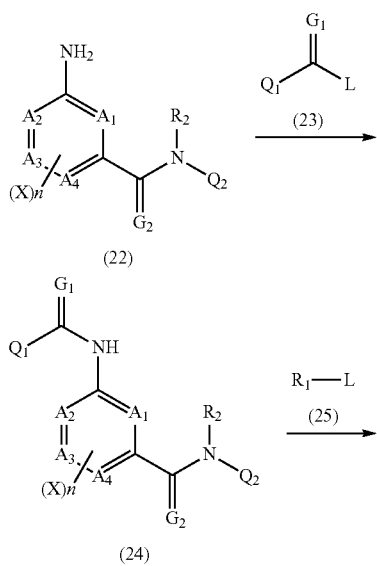

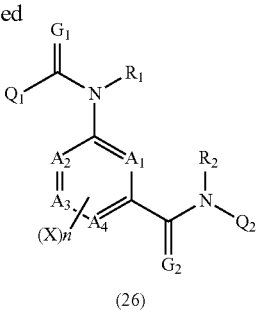

(26)

wherein $A_1$, $A_2$, $A_3$, $A_4$, $G_1$, $G_2$, $R_1$, $R_2$, X, n, $Q_1$ and $Q_2$ have the same meaning as described above, and L represents a functionality capable of leaving such as a halogen atom or a hydroxyl group.

1-(i) Formula (19)+Formula (20)→Formula (21)

An aromatic carboxamide derivative having a nitro group represented by Formula (21) can be prepared by reacting an m-nitro aromatic carboxylic acid derivative having a leaving group represented by Formula (19) with an aromatic amine derivative represented by Formula (20) in a suitable solvent or without a solvent. In this step, an appropriate base can be also used.

For the solvent, use can be made of any solvent which does not impede the reaction significantly, for example, water; aromatic hydrocarbons such as benzene, toluene and xylene; halogenated hydrocarbons such as dichloromethane, chloroform and tetrachlorocarbon; chained or cyclic ethers such as diethyl ether, dioxane, tetrahydrofuran and 1,2-dimethoxyethane; esters such as ethyl acetate and butyl acetate; alcohols such as methanol and ethanol; ketones such as acetone, methyl isobutyl ketone and cyclohexanone; amides such as dimethyl formamide and dimethyl acetamide; nitriles such as acetonitrile; and inert solvents such as 1,3-dimethyl-2-imidazolidinone, which may be used alone or in combination of two or more.

Further, for the base, use can be made of organic bases such as triethylamine, tri-n-butylamine, pyridine and 4-dimethyl aminopyridine; alkali metal hydroxides such as sodium hydroxide and potassium hydroxide; carbonates such as sodium hydrogen carbonate and potassium carbonate; phosphates such as dipotassium hydrogen phosphate and trisodium phosphate; alkali metal hydrides such as sodium hydride; and alkali metal alcoholates such as sodium methoxide and sodium ethoxide. These bases may be appropriately used in a quantity of 0.01 to 5-fold molar equivalents with respect to the compound represented by Formula (19).

The reaction temperature may be suitably selected within the range of −20° C. to the reflux temperature of the solvent used, and the reaction time within the range of several minutes to 96 hours.

Among the compounds represented by Formula (19), an aromatic carboxylic acid halide derivative may be prepared easily from an aromatic carboxylic acid by a conventional process using a halogenating agent. A halogenating agent may be, for example, thionyl chloride, thionyl bromide, phosphorus oxychloride, oxalyl chloride, phosphorus trichloride and the like.

Meanwhile, it is possible to prepare the compound represented by Formula (21) from an m-nitro aromatic carboxylic acid derivative and the compound represented by Formula (20) without using a halogenating agent. The process is described in, for example, Chem. Ber. p. 788 (1970), in which a condensing agent comprising N,N'-dicyclohexylcarbodiimide is used, suitably with an additive such as 1-hydroxybenzotriazole. Other condensing agents that can be used in this case may include 1-ethyl-3-(3-dimethylaminopropyl)carbodiimide, 1,1'-carbonylbis-1H-imidazole and the like.

Furthermore, for other processes for preparation of the compounds represented by Formula (21), there can be used a mixed acid anhydride process using chloroformic acid esters or a process described in J. Am. Chem. Soc., p. 5012 (1967) in order to prepare the compound represented by Formula (21). The chloroformic acid esters used in this case may include isobutyl chloroformate, isopropyl chloroformate and the like. In addition to chloroformic acid esters, diethylacetyl chloride, trimethylacetyl chloride and the like can also be used.

Both the process using a condensing agent and the mixed acid anhydride process are not limited by the solvent, the reaction temperature and the reaction time as described in the references above. An inert solvent may be used which does not impede the reaction significantly, and the reaction temperature and the reaction time may also be selected appropriately in accordance with the proceeding of the reaction.

1-(ii) Formula (21)→Formula (22)

An aromatic carboxamide derivative having an amino group represented by Formula (22) can be derived from the aromatic carboxamide derivative having a nitro group represented by Formula (21) by means of reduction. Such reduction is illustrated by a process using hydrogenation and a process using a metal compound (for example, tin(II) chloride (anhydride), iron powder, zinc powder and the like).

The reaction of the former process can be carried out in a suitable solvent in the presence of catalyst at atmospheric pressure or a higher pressure under a hydrogen atmosphere. Examples of the catalyst may include palladium catalysts such as palladium-carbon, nickel catalysts such as Raney nickel, cobalt catalysts, ruthenium catalysts, rhodium catalysts, platinum catalysts and the like, and examples of the solvent may include water; alcohols such as methanol and ethanol; aromatic hydrocarbons such as benzene, toluene; chained or cyclic ethers such as ether, dioxane, tetrahydrofuran, etc.; and esters such as ethyl acetate. The compound of Formula (22) can be efficiently prepared by appropriately selecting the pressure within a range of 0.1 to 10 Mpa, the reaction temperature within a range of −20° C. to the reflux temperature of the solvent used, and the reaction time within a range of several minutes to 96 hours.

For the latter process, there can be used a method using tin (II) chloride (anhydride) as a metal compound under the conditions described in "Organic Syntheses" Coll. Vol. III, P. 453.

1-(iii) Formula (22)+Formula (23)→Formula (24)

A compound of the invention represented by Formula (24) can be prepared by reacting the aromatic carboxamide derivative having an amino group represented by Formula (22) with the compound represented by Formula (23) in a suitable solvent. In this step, a suitable base can also be used.

For the solvent, use can be made of any solvent which does not impede the reaction significantly, for example, water; aromatic hydrocarbons such as benzene, toluene and xylene; halogenated hydrocarbons such as dichloromethane, chloroform and tetrachlorocarbon; chained or cyclic ethers such as diethyl ether, dioxane, tetrahydrofuran and 1,2-dimethoxyethane; esters such as ethyl acetate and butyl acetate; alcohols such as methanol and ethanol; ketones such as acetone, methyl isobutyl ketone and cyclohexanone; amides such as dimethyl formamide and dimethyl acetamide; nitriles such as acetonitrile; and inert solvents such as 1,3-dimethyl-2-imidazolidinone, which may be used alone or in combination of two or more.

Further, for the base, use can be made of organic bases such as triethylamine, tri-n-butylamine, pyridine and 4-dimethyl aminopyridine; alkali metal hydroxides such as sodium hydroxide and potassium hydroxide; carbonates such as sodium hydrogen carbonate and potassium carbonate; phosphates such as dipotassium hydrogen phosphate and trisodium phosphate; alkali metal hydrides such as sodium hydride; and alkali metal alcoholates such as sodium methoxide and sodium ethoxide. Such base may be appropriately used in a quantity of 0.01 to 5-fold molar equivalents with respect to the compound represented by Formula (22). The reaction temperature may be suitably selected within the range of −20° C. to the reflux temperature of the solvent used, and the reaction time within the range of several minutes to 96 hours. It is also possible to prepare by the method using a condensing agent as described in 1-(i) or the mixed acid anhydride method.

1-(iv) Formula (24)+Formula (25)→Formula (26)

A compound represented by Formula (26) of the invention can be prepared by reacting a compound represented by Formula (24) with an alkyl compound having a leaving group represented by Formula (25) in a solvent or without a solvent. The compound represented by Formula (25) may include an alkyl halide such as methyl iodide, ethyl iodide or n-propyl bromide. Further, in this step, it is possible to use a suitable base or a solvent, and for such base or solvent, those exemplified in 1-(i) may be used. The reaction temperature, the reaction time and the like may be selected according to the examples as given in 1-(i).

Alternatively, it is also possible to prepare the compound represented by Formula (26) by reacting the compound represented by Formula (24) with an alkylating agent such as dimethyl sulfate, diethyl sulfate and the like, instead of the compound represented by Formula (25).

Preparation Process 2

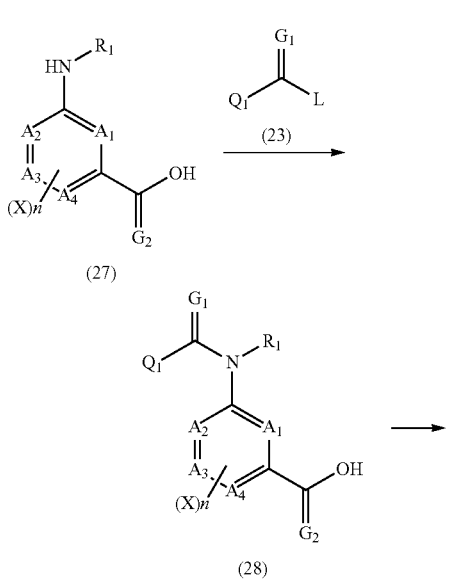

-continued

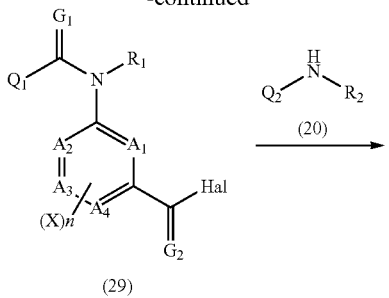

(29)

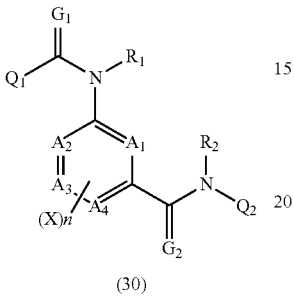

(30)

wherein $A_1$, $A_2$, $A_3$, $A_4$, $G_1$, $G_2$, $R_1$, $R_2$, X, n, $Q_1$, $Q_2$, L and Hal have the same meaning as those described in the above.

2-(i) Formula (27)+Formula (23)→Formula (28)

Carboxylic acids having an acylamino group represented by Formula (28) can be prepared by reacting carboxylic acids having an amino group represented by Formula (27) as starting material with the compound represented by Formula (23) according to the conditions described in 1-(i).

2-(ii) Formula (28)→Formula (29)

A compound represented by Formula (29) can be prepared by a known conventional method in which the compound represented by Formula (28) is reacted with thionyl chloride, oxalyl chloride, phosgene, phosphorus oxychloride, phosphorus pentachloride, phosphorus trichloride, thionyl bromide, phosphorus tribromide, diethylaminosulfur trifluoride and the like.

2-(iii) Formula (29)+Formula (20)→Formula (30)

A compound represented by Formula (30) can be prepared by reacting the compound represented by Formula (29) with a compound represented by Formula (20) according to the conditions described in 1-(i).

2-(iv) Formula (28)+Formula (20)→Formula (30)

The compound represented by Formula (30) can be also prepared by reacting the compound represented by Formula (28) with the compound represented by Formula (20) according to the conditions of using a condensing agent as described in 1-(i) or the conditions of using the mixed acid anhydride method.

Preparation Process 3

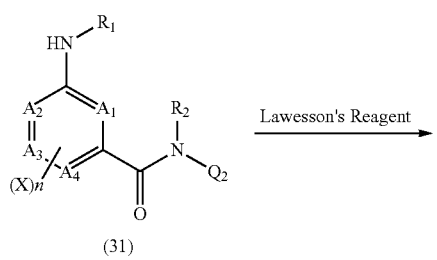

(31)

-continued

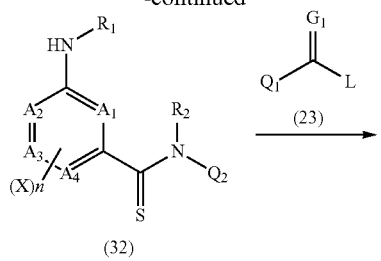

(32)

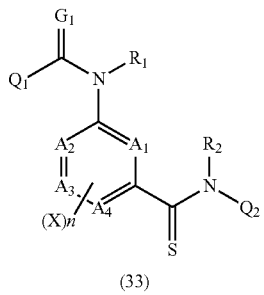

(33)

wherein $A_1$, $A_2$, $A_3$, $A_4$, $G_1$, $R_1$, $R_2$, X, n, $Q_1$, $Q_2$ and L have the same meaning as those described in the above.

3-(i) Formula (31)→Formula (32)

A compound represented by Formula (32) can be prepared by reacting a compound represented by Formula (31) with the Lawesson's reagent according to the known conditions as described in Synthesis, p. 463 (1993) or in Synthesis, p. 829 (1984). Conditions such as a solvent, a reaction temperature and the like are not limited to those as described in the literature.

3-(ii) Formula (32)+Formula (23)→Formula (33)

A compound represented by Formula (33) can be prepared by reacting the compound represented by Formula (32) with the compound represented by Formula (23) according to the conditions as described in 1-(i).

Preparation Process 4

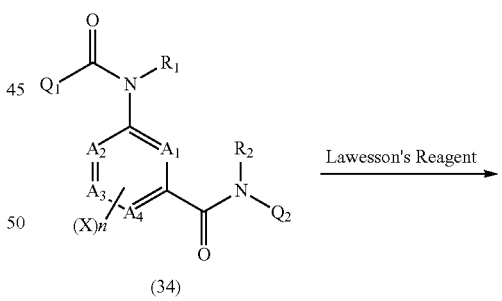

(34)

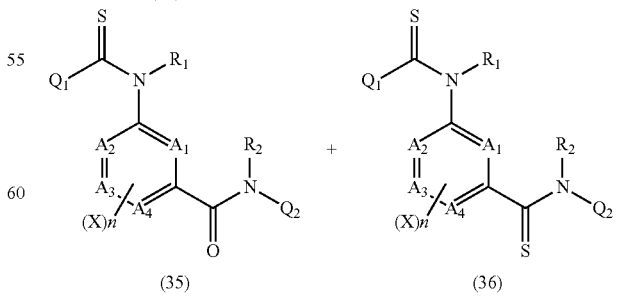

(35)     (36)

wherein $A_1$, $A_2$, $A_3$, $A_4$, $R_1$, $R_2$, X, n, $Q_1$ and $Q_2$ have the same meaning as those described in the above.

A compound represented by Formula (35) and a compound represented by Formula (36) can be prepared from the compound represented by Formula (34) according to the conditions as described in 3-(i). Conditions such as a solvent, a reaction temperature and the like are not limited to those as described in the literature. These two compounds can be easily separated and purified by means of a known separation and purification technique such as silica gel column chromatography.

Preparation Process 5

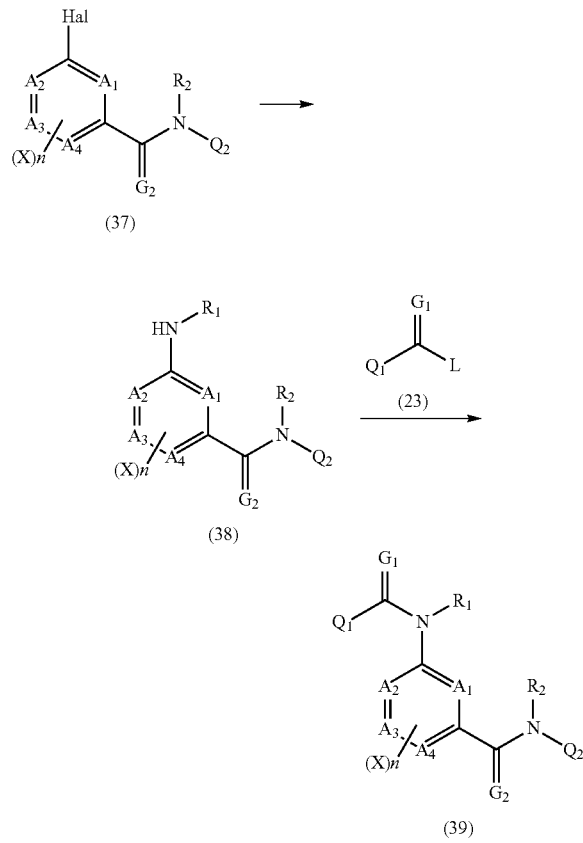

wherein $A_1$, $A_2$, $A_3$, $A_4$, $G_1$, $G_2$, $R_1$, $R_2$, X, n, $Q_1$, $Q_2$ and L have the same meaning as those described in the above.

5-(i) Formula (37)→Formula (38)

A compound represented by Formula (38) can be prepared by carrying out an amination reaction using ammonia according to the conditions as described in, for example, J. Org. Chem., p. 280 (1958). Conditions such as a reaction solvent are not limited to those as described in the literature, and any inert solvent which does not impede the reaction significantly may be used. A reaction temperature and a reaction time may also be selected in accordance with the proceeding of the reaction. Further, it is also possible to use methylamine, ethylamine and the like, in addition to ammonia, as the aminating agent.

5-(ii) Formula (38)+Formula (23)→Formula (39)

A compound represented by Formula (39) can be prepared by reacting the compound represented by Formula (38) with a compound represented by Formula (23) according to the conditions as described in 1-(i).

Preparation Process 6

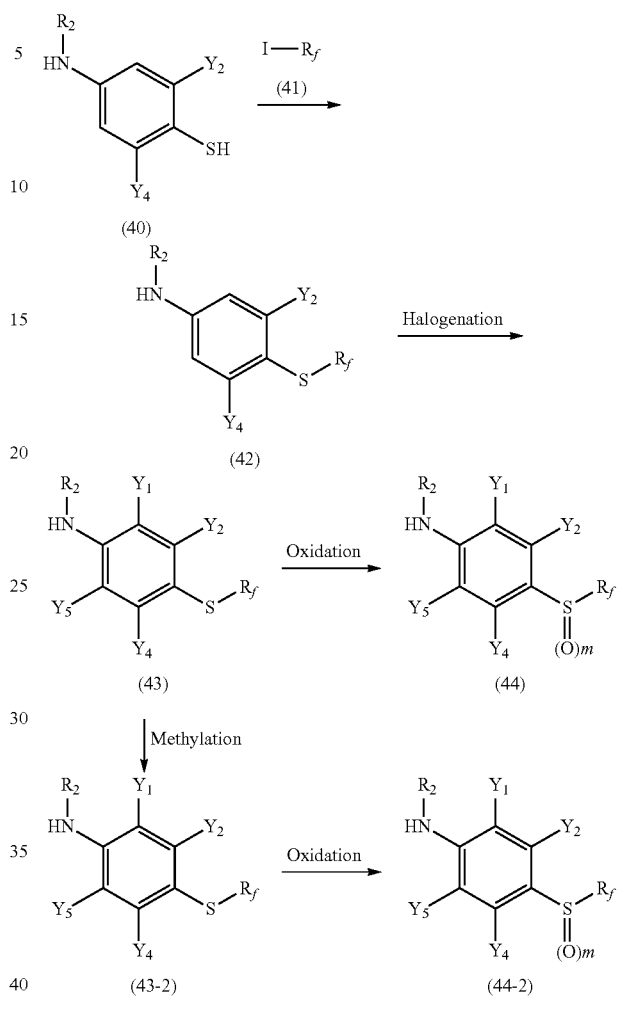

wherein $R_2$ has the same meaning as described in the above; $Y_1$ and $Y_5$ each represent a methyl group, a chlorine atom, a bromine atom or an iodine atom; $Y_2$ and $Y_4$ have the same meaning as those described in the above; $R_f$ represents a C1-C6 perfluoroalkyl group; and m represents 1 or 2.

6-(i) Formula (40)+Formula (41)→Formula (42)

A compound represented by Formula (42) can be prepared by reacting an aminothiophenol represented by Formula (40) with a haloalkyl iodide represented by Formula (41) according to the method as described in J. Fluorine Chem., p. 207 (1994).

The haloalkyl iodide represented by Formula (41) may include, for example, trifluoromethyl iodide, pentafluoroethyl iodide, heptafluoro-n-propyl iodide, heptafluoroisopropyl iodide, nonafluoro-n-butyl iodide, nonafluoro-2-butyl iodide and the like, and these compounds represented by Formula (40) may be suitably used in the range of 1 to 10-fold molar equivalents.

The solvent used in this step is not limited to those solvents as described in the above literature, and the solvent may be any of those not impeding the reaction significantly, for example, water; aromatic hydrocarbons such as benzene, toluene and xylene; halogenated hydrocarbons such as dichloromethane, chloroform and tetrachlorocarbon; chained or cyclic ethers such as diethyl ether, dioxane, tetrahydrofuran and 1,2-dimethoxyethane; esters such as ethyl acetate and butyl acetate; alcohols such as methanol and ethanol; ketones such as acetone, methyl isobutyl ketone and cyclohexanone; amides such as dimethyl formamide and dimethylacetamide; nitriles such as acetonitrile; or inert solvents such as 1,3-dimethyl-2-imidazolidinone, hexamethylphosphate triamide and the like, which may used alone or in combination of two or more. A polar solvent is particularly preferred. The reaction temperature may be suitably selected within the range of −20° C. to the reflux temperature of the solvent used, and the reaction time within the range of several minutes to 96 hours.

6-(ii) Formula (42)→Formula (43)

A compound represented by Formula (43) can be prepared using a suitable halogenating agent, for example, according to the method as described in Synth. Commun., p. 1261 (1989).

The halogenating agent may include, for example, chlorine, bromine, iodine, N-chlorosuccinimide, N-bromosuccinimide, N-iodosuccinimide and the like, and these compounds represented by Formula (42) may be suitably used in the range of 1 to 10-fold molar equivalents.

In this step, it is possible to use a suitable solvent. Such solvent for use is not limited to the solvents as described in the above literature, and the solvent may be any of those not impeding the reaction significantly, for example, water; aromatic hydrocarbons such as benzene, toluene and xylene; halogenated hydrocarbons such as dichloromethane, chloroform and tetrachlorocarbon; chained or cyclic ethers such as diethyl ether, dioxane, tetrahydrofuran and 1,2-dimethoxyethane; esters such as ethyl acetate and butyl acetate; alcohols such as methanol and ethanol; ketones such as acetone, methyl isobutyl ketone and cyclohexanone; amides such as dimethyl formamide and dimethylacetamide; nitriles such as acetonitrile; or inert solvents such as 1,3-dimethyl-2-imidazolidinone, hexamethylphosphate triamide and the like, which may used alone or in combination of two or more. A polar solvent is particularly preferred. The reaction temperature may be suitably selected within the range of −20° C. to the reflux temperature of the solvent used, and the reaction time within the range of several minutes to 96 hours.

6-(iii) Formula (43)→Formula (44)

A compound represented by Formula (44) can be prepared using a suitable oxidizing agent, for example, according to the method as described in Tetrahedron Lett., p. 4955 (1994).

The oxidizing agent may include, for example, an organic peracid such as m-chloroperbenzoic acid, sodium metaperiodate, hydrogen peroxide, ozone, selenium dioxide, chromic acid, dinitrogen tetraoxide, acyl nitrate, iodine, bromine, N-bromosuccinimide, iodosyl benzyl, t-butyl hypochlorite and the like.

The solvent used in this step is not limited to the solvents described in the above literature, and the solvent may be any of those not impeding the reaction of the invention significantly. The solvent can be used alone or in combination of two or more. A polar solvent is particularly preferred. The reaction temperature may be suitably selected within the range of −20° C. to the reflux temperature of the solvent used, and the reaction time within the range of several minutes to 96 hours.

6-(iv) Formula (43)→Formula (43-2)

A compound represented by Formula (43-2), wherein either of $Y_1$ and $Y_5$ essentially represents a methyl group, can be prepared from the compound represented by Formula (43) using a suitable methylating agent. In this step, for example, the process described in Tetrahedron Lett., p. 6237 (2000) can be carried out.

6-(v) Formula (43-2)→Formula (44-2)

A compound represented by Formula (44-2), wherein either of $Y_1$ and $Y_5$ essentially represents a methyl group, can be prepared according to the process described in 6-(iii).

Further, the compound of the present invention can be prepared using the aniline derivatives represented by Formula (43), Formula (44), Formula (43-2) and Formula (44-2), by selecting a suitable production process as described in the invention.

Preparation Process 7

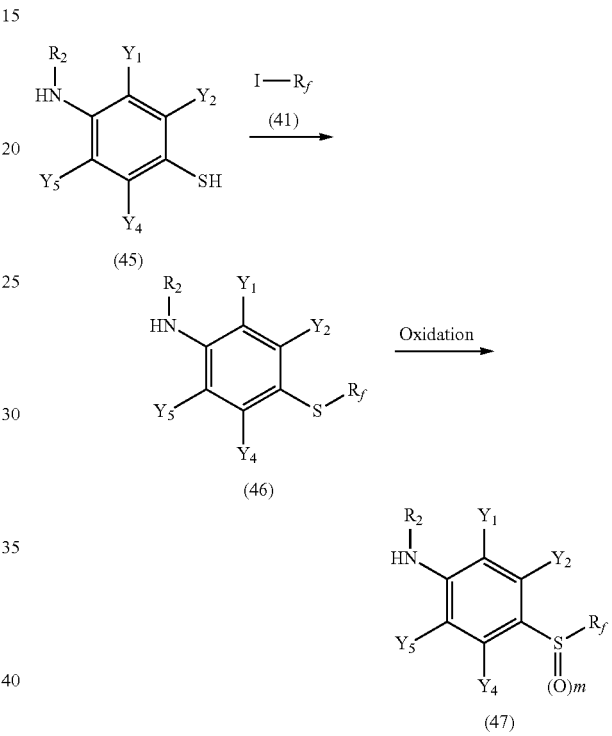

wherein $R_2$, $Y_1$, $Y_2$, $Y_4$, $Y_5$, $R_f$ and m have the same meaning as those described in Preparation Process 6.

The aniline derivative represented by Formula (47) can be prepared according to Preparation Process 6 using a compound represented by Formula (45) as starting material, and further the compound of the invention can be prepared by selecting a suitable production process as described in the invention.

Preparation Process 8

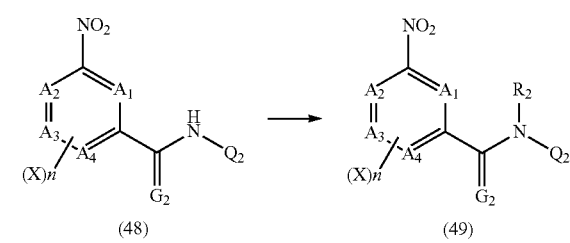

wherein $A_1$, $A_2$, $A_3$, $A_4$, X, n, $G_2$, $R_2$ and $Q_2$ have the same meaning as those described above.

A compound represented by Formula (49) can be prepared by reacting a compound represented by Formula (48) with a suitable reacting agent in a suitable solvent using a suitable base.

For the solvent, it may be any of those which do not impede the reaction significantly, for example, aliphatic hydrocarbons such as hexane, cyclohexane and methylcyclohexane; aromatic hydrocarbons such as benzene, xylene and toluene; halogenated hydrocarbons such as dichloromethane, chloroform, tetrachlorocarbon and 1,2-dichloroethane; ethers such as diethyl ether, dioxane, tetrahydrofuran and 1,2-dimethoxyethane; amides such as dimethylformamide and dimethylacetamide; nitriles such as acetonitrile and propionitrile; ketones such as acetone, methyl isobutyl ketone, cyclohexanone and methyl ethyl ketone; esters such as ethyl acetate and butyl acetate; alcohols such as methanol and ethanol; 1,3-dimehtyl-2-imidazolidinone, sulfolane, dimethylsulfoxide, water and the like, which can be used alone or in combination of two or more.

For the base, use can be made of, for example, organic bases such as triethylamine, tributylamine, pyridine, 4-dimethylaminopyridine; an alkali metal hydroxide such as sodium hydroxide and potassium hydroxide; a carbonate such as sodium hydrogen carbonate and potassium carbonate; a phosphate such as potassium monohydrogen phosphate, trisodium phosphate; an alkali metal hydride such as sodium hydride; an alkali metal alkoxide such as sodium methoxide, sodium ethoxide; an organic lithium such as n-butyllithium; a Grignard reagent such as ethylmagnesium bromide; and the like.

Such base can be appropriately selected or used as solvent, in the range of 0.01 to 5-fold molar equivalents with respect to the compound represented by Formula (48).

For the reacting agent, use can be made of, for example, an alkyl halide such as methyl iodide, ethyl bromide, trifluoromethyl iodide, 2,2,2-trifluoroethyl iodide; an aryl halide such as aryl iodide; a propargyl halide such as propargyl bromide; an acyl halide such as acetyl chloride; an acid anhydride such as trifluoroacetic acid anhydride; an alkyl sulfate such as dimethyl sulfate, diethyl sulfate; and the like.

Such reacting agent can be appropriately selected or used as solvent, in the range of 1 to 5-fold molar equivalents with respect to the compound represented by Formula (48).

The reaction temperature may be appropriately selected in the range from −80° C. to the reflux temperature of the solvent used, and the reaction time in the range from several minutes to 96 hours.

Preparation Process 9

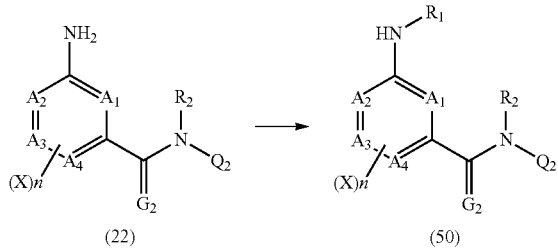

wherein $A_1$, $A_2$, $A_3$, $A_4$, X, n, $G_2$, $R_1$, $R_2$ and $Q_2$ have the same meaning as those described above.

9-(i) Formula (22)→Formula (50)

A compound represented by Formula (50) can be prepared by reacting a compound represented by Formula (22) with aldehydes or ketones in a suitable solvent, and reacting under a hydrogen atmosphere in the presence of a suitable catalyst.

The solvent may be any of those which do not impede the reaction significantly, for example, aliphatic hydrocarbons such as hexane, cyclohexane and methylcyclohexane; aromatic hydrocarbons such as benzene, xylene and toluene; halogenated hydrocarbons such as dichloromethane, chloroform, tetrachlorocarbon and 1,2-dichloroethane; ethers such as diethyl ether, dioxane, tetrahydrofuran and 1,2-dimethoxyethane; amides such as dimethylformamide and dimethylacetamide; nitriles such as acetonitrile and propionitrile; ketones such as acetone, methyl isobutyl ketone, cyclohexanone and methyl ethyl ketone; esters such as ethyl acetate and butyl acetate; alcohols such as methanol and ethanol; 1,3-dimehtyl-2-imidazolidinone, sulfolane, dimethylsulfoxide, water and the like, which can be used alone or in combination of two or more.

Examples of the catalyst may include palladium-based catalysts such as palladium-carbon, palladium hydroxide-carbon; nickel-based catalysts such as Raney nickel; cobalt catalysts, platinum catalysts, ruthenium catalysts, rhodium catalysts and the like.

Examples of the aldehydes may include, for example, formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde and the like.

Examples of the ketones may include, for example, acetone, perfluoroacetone, methyl ethyl ketone and the like.

The reaction pressure may be appropriately selected in the range of 1 atm to 100 atm.

The reaction temperature may be appropriately selected in the range from −20° C. to the reflux temperature of the solvent used, and the reaction time may be appropriately selected in the range from several minutes to 96 hours.

9-(ii) Formula (22)→Formula (50) (Alternative process 1)

The compound represented by Formula (50) can be prepared by reacting the compound represented by Formula (22) with an aldehyde or a ketone in a suitable solvent, and treating the product with a suitable reducing agent.

The solvent may be any of those which do not impede the reaction significantly, for example, aliphatic hydrocarbons such as hexane, cyclohexane and methylcyclohexane; aromatic hydrocarbons such as benzene, xylene and toluene; halogenated hydrocarbons such as dichloromethane, chloroform, tetrachlorocarbon and 1,2-dichloroethane; ethers such as diethyl ether, dioxane, tetrahydrofuran and 1,2-dimethoxyethane; amides such as dimethylformamide and dimethylacetamide; nitriles such as acetonitrile and propionitrile; ketones such as acetone, methyl isobutyl ketone, cyclohexanone and methyl ethyl ketone; esters such as ethyl acetate and butyl acetate; alcohols such as methanol and ethanol; 1,3-dimehtyl-2-imidazolidinone, sulfolane, dimethylsulfoxide, water and the like, which can be used alone or in combination of two or more.

Examples of the reducing agent may include, for example, borohydrides such as sodium borohydride, sodium cyanoborohydride, sodium triacetate borohydride and the like.

Examples of the aldehydes may include, for example, formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde and the like.

Examples of the ketones may include, for example, acetone, perfluoroacetone, methyl ethyl ketone and the like.

The reaction temperature may be appropriately selected in the range from −20° C. to the reflux temperature of the solvent used, and the reaction time may be appropriately selected in the range from several minutes to 96 hours.

9-(iii) Formula (22)→Formula (50) (Alternative process 2)

The compound represented by Formula (50), wherein $R_1$ is methyl, can be prepared by reacting the compound represented by Formula (22) with a formylating agent in a suitable solvent or without solvent, and treating the product with a suitable reducing agent.

The solvent may be any of those which do not impede the reaction significantly, for example, aliphatic hydrocarbons such as hexane, cyclohexane and methylcyclohexane; aromatic hydrocarbons such as benzene, xylene and toluene; halogenated hydrocarbons such as dichloromethane, chloroform, tetrachlorocarbon and 1,2-dichloroethane; ethers such as diethyl ether, dioxane, tetrahydrofuran and 1,2-dimethoxyethane; amides such as dimethylformamide and dimethylacetamide; nitriles such as acetonitrile and propionitrile; ketones such as acetone, methyl isobutyl ketone, cyclohexanone and methyl ethyl ketone; esters such as ethyl acetate and butyl acetate; alcohols such as methanol and ethanol; 1,3-dimehtyl-2-imidazolidinone, sulfolane, dimethylsulfoxide, water and the like, which can be used alone or in combination of two or more.

Examples of the formylating agent may include, for example, formaldehyde, formic acid, fluoroformic acid, formic acid anhydrides such as formyl(2,2-dimethylpropioic acid), formic acid esters such as phenyl formate, pentafluorobenzaldehyde, oxazole and the like.

Examples of the reducing agent may include, for example, inorganic acids such as sulfuric acid, organic acids such as formic acid, borohydrides such as sodium borohydride and sodium cyanoborohydride, boronic acid, lithium aluminum hydride and the like.

The reaction temperature may be appropriately selected in the range from −20° C. to the reflux temperature of the solvent used, and the reaction time may be appropriately selected in the range from several minutes to 96 hours.

Preparation Process 10

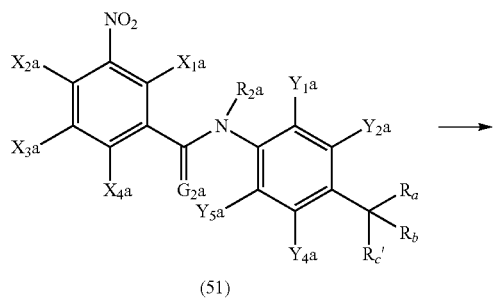

(51)

→

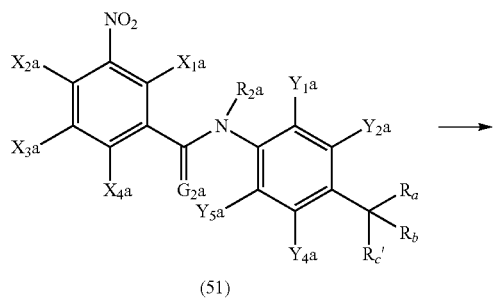

(52)

wherein $X_1a$, $X_2a$, $X_3a$, $X_4a$, $Y_1a$, $Y_2a$, $Y_4a$, $Y_5a$, $G_2a$, $R_2a$, $R_a$ and $R_b$ have the same meaning as those described above; $R_c'$ in Formula (51) represents a hydroxyl group or a group —O—$R_d$ (wherein $R_d$ has the same meaning as described above); and $R_c''$ in Formula (52) represents a chlorine atom, a bromine atom or an iodine atom.

A chlorine compound (or a bromine compound, an iodine compound) represented by Formula (52) can be prepared by reacting a compound represented by Formula (51) with a suitable halogenating agent in a suitable solvent or without a solvent. In this step, a suitable additive may also be used.

The solvent may be any of those which do not impede the reaction significantly, for example, aliphatic hydrocarbons such as hexane, cyclohexane and methylcyclohexane; aromatic hydrocarbons such as benzene, xylene and toluene; halogenated hydrocarbons such as dichloromethane, chloroform, tetrachlorocarbon and 1,2-dichloroethane; ethers such as diethyl ether, dioxane, tetrahydrofuran and 1,2-dimethoxyethane; amides such as dimethylformamide and dimethylacetamide; nitriles such as acetonitrile and propionitrile; ketones such as acetone, methyl isobutyl ketone and cyclohexanone; esters such as ethyl acetate and butyl acetate; alcohols such as methanol and ethanol; 1,3-dimehtyl-2-imidazolidinone, sulfolane, dimethylsulfoxide, water and the like, which can be used alone or in combination of two or more.

Examples of the halogenating agent may include, for example, thionyl chloride, thionyl bromide, phosphorus oxychloride, oxalyl chloride, phosphorus trichloride, phosphorus tribromide, phosphorus pentachloride, a Rydon's reagent, sulfonyl halides such as methanesulfonyl chloride, p-toluenesulfonyl chloride and benzenesulfonyl chloride, sulfonium halide, a sulfonic acid ester, chlorine, bromine, iodine, hypohalogenic acid ester, N-halogenoamine, hydrogen chloride, hydrogen bromide, sodium bromide, potassium bromide, cyanuric chloride, 1,3-dichloro-1,2,4-triazole, titanium(IV) chloride, vanadium(IV) chloride, arsenic (III) chloride, N,N-diethyl-1,2,2-trichlorovinylamine, trichloroacetonitrile, sodium chloride, ammonium bromide, N,N-dimethylchloroforminium chloride, N,N-dimethylchloroforminium bromide, phosphorus trichloride, phosphorus tribromide, N,N-dimethylphosphoamidine dichloride and the like.

An additive may include, for example, metal salts such as zinc chloride, lithium bromide and the like, phase-transfer catalysts, organic bases such as hexamethyl phosphoric acid triamide, inorganic acids such as sulfuric acid, N,N-dimethyl formamide and the like.

Such halogenating agent may be appropriately selected or used as solvent, in the range of 0.01 to 10-fold molar equivalents with respect to the compound represented by Formula (1).

The reaction temperature may be appropriately selected in the range from −80° C. to the reflux temperature of the solvent used, and the reaction time may be appropriately selected in the range from several minutes to 96 hours.

Preparation Process 11

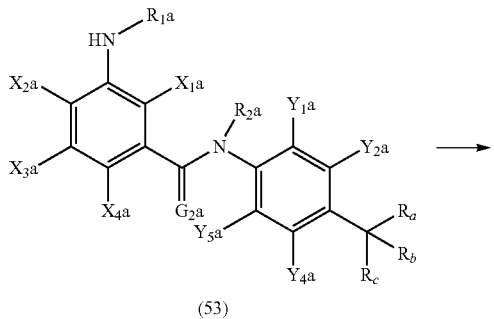

(53)

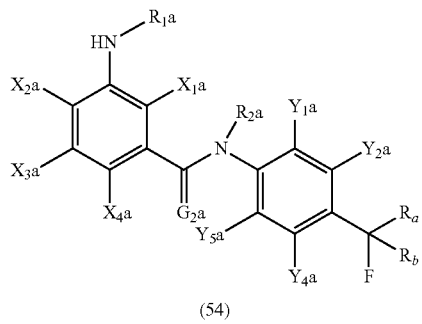

(54)

wherein $X_1a$, $X_2a$, $X_3a$, $X_4a$, $Y_1a$, $Y_2a$, $Y_4a$, $Y_5a$, $G_2a$, $R_1a$, $R_2a$, $R_a$, $R_b$ and $R_c$ have the same meaning as those described above.

A compound represented by Formula (54) can be prepared by reacting a compound represented by Formula (53) with a suitable fluorinating agent in a suitable solvent or without a solvent.

The solvent may be any of those which do not impede the reaction significantly, for example, aliphatic hydrocarbons such as hexane, cyclohexane and methylcyclohexane; aromatic hydrocarbons such as benzene, xylene and toluene; halogenated hydrocarbons such as dichloromethane, chloroform, tetrachlorocarbon and 1,2-dichloroethane; ethers such as diethyl ether, dioxane, tetrahydrofuran and 1,2-dimethoxyethane; amides such as dimethylformamide and dimethylacetamide; nitriles such as acetonitrile and propionitrile; ketones such as acetone, methyl isobutyl ketone, cyclohexanone and methyl ethyl ketone; esters such as ethyl acetate and butyl acetate; alcohols such as methanol and ethanol; 1,3-dimehtyl-2-imidazolidinone, sulfolane, dimethylsulfoxide, water and the like, which can be used alone or in combination of two or more.

Examples of the fluorinating agent may include 1,1,2,2-tetrafluoroethyl diethylamine, 2-chloro-1,1,2-trifluoroethyl diethylamine, trifluorodiphenylphospholane, difluorotriphenylphospholane, fluoroformic acid esters, sulfur tetrafluoride, potassium fluoride, potassium hydrogen fluoride, cesium fluoride, rubidium fluoride, sodium fluoride, lithium fluoride, antimony(III) fluoride, antimony(V) fluoride, zinc fluoride, cobalt fluoride, lead fluoride, copper fluoride, mercury(II) fluoride, silver fluoride, silver fluoroborate, thallium (I) fluoride, molybdenum(VI) fluoride, arsenic(III) fluoride, bromine fluoride, selenium tetrafluoride, tris(dimethylamino)sulfonium difluorotrimethylsilicate, sodium hexafluorosilicate, quaternary ammonium fluorides, (2-chloroethyl) diethylamine, diethylaminosulfur trifluoride, morpholinosulfur trifluoride, silicon tetrafluoride, hydrogen fluoride, hydrofluoric acid, hydrogen fluoride-pyridine complex, hydrogen fluoride-triethylamine complex, hydrogen fluoride salts, bis(2-methoxyethyl)amino sulfurtrifluoride, 2,2-difluoro-1,3-dimethyl-2-imidazolidinone, iodine pentafluoride, tris(diethylamino)phosphonium 2,2,3,3,4,4-hexafluorocyclobutanilide, triethylammonium hexafluorocylcobutanilide, hexafluoropropene and the like. Such fluorinating agent can be used alone or in combination of two or more. The fluorinating agent may be appropriately selected or used as solvent, in the range of 1 to 10-fold molar equivalents with respect to the compound represented by Formula (53).

Additives may be used, and examples thereof may include crown ethers such as 18-crown-6, interline transfer catalysts such as a tetraphenylphosphonium salt, inorganic salts such as calcium fluoride and calcium chloride, metal oxides such as mercury oxide, ion exchange resin and the like. Such additives can be not only added to the reaction system but also used as a pretreating agent for the fluorinating agent.

The reaction temperature may be appropriately selected in the range from −80° C. to the reflux temperature of the solvent used, and the reaction time may be appropriately selected in the range from several minutes to 96 hours.

Preparation Process 12

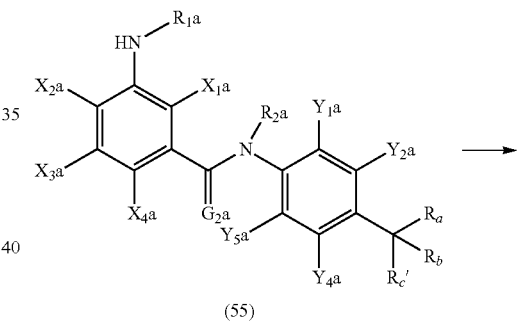

(55)

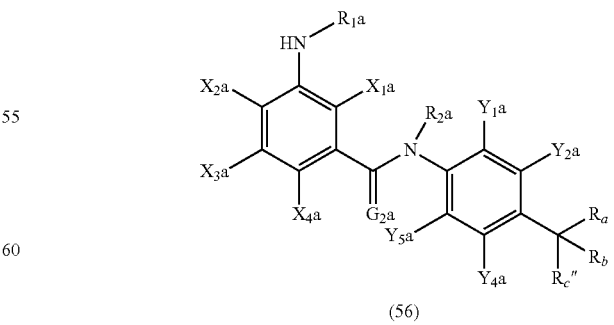

(56)

wherein $X_1a$, $X_2a$, $X_3a$, $X_4a$, $Y_1a$, $Y_2a$, $Y_4a$, $Y_5a$, $G_2a$, $R_1a$, $R_2a$, $R_a$, $R_b$, $R_c'$ and $R_c''$ have the same meaning as those described above.

A compound represented by Formula (56) can be prepared from the compound represented by Formula (55) according to the process described in Preparation Process 10.

Preparation Process 13

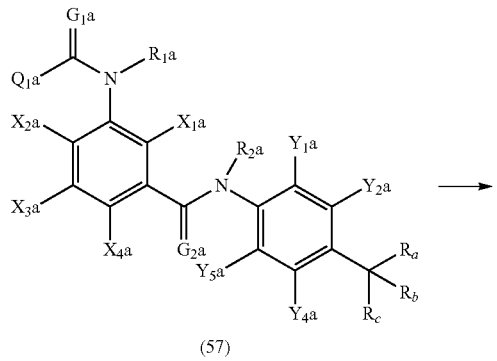

(57)

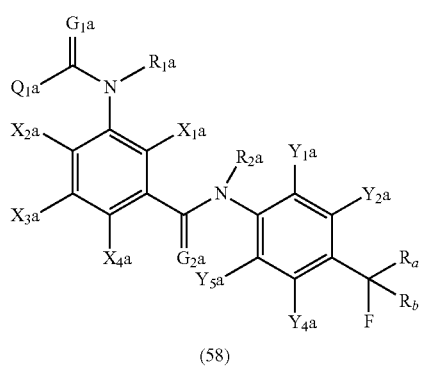

(58)

wherein $X_1a$, $X_2a$, $X_3a$, $X_4a$, $Y_1a$, $Y_2a$, $Y_4a$, $Y_5a$, $G_1a$, $G_2a$, $R_1a$, $R_2a$, $R_a$, $R_b$, $R_c$ and $Q_1a$ have the same meaning as those described above.

A compound represented by Formula (58) can be prepared from the compound represented by Formula (57) according to the process described in Preparation Process 11.

Preparation Process 14

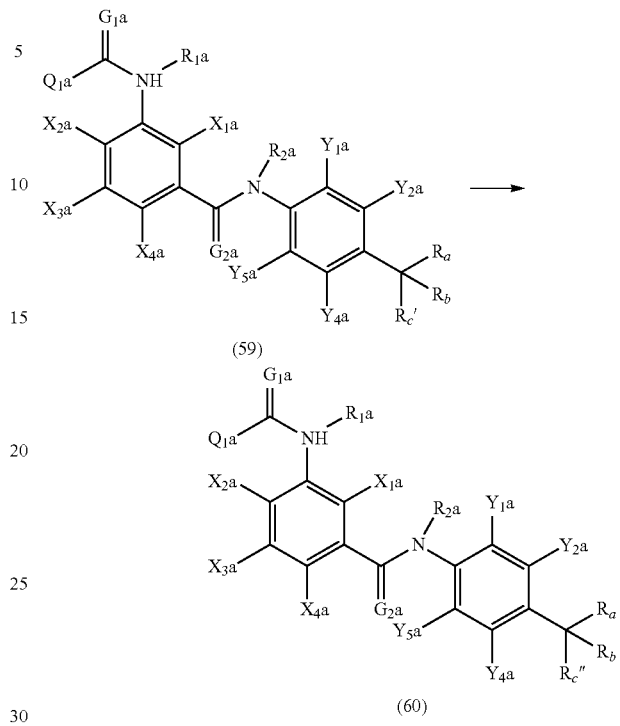

wherein $X_1a$, $X_2a$, $X_3a$, $X_4a$, $Y_1a$, $Y_2a$, $Y_4a$, $Y_5a$, $G_1a$, $G_2a$, $R_1a$, $R_2a$, $R_a$, $R_b$, $R_c'$, $R_c''$ and $Q_1a$ have the same meaning as those described above.

A compound represented by Formula (60) can be prepared from the compound represented by Formula (59) according to the process described in Preparation Process 10.

In all of the processes for preparation as described in the above, the desired products may be isolated from the reaction system after the reaction is completed according to conventional methods, but if required, purification can be carried out by operations such as recrystallization, column chromatography, distillation and the like. Further, the desired product can be also provided to the subsequent reaction process without being separated from the reaction system.

Hereinbelow, the representative compounds among the compounds represented by Formula (1) as the active ingredient for the insecticide of the invention will be given in Table 1 to Table 5, but the invention is not intended to be limited thereto.

In Table 6 and Table 7, the compound representative of the compound of Formula (6) will be given, but the invention is not intended to be limited thereto.

In Table 8 to Table 10, the compounds representative of the compounds of Formula (8), Formula (11) and Formula (13), but the invention is not intended to be limited thereto.

In addition, the abbreviations in the tables have the following meanings: "n-" represents normal, "Me" a methyl group, "Et" an ethyl group, "n-Pr" a normal propyl group, "i-Pr" an isopropyl group, "n-Bu" a normal butyl group, "i-Bu" an isobutyl group, "s-Bu" a secondary butyl group, "t-Bu" a tertiary butyl group, "H" a hydrogen atom, "O" an oxygen atom, "S" a sulfur atom, "C" a carbon atom, "N" a nitrogen atom, "F" a fluorine atom, "Cl" a chlorine atom, "Br" a bromine atom, "I" an iodine atom, "$CF_3$" a trifluoromethyl group, "MeS" a methylthio group, "MeSO" methylsulfinyl group, "MeSO$_2$" a methylsulfonyl group, "MeO" a methoxy group, "NH$_2$" an amino group, "MeNH" a methylamino group, and "Me$_2$N" is a dimethylamino group; and "OH" a hydroxyl group, respectively.

TABLE 1

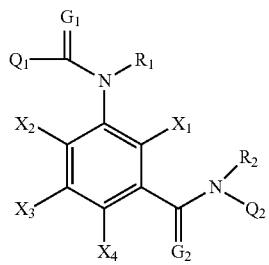

($X_1$, $X_2$, $X_3$, $X_4$, $R_1$, $R_2$ = a hydrogen atom, $G_1$, $G_2$ = an oxygen atom)

| Comp. No. | Q$_1$ | Q$_2$ |
|---|---|---|
| 1 | phenyl | 2,6-dimethyl-4-(pentafluoroethyl)phenyl |
| 2 | phenyl | 2,6-dichloro-4-(pentafluoroethyl)phenyl |
| 3 | 2-fluorophenyl | 2,6-dichloro-4-(pentafluoroethyl)phenyl |
| 4 | phenyl | 2,6-dibromo-4-(pentafluoroethyl)phenyl |
| 5 | 2-fluorophenyl | 2,6-dibromo-4-(pentafluoroethyl)phenyl |
| 6 | phenyl | 2,6-dichloro-4-(heptafluoroisopropyl)phenyl |
| 7 | phenyl | 2,6-dibromo-4-(heptafluoroisopropyl)phenyl |
| 8 | 2-fluorophenyl | 2,6-dibromo-4-(heptafluoroisopropyl)phenyl |
| 9 | phenyl | 2,6-dimethyl-4-(heptafluoro-n-propyl)phenyl |
| 10 | phenyl | 2,6-dimethyl-4-(heptafluoroisopropyl)phenyl |
| 11 | 2-methylphenyl | 2,6-dimethyl-4-(heptafluoroisopropyl)phenyl |
| 12 | 3-methylphenyl | 2,6-dimethyl-4-(heptafluoroisopropyl)phenyl |
| 13 | 4-methylphenyl | 2,6-dimethyl-4-(heptafluoroisopropyl)phenyl |
| 14 | 2-ethylphenyl | 2,6-dimethyl-4-(heptafluoroisopropyl)phenyl |
| 15 | 3-ethylphenyl | 2,6-dimethyl-4-(heptafluorolsopropyl)phenyl |
| 16 | 4-ethylphenyl | 2,6-dimethyl-4-(heptafluoroisopropyl)phenyl |
| 17 | 2-fluorophenyl | 2,6-dimethyl-4-(heptafluoroisopropyl)phenyl |
| 18 | 3-fluorophenyl | 2,6-dimethyl-4-(heptafluoroisopropyl)phenyl |
| 19 | 4-fluorophenyl | 2,6-dimethyl-4-(heptafluoroisopropyl)phenyl |
| 20 | 2-chlorophenyl | 2,6-dimethyl-4-(heptafluoroisopropyl)phenyl |
| 21 | 3-chlorophenyl | 2,6-dimethyl-4-(heptafluoroisopropyl)phenyl |
| 22 | 4-chlorophenyl | 2,6-dimethyl-4-(heptafluoroisopropyl)phenyl |
| 23 | 2-bromophenyl | 2,6-dimethyl-4-(heptafluoroisopropyl)phenyl |
| 24 | 3-bromophenyl | 2,6-dimethyl-4-(heptafluoroisopropyl)phenyl |
| 25 | 4-bromophenyl | 2,6-dimethyl-4-(heptafluoroisopropyl)phenyl |
| 26 | 2-iodophenyl | 2,6-dimethyl-4-(heptafluoroisopropyl)phenyl |
| 27 | 3-iodophenyl | 2,6-dimethyl-4-(heptafluoroisopropyl)phenyl |
| 28 | 4-iodophenyl | 2,6-dimethyl-4-(heptafluoroisopropyl)phenyl |
| 29 | 3-cyanophenyl | 2,6-dimethyl-4-(heptafloorolsopropyl)phenyl |
| 30 | 4-cyanophenyl | 2,6-dimethyl-4-(heptafluoroisopropyl)phenyl |
| 31 | 2-nitrophenyl | 2,6-dimethyl-4-(heptafluoroisopropyl)phenyl |
| 32 | 3-nitrophenyl | 2,6-dimethyl-4-(heptafluoroisopropyl)phenyl |
| 33 | 4-nitrophenyl | 2,6-dimethyl-4-(heptafluoroisopropyl)phenyl |
| 34 | 2-aminophenyl | 2,6-dimethyl-4-(heptafluoroisopropyl)phenyl |
| 35 | 3-aminophenyl | 2,6-dimethyl-4-(heptafluoroisopropyl)phenyl |
| 36 | 4-aminophenyl | 2,6-dimethyl-4-(heptafluoroisopropyl)phenyl |
| 37 | 2-trifluoromethylphenyl | 2,6-dimethyl-4-(heptafluoroisopropyl)phenyl |
| 38 | 3-trifluoromethylphenyl | 2,6-dimethyl-4-(heptafluoroisopropyl)phenyl |
| 39 | 4-trifluoromethylphenyl | 2,6-dimethyl-4-(heptafluoroisopropyl)phenyl |
| 40 | 2-hydroxyphenyl | 2,6-dimethyl-4-(heptafluoroisopropyl)phenyl |
| 41 | 2-methoxyphenyl | 2,6-dimethyl-4-(heptafluoroisopropyl)phenyl |
| 42 | 3-methoxyphenyl | 2,6-dimethyl-4-(heptarluoroisopropyl)phenyl |
| 43 | 4-methoxyphenyl | 2,6-dimethyl-4-(heptafluoroisopropyl)phenyl |
| 44 | 2-phenoxyphenyl | 2,6-dimethyl-4-(heptafluoroisopropyl)phenyl |
| 45 | 4-(1,1-dimethylethyl)phenyl | 2,6-dimethyl-4-(heptafluoroisopropyl)phenyl |
| 46 | 3-(dimethylamino)phenyl | 2,6-dimethyl-4-(heptafluoroisopropyl)phenyl |
| 47 | 4-(dimethylamino)phenyl | 2,6-dimethyl-4-(heptafluoroisopropyl)phenyl |
| 48 | 4-trifluoromethoxyphenyl | 2,6-dimethyl-4-(heptafluoroisopropyl)phenyl |
| 49 | 2-(acetylamino)phenyl | 2,6-dimethyl-4-(heptafluoroisopropyl)phenyl |
| 50 | 3-(acetylamino)phenyl | 2,6-dimethyl-4-(heptafluoroisopropyl)phenyl |
| 51 | 4-(acetylamino)phenyl | 2,6-dimethyl-4-(heptafluoroisopropyl)phenyl |
| 52 | 2-acetoxyphenyl | 2,6-dimethyl-4-(heptafluoroisopropyl)phenyl |
| 53 | 2-(methoxycarbonyl)phenyl | 2,6-dimethyl-4-(heptafluoroisopropyl)phenyl |
| 54 | 4-(methoxycarbonyl)phenyl | 2,6-dimethyl-4-(heptafluoroisopropyl)phenyl |
| 55 | 2-(4-trifluoromethylphenyl)phenyl | 2,6-dimethyl-4-(heptafluoroisopropyl)phenyl |
| 56 | 2,3-dimethylphenyl | 2,6-dimethyl-4-(heptafluoroisopropyl)phenyl |
| 57 | 2,4-dimethylphenyl | 2,6-dimethyl-4-(heptafluoroisopropyl)phenyl |
| 58 | 2,6-dimethylphenyl | 2,6-dimethyl-4-(heptafluoroisopropyl)phenyl |
| 59 | 2,3-difluorophenyl | 2,6-dimethyl-4-(heptafluoroisopropyl)phenyl |
| 60 | 2,4-difluorophenyl | 2,6-dimethyl-4-(heptafluoroisopropyl)phenyl |

TABLE 1-continued

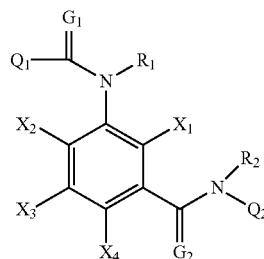

($X_1$, $X_2$, $X_3$, $X_4$, $R_1$, $R_2$ = a hydrogen atom, $G_1$, $G_2$ = an oxygen atom)

| Comp. No. | $Q_1$ | $Q_2$ |
|---|---|---|
| 61 | 2,5-difluorophenyl | 2,6-dimethyl-4-(heptafluoroisopropyl)phenyl |
| 62 | 2,6-difluorophenyl | 2,6-dimethyl-4-(heptafluoroisopropyl)phenyl |
| 63 | 3,4-difluorophenyl | 2,6-dimethyl-4-(heptafluoroisopropyl)phenyl |
| 64 | 3,5-difluorophenyl | 2,6-dimethyl-4-(heptafluoroisopropyl)phenyl |
| 65 | 2,3-dichlorophenyl | 2,6-dimethyl-4-(heptafluoroisopropyl)phenyl |
| 66 | 2,4-dichlorophenyl | 2,6-dimethyl-4-(heptafluoroisopropyl)phenyl |
| 67 | 2,5-dichlorophenyl | 2,6-dimethyl-4-(heptafluoroisopropyl)phenyl |
| 68 | 2,6-dichlorophenyl | 2,6-dimethyl-4-(heptafluoroisopropyl)phenyl |
| 69 | 3,4-dichlorophenyl | 2,6-dimethyl-4-(heptafluoroisopropyl)phenyl |
| 70 | 2,4-dinitrophenyl | 2,6-dimethyl-4-(heptafluoroisopropyl)phenyl |
| 71 | 3,4-dinitrophenyl | 2,6-dimethyl-4-(heptafluoroisopropyl)phenyl |
| 72 | 2,6-dimethoxyphenyl | 2,6-dimethyl-4-(heptafluoroisopropyl)phenyl |
| 73 | 3,5-dimethoxyphenyl | 2,6-dimethyl-4-(heptafluoroisopropyl)phenyl |
| 74 | 3-methyl-4-nitrophenyl | 2,6-dimethyl-4-(heptafluoroisopropyl)phenyl |
| 75 | 5-amino-2-fluorophenyl | 2,6-dimethyl-4-(heptafluoroisopropyl)phenyl |
| 76 | 3-fluoro-2-methylphenyl | 2,6-dimethyl-4-(heptafluoroisopropyl)phenyl |
| 77 | 2-fluoro-5-nitrophenyl | 2,6-dimethyl-4-(heptafluoroisopropyl)phenyl |
| 78 | 4-fluoro-3-nitrophenyl | 2,6-dimethyl-4-(heptafluoroisopropyl)phenyl |
| 79 | 5-fluoro-2-nitrophenyl | 2,6-dimethyl-4-(heptafluoroisopropyl)phenyl |
| 80 | 2-fluoro-6-iodophenyl | 2,6-dimethyl-4-(heptafluoroisopropyl)phenyl |
| 81 | 2-fluoro-5-trifluoromethylphenyl | 2,6-dimethyl-4-(heptafluoroisopropyl)phenyl |
| 82 | 2-chloro-4-nitrophenyl | 2,6-dimethyl-4-(heptafluoroisopropyl)phenyl |
| 83 | 2-chloro-4-fluorophenyl | 2,6-dimethyl-4-(heptafluoroisopropyl)phenyl |
| 84 | 2-chloro-6-fluorophenyl | 2,6-dimethyl-4-(heptafluoroisopropyl)phenyl |
| 85 | 3-chloro-4-fluorophenyl | 2,6-dimethyl-4-(heptafluoroisopropyl)phenyl |
| 86 | 4-chloro-2-fluorophenyl | 2,6-dimethyl-4-(heptafluoroisopropyl)phenyl |
| 87 | 4-chloro-2-nitrophenyl | 2,6-dimethyl-4-(heptafluoroisopropyl)phenyl |
| 88 | 3-methoxy-4-nitrophenyl | 2,6-dimethyl-4-(heptafluoroisopropyl)phenyl |
| 89 | 2-methoxy-4-nitrophenyl | 2,6-dimethyl-4-(heptafluoroisopropyl)phenyl |
| 90 | 2,3,4-trifluorophenyl | 2,6-dimethyl-4-(heptafluoroisopropyl)phenyl |
| 91 | 2,4,6-trimethylphenyl | 2,6-dimethyl-4-(heptafluoroisopropyl)phenyl |
| 92 | 2,3,6-trifluorophenyl | 2,6-dimethyl-4-(heptafluoroisopropyl)phenyl |
| 93 | 2,4,5-trimethoxyphenyl | 2,6-dimethyl-4-(heptafluoroisopropyl)phenyl |
| 94 | 3,4,5-trimethoxyphenyl | 2,6-dimethyl-4-(heptafluoroisopropyl)phenyl |
| 95 | 2,3,4,5,6-pentafluorophenyl | 2,6-dimethyl-4-(heptafluoroisopropyl)phenyl |
| 96 | 2-biphenyl | 2,6-dimethyl-4-(heptafluoroisopropyl)phenyl |
| 97 | 3-biphenyl | 2,6-dimethyl-4-(heptafluoroisopropyl)phenyl |
| 98 | 1-naphthyl | 2,6-dimethyl-4-(heptafluoroisopropyl)phenyl |
| 99 | 2-naphthyl | 2,6-dimethyl-4-(heptafluoroisopropyl)phenyl |
| 100 | pyridin-2-yl | 2,6-dimethyl-4-(heptafluoroisopropyl)phenyl |
| 101 | pyridin-3-yl | 2,6-dimethyl-4-(heptafluoroisopropyl)phenyl |
| 102 | pyridin-4-yl | 2,6-dimethyl-4-(heptafluoroisopropyl)phenyl |
| 103 | 2-methylpyridin-5-yl | 2,6-dimethyl-4-(heptafluoroisopropyl)phenyl |
| 104 | 3-methylpyridin-2-yl | 2,6-dimethyl-4-(heptafluoroisopropyl)phenyl |
| 105 | 2-fluoropyridin-3-yl | 2,6-dimethyl-4-(heptafluoroisopropyl)phenyl |
| 106 | 2-chloropyridin-3-yl | 2,6-dimethyl-4-(heptafluoroisopropyl)phenyl |
| 107 | 2-chloropyridin-4-yl | 2,6-dimethyl-4-(heptafluoroisopropyl)phenyl |
| 108 | 2-chloropyridin-6-yl | 2,6-dimethyl-4-(heptafluoroisopropyl)phenyl |
| 109 | 2-chloropyridin-5-yl | 2,6-dimethyl-4-(heptafluoroisopropyl)phenyl |
| 110 | 5-chloropyridin-2-yl | 2,6-dimethyl-4-(heptafluoroisopropyl)phenyl |
| 111 | 4-trifluoromethylpyridin-3-yl | 2,6-dimethyl-4-(heptafluoroisopropyl)phenyl |
| 112 | 3-hydroxypyridin-2-yl | 2,6-dimethyl-4-(heptafluoroisopropyl)phenyl |
| 113 | 2-phenoxypyridin-3-yl | 2,6-dimethyl-4-(heptafluoroisopropyl)phenyl |
| 114 | 2-methylthiopyridin-3-yl | 2,6-dimethyl-4-(heptafluoroisopropyl)phenyl |
| 115 | 2,6-dimethoxypyridin-3-yl | 2,6-dimethyl-4-(heptafluoroisopropyl)phenyl |
| 116 | 2,3-dichloropyridin-5-yl | 2,6-dimethyl-4-(heptafluoroisopropyl)phenyl |
| 117 | 2,5-dichloropyridin-3-yl | 2,6-dimethyl-4-(heptafluoroisopropyl)phenyl |
| 118 | 2,6-dichloropyridin-3-yl | 2,6-dimethyl-4-(heptafluoroisopropyl)phenyl |
| 119 | 3,5-dichloropyridin-4-yl | 2,6-dimethyl-4-(heptafluoroisopropyl)phenyl |
| 120 | (pyridine-N-oxide)-2-yl | 2,6-dimethyl-4-(heptafluoroisopropyl)phenyl |
| 121 | N-methylpyrrol-2-yl | 2,6-dimethyl-4-(heptafluoroisopropyl)phenyl |
| 122 | pyrazin-2-yl | 2,6-dimethyl-4-(heptafluoroisopropyl)phenyl |
| 123 | 2-methylpyrazin-5-yl | 2,6-dimethyl-4-(heptafluoroisopropyl)phenyl |

TABLE 1-continued

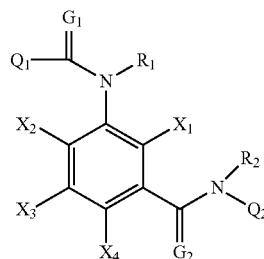

($X_1$, $X_2$, $X_3$, $X_4$, $R_1$, $R_2$ = a hydrogen atom, $G_1$, $G_2$ = an oxygen atom)

| Comp. No. | $Q_1$ | $Q_2$ |
|---|---|---|
| 124 | 4-trifluoromethylpyrimidin-5-yl | 2,6-dimethyl-4-(heptafluoroisopropyl)phenyl |
| 125 | furan-2-yl | 2,6-dimethyl-4-(heptafluoroisopropyl)phenyl |
| 126 | furan-3-yl | 2,6-dimethyl-4-(heptafluoroisopropyl)phenyl |
| 127 | 2-tetrahydrofuranyl | 2,6-dimethyl-4-(heptafluoroisopropyl)phenyl |
| 128 | 3-tetrahydrofuranyl | 2,6-dimethyl-4-(heptafluoroisopropyl)phenyl |
| 129 | benzofuran-2-yl | 2,6-dimethyl-4-(heptafluoroisopropyl)phenyl |
| 130 | tetrahydropyran-2-yl | 2,6-dimethyl-4-(heptafluoroisopropyl)phenyl |
| 131 | 2-methyl-5,6-dihydro-4Hpyran-3-yl | 2,6-dimethyl-4-(heptafluoroisopropyl)phenyl |
| 132 | thiophen-2-yl | 2,6-dimethyl-4-(heptafluoroisopropyl)phenyl |
| 133 | thiophen-3-yl | 2,6-dimethyl-4-(heptafluoroisopropyl)phenyl |
| 134 | 3-methylthiophen-2-yl | 2,6-dimethyl-4-(heptafluoroisopropyl)phenyl |
| 135 | 2-nitrothiophen-4-yl | 2,6-dimethyl-4-(heptafluoroisopropyl)phenyl |
| 136 | 2-methylthiophen-5-yl | 2,6-dimethyl-4-(heptafluoroisopropyl)phenyl |
| 137 | 3-chlorothiophen-2-yl | 2,6-dimethyl-4-(heptafluoroisopropyl)phenyl |
| 138 | 2-chlorothiophen-5-yl | 2,6-dimethyl-4-(heptafluoroisopropyl)phenyl |
| 139 | 3-bromothiophen-2-yl | 2,6-dimethyl-4-(heptafluoroisopropyl)phenyl |
| 140 | 2-bromothiophen-5-yl | 2,6-dimethyl-4-(heptafluoroisopropyl)phenyl |
| 141 | 3-iodothiophen-2-yl | 2,6-dimethyl-4-(heptafluoroisopropyl)phenyl |
| 142 | 3-phenylthiophen-2-yl | 2,6-dimethyl-4-(heptafluoroisopropyl)phenyl |
| 143 | 2,4-dimethylthiophen-5-yl | 2,6-dimethyl-4-(heptafluoroisopropyl)phenyl |
| 144 | benzothiophen-2-yl | 2,6-dimethyl-4-(heptafluoroisopropyl)phenyl |
| 145 | 4-nitro-1H-pyrrol-2-yl | 2,6-dimethyl-4-(heptafluoroisopropyl)phenyl |
| 146 | 3-ethyl-3H-pyrazol-4-yl | 2,6-dimethyl-4-(heptafluoroisopropyl)phenyl |
| 147 | 1-methyl-3-nitro-1H-pyrazol-4-yl | 2,6-dimethyl-4-(heptafluoroisopropyl)phenyl |
| 148 | 3-chloro-1-methyl-1H-pyrazol-4-yl | 2,6-dimethyl-4-(heptafluoroisopropyl)phenyl |
| 149 | 3-bromo-1-methyl-1H-pyrazol-4-yl | 2,6-dimethyl-4-(heptafluoroisopropyl)phenyl |
| 150 | 1-methyl-3-trifluoromethyl-1H-pyrazol-4-yl | 2,6-dimethyl-4-(heptafluoroisopropyl)phenyl |
| 151 | 1-methyl-5-trifluoromethyl-1H-pyrazol-4-yl | 2,6-dimethyl-4-(heptafluoroisopropyl)phenyl |
| 152 | isoxazol-5-yl | 2,6-dimethyl-4-(heptafluoroisopropyl)phenyl |
| 153 | 4-trifluoromethylthiazol-5-yl | 2,6-dimethyl-4-(heptafluoroisopropyl)phenyl |
| 154 | 2,4-dimethylthiazol-5-yl | 2,6-dimethyl-4-(heptafluoroisopropyl)phenyl |
| 155 | 2-ethyl-4-methylthiazol-5-yl | 2,6-dimethyl-4-(heptafluoroisopropyl)phenyl |
| 156 | 2-chloro-4-methylthiazol-5-yl | 2,6-dimethyl-4-(heptafluoroisopropyl)phenyl |
| 157 | 3-methyl-isothiazol-5-yl | 2,6-dimethyl-4-(heptafluoroisopropyl)phenyl |
| 158 | 3,4-dichloro-isothiazol-5-yl | 2,6-dimethyl-4-(heptafluoroisopropyl)phenyl |
| 159 | 3-chlorobenzothiazol-2-yl | 2,6-dimethyl-4-(heptafluoroisopropyl)phenyl |
| 160 | 2,2-difluoro-benzo[1.3]dioxol-5-yl | 2,6-dimethyl-4-(heptafluoroisopropyl)phenyl |
| 161 | 2,2-difluoro-benzo[1.3]dioxol-4-yl | 2,6-dimethyl-4-(heptafluoroisopropyl)phenyl |
| 162 | 2-phenylquinolin-4-yl | 2,6-dimethyl-4-(heptafluoroisopropyl)phenyl |
| 163 | phenyl | 2-bromo-4-(heptafluoroisopropyl)-6-methylphenyl |
| 164 | phenyl | 2-ethyl-4-(heptafluoroisopropyl)-6-methylphenyl |
| 165 | 2-fluorophenyl | 2-ethyl-4-(heptafluoroisopropyl)-6-methylphenyl |
| 166 | phenyl | 4-(heptafluoroisopropyl)-2-iodo-6-methylphenyl |
| 167 | phenyl | 4-(heptafluoroisopropyl)-2-hydroxy-6-methylphenyl |
| 168 | phenyl | 2-chloro-6-ethyl-4-(heptafluoroisopropyl)phenyl |
| 169 | phenyl | 2-bromo-6-ethyl-4-(heptafluoroisopropyl)phenyl |
| 170 | 2-fluorophenyl | 2-bromo-6-ethyl-4-(heptafluoroisopropyl)phenyl |
| 171 | phenyl | 2-ethyl-4-(heptafluoroisopropyl)-6-iodophenyl |
| 172 | 2-fluorophenyl | 2-ethyl-4-(heptafluoroisopropyl)-6-iodophenyl |
| 173 | 4-nitrophenyl | 2-ethyl-4-(heptafluoroisopropyl)-6-iodophenyl |
| 174 | 4-cyanophenyl | 2-ethyl-4-(heptafluoroisopropyl)-6-iodophenyl |
| 175 | 4-nitrophenyl | 4-(heptafluoroisopropyl)-2-methyl-6-n-propylphenyl |
| 176 | phenyl | 4-(heptafluoroisopropyl)-2-isopropyl-6-methylphenyl |
| 177 | 2-fluorophenyl | 4-(heptafluoroisopropyl)-2-isopropyl-6-methylphenyl |
| 178 | phenyl | 2-bromo-4-(heptafluoroisopropyl)-6-n-propylphenyl |
| 179 | 2-fluorophenyl | 2-bromo-4-(heptafluoroisopropyl)-6-n-propylphenyl |
| 180 | 4-nitrophenyl | 2-bromo-4-(heptafluoroisopropyl)-6-n-propylphenyl |
| 181 | 4-cyanophenyl | 2-bromo-4-(heptafluoroisopropyl)-6-n-propylphenyl |
| 182 | phenyl | 4-(heptafluoroisopropyl)-2-iodo-6-n-propylphenyl |
| 183 | 2-fluorophenyl | 4-(heptafluoroisopropyl)-2-iodo-6-n-propylphenyl |
| 184 | 4-nitrophenyl | 4-(heptafluoroisopropyl)-2-iodo-6-n-propylphenyl |
| 185 | 4-cyanophenyl | 4-(heptafluoroisopropyl)-2-iodo-6-n-propylphenyl |
| 186 | 4-trifluoromethylphenyl | 4-(heptafluoroisopropyl)-2-iodo-6-n-propylphenyl |

TABLE 1-continued

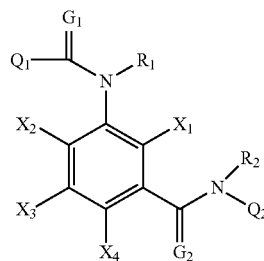

($X_1$, $X_2$, $X_3$, $X_4$, $R_1$, $R_2$ = a hydrogen atom, $G_1$, $G_2$ = an oxygen atom)

| Comp. No. | $Q_1$ | $Q_2$ |
|---|---|---|
| 187 | phenyl | 2-chloro-4-(heptafluoroisopropyl)-6-n-butylphenyl |
| 188 | 2-fluorophenyl | 2-chloro-4-(heptafluoroisopropyl)-6-n-butylphenyl |
| 189 | phenyl | 2-bromo-4-(heptafluoroisopropyl)-6-n-butylphenyl |
| 190 | 2-fluorophenyl | 2-bromo-4-(heptafluoroisopropyl)-6-n-butylphenyl |
| 191 | phenyl | 4-(heptafluoroisopropyl)-2-iodo-6-n-butylphenyl |
| 192 | 2-fluorophenyl | 4-(heptafluoroisopropyl)-2-iodo-6-n-butylphenyl |
| 193 | phenyl | 2-(2-butyl)-6-chloro-4-(heptafluoroisopropyl)phenyl |
| 194 | phenyl | 2-bromo-6-(2-butyl)-4-(heptafluoroisopropyl)phenyl |
| 195 | 2-fluorophenyl | 2-bromo-6-(2-butyl)-4-(heptafluoroisopropyl)phenyl |
| 196 | phenyl | 2-(2-butyl)-4-(heptafluoroisopropyl)-6-iodophenyl |
| 197 | 2-fluorophenyl | 2-bromo-6-cyano-4-(heptafluoroisopropyl)phenyl |
| 198 | phenyl | 2-bromo-4-(heptafluoroisopropyl)-6-methylthiophenyl |
| 199 | 2-fluorophenyl | 2-bromo-4-(heptafluoroisopropyl)-6-methylthiophenyl |
| 200 | phenyl | 2-bromo-4-(heptafluoroisopropyl)-6-(methylsulfinyl)phenyl |
| 201 | 2-fluorophenyl | 2-chloro-4-(heptafluoroisopropyl)-6-(methylsulfonyl)phenyl |
| 202 | 2-chloropyridin-3-yl | 2-chloro-4-(heptafluoroisopropyl)-6-(methylsulfonyl)phenyl |
| 203 | phenyl | 2-bromo-4-(heptafluoroisopropyl)-6-(methylsulfonyl)phenyl |
| 204 | 2-fluorophenyl | 2-bromo-4-(heptafluoroisopropyl)-6-(methylsulfonyl)phenyl |
| 205 | 4-fluorophenyl | 2-bromo-4-(heptafluoroisopropyl)-6-(methylsulfonyl)phenyl |
| 206 | 4-nitrophenyl | 2-bromo-4-(heptafluoroisopropyl)-6-(methylsulfonyl)phenyl |
| 207 | 4-cyanophenyl | 2-bromo-4-(heptafluoroisopropyl)-6-(methylsulfonyl)phenyl |
| 208 | 2-chloropyridin-3-yl | 2-bromo-4-(heptafluoroisopropyl)-6-(methylsulfonyl)phenyl |
| 209 | phenyl | 4-(heptafluoroisopropyl)-2-methylthiomethyl-6-trifluoromethylphenyl |
| 210 | phenyl | 2-bromo-4-(heptafluoroisopropyl)-6-(trifluoromethylthio)phenyl |
| 211 | phenyl | 2,6-dimethyl-4-(nonafluoro-n-butyl)phenyl |
| 212 | phenyl | 2,6-dimethyl-4-(nonafluoro-2-butyl)phenyl |
| 213 | 2-methylphenyl | 2,6-dimethyl-4-(nonafluoro-2-butyl)phenyl |
| 214 | 4-methylphenyl | 2,6-dimethyl-4-(nonafluoro-2-butyl)phenyl |
| 215 | 2-fluorophenyl | 2,6-dimethyl-4-(nonafluoro-2-butyl)phenyl |
| 216 | 3-fluorophenyl | 2,6-dimethyl-4-(nonafluoro-2-butyl)phenyl |
| 217 | 4-fluorophenyl | 2,6-dimethyl-4-(nonafluoro-2-butyl)phenyl |
| 218 | 2-chlorophenyl | 2,6-dimethyl-4-(nonafluoro-2-butyl)phenyl |
| 219 | 4-chlorophenyl | 2,6-dimethyl-4-(nonafluoro-2-butyl)phenyl |
| 220 | 2-bromophenyl | 2,6-dimethyl-4-(nonafluoro-2-butyl)phenyl |
| 221 | 2-iodophenyl | 2,6-dimethyl-4-(nonafluoro-2-butyl)phenyl |
| 222 | 3-cyanophenyl | 2,6-dimethyl-4-(nonafluoro-2-butyl)phenyl |
| 223 | 4-cyanophenyl | 2,6-dimethyl-4-(nonafluoro-2-butyl)phenyl |
| 224 | 2-nitrophenyl | 2,6-dimethyl-4-(nonafluoro-2-butyl)phenyl |
| 225 | 3-nitrophenyl | 2,6-dimethyl-4-(nonafluoro-2-butyl)phenyl |
| 226 | 4-nitrophenyl | 2,6-dimethyl-4-(nonafluoro-2-butyl)phenyl |
| 227 | 2-trifluoromethylphenyl | 2,6-dimethyl-4-(nonafluoro-2-butyl)phenyl |
| 228 | 4-trifluoromethylphenyl | 2,6-dimethyl-4-(nonafluoro-2-butyl)phenyl |
| 229 | 4-trifluoromethoxyphenyl | 2,6-dimethyl-4-(nonafluoro-2-butyl)phenyl |
| 230 | 2,3-difluorophenyl | 2,6-dimethyl-4-(nonafluoro-2-butyl)phenyl |
| 231 | 2,4-difluorophenyl | 2,6-dimethyl-4-(nonafluoro-2-butyl)phenyl |
| 232 | 2,5-difluorophenyl | 2,6-dimethyl-4-(nonafluoro-2-butyl)phenyl |
| 233 | 2,6-difluorophenyl | 2,6-dimethyl-4-(nonafluoro-2-butyl)phenyl |
| 234 | 2,4-dichlorophenyl | 2,6-dimethyl-4-(nonafluoro-2-butyl)phenyl |
| 235 | 2,6-dichlorophenyl | 2,6-dimethyl-4-(nonafluoro-2-butyl)phenyl |
| 236 | 3,4-dichlorophenyl | 2,6-dimethyl-4-(nonafluoro-2-butyl)phenyl |
| 237 | 2-chloro-4-nitrophenyl | 2,6-dimethyl-4-(nonafluoro-2-butyl)phenyl |
| 238 | 2-chloro-4-fluorophenyl | 2,6-dimethyl-4-(nonafluoro-2-butyl)phenyl |
| 239 | 2-chloro-6-fluorophenyl | 2,6-dimethyl-4-(nonafluoro-2-butyl)phenyl |
| 240 | 4-chloro-2-fluorophenyl | 2,6-dimethyl-4-(nonafluoro-2-butyl)phenyl |
| 241 | 4-chloro-2-nitrophenyl | 2,6-dimethyl-4-(nonafluoro-2-butyl)phenyl |
| 242 | 2,3,6-trifluorophenyl | 2,6-dimethyl-4-(nonafluoro-2-butyl)phenyl |
| 243 | pyridin-2-yl | 2,6-dimethyl-4-(nonafluoro-2-butyl)phenyl |
| 244 | pyridin-3-yl | 2,6-dimethyl-4-(nonafluoro-2-butyl)phenyl |
| 245 | 2-fluoropyridin-3-yl | 2,6-dimethyl-4-(nonafluoro-2-butyl)phenyl |
| 246 | 2-chloropyridin-3-yl | 2,6-dimethyl-4-(nonafluoro-2-butyl)phenyl |
| 247 | 2-chloropyridin-5-yl | 2,6-dimethyl-4-(nonafluoro-2-butyl)phenyl |
| 248 | 2-methylthiopyridin-3-yl | 2,6-dimethyl-4-(nonafluoro-2-butyl)phenyl |
| 249 | pyrazin-2-yl | 2,6-dimethyl-4-(nonafluoro-2-butyl)phenyl |

TABLE 1-continued

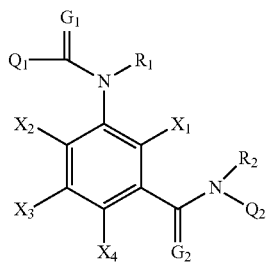

($X_1$, $X_2$, $X_3$, $X_4$, $R_1$, $R_2$ = a hydrogen atom, $G_1$, $G_2$ = an oxygen atom)

| Comp. No. | $Q_1$ | $Q_2$ |
| --- | --- | --- |
| 250 | furan-2-yl | 2,6-dimethyl-4-(nonafluoro-2-butyl)phenyl |
| 251 | furan-3-yl | 2,6-dimethyl-4-(nonafluoro-2-butyl)phenyl |
| 252 | 2-tetrahydrofuranyl | 2,6-dimethyl-4-(nonafluoro-2-butyl)phenyl |
| 253 | benzofuran-2-yl | 2,6-dimethyl-4-(nonafluoro-2-butyl)phenyl |
| 254 | thiophen-2-yl | 2,6-dimethyl-4-(nonafluoro-2-butyl)phenyl |
| 255 | 2,6-difluorophenyl | 2,6-dichloro-4-(trifluoromethylthio)phenyl |
| 256 | phenyl | 2,6-dibromo-4-(trifluoromethylthio)phenyl |
| 257 | 2,6-difluorophenyl | 2,6-dibromo-4-(trifluoromethylthio)phenyl |
| 258 | phenyl | 2,6-dibromo-4-(pentafluoroethylthio)phenyl |
| 259 | 2-fluorophenyl | 2,6-dibromo-4-(pentafluoroethylthio)phenyl |
| 260 | phenyl | 2,6-dimethyl-4-(heptafluoro-n-propylthio)phenyl |
| 261 | 2-fluorophenyl | 2,6-dimethyl-4-(heptafluoro-n-propylthio)phenyl |
| 262 | phenyl | 2,6-dichloro-4-(heptafluoro-n-propylthio)phenyl |
| 263 | phenyl | 2,6-dibromo-4-(heptafluoro-n-propylthio)phenyl |
| 264 | 2-methylphenyl | 2,6-dibromo-4-(heptafluoro-n-propylthio)phenyl |
| 265 | 4-methylphenyl | 2,6-dibromo-4-(heptafluoro-n-propylthio)phenyl |
| 266 | 2-fluorophenyl | 2,6-dibromo-4-(heptafluoro-n-propylthio)phenyl |
| 267 | 3-fluorophenyl | 2,6-dibromo-4-(heptafluoro-n-propylthio)phenyl |
| 268 | 4-fluorophenyl | 2,6-dibromo-4-(heptafluoro-n-propylthio)phenyl |
| 269 | 2-chlorophenyl | 2,6-dibromo-4-(heptafluoro-n-propylthio)phenyl |
| 270 | 4-chlorophenyl | 2,6-dibromo-4-(heptafluoro-n-propylthio)phenyl |
| 271 | 2-bromophenyl | 2,6-dibromo-4-(heptafluoro-n-propylthio)phenyl |
| 272 | 2-iodophenyl | 2,6-dibromo-4-(heptafluoro-n-propylthio)phenyl |
| 273 | 3-cyanophenyl | 2,6-dibromo-4-(heptafluoro-n-propylthio)phenyl |
| 274 | 4-cyanophenyl | 2,6-dibromo-4-(heptafluoro-n-propylthio)phenyl |
| 275 | 2-nitrophenyl | 2,6-dibromo-4-(heptafluoro-n-propylthio)phenyl |
| 276 | 3-nitrophenyl | 2,6-dibromo-4-(heptafluoro-n-propylthio)phenyl |
| 277 | 4-nitrophenyl | 2,6-dibromo-4-(heptafluoro-n-propylthio)phenyl |
| 278 | 2-trifluoromethylphenyl | 2,6-dibromo-4-(heptafluoro-n-propylthio)phenyl |
| 279 | 4-trifluoromethylphenyl | 2,6-dibromo-4-(heptafluoro-n-propylthio)phenyl |
| 280 | 4-trifluoromethoxyphenyl | 2,6-dibromo-4-(heptafluoro-n-propylthio)phenyl |
| 281 | 2,3-difluorophenyl | 2,6-dibromo-4-(heptafluoro-n-propylthio)phenyl |
| 282 | 2,4-difluorophenyl | 2,6-dibromo-4-(heptafluoro-n-propylthio)phenyl |
| 283 | 2,5-difluorophenyl | 2,6-dibromo-4-(heptafluoro-n-propylthio)phenyl |
| 284 | 2,6-difluorophenyl | 2,6-dibromo-4-(heptafluoro-n-propylthio)phenyl |
| 285 | 3-aminophenyl | 2,6-dibromo-4-(heptafluoro-n-propylthio)phenyl |
| 286 | 3-(acetylamino)phenyl | 2,6-dibromo-4-(heptafluoro-n-propylthio)phenyl |
| 287 | 3-(methylsulfonylamino)phenyl | 2,6-dibromo-4-(heptafluoro-n-propylthio)phenyl |
| 288 | 2,4-dinitrophenyl | 2,6-dibromo-4-(heptafluoro-n-propylthio)phenyl |
| 289 | 3,4-dinitrophenyl | 2,6-dibromo-4-(heptafluoro-n-propylthio)phenyl |
| 290 | 3-methyl-4-nitrophenyl | 2,6-dibromo-4-(heptafluoro-n-propylthio)phenyl |
| 291 | 5-amino-2-fluorophenyl | 2,6-dibromo-4-(heptafluoro-n-propylthio)phenyl |
| 292 | 2-fluoro-5-nitrophenyl | 2,6-dibromo-4-(heptafluoro-n-propylthio)phenyl |
| 293 | 2-fluoro-5-(methylsulfonylamino)phenyl | 2,6-dibromo-4-(heptafluoro-n-propylthio)phenyl |
| 294 | 2-methoxy-4-nitrophenyl | 2,6-dibromo-4-(heptafluoro-n-propylthio)phenyl |
| 295 | 3-methoxy-4-nitrophenyl | 2,6-dibromo-4-(heptafluoro-n-propylthio)phenyl |
| 296 | 5-(acetylamino)-2-fluorophenyl | 2,6-dibromo-4-(heptafluoro-n-propylthio)phenyl |
| 297 | 2,4-dichlorophenyl | 2,6-dibromo-4-(heptafluoro-n-propylthio)phenyl |
| 298 | 2,6-dichlorophenyl | 2,6-dibromo-4-(heptafluoro-n-propylthio)phenyl |
| 299 | 3,4-dichlorophenyl | 2,6-dibromo-4-(heptafluoro-n-propylthio)phenyl |
| 300 | 2-chloro-4-nitrophenyl | 2,6-dibromo-4-(heptafluoro-n-propylthio)phenyl |
| 301 | 2-chloro-4-fluorophenyl | 2,6-dibromo-4-(heptafluoro-n-propylthio)phenyl |
| 302 | 2-chloro-6-fluorophenyl | 2,6-dibromo-4-(heptafluoro-n-propylthio)phenyl |
| 303 | 4-chloro-2-fluorophenyl | 2,6-dibromo-4-(heptafluoro-n-propylthio)phenyl |
| 304 | 4-chloro-2-nitrophenyl | 2,6-dibromo-4-(heptafluoro-n-propylthio)phenyl |
| 305 | 2,3,6-trifluorophenyl | 2,6-dibromo-4-(heptafluoro-n-propylthio)phenyl |
| 306 | pyridin-2-yl | 2,6-dibromo-4-(heptafluoro-n-propylthio)phenyl |
| 307 | pyridin-3-yl | 2,6-dibromo-4-(heptafluoro-n-propylthio)phenyl |
| 308 | 2-fluoropyridin-3-yl | 2,6-dibromo-4-(heptafluoro-n-propylthio)phenyl |
| 309 | 2-chloropyridin-3-yl | 2,6-dibromo-4-(heptafluoro-n-propylthio)phenyl |
| 310 | 2-chloropyridin-5-yl | 2,6-dibromo-4-(heptatluoro-n-propylthio)phenyl |
| 311 | 2-methylthiopyridin-3-yl | 2,6-dibromo-4-(heptafluoro-n-propylthio)phenyl |
| 312 | 2,6-dichloropyridin-3-yl | 2,6-dibromo-4-(heptafluoro-n-propylthio)phenyl |

TABLE 1-continued

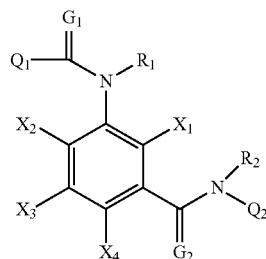

($X_1$, $X_2$, $X_3$, $X_4$, $R_1$, $R_2$ = a hydrogen atom, $G_1$, $G_2$ = an oxygen atom)

| Comp. No. | $Q_1$ | $Q_2$ |
|---|---|---|
| 313 | 2,6-dichloropyridin-4-yl | 2,6-dibromo-4-(heptafluoro-n-propylthio)phenyl |
| 314 | 2-chloro-6-methylpyridin-3-yl | 2,6-dibromo-4-(heptafluoro-n-propylthio)phenyl |
| 315 | pyridin-N-oxide-2-yl | 2,6-dibromo-4-(heptafluoro-n-propylthio)phenyl |
| 316 | pyrazin-2-yl | 2,6-dibromo-4-(heptafluoro-n-propylthio)phenyl |
| 317 | 1-methyl-3-nitro-1Hpyrazol-4-yl | 2,6-dibromo-4-(heptafluoro-n-propylthio)phenyl |
| 318 | 1-methyl-3-trifluoromethyl-1Hpyrazol-4-yl | 2,6-dibromo-4-(heptafluoro-n-propylthio)phenyl |
| 319 | 1-methyl-5-trifluoromethyl-1Hpyrazol-4-yl | 2,6-dibromo-4-(heptafluoro-n-propylthio)phenyl |
| 320 | 2-tetrahydrofuranyl | 2,6-dibromo-4-(heptafluoro-n-propylthio)phenyl |
| 321 | 2-phenylthiazol-4-yl | 2,6-dibromo-4-(heptafluoro-n-propylthio)phenyl |
| 322 | furan-2-yl | 2,6-dibromo-4-(heptafluoro-n-propylthio)phenyl |
| 323 | furan-3-yl | 2,6-dibromo-4-(heptafluoro-n-propylthio)phenyl |
| 324 | 2-tetrahydrofuranyl | 2,6-dibromo-4-(heptafluoro-n-propylthio)phenyl |
| 325 | benzofuran-2-yl | 2,6-dibromo-4-(heptafluoro-n-propylthio)phenyl |
| 326 | thiophen-2-yl | 2,6-dibromo-4-(heptafluoro-n-propylthio)phenyl |
| 327 | phenyl | 2,6-diiodo-4-(heptafluoro-n-propylthio)phenyl |
| 328 | 2-fluorophenyl | 2,6-diiodo-4-(heptafluoro-n-propylthio)phenyl |
| 329 | phenyl | 2,6-dichloro-4-(heptafluoroisopropylthio)phenyl |
| 330 | 2-fluorophenyl | 2,6-dichloro-4-(heptafluoroisopropylthio)phenyl |
| 331 | 2-chloropyridin-3-yl | 2,6-dichloro-4-(heptafluoroisopropylthio)phenyl |
| 332 | phenyl | 2,6-dibromo-4-(heptafluoroisopropylthio)phenyl |
| 333 | phenyl | 2,6-dibromo-4-(nonafluoro-n-butylthio)phenyl |
| 334 | 2-fluorophenyl | 2,6-dibromo-4-(nonafluoro-n-butylthio)phenyl |
| 335 | phenyl | 2,6-dibromo-4-(heptafluoro-n-propylsulfinyl)phenyl |
| 336 | 2-methylphenyl | 2,6-dibromo-4-(heptafluoro-n-propylsulfinyl)phenyl |
| 337 | 4-methylphenyl | 2,6-dibromo-4-(heptafluoro-n-propylsulfinyl)phenyl |
| 338 | 2-fluorophenyl | 2,6-dibromo-4-(heptafluoro-n-propylsulfinyl)phenyl |
| 339 | 3-fluorophenyl | 2,6-dibromo-4-(heptafluoro-n-propylsulfinyl)phenyl |
| 340 | 4-fluorophenyl | 2,6-dibromo-4-(heptafluoro-n-propylsulfinyl)phenyl |
| 341 | 2-chlorophenyl | 2,6-dibromo-4-(heptafluoro-n-propylsulfinyl)phenyl |
| 342 | 4-chlorophenyl | 2,6-dibromo-4-(heptafluoro-n-propylsulfinyl)phenyl |
| 343 | 2-bromophenyl | 2,6-dibromo-4-(heptafluoro-n-propylsulfinyl)phenyl |
| 344 | 2-iodophenyl | 2,6-dibromo-4-(heptafluoro-n-propylsulfinyl)phenyl |
| 345 | 3-cyanophenyl | 2,6-dibromo-4-(heptafluoro-n-propylsulfinyl)phenyl |
| 346 | 4-cyanophenyl | 2,6-dibromo-4-(heptafluoro-n-propylsulfinyl)phenyl |
| 347 | 2-nitrophenyl | 2,6-dibromo-4-(heptafluoro-n-propylsulfinyl)phenyl |
| 348 | 3-nitrophenyl | 2,6-dibromo-4-(heptafluoro-n-propylsulfinyl)phenyl |
| 349 | 4-nitrophenyl | 2,6-dibromo-4-(heptafluoro-n-propylsulfinyl)phenyl |
| 350 | 2-trifluoromethylphenyl | 2,6-dibromo-4-(heptafluoro-n-propylsulfinyl)phenyl |
| 351 | 4-trifluoromethylphenyl | 2,6-dibromo-4-(heptafluoro-n-propylsulfinyl)phenyl |
| 352 | 4-trifluoromethoxyphenyl | 2,6-dibromo-4-(heptafluoro-n-propylsulfinyl)phenyl |
| 353 | 2,3-difluorophenyl | 2,6-dibromo-4-(heptafluoro-n-propylsulfinyl)phenyl |
| 354 | 2,4-difluorophenyl | 2,6-dibromo-4-(heptafluoro-n-propylsulfinyl)phenyl |
| 355 | 2,5-difluorophenyl | 2,6-dibromo-4-(heptafluoro-n-propylsulfinyl)phenyl |
| 356 | 2,6-difluorophenyl | 2,6-dibromo-4-(heptafluoro-n-propylsulfinyl)phenyl |
| 357 | 2,4-dichlorophenyl | 2,6-dibromo-4-(heptafluoro-n-propylsulfinyl)phenyl |
| 358 | 2,6-dichlorophenyl | 2,6-dibromo-4-(heptafluoro-n-propylsulfinyl)phenyl |
| 359 | 3,4-dichlorophenyl | 2,6-dibromo-4-(heptafluoro-n-propylsulfinyl)phenyl |
| 360 | 2-chloro-4-nitrophenyl | 2,6-dibromo-4-(heptafluoro-n-propylsulfinyl)phenyl |
| 361 | 2-chloro-4-fluorophenyl | 2,6-dibromo-4-(heptatluoro-n-propylsulfinyl)phenyl |
| 362 | 2-chloro-6-fluorophenyl | 2,6-dibromo-4-(heptafluoro-n-propylsulfinyl)phenyl |
| 363 | 4-chloro-2-fluorophenyl | 2,6-dibromo-4-(heptafluoro-n-propylsulfinyl)phenyl |
| 364 | 4-chloro-2-nitrophenyl | 2,6-dibromo-4-(heptafluoro-n-propylsulfinyl)phenyl |
| 365 | 2,3,6-trifluorophenyl | 2,6-dibromo-4-(heptafluoro-n-propylsulfinyl)phenyl |
| 366 | pyridin-2-yl | 2,6-dibromo-4-(heptafluoro-n-propylsulfinyl)phenyl |
| 367 | pyridin-3-yl | 2,6-dibromo-4-(heptafluoro-n-propylsulfinyl)phenyl |
| 368 | 2-fluoropyridin-3-yl | 2,6-dibromo-4-(heptafluoro-n-propylsulfinyl)phenyl |
| 369 | 2-chloropyridin-3-yl | 2,6-dibromo-4-(heptafluoro-n-propylsulfinyl)phenyl |
| 370 | 2-chloropyridin-5-yl | 2,6-dibromo-4-(heptafluoro-n-propylsulfinyl)phenyl |
| 371 | 2-methylthiopyridin-3-yl | 2,6-dibromo-4-(heptafluoro-n-propylsulfinyl)phenyl |
| 372 | pyrazin-2-yl | 2,6-dibromo-4-(heptafluoro-n-propylsulfinyl)phenyl |
| 373 | furan-2-yl | 2,6-dibromo-4-(heptafluoro-n-propylsulfinyl)phenyl |
| 374 | thiophen-2-yl | 2,6-dibromo-4-(heptafluoro-n-propylsulfinyl)phenyl |
| 375 | 2,6-difluorophenyl | 2,6-dichloro-4-(trifluoromethylsulfonyl)phenyl |

TABLE 1-continued

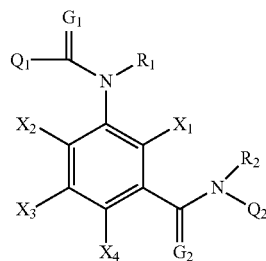

($X_1$, $X_2$, $X_3$, $X_4$, $R_1$, $R_2$ = a hydrogen atom, $G_1$, $G_2$ = an oxygen atom)

| Comp. No. | $Q_1$ | $Q_2$ |
| --- | --- | --- |
| 376 | phenyl | 2,6-dibromo-4-(trifluoromethylsulfonyl)phenyl |
| 377 | 2,6-difluorophenyl | 2,6-dibromo-4-(trifluoromethylsulfonyl)phenyl |
| 378 | 2-fluorophenyl | 2,6-dichloro-4-(heptafluoroisopropylsulfonyl)phenyl |
| 379 | phenyl | 2,6-dichloro-4-(heptafluoroisopropylsulfonyl)phenyl |
| 380 | phenyl | 2,6-dibromo-4-(heptafluoro-n-propylsulfonyl)phenyl |
| 381 | 2-methylphenyl | 2,6-dibromo-4-(heptafluoro-n-propylsulfonyl)phenyl |
| 382 | 4-methylphenyl | 2,6-dibromo-4-(heptafluoro-n-propylsulfonyl)phenyl |
| 383 | 2-fluorophenyl | 2,6-dibromo-4-(heptafluoro-n-propylsulfonyl)phenyl |
| 384 | 3-fluorophenyl | 2,6-dibromo-4-(heptafluoro-n-propylsulfonyl)phenyl |
| 385 | 4-fluorophenyl | 2,6-dibromo-4-(heptafluoro-n-propylsulfonyl)phenyl |
| 386 | 2-chlorophenyl | 2,6-dibromo-4-(heptafluoro-n-propylsulfonyl)phenyl |
| 387 | 4-chlorophenyl | 2,6-dibromo-4-(heptafluoro-n-propylsulfonyl)phenyl |
| 388 | 2-bromophenyl | 2,6-dibromo-4-(heptafluoro-n-propylsulfonyl)phenyl |
| 389 | 2-iodophenyl | 2,6-dibromo-4-(heptafluoro-n-propylsulfonyl)phenyl |
| 390 | 3-cyanophenyl | 2,6-dibromo-4-(heptafluoro-n-propylsulfonyl)phenyl |
| 391 | 4-cyanophenyl | 2,6-dibromo-4-(heptafluoro-n-propylsulfonyl)phenyl |
| 392 | 2-nitrophenyl | 2,6-dibromo-4-(heptafluoro-n-propylsulfonyl)phenyl |
| 393 | 3-nitrophenyl | 2,6-dibromo-4-(heptafluoro-n-propylsulfonyl)phenyl |
| 394 | 4-nitrophenyl | 2,6-dibromo-4-(heptafluoro-n-propylsulfonyl)phenyl |
| 395 | 2-trifluoromethylphenyl | 2,6-dibromo-4-(heptafluoro-n-propylsulfonyl)phenyl |
| 396 | 4-trifluoromethylphenyl | 2,6-dibromo-4-(heptafluoro-n-propylsulfonyl)phenyl |
| 397 | 4-trifluoromethoxyphenyl | 2,6-dibromo-4-(heptafluoro-n-propylsulfonyl)phenyl |
| 398 | 2,3-difluorophenyl | 2,6-dibromo-4-(heptafluoro-n-propylsulfonyl)phenyl |
| 399 | 2,4-difluorophenyl | 2,6-dibromo-4-(heptafluoro-n-propylsulfonyl)phenyl |
| 400 | 2,5-difluorophenyl | 2,6-dibromo-4-(heptafluoro-n-propylsulfonyl)phenyl |
| 401 | 2,6-difluorophenyl | 2,6-dibromo-4-(heptafluoro-n-propylsulfonyl)phenyl |
| 402 | 2,4-dichlorophenyl | 2,6-dibromo-4-(heptafluoro-n-propylsulfonyl)phenyl |
| 403 | 2,6-dichlorophenyl | 2,6-dibromo-4-(heptafluoro-n-propylsulfonyl)phenyl |
| 404 | 3,4-dichlorophenyl | 2,6-dibromo-4-(heptafluoro-n-propylsulfonyl)phenyl |
| 405 | 2-chloro-4-nitrophenyl | 2,6-dibromo-4-(heptafluoro-n-propylsulfonyl)phenyl |
| 406 | 2-chloro-4-fluorophenyl | 2,6-dibromo-4-(heptafluoro-n-propylsulfonyl)phenyl |
| 407 | 2-chloro-6-fluorophenyl | 2,6-dibromo-4-(heptafluoro-n-propylsulfonyl)phenyl |
| 408 | 4-chloro-2-fluorophenyl | 2,6-dibromo-4-(heptafluoro-n-propylsulfonyl)phenyl |
| 409 | 4-chloro-2-nitrophenyl | 2,6-dibromo-4-(heptafluoro-n-propylsulfonyl)phenyl |
| 410 | 2,3,6-trifluorophenyl | 2,6-dibromo-4-(heptafluoro-n-propylsulfonyl)phenyl |
| 411 | pyridin-2-yl | 2,6-dibromo-4-(heptafluoro-n-propylsulfonyl)phenyl |
| 412 | pyridin-3-yl | 2,6-dibromo-4-(heptafluoro-n-propylsulfonyl)phenyl |
| 413 | 2-fluoropyridin-3-yl | 2,6-dibromo-4-(heptafluoro-n-propylsulfonyl)phenyl |
| 414 | 2-chloropyridin-3-yl | 2,6-dibromo-4-(heptafluoro-n-propylsulfonyl)phenyl |
| 415 | 2-chloropyridin-5-yl | 2,6-dibromo-4-(heptafluoro-n-propylsulfonyl)phenyl |
| 416 | 2-methylthiopyridin-3-yl | 2,6-dibromo-4-(heptafluoro-n-propylsulfonyl)phenyl |
| 417 | pyrazin-2-yl | 2,6-dibromo-4-(heptafluoro-n-propylsulfonyl)phenyl |
| 418 | furan-2-yl | 2,6-dibromo-4-(heptafluoro-n-propylsulfonyl)phenyl |
| 419 | thiophen-2-yl | 2,6-dibromo-4-(heptafluoro-n-propylsulfonyl)phenyl |
| 420 | phenyl | 2,6-dimethyl-4-(heptafluoro-n-propylthio)phenyl |
| 421 | 2-methylphenyl | 2,6-dimethyl-4-(heptafluoro-n-propylthio)phenyl |
| 422 | 4-methylphenyl | 2,6-dimethyl-4-(heptafluoro-n-propylthio)phenyl |
| 423 | 2-fluorophenyl | 2,6-dimethyl-4-(heptafluoro-n-propylthio)phenyl |
| 424 | 3-fluorophenyl | 2,6-dimethyl-4-(heptafluoro-n-propylthio)phenyl |
| 425 | 4-fluorophenyl | 2,6-dimethyl-4-(heptafluoro-n-propylthio)phenyl |
| 426 | 2-chlorophenyl | 2,6-dimethyl-4-(heptafluoro-n-propylthio)phenyl |
| 427 | 4-chlorophenyl | 2,6-dimethyl-4-(heptafluoro-n-propylthio)phenyl |
| 428 | 2-bromophenyl | 2,6-dimethyl-4-(heptafluoro-n-propylthio)phenyl |
| 429 | 2-iodophenyl | 2,6-dimethyl-4-(heptafluoro-n-propylthio)phenyl |
| 430 | 3-cyanophenyl | 2,6-dimethyl-4-(heptafluoro-n-propylthio)phenyl |
| 431 | 4-cyanophenyl | 2,6-dimethyl-4-(heptafluoro-n-propylthio)phenyl |
| 432 | 2-nitrophenyl | 2,6-dimethyl-4-(heptafluoro-n-propylthio)phenyl |
| 433 | 3-nitrophenyl | 2,6-dimethyl-4-(heptafluoro-n-propylthio)phenyl |
| 434 | 4-nitrophenyl | 2,6-dimethyl-4-(heptafluoro-n-propylthio)phenyl |
| 435 | 2-trifluoromethylphenyl | 2,6-dimethyl-4-(heptafluoro-n-propylthio)phenyl |
| 436 | 4-trifluoromethylphenyl | 2,6-dimethyl-4-(heptafluoro-n-propylthio)phenyl |
| 437 | 4-trifluoromethoxyphenyl | 2,6-dimethyl-4-(heptafluoro-n-propylthio)phenyl |
| 438 | 2,3-difluorophenyl | 2,6-dimethyl-4-(heptafluoro-n-propylthio)phenyl |

TABLE 1-continued

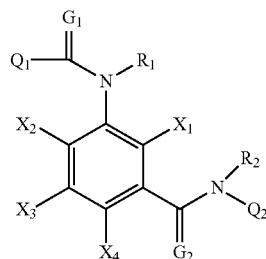

($X_1$, $X_2$, $X_3$, $X_4$, $R_1$, $R_2$ = a hydrogen atom, $G_1$, $G_2$ = an oxygen atom)

| Comp. No. | $Q_1$ | $Q_2$ |
| --- | --- | --- |
| 439 | 2,4-difluorophenyl | 2,6-dimethyl-4-(heptafluoro-n-propylthio)phenyl |
| 440 | 2,5-difluorophenyl | 2,6-dimethyl-4-(heptafluoro-n-propylthio)phenyl |
| 441 | 2,6-difluorophenyl | 2,6-dimethyl-4-(heptafluoro-n-propylthio)phenyl |
| 442 | 2,4-dichlorophenyl | 2,6-dimethyl-4-(heptafluoro-n-propylthio)phenyl |
| 443 | 2,6-dichlorophenyl | 2,6-dimethyl-4-(heptafluoro-n-propylthio)phenyl |
| 444 | 3,4-dichlorophenyl | 2,6-dimethyl-4-(heptafluoro-n-propylthio)phenyl |
| 445 | 2-chloro-4-nitrophenyl | 2,6-dimethyl-4-(heptafluoro-n-propylthio)phenyl |
| 446 | 2-chloro-4-fluorophenyl | 2,6-dimethyl-4-(heptafluoro-n-propylthio)phenyl |
| 447 | 2-chloro-6-fluorophenyl | 2,6-dimethyl-4-(heptafluoro-n-propylthio)phenyl |
| 448 | 4-chloro-2-fluorophenyl | 2,6-dimethyl-4-(heptafluoro-n-propylthio)phenyl |
| 449 | 4-chloro-2-nitrophenyl | 2,6-dimethyl-4-(heptafluoro-n-propylthio)phenyl |
| 450 | 2,3,6-trifluorophenyl | 2,6-dimethyl-4-(heptafluoro-n-propylthio)phenyl |
| 451 | pyridin-2-yl | 2,6-dimethyl-4-(heptafluoro-n-propylthio)phenyl |
| 452 | pyridin-3-yl | 2,6-dimethyl-4-(heptafluoro-n-propylthio)phenyl |
| 453 | 2-fluoropyridin-3-yl | 2,6-dimethyl-4-(heptafluoro-n-propylthio)phenyl |
| 454 | 2-chloropyridin-3-yl | 2,6-dimethyl-4-(heptafluoro-n-propylthio)phenyl |
| 455 | 2-chloropyridin-5-yl | 2,6-dimethyl-4-(heptafluoro-n-propylthio)phenyl |
| 456 | 2-methylthiopyridin-3-yl | 2,6-dimethyl-4-(heptafluoro-n-propylthio)phenyl |
| 457 | pyrazin-2-yl | 2,6-dimethyl-4-(heptafluoro-n-propylthio)phenyl |
| 458 | furan-2-yl | 2,6-dimethyl-4-(heptafluoro-n-propylthio)phenyl |
| 459 | thiophen-2-yl | 2,6-dimethyl-4-(heptafluoro-n-propylthio)phenyl |
| 460 | 2,6-difluorophenyl | 2,6-dichloro-4-(trifluoromethylsulfonyl)phenyl |
| 461 | phenyl | 2-bromo-6-(heptafluoroisopropyloxy)-4-methylpyridin-3-yl |
| 462 | 2-fluorophenyl | 2-bromo-6-(heptafluoroisopropyloxy)-4-methylpyridin-3-yl |
| 463 | phenyl | 2,4-dimethyl-6-(2,2,2-trifluoro-1-trifluoromethylethoxy)pyridin-3-yl |
| 464 | phenyl | 2-chloro-4-methyl-6-(2,2,2-trifluoro-1-trifluoromethylethoxy)pyridin-3-yl |
| 465 | phenyl | 2-bromo-4-methyl-6-(2,2,2-trifluoro-1-trifluoromethylethoxy)pyridin-3-yl |
| 466 | 2-fluorophenyl | 2-bromo-4-methyl-6-(2,2,2-trifluoro-1-trifluoromethylethoxy)pyridin-3-yl |
| 467 | phenyl | 2-iodo-4-methyl-6-(2,2,2-trifluoro-1-trifluoromethylethoxy)pyridin-3-yl |

TABLE 2

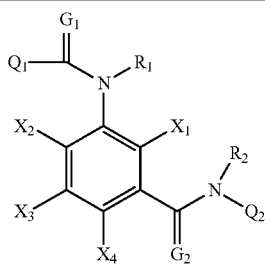

($R_1$, $R_2$ = a hydrogen atom, $G_1$, $G_2$ = an oxygen atom)

| Comp. No. | $Q_1$ | $X_1$ | $X_2$ | $X_3$ | $X_4$ | $Q_2$ |
| --- | --- | --- | --- | --- | --- | --- |
| 601 | phenyl | F | H | H | H | 2,6-dimethyl-4-(heptafluoroisopropyl)phenyl |
| 602 | 2-methylphenyl | F | H | H | H | 2,6-dimethyl-4-(heptafluoroisopropyl)phenyl |
| 603 | 3-methylphenyl | F | H | H | H | 2,6-dimethyl-4-(heptafluoroisopropyl)phenyl |
| 604 | 4-methylphenyl | F | H | H | H | 2,6-dimethyl-4-(heptafluoroisopropyl)phenyl |
| 605 | 2-nitrophenyl | F | H | H | H | 2,6-dimethyl-4-(heptafluoroisopropyl)phenyl |
| 606 | 3-nitrophenyl | F | H | H | H | 2,6-dimethyl-4-(heptafluoroisopropyl)phenyl |
| 607 | 4-nitrophenyl | F | H | H | H | 2,6-dimethyl-4-(heptafluoroisopropyl)phenyl |
| 608 | 3-cyanophenyl | F | H | H | H | 2,6-dimethyl-4-(heptafluoroisopropyl)phenyl |
| 609 | 4-cyanophenyl | F | H | H | H | 2,6-dimethyl-4-(heptafluoroisopropyl)phenyl |
| 610 | 2-fluorophenyl | F | H | H | H | 2,6-dimethyl-4-(heptafluoroisopropyl)phenyl |
| 611 | 3-fluorophenyl | F | H | H | H | 2,6-dimethyl-4-(heptafluoroisopropyl)phenyl |
| 612 | 4-fluorophenyl | F | H | H | H | 2,6-dimethyl-4-(heptafluoroisopropyl)phenyl |

TABLE 2-continued

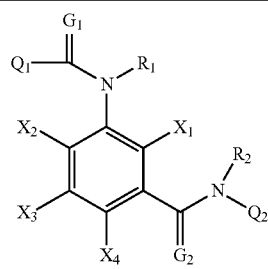

($R_1$, $R_2$ = a hydrogen atom, $G_1$, $G_2$ = an oxygen atom)

| Comp. No. | $Q_1$ | $X_1$ | $X_2$ | $X_3$ | $X_4$ | $Q_2$ |
|---|---|---|---|---|---|---|
| 613 | 2-chlorophenyl | F | H | H | H | 2,6-dimethyl-4-(heptafluoroisopropyl)phenyl |
| 614 | 4-chlorophenyl | F | H | H | H | 2,6-dimethyl-4-(heptafluoroisopropyl)phenyl |
| 615 | 2-bromophenyl | F | H | H | H | 2,6-dimethyl-4-(heptafluoroisopropyl)phenyl |
| 616 | 2-iodophenyl | F | H | H | H | 2,6-dimethyl-4-(heptafluoroisopropyl)phenyl |
| 617 | 2-trifluoromethyl phenyl | F | H | H | H | 2,6-dimethyl-4-(heptafluoroisopropyl)phenyl |
| 618 | 4-trifluoromethyl phenyl | F | H | H | H | 2,6-dimethyl-4-(heptafluoroisopropyl)phenyl |
| 619 | 4-trifluoromethoxy phenyl | F | H | H | H | 2,6-dimethyl-4-(heptafluoroisopropyl)phenyl |
| 620 | 4-(dimethylamino) phenyl | F | H | H | H | 2,6-dimethyl-4-(heptafluoroisopropyl)phenyl |
| 621 | 2.3-difluorophenyl | F | H | H | H | 2,6-dimethyl-4-(heptafluoroisopropyl)phenyl |
| 622 | 2.4-difluorophenyl | F | H | H | H | 2,6-dimethyl-4-(heptafluoroisopropyl)phenyl |
| 623 | 2.5-difluorophenyl | F | H | H | H | 2,6-dimethyl-4-(heptafluoroisopropyl)phenyl |
| 624 | 2,6-difluorophenyl | F | H | H | H | 2,6-dimethyl-4-(heptafluoroisopropyl)phenyl |
| 625 | 2,4-dichlorophenyl | F | H | H | H | 2,6-dimethyl-4-(heptafluoroisopropyl)phenyl |
| 626 | 2,6-dichlorophenyl | F | H | H | H | 2,6-dimethyl-4-(heptafluoroisopropyl)phenyl |
| 627 | 3,4-dichlorophenyl | F | H | H | H | 2,6-dimethyl-4-(heptafluoroisopropyl)phenyl |
| 628 | 2-fluoro-4-nitrophenyl | F | H | H | H | 2,6-dimethyl-4-(heptafluoroisopropyl)phenyl |
| 629 | 4-fluoro-2-nitrophenyl | F | H | H | H | 2,6-dimethyl-4-(heptafluoroisopropyl)phenyl |
| 630 | 2-chloro-4-fluorophenyl | F | H | H | H | 2,6-dimethyl-4-(heptafluoroisopropyl)phenyl |
| 631 | 4-chloro-2-fluorophenyl | F | H | H | H | 2,6-dimethyl-4-(heptafluoroisopropyl)phenyl |
| 632 | 2-chloro-6-fluorophenyl | F | H | H | H | 2,6-dimethyl-4-(heptafluoroisopropyl)phenyl |
| 633 | 2-chloro-4-nitrophenyl | F | H | H | H | 2,6-dimethyl-4-(heptafluoroisopropyl)phenyl |
| 634 | 4-chloro-2-nitrophenyl | F | H | H | H | 2,6-dimethyl-4-(heptafluoroisopropyl)phenyl |
| 635 | 2,3,6-trifluorophenyl | F | H | H | H | 2,6-dimethyl-4-(heptafluoroisopropyl)phenyl |
| 636 | pyridin-2-yl | F | H | H | H | 2,6-dimethyl-4-(heptafluoroisopropyl)phenyl |
| 637 | pyridin-3-yl | F | H | H | H | 2,6-dimethyl-4-(heptafluoroisopropyl)phenyl |
| 638 | 2-fluoropyridin-3-yl | F | H | H | H | 2,6-dimethyl-4-(heptafluoroisopropyl)phenyl |
| 639 | 2-chloropyridin-3-yl | F | H | H | H | 2,6-dimethyl-4-(heptafluoroisopropyl)phenyl |
| 640 | 2-chloropyridin-5-yl | F | H | H | H | 2,6-dimethyl-4-(heptafluoroisopropyl)phenyl |
| 641 | 2-methylthiopyridin-3-yl | F | H | H | H | 2,6-dimethyl-4-(heptafluoroisopropyl)phenyl |
| 642 | pyrazin-2-yl | F | H | H | H | 2,6-dimethyl-4-(heptafluoroisopropyl)phenyl |
| 643 | furan-2-yl | F | H | H | H | 2,6-dimethyl-4-(heptafluoroisopropyl)phenyl |
| 644 | furan-3-yl | F | H | H | H | 2,6-dimethyl-4-(heptafluoroisopropyl)phenyl |
| 645 | 2-tetrahydrofuranyl | F | H | H | H | 2,6-dimethyl-4-(heptafluoroisopropyl)phenyl |
| 646 | benzofuran-2-yl | F | H | H | H | 2,6-dimethyl-4-(heptafluoroisopropyl)phenyl |
| 647 | thiophen-2-yl | F | H | H | H | 2,6-dimethyl-4-(heptafluoroisopropyl)phenyl |
| 648 | 2-methyl-5,6-dihydro-4H-pyran-3-yl | F | H | H | H | 2,6-dimethyl-4-(heptafluoroisopropyl)phenyl |
| 649 | phenyl | H | Cl | H | H | 2,6-dimethyl-4-(heptafluoroisopropyl)phenyl |
| 650 | phenyl | H | F | H | H | 2,6-dimethyl-4-(heptafluoroisopropyl)phenyl |
| 651 | 4-nitrophenyl | H | F | H | H | 2,6-dimethyl-4-(heptafluoroisopropyl)phenyl |
| 652 | 4-cyanophenyl | H | F | H | H | 2,6-dimethyl-4-(heptafluoroisopropyl)phenyl |
| 653 | 2-fluorophenyl | H | F | H | H | 2,6-dimethyl-4-(heptafluoroisopropyl)phenyl |
| 654 | 4-fluorophenyl | H | F | H | H | 2,6-dimethyl-4-(heptafluoroisopropyl)phenyl |
| 655 | 4-trifluoromethylphenyl | H | F | H | H | 2,6-dimethyl-4-(heptafluoroisopropyl)phenyl |
| 656 | 2.4-difluorophenyl | H | F | H | H | 2,6-dimethyl-4-(heptafluoroisopropyl)phenyl |
| 657 | 2-chloropyridin-3-yl | H | F | H | H | 2,6-dimethyl-4-(heptafluoroisopropyl)phenyl |
| 658 | phenyl | H | H | $CF_3$ | H | 2,6-dimethyl-4-(heptafluoroisopropyl)phenyl |
| 659 | phenyl | H | H | H | F | 2,6-dimethyl-4-(heptafluoroisopropyl)phenyl |
| 660 | phenyl | H | H | H | Cl | 2,6-dimethyl-4-(heptafluoroisopropyl)phenyl |
| 661 | phenyl | H | H | H | Br | 2,6-dimethyl-4-(heptafluoroisopropyl)phenyl |
| 662 | phenyl | H | H | H | I | 2,6-dimethyl-4-(heptafluoroisopropyl)phenyl |
| 663 | phenyl | F | H | H | F | 2,6-dimethyl-4-(heptafluoroisopropyl)phenyl |
| 664 | phenyl | H | Br | H | Br | 2,6-dimethyl-4-(heptafluoroisopropyl)phenyl |
| 665 | phenyl | F | H | H | H | 2,6-dimethyl-4-(nonafluoro-2-butyl)phenyl |
| 666 | 2-methylphenyl | F | H | H | H | 2,6-dimethyl-4-(nonafluoro-2-butyl)phenyl |
| 667 | 4-methylphenyl | F | H | H | H | 2,6-dimethyl-4-(nonafluoro-2-butyl)phenyl |
| 668 | 2-fluorophenyl | F | H | H | H | 2,6-dimethyl-4-(nonafluoro-2-butyl)phenyl |
| 669 | 3-fluorophenyl | F | H | H | H | 2,6-dimethyl-4-(nonafluoro-2-butyl)phenyl |
| 670 | 4-fluorophenyl | F | H | H | H | 2,6-dimethyl-4-(nonafluoro-2-butyl)phenyl |

TABLE 2-continued

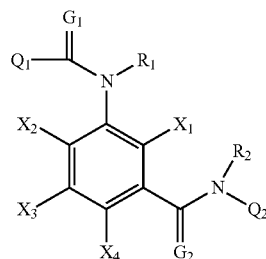

($R_1$, $R_2$ = a hydrogen atom, $G_1$, $G_2$ = an oxygen atom)

| Comp. No. | $Q_1$ | $X_1$ | $X_2$ | $X_3$ | $X_4$ | $Q_2$ |
|---|---|---|---|---|---|---|
| 671 | 2-chlorophenyl | F | H | H | H | 2,6-dimethyl-4-(nonafluoro-2-butyl)phenyl |
| 672 | 4-chlorophenyl | F | H | H | H | 2,6-dimethyl-4-(nonafluoro-2-butyl)phenyl |
| 673 | 2-bromophenyl | F | H | H | H | 2,6-dimethyl-4-(nonafluoro-2-butyl)phenyl |
| 674 | 2-iodophenyl | F | H | H | H | 2,6-dimethyl-4-(nonafluoro-2-butyl)phenyl |
| 675 | 3-cyanophenyl | F | H | H | H | 2,6-dimethyl-4-(nonafluoro-2-butyl)phenyl |
| 676 | 4-cyanophenyl | F | H | H | H | 2,6-dimethyl-4-(nonafluoro-2-butyl)phenyl |
| 677 | 2-nitrophenyl | F | H | H | H | 2,6-dimethyl-4-(nonafluoro-2-butyl)phenyl |
| 678 | 3-nitrophenyl | F | H | H | H | 2,6-dimethyl-4-(nonafluoro-2-butyl)phenyl |
| 679 | 4-nitrophenyl | F | H | H | H | 2,6-dimethyl-4-(nonafluoro-2-butyl)phenyl |
| 680 | 2-trifluoromethylphenyl | F | H | H | H | 2,6-dimethyl-4-(nonafluoro-2-butyl)phenyl |
| 681 | 4-trifluoromethylphenyl | F | H | H | H | 2,6-dimethyl-4-(nonafluoro-2-butyl)phenyl |
| 682 | 4-trifluoromethoxy-phenyl | F | H | H | H | 2,6-dimethyl-4-(nonafluoro-2-butyl)phenyl |
| 683 | 2.3-difluorophenyl | F | H | H | H | 2,6-dimethyl-4-(nonafluoro-2-butyl)phenyl |
| 684 | 2.4-difluorophenyl | F | H | H | H | 2,6-dimethyl-4-(nonafluoro-2-butyl)phenyl |
| 685 | 2.5-difluorophenyl | F | H | H | H | 2,6-dimethyl-4-(nonafluoro-2-butyl)phenyl |
| 686 | 2,6-difluorophenyl | F | H | H | H | 2,6-dimethyl-4-(nonafluoro-2-butyl)phenyl |
| 687 | 2,4-dichlorophenyl | F | H | H | H | 2,6-dimethyl-4-(nonafluoro-2-butyl)phenyl |
| 688 | 2,6-dichlorophenyl | F | H | H | H | 2,6-dimethyl-4-(nonafluoro-2-butyl)phenyl |
| 689 | 3,4-dichlorophenyl | F | H | H | H | 2,6-dimethyl-4-(nonafluoro-2-butyl)phenyl |
| 690 | 2-chloro-4-nitrophenyl | F | H | H | H | 2,6-dimethyl-4-(nonafluoro-2-butyl)phenyl |
| 691 | 2-chloro-4-fluorophenyl | F | H | H | H | 2,6-dimethyl-4-(nonafluoro-2-butyl)phenyl |
| 692 | 2-chloro-6-fluorophenyl | F | H | H | H | 2,6-dimethyl-4-(nonafluoro-2-butyl)phenyl |
| 693 | 4-chloro-2-fluorophenyl | F | H | H | H | 2,6-dimethyl-4-(nonafluoro-2-butyl)phenyl |
| 694 | 4-chloro-2-nitrophenyl | F | H | H | H | 2,6-dimethyl-4-(nonafluoro-2-butyl)phenyl |
| 695 | 2,3,6-trifluorophenyl | F | H | H | H | 2,6-dimethyl-4-(nonafluoro-2-butyl)phenyl |
| 696 | pyridin-2-yl | F | H | H | H | 2,6-dimethyl-4-(nonafluoro-2-butyl)phenyl |
| 697 | pyridin-3-yl | F | H | H | H | 2,6-dimethyl-4-(nonafluoro-2-butyl)phenyl |
| 698 | 2-fluoropyridin-3-yl | F | H | H | H | 2,6-dimethyl-4-(nonafluoro-2-butyl)phenyl |
| 699 | 2-chloropyridin-3-yl | F | H | H | H | 2,6-dimethyl-4-(nonafluoro-2-butyl)phenyl |
| 700 | 2-chloropyridin-5-yl | F | H | H | H | 2,6-dimethyl-4-(nonafluoro-2-butyl)phenyl |
| 701 | 2-methylthiopyridin-3-yl | F | H | H | H | 2,6-dimethyl-4-(nonafluoro-2-butyl)phenyl |
| 702 | pyrazin-2-yl | F | H | H | H | 2,6-dimethyl-4-(nonafluoro-2-butyl)phenyl |
| 703 | furan-2-yl | F | H | H | H | 2,6-dimethyl-4-(nonafluoro-2-butyl)phenyl |
| 704 | furan-3-yl | F | H | H | H | 2,6-dimethyl-4-(nonafluoro-2-butyl)phenyl |
| 705 | 2-tetrahydrofuranyl | F | H | H | H | 2,6-dimethyl-4-(nonafluoro-2-butyl)phenyl |
| 706 | benzofuran-2-yl | F | H | H | H | 2,6-dimethyl-4-(nonafluoro-2-butyl)phenyl |
| 707 | thiophen-2-yl | F | H | H | H | 2,6-dimethyl-4-(nonafluoro-2-butyl)phenyl |
| 708 | phenyl | F | H | H | H | 2,6-dibromo-4-(heptafluoro-n-propylthio)phenyl |
| 709 | 2-methylphenyl | F | H | H | H | 2,6-dibromo-4-(heptafluoro-n-propylthio)phenyl |
| 710 | 4-methylphenyl | F | H | H | H | 2,6-dibromo-4-(heptafluoro-n-propylthio)phenyl |
| 711 | 2-fluorophenyl | F | H | H | H | 2,6-dibromo-4-(heptafluoro-n-propylthio)phenyl |
| 712 | 3-fluorophenyl | F | H | H | H | 2,6-dibromo-4-(heptafluoro-n-propylthio)phenyl |
| 713 | 4-fluorophenyl | F | H | H | H | 2,6-dibromo-4-(heptafluoro-n-propylthio)phenyl |
| 714 | 2-chlorophenyl | F | H | H | H | 2,6-dibromo-4-(heptafluoro-n-propylthio)phenyl |
| 715 | 4-chlorophenyl | F | H | H | H | 2,6-dibromo-4-(heptafluoro-n-propylthio)phenyl |
| 716 | 2-bromophenyl | F | H | H | H | 2,6-dibromo-4-(heptafluoro-n-propylthio)phenyl |
| 717 | 2-iodophenyl | F | H | H | H | 2,6-dibromo-4-(heptafluoro-n-propylthio)phenyl |
| 718 | 3-cyanophenyl | F | H | H | H | 2,6-dibromo-4-(heptafluoro-n-propylthio)phenyl |
| 719 | 4-cyanophenyl | F | H | H | H | 2,6-dibromo-4-(heptafluoro-n-propylthio)phenyl |

TABLE 2-continued

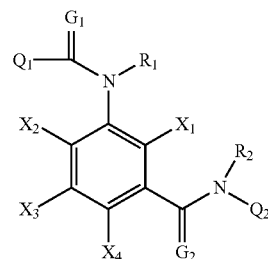

($R_1$, $R_2$ = a hydrogen atom, $G_1$, $G_2$ = an oxygen atom)

| Comp. No. | $Q_1$ | $X_1$ | $X_2$ | $X_3$ | $X_4$ | $Q_2$ |
|---|---|---|---|---|---|---|
| 720 | 2-nitrophenyl | F | H | H | H | 2,6-dibromo-4-(heptafluoro-n-propylthio)phenyl |
| 721 | 3-nitrophenyl | F | H | H | H | 2,6-dibromo-4-(heptafluoro-n-propylthio)phenyl |
| 722 | 4-nitrophenyl | F | H | H | H | 2,6-dibromo-4-(heptafluoro-n-propylthio)phenyl |
| 723 | 2-trifluoromethylphenyl | F | H | H | H | 2,6-dibromo-4-(heptafluoro-n-propylthio)phenyl |
| 724 | 4-trifluoromethylphenyl | F | H | H | H | 2,6-dibromo-4-(heptafluoro-n-propylthio)phenyl |
| 725 | 4-trifluoromethoxy-phenyl | F | H | H | H | 2,6-dibromo-4-(heptafluoro-n-propylthio)phenyl |
| 726 | 2,3-difluorophenyl | F | H | H | H | 2,6-dibromo-4-(heptafluoro-n-propylthio)phenyl |
| 727 | 2,4-difluorophenyl | F | H | H | H | 2,6-dibromo-4-(heptafluoro-n-propylthio)phenyl |
| 728 | 2,5-difluorophenyl | F | H | H | H | 2,6-dibromo-4-(heptafluoro-n-propylthio)phenyl |
| 729 | 2,6-difluorophenyl | F | H | H | H | 2,6-dibromo-4-(heptafluoro-n-propylthio)phenyl |
| 730 | 2,4-dichlorophenyl | F | H | H | H | 2,6-dibromo-4-(heptafluoro-n-propylthio)phenyl |
| 731 | 2,6-dichlorophenyl | F | H | H | H | 2,6-dibromo-4-(heptafluoro-n-propylthio)phenyl |
| 732 | 3,4-dichlorophenyl | F | H | H | H | 2,6-dibromo-4-(heptafluoro-n-propylthio)phenyl |
| 733 | 2-chloro-4-nitrophenyl | F | H | H | H | 2,6-dibromo-4-(heptafluoro-n-propylthio)phenyl |
| 734 | 2-chloro-4-fluorophenyl | F | H | H | H | 2,6-dibromo-4-(heptafluoro-n-propylthio)phenyl |
| 735 | 2-chloro-6-fluorophenyl | F | H | H | H | 2,6-dibromo-4-(heptafluoro-n-propylthio)phenyl |
| 736 | 4-chloro-2-fluorophenyl | F | H | H | H | 2,6-dibromo-4-(heptafluoro-n-propylthio)phenyl |
| 737 | 4-chloro-2-nitrophenyl | F | H | H | H | 2,6-dibromo-4-(heptafluoro-n-propylthio)phenyl |
| 738 | 2,3,6-trifluorophenyl | F | H | H | H | 2,6-dibromo-4-(heptafluoro-n-propylthio)phenyl |
| 739 | pyridin-2-yl | F | H | H | H | 2,6-dibromo-4-(heptafluoro-n-propylthio)phenyl |
| 740 | pyridin-3-yl | F | H | H | H | 2,6-dibromo-4-(heptafluoro-n-propylthio)phenyl |
| 741 | 2-fluoropyridin-3-yl | F | H | H | H | 2,6-dibromo-4-(heptafluoro-n-propylthio)phenyl |
| 742 | 2-chloropyridin-3-yl | F | H | H | H | 2,6-dibromo-4-(heptafluoro-n-propylthio)phenyl |
| 743 | 2-chloropyridin-5-yl | F | H | H | H | 2,6-dibromo-4-(heptafluoro-n-propylthio)phenyl |
| 744 | 2-methylthiopyridin-3-yl | F | H | H | H | 2,6-dibromo-4-(heptafluoro-n-propylthio)phenyl |
| 745 | pyrazin-2-yl | F | H | H | H | 2,6-dibromo-4-(heptafluoro-n-propylthio)phenyl |
| 746 | furan-2-yl | F | H | H | H | 2,6-dibromo-4-(heptafluoro-n-propylthio)phenyl |
| 747 | furan-3-yl | F | H | H | H | 2,6-dibromo-4-(heptafluoro-n-propylthio)phenyl |
| 748 | 2-tetrahydrofuranyl | F | H | H | H | 2,6-dibromo-4-(heptafluoro-n-propylthio)phenyl |
| 749 | benzofuran-2-yl | F | H | H | H | 2,6-dibromo-4-(heptafluoro-n-propylthio)phenyl |
| 750 | thiophen-2-yl | F | H | H | H | 2,6-dibromo-4-(heptafluoro-n-propylthio)phenyl |
| 751 | phenyl | F | H | H | H | 2,6-dibromo-4-(heptafluoro- |

TABLE 2-continued

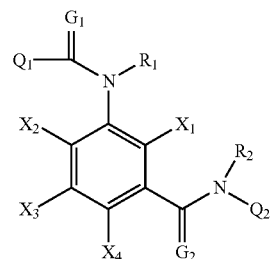

(R₁, R₂ = a hydrogen atom, G₁, G₂ = an oxygen atom)

| Comp. No. | Q₁ | X₁ | X₂ | X₃ | X₄ | Q₂ |
|---|---|---|---|---|---|---|
| 752 | 2-methylphenyl | F | H | H | H | 2,6-dibromo-4-(heptafluoro-n-propylsulfinyl)phenyl |
| 753 | 4-methylphenyl | F | H | H | H | 2,6-dibromo-4-(heptafluoro-n-propylsulfinyl)phenyl |
| 754 | 2-fluorophenyl | F | H | H | H | 2,6-dibromo-4-(heptafluoro-n-propylsulfinyl)phenyl |
| 755 | 3-fluorophenyl | F | H | H | H | 2,6-dibromo-4-(heptafluoro-n-propylsulfinyl)phenyl |
| 756 | 4-fluorophenyl | F | H | H | H | 2,6-dibromo-4-(heptafluoro-n-propylsulfinyl)phenyl |
| 757 | 2-chlorophenyl | F | H | H | H | 2,6-dibromo-4-(heptafluoro-n-propylsulfinyl)phenyl |
| 758 | 4-chlorophenyl | F | H | H | H | 2,6-dibromo-4-(heptafluoro-n-propylsulfinyl)phenyl |
| 759 | 2-bromophenyl | F | H | H | H | 2,6-dibromo-4-(heptafluoro-n-propylsulfinyl)phenyl |
| 760 | 2-iodophenyl | F | H | H | H | 2,6-dibromo-4-(heptafluoro-n-propylsulfinyl)phenyl |
| 761 | 3-cyanophenyl | F | H | H | H | 2,6-dibromo-4-(heptafluoro-n-propylsulfinyl)phenyl |
| 762 | 4-cyanophenyl | F | H | H | H | 2,6-dibromo-4-(heptafluoro-n-propylsulfinyl)phenyl |
| 763 | 2-nitrophenyl | F | H | H | H | 2,6-dibromo-4-(heptafluoro-n-propylsulfinyl)phenyl |
| 764 | 3-nitrophenyl | F | H | H | H | 2,6-dibromo-4-(heptafluoro-n-propylsulfinyl)phenyl |
| 765 | 4-nitrophenyl | F | H | H | H | 2,6-dibromo-4-(heptafluoro-n-propylsulfinyl)phenyl |
| 766 | 2-trifluoromethylphenyl | F | H | H | H | 2,6-dibromo-4-(heptafluoro-n-propylsulfinyl)phenyl |
| 767 | 4-trifluoromethylphenyl | F | H | H | H | 2,6-dibromo-4-(heptafluoro-n-propylsulfinyl)phenyl |
| 768 | 4-trifluoromethoxy-phenyl | F | H | H | H | 2,6-dibromo-4-(heptafluoro-n-propylsulfinyl)phenyl |
| 769 | 2,3-difluorophenyl | F | H | H | H | 2,6-dibromo-4-(heptafluoro-n-propylsulfinyl)phenyl |
| 770 | 2,4-difluorophenyl | F | H | H | H | 2,6-dibromo-4-(heptafluoro-n-propylsulfinyl)phenyl |
| 771 | 2,5-difluorophenyl | F | H | H | H | 2,6-dibromo-4-(heptafluoro-n-propylsulfinyl)phenyl |
| 772 | 2,6-difluorophenyl | F | H | H | H | 2,6-dibromo-4-(heptafluoro-n-propylsulfinyl)phenyl |
| 773 | 2,4-dichlorophenyl | F | H | H | H | 2,6-dibromo-4-(heptafluoro-n-propylsulfinyl)phenyl |
| 774 | 2,6-dichlorophenyl | F | H | H | H | 2,6-dibromo-4-(heptafluoro-n-propylsulfinyl)phenyl |
| 775 | 3,4-dichlorophenyl | F | H | H | H | 2,6-dibromo-4-(heptafluoro-n-propylsulfinyl)phenyl |
| 776 | 2-chloro-4-nitrophenyl | F | H | H | H | 2,6-dibromo-4-(heptafluoro-n-propylsulfinyl)phenyl |
| 777 | 2-chloro-4-fluorophenyl | F | H | H | H | 2,6-dibromo-4-(heptafluoro-n-propylsulfinyl)phenyl |
| 778 | 2-chloro-6-fluorophenyl | F | H | H | H | 2,6-dibromo-4-(heptafluoro-n-propylsulfinyl)phenyl |
| 779 | 4-chloro-2-fluorophenyl | F | H | H | H | 2,6-dibromo-4-(heptafluoro-n-propylsulfinyl)phenyl |
| 780 | 4-chloro-2-nitrophenyl | F | H | H | H | 2,6-dibromo-4-(heptafluoro-n-propylsulfinyl)phenyl |
| 781 | 2,3,6-trifluorophenyl | F | H | H | H | 2,6-dibromo-4-(heptafluoro-n-propylsulfinyl)phenyl |
| 782 | pyridin-2-yl | F | H | H | H | 2,6-dibromo-4-(heptafluoro-n-propylsulfinyl)phenyl |

TABLE 2-continued

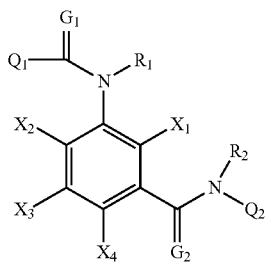

($R_1$, $R_2$ = a hydrogen atom, $G_1$, $G_2$ = an oxygen atom)

| Comp. No. | $Q_1$ | $X_1$ | $X_2$ | $X_3$ | $X_4$ | $Q_2$ |
|---|---|---|---|---|---|---|
| 783 | pyridin-3-yl | F | H | H | H | 2,6-dibromo-4-(heptafluoro-n-propylsulfinyl)phenyl |
| 784 | 2-fluoropyridin-3-yl | F | H | H | H | 2,6-dibromo-4-(heptafluoro-n-propylsulfinyl)phenyl |
| 785 | 2-chloropyridin-3-yl | F | H | H | H | 2,6-dibromo-4-(heptafluoro-n-propylsulfinyl)phenyl |
| 786 | 2-chloropyridin-5-yl | F | H | H | H | 2,6-dibromo-4-(heptafluoro-n-propylsulfinyl)phenyl |
| 787 | 2-methylthiopyridin-3-yl | F | H | H | H | 2,6-dibromo-4-(heptafluoro-n-propylsulfinyl)phenyl |
| 788 | pyrazin-2-yl | F | H | H | H | 2,6-dibromo-4-(heptafluoro-n-propylsulfinyl)phenyl |
| 789 | furan-2-yl | F | H | H | H | 2,6-dibromo-4-(heptafluoro-n-propylsulfinyl)phenyl |
| 790 | thiophen-2-yl | F | H | H | H | 2,6-dibromo-4-(heptafluoro-n-propylsulfinyl)phenyl |
| 791 | phenyl | F | H | H | H | 2,6-dimethyl-4-(heptafluoro-n-propylthio)phenyl |
| 792 | 2-methylphenyl | F | H | H | H | 2,6-dimethyl-4-(heptafluoro-n-propylthio)phenyl |
| 793 | 4-methylphenyl | F | H | H | H | 2,6-dimethyl-4-(heptafluoro-n-propylthio)phenyl |
| 794 | 2-fluorophenyl | F | H | H | H | 2,6-dimethyl-4-(heptafluoro-n-propylthio)phenyl |
| 795 | 3-fluorophenyl | F | H | H | H | 2,6-dimethyl-4-(heptafluoro-n-propylthio)phenyl |
| 796 | 4-fluorophenyl | F | H | H | H | 2,6-dimethyl-4-(heptafluoro-n-propylthio)phenyl |
| 797 | 2-chlorophenyl | F | H | H | H | 2,6-dimethyl-4-(heptafluoro-n-propylthio)phenyl |
| 798 | 4-chlorophenyl | F | H | H | H | 2,6-dimethyl-4-(heptafluoro-n-propylthio)phenyl |
| 799 | 2-bromophenyl | F | H | H | H | 2,6-dimethyl-4-(heptafluoro-n-propylthio)phenyl |
| 800 | 2-iodophenyl | F | H | H | H | 2,6-dimethyl-4-(heptafluoro-n-propylthio)phenyl |
| 801 | 3-cyanophenyl | F | H | H | H | 2,6-dimethyl-4-(heptafluoro-n-propylthio)phenyl |
| 802 | 4-cyanophenyl | F | H | H | H | 2,6-dimethyl-4-(heptafluoro-n-propylthio)phenyl |
| 803 | 2-nitrophenyl | F | H | H | H | 2,6-dimethyl-4-(heptafluoro-n-propylthio)phenyl |
| 804 | 3-nitrophenyl | F | H | H | H | 2,6-dimethyl-4-(heptafluoro-n-propylthio)phenyl |
| 805 | 4-nitrophenyl | F | H | H | H | 2,6-dimethyl-4-(heptafluoro-n-propylthio)phenyl |
| 806 | 2-trifluoromethylphenyl | F | H | H | H | 2,6-dimethyl-4-(heptafluoro-n-propylthio)phenyl |
| 807 | 4-trifluoromethylphenyl | F | H | H | H | 2,6-dimethyl-4-(heptafluoro-n-propylthio)phenyl |
| 808 | 4-trifluoromethoxy-phenyl | F | H | H | H | 2,6-dimethyl-4-(heptafluoro-n-propylthio)phenyl |
| 809 | 2,3-difluorophenyl | F | H | H | H | 2,6-dimethyl-4-(heptafluoro-n-propylthio)phenyl |
| 810 | 2,4-difluorophenyl | F | H | H | H | 2,6-dimethyl-4-(heptafluoro-n-propylthio)phenyl |
| 811 | 2,5-difluorophenyl | F | H | H | H | 2,6-dimethyl-4-(heptafluoro-n-propylthio)phenyl |
| 812 | 2,6-difluorophenyl | F | H | H | H | 2,6-dimethyl-4-(heptafluoro-n-propylthio)phenyl |
| 813 | 2,4-dichlorophenyl | F | H | H | H | 2,6-dimethyl-4-(heptafluoro-n-propylthio)phenyl |

TABLE 2-continued

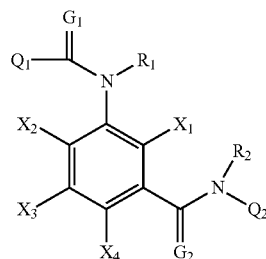

($R_1$, $R_2$ = a hydrogen atom, $G_1$, $G_2$ = an oxygen atom)

| Comp. No. | $Q_1$ | $X_1$ | $X_2$ | $X_3$ | $X_4$ | $Q_2$ |
|---|---|---|---|---|---|---|
| 814 | 2,6-dichlorophenyl | F | H | H | H | 2,6-dimethyl-4-(heptafluoro-n-propylthio)phenyl |
| 815 | 3,4-dichlorophenyl | F | H | H | H | 2,6-dimethyl-4-(heptafluoro-n-propylthio)phenyl |
| 816 | 2-chloro-4-nitrophenyl | F | H | H | H | 2,6-dimethyl-4-(heptafluoro-n-propylthio)phenyl |
| 817 | 2-chloro-4-fluorophenyl | F | H | H | H | 2,6-dimethyl-4-(heptafluoro-n-propylthio)phenyl |
| 818 | 2-chloro-6-fluorophenyl | F | H | H | H | 2,6-dimethyl-4-(heptafluoro-n-propylthio)phenyl |
| 819 | 4-chloro-2-fluorophenyl | F | H | H | H | 2,6-dimethyl-4-(heptafluoro-n-propylthio)phenyl |
| 820 | 4-chloro-2-nitrophenyl | F | H | H | H | 2,6-dimethyl-4-(heptafluoro-n-propylthio)phenyl |
| 821 | 2,3,6-trifluorophenyl | F | H | H | H | 2,6-dimethyl-4-(heptafluoro-n-propylthio)phenyl |
| 822 | pyridin-2-yl | F | H | H | H | 2,6-dimethyl-4-(heptafluoro-n-propylthio)phenyl |
| 823 | pyridin-3-yl | F | H | H | H | 2,6-dimethyl-4-(heptafluoro-n-propylthio)phenyl |
| 824 | 2-fluoropyridin-3-yl | F | H | H | H | 2,6-dimethyl-4-(heptafluoro-n-propylthio)phenyl |
| 825 | 2-chloropyridin-3-yl | F | H | H | H | 2,6-dimethyl-4-(heptafluoro-n-propylthio)phenyl |
| 826 | 2-chloropyridin-5-yl | F | H | H | H | 2,6-dimethyl-4-(heptafluoro-n-propylthio)phenyl |
| 827 | 2-methylthiopyridin-3-yl | F | H | H | H | 2,6-dimethyl-4-(heptafluoro-n-propylthio)phenyl |
| 828 | pyrazin-2-yl | F | H | H | H | 2,6-dimethyl-4-(heptafluoro-n-propylthio)phenyl |
| 829 | furan-2-yl | F | H | H | H | 2,6-dimethyl-4-(heptafluoro-n-propylthio)phenyl |
| 830 | thiophen-2-yl | F | H | H | H | 2,6-dimethyl-4-(heptafluoro-n-propylthio)phenyl |
| 831 | phenyl | Cl | H | H | H | 2,6-dibromo-4-(heptafluoro-n-propylthio)phenyl |
| 832 | 2-fluorophenyl | Cl | H | H | H | 2,6-dibromo-4-(heptafluoro-n-propylthio)phenyl |
| 833 | 2-chloropyridin-3-yl | Cl | H | H | H | 2,6-dibromo-4-(heptafluoro-n-propylthio)phenyl |

TABLE 3

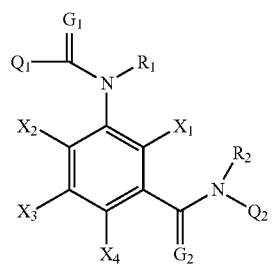

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1001 | phenyl | Me | H | H | H | 2,6-dimethyl-4-(heptafluoroisopropyl)phenyl |

TABLE 3-continued

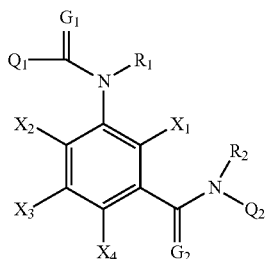

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1002 | 2-methylphenyl | Me | H | H | H | 2,6-dimethyl-4-(heptafluoroisopropyl)phenyl |
| 1003 | 4-methylphenyl | Me | H | H | H | 2,6-dimethyl-4-(heptafluoroisopropyl)phenyl |
| 1004 | 2-fluorophenyl | Me | H | H | H | 2,6-dimethyl-4-(heptafluoroisopropyl)phenyl |
| 1005 | 3-fluorophenyl | Me | H | H | H | 2,6-dimethyl-4-(heptafluoroisopropyl)phenyl |
| 1006 | 4-fluorophenyl | Me | H | H | H | 2,6-dimethyl-4-(heptafluoroisopropyl)phenyl |
| 1007 | 2-chlorophenyl | Me | H | H | H | 2,6-dimethyl-4-(heptafluoroisopropyl)phenyl |
| 1008 | 4-chlorophenyl | Me | H | H | H | 2,6-dimethyl-4-(heptafluoroisopropyl)phenyl |
| 1009 | 2-bromophenyl | Me | H | H | H | 2,6-dimethyl-4-(heptafluoroisopropyl)phenyl |
| 1010 | 2-iodophenyl | Me | H | H | H | 2,6-dimethyl-4-(heptafluoroisopropyl)phenyl |
| 1011 | 3-cyanophenyl | Me | H | H | H | 2,6-dimethyl-4-(heptafluoroisopropyl)phenyl |
| 1012 | 4-cyanophenyl | Me | H | H | H | 2,6-dimethyl-4-(heptafluoroisopropyl)phenyl |
| 1013 | 2-nitrophenyl | Me | H | H | H | 2,6-dimethyl-4-(heptafluoroisopropyl)phenyl |
| 1014 | 3-nitrophenyl | Me | H | H | H | 2,6-dimethyl-4-(heptafluoroisopropyl)phenyl |
| 1015 | 4-nitrophenyl | Me | H | H | H | 2,6-dimethyl-4-(heptafluoroisopropyl)phenyl |
| 1016 | 2-trifluoromethyl phenyl | Me | H | H | H | 2,6-dimethyl-4-(heptafluoroisopropyl)phenyl |
| 1017 | 4-trifluoromethyl phenyl | Me | H | H | H | 2,6-dimethyl-4-(heptafluoroisopropyl)phenyl |
| 1018 | 4-trifluoromethoxy phenyl | Me | H | H | H | 2,6-dimethyl-4-(heptafluoroisopropyl)phenyl |
| 1019 | 2,3-difluorophenyl | Me | H | H | H | 2,6-dimethyl-4-(heptafluoroisopropyl)phenyl |
| 1020 | 2,4-difluorophenyl | Me | H | H | H | 2,6-dimethyl-4-(heptafluoroisopropyl)phenyl |
| 1021 | 2,5-difluorophenyl | Me | H | H | H | 2,6-dimethyl-4-(heptafluoroisopropyl)phenyl |
| 1022 | 2,6-difluorophenyl | He | H | H | H | 2,6-dimethyl-4-(heptafluoroisopropyl)phenyl |
| 1023 | 2,4-dichlorophenyl | Me | H | H | H | 2,6-dimethyl-4-(heptafluoro isopropyl)phenyl |
| 1024 | 2,6-dichlorophenyl | Me | H | H | H | 2,6-dimethyl-4-(heptafluoro isopropyl)phenyl |
| 1025 | 3,4-dichlorophenyl | Me | H | H | H | 2,6-dimethyl-4-(heptafluoro isopropyl)phenyl |
| 1026 | 2-chloro-4-nitrophenyl | Me | H | H | H | 2,6-dimethyl-4-(heptafluoro isopropyl)phenyl |
| 1027 | 2-chloro-4-fluorophenyl | Me | H | H | H | 2,6-dimethyl-4-(heptafluoro isopropyl)phenyl |
| 1028 | 2-chloro-6-fluorophenyl | Me | H | H | H | 2,6-dimethyl-4-(heptafluoro isopropyl)phenyl |
| 1029 | 4-chloro-2-fluorophenyl | Me | H | H | H | 2,6-dimethyl-4-(heptafluoro isopropyl)phenyl |
| 1030 | 4-chloro-2-nitrophenyl | Me | H | H | H | 2,6-dimethyl-4-(heptafluoro isopropyl)phenyl |
| 1031 | 2,3,6-trifluorophenyl | Me | H | H | H | 2,6-dimethyl-4-(heptafluoro isopropyl)phenyl |
| 1032 | 3-(acetylamino)phenyl | Me | H | H | H | 2,6-dimethyl-4-(heptafluoro isopropyl)phenyl |

TABLE 3-continued

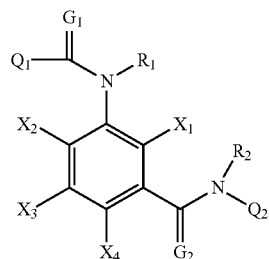

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1033 | pyridin-2-yl | Me | H | H | H | 2,6-dimethyl-4-(heptafluoroisopropyl)phenyl |
| 1034 | pyridin-3-yl | Me | H | H | H | 2,6-dimethyl-4-(heptafluoroisopropyl)phenyl |
| 1035 | 2-fluoropyridin-3-yl | Me | H | H | H | 2,6-dimethyl-4-(heptafluoroisopropyl)phenyl |
| 1036 | 2-chloropyridin-3-yl | Me | H | H | H | 2,6-dimethyl-4-(heptafluoroisopropyl)phenyl |
| 1037 | 2-chloropyridin-5-yl | Me | H | H | H | 2,6-dimethyl-4-(heptafluoroisopropyl)phenyl |
| 1038 | 2-trifluoromethylpyridin-3-yl | Me | H | H | H | 2,6-dimethyl-4-(heptafluoroisopropyl)phenyl |
| 1039 | 2-methylthiopyridin-3-yl | Me | H | H | H | 2,6-dimethyl-4-(heptafluoroisopropyl)phenyl |
| 1040 | pyrazin-2-yl | Me | H | H | H | 2,6-dimethyl-4-(heptafluoroisopropyl)phenyl |
| 1041 | furan-2-yl | Me | H | H | H | 2,6-dimethyl-4-(heptafluoroisopropyl)phenyl |
| 1042 | furan-3-yl | Me | H | H | H | 2,6-dimethyl-4-(heptafluoroisopropyl)phenyl |
| 1043 | 2-tetrahydrofuranyl | Me | H | H | H | 2,6-dimethyl-4-(heptafluoroisopropyl)phenyl |
| 1044 | benzofuran-2-yl | Me | H | H | H | 2,6-dimethyl-4-(heptafluoroisopropyl)phenyl |
| 1045 | thiophen-2-yl | Me | H | H | H | 2,6-dimethyl-4-(heptafluoroisopropyl)phenyl |
| 1046 | phenyl | Me | H | H | H | 2-bromo-4-(heptafluoroisopropyl)-6-(methylsulfonyl)phenyl |
| 1047 | 2-methylphenyl | Me | H | H | H | 2-bromo-4-(heptafluoroisopropyl)-6-(methylsulfonyl)phenyl |
| 1048 | 4-methylphenyl | Me | H | H | H | 2-bromo-4-(heptafluoroisopropyl)-6-(methylsulfonyl)phenyl |
| 1049 | 2-fluorophenyl | Me | H | H | H | 2-bromo-4-(heptafluoroisopropyl)-6-(methylsulfonyl)phenyl |
| 1050 | 3-fluorophenyl | Me | H | H | H | 2-bromo-4-(heptafluoroisopropyl)-6-(methylsulfonyl)phenyl |
| 1051 | 4-fluorophenyl | Me | H | H | H | 2-bromo-4-(heptafluoroisopropyl)-6-(methylsulfonyl)phenyl |
| 1052 | 2-chlorophenyl | Me | H | H | H | 2-bromo-4-(heptafluoroisopropyl)-6-(methylsulfonyl)phenyl |
| 1053 | 4-chlorophenyl | Me | H | H | H | 2-bromo-4-(heptafluoroisopropyl)-6-(methylsulfonyl)phenyl |
| 1054 | 2-bromophenyl | Me | H | H | H | 2-bromo-4-(heptafluoroisopropyl)-6-(methylsulfonyl)phenyl |
| 1055 | 2-iodophenyl | Me | H | H | H | 2-bromo-4-(heptafluoroisopropyl)-6-(methylsulfonyl)phenyl |
| 1056 | 3-cyanophenyl | Me | H | H | H | 2-bromo-4-(heptafluoroisopropyl)-6-(methylsulfonyl)phenyl |
| 1057 | 4-cyanophenyl | Me | H | H | H | 2-bromo-4-(heptafluoroisopropyl)-6-(methylsulfonyl)phenyl |
| 1058 | 2-nitrophenyl | Me | H | H | H | 2-bromo-4-(heptafluoroisopropyl)-6-(methylsulfonyl)phenyl |
| 1059 | 3-nitrophenyl | Me | H | H | H | 2-bromo-4-(heptafluoroisopropyl)-6-(methylsulfonyl)phenyl |
| 1060 | 4-nitrophenyl | Me | H | H | H | 2-bromo-4-(heptafluoroisopropyl)-6-(methylsulfonyl)phenyl |
| 1061 | 2-trifluoromethylphenyl | Me | H | H | H | 2-bromo-4-(heptafluoroisopropyl)-6-(methylsulfonyl)phenyl |
| 1062 | 4-trifluoromethylphenyl | Me | H | H | H | 2-bromo-4-(heptafluoroisopropyl)-6-(methylsulfonyl)phenyl |
| 1063 | 4-trifluoromethoxyphenyl | Me | H | H | H | 2-bromo-4-(heptafluoroisopropyl)-6-(methylsulfonyl)phenyl |

TABLE 3-continued

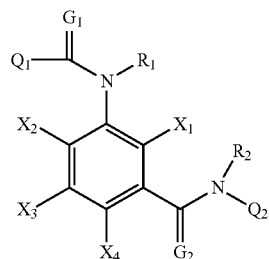

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1064 | 2,3-difluorophenyl | Me | H | H | H | 2-bromo-4-(heptafluoroisopropyl)-6-(methylsulfonyl)phenyl |
| 1065 | 2,4-difluorophenyl | Me | H | H | H | 2-bromo-4-(heptafluoroisopropyl)-6-(methylsulfonyl)phenyl |
| 1066 | 2,5-difluorophenyl | Me | H | H | H | 2-bromo-4-(heptafluoroisopropyl)-6-(methylsulfonyl)phenyl |
| 1067 | 2,6-difluorophenyl | Me | H | H | H | 2-bromo-4-(heptafluoroisopropyl)-6-(methylsulfonyl)phenyl |
| 1068 | 2,4-dichlorophenyl | Me | H | H | H | 2-bromo-4-(heptafluoroisopropyl)-6-(methylsulfonyl)phenyl |
| 1069 | 2,6-dichlorophenyl | Me | H | H | H | 2-bromo-4-(heptafluoroisopropyl)-6-(methylsulfonyl)phenyl |
| 1070 | 3,4-dichlorophenyl | Me | H | H | H | 2-bromo-4-(heptafluoroisopropyl)-6-(methylsulfonyl)phenyl |
| 1071 | 2-chloro-4-nitrophenyl | Me | H | H | H | 2-bromo-4-(heptafluoroisopropyl)-6-(methylsulfonyl)phenyl |
| 1072 | 2-chloro-4-fluorophenyl | Me | H | H | H | 2-bromo-4-(heptafluoroisopropyl)-6-(methylsulfonyl)phenyl |
| 1073 | 2-chloro-6-fluorophenyl | Me | H | H | H | 2-bromo-4-(heptafluoroisopropyl)-6-(methylsulfonyl)phenyl |
| 1074 | 4-chloro-2-fluorophenyl | Me | H | H | H | 2-bromo-4-(heptafluoroisopropyl)-6-(methylsulfonyl)phenyl |
| 1075 | 4-chloro-2-nitrophenyl | Me | H | H | H | 2-bromo-4-(heptafluoroisopropyl)-6-(methylsulfonyl)phenyl |
| 1076 | 2,3,6-trifluorophenyl | Me | H | H | H | 2-bromo-4-(heptafluoroisopropyl)-6-(methylsulfonyl)phenyl |
| 1077 | pyridin-2-yl | Me | H | H | H | 2-bromo-4-(heptafluoroisopropyl)-6-(methylsulfonyl)phenyl |
| 1078 | pyridin-3-yl | Me | H | H | H | 2-bromo-4-(heptafluoroisopropyl)-6-(methylsulfonyl)phenyl |
| 1079 | 2-fluoropyridin-3-yl | Me | H | H | H | 2-bromo-4-(heptafluoroisopropyl)-6-(methylsulfonyl)phenyl |
| 1080 | 2-chloropyridin-3-yl | Me | H | H | H | 2-bromo-4-(heptafluoroisopropyl)-6-(methylsulfonyl)phenyl |
| 1081 | 2-chloropyridin-5-yl | Me | H | H | H | 2-bromo-4-(heptafluoroisopropyl)-6-(methylsulfonyl)phenyl |
| 1082 | 2-methylthiopyridin-3-yl | Me | H | H | H | 2-bromo-4-(heptafluoroisopropyl)-6-(methylsulfonyl)phenyl |
| 1083 | pyrazin-2-yl | Me | H | H | H | 2-bromo-4-(heptafluoroisopropyl)-6-(methylsulfonyl)phenyl |
| 1084 | furan-2-yl | Me | H | H | H | 2-bromo-4-(heptafluoroisopropyl)-6-(methylsulfonyl)phenyl |
| 1085 | thiophen-2-yl | Me | H | H | H | 2-bromo-4-(heptafluoroisopropyl)-6-(methylsulfonyl)phenyl |
| 1086 | phenyl | Me | H | H | H | 2-n-propyl-6-iodo-4-(heptafluoroisopropyl)phenyl |
| 1087 | 2-methylphenyl | Me | H | H | H | 2-n-propyl-6-iodo-4-(heptafluoroisopropyl)phenyl |
| 1088 | 4-methylphenyl | Me | H | H | H | 2-n-propyl-6-iodo-4-(heptafluoroisopropyl)phenyl |
| 1089 | 2-fluorophenyl | Me | H | H | H | 2-n-propyl-6-iodo-4-(heptafluoroisopropyl)phenyl |
| 1090 | 3-fluorophenyl | Me | H | H | | 2-n-propyl-6-iodo-4-(heptafluoroisopropyl)phenyl |
| 1091 | 4-fluorophenyl | Me | H | H | H | 2-n-propyl-6-iodo-4-(heptafluoroisopropyl)phenyl |
| 1092 | 2-chlorophenyl | Me | H | H | H | 2-n-propyl-6-iodo-4-(heptafluoroisopropyl)phenyl |
| 1093 | 4-chlorophenyl | Me | H | H | H | 2-n-propyl-6-iodo-4-(heptafluoroisopropyl)phenyl |
| 1094 | 2-bromophenyl | Me | H | H | H | 2-n-propyl-6-iodo-4-(heptafluoroisopropyl)phenyl |

TABLE 3-continued

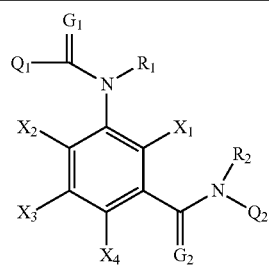

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1095 | 2-iodophenyl | Me | H | H | H | 2-n-propyl-6-iodo-4-(heptafluoroisopropyl)phenyl |
| 1096 | 3-cyanophenyl | Me | H | H | H | 2-n-propyl-6-iodo-4-(heptafluoroisopropyl)phenyl |
| 1097 | 4-cyanophenyl | Me | H | H | H | 2-n-propyl-6-iodo-4-(heptafluoroisopropyl)phenyl |
| 1098 | 2-nitrophenyl | Me | H | H | H | 2-n-propyl-6-iodo-4-(heptafluoroisopropyl)phenyl |
| 1099 | 3-nitrophenyl | Me | H | H | H | 2-n-propyl-6-iodo-4-(heptafluoroisopropyl)phenyl |
| 1100 | 4-nitrophenyl | Me | H | H | H | 2-n-propyl-6-iodo-4-(heptafluoroisopropyl)phenyl |
| 1101 | 2-trifluoromethylphenyl | Me | H | H | H | 2-n-propyl-6-iodo-4-(heptafluoroisopropyl)phenyl |
| 1102 | 4-trifluoromethylphenyl | Me | H | H | H | 2-n-propyl-6-iodo-4-(heptafluoroisopropyl)phenyl |
| 1103 | 4-trifluoromethoxyphenyl | Me | H | H | H | 2-n-propyl-6-iodo-4-(heptafluoroisopropyl)phenyl |
| 1104 | 2,3-difluorophenyl | Me | H | H | H | 2-n-propyl-6-iodo-4-(heptafluoroisopropyl)phenyl |
| 1105 | 2,4-difluorophenyl | Me | H | H | H | 2-n-propyl-6-iodo-4-(heptafluoroisopropyl)phenyl |
| 1106 | 2,5-difluorophenyl | Me | H | H | H | 2-n-propyl-6-iodo-4-(heptafluoroisopropyl)phenyl |
| 1107 | 2,6-difluorophenyl | Me | H | H | H | 2-n-propyl-6-iodo-4-(heptafluoroisopropyl)phenyl |
| 1108 | 2,4-dichlorophenyl | Me | H | H | H | 2-n-propyl-6-iodo-4-(heptafluoroisopropyl)phenyl |
| 1109 | 2,6-dichlorophenyl | Me | H | H | H | 2-n-propyl-6-iodo-4-(heptafluoroisopropyl)phenyl |
| 1110 | 3,4-dichlorophenyl | Me | H | H | H | 2-n-propyl-6-iodo-4-(heptafluoroisopropyl)phenyl |
| 1111 | 2-chloro-4-nitrophenyl | Me | H | H | H | 2-n-propyl-6-iodo-4-(heptafluoroisopropyl)phenyl |
| 1112 | 2-chloro-4-fluorophenyl | Me | H | H | H | 2-n-propyl-6-iodo-4-(heptafluoroisopropyl)phenyl |
| 1113 | 2-chloro-6-fluorophenyl | Me | H | H | H | 2-n-propyl-6-iodo-4-(heptafluoroisopropyl)phenyl |
| 1114 | 4-chloro-2-fluorophenyl | Me | H | H | H | 2-n-propyl-6-iodo-4-(heptafluoroisopropyl)phenyl |
| 1115 | 4-chloro-2-nitrophenyl | Me | H | H | H | 2-n-propyl-6-iodo-4-(heptafluoroisopropyl)phenyl |
| 1116 | 2,3,6-trifluorophenyl | Me | H | H | H | 2-n-propyl-6-iodo-4-(heptafluoroisopropyl)phenyl |
| 1117 | pyridin-2-yl | Me | H | H | H | 2-n-propyl-6-iodo-4-(heptafluoroisopropyl)phenyl |
| 1118 | pyridin-3-yl | Me | H | H | H | 2-n-propyl-6-iodo-4-(heptafluoroisopropyl)phenyl |
| 1119 | 2-fluoropyridin-3-yl | Me | H | H | H | 2-n-propyl-6-iodo-4-(heptafluoroisopropyl)phenyl |
| 1120 | 2-chloropyridin-3-yl | Me | H | H | H | 2-n-propyl-6-iodo-4-(heptafluoroisopropyl)phenyl |
| 1121 | 2-chloropyridin-5-yl | Me | H | H | H | 2-n-propyl-6-iodo-4-(heptafluoroisopropyl)phenyl |
| 1122 | 2-methylthiopyridin-3-yl | Me | H | H | H | 2-n-propyl-6-iodo-4-(heptafluoroisopropyl)phenyl |
| 1123 | pyrazin-2-yl | Me | H | H | H | 2-n-propyl-6-iodo-4-(heptafluoroisopropyl)phenyl |
| 1124 | furan-2-yl | Me | H | H | H | 2-n-propyl-6-iodo-4-(heptafluoroisopropyl)phenyl |
| 1125 | 2-fluorophenyl | Me | H | H | H | 2,6-dimethyl-4-(heptafluoro-n-propylthio)phenyl |

TABLE 3-continued

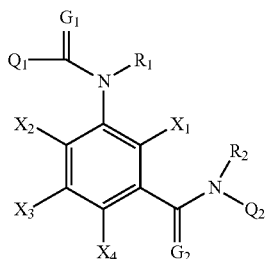

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1126 | phenyl | Me | H | H | H | 2,6-dibromo-4-(heptafluoro-n-propylthio)phenyl |
| 1127 | 2-methylphenyl | Me | H | H | H | 2,6-dibromo-4-(heptafluoro-n-propylthio)phenyl |
| 1128 | 4-methylphenyl | Me | H | H | H | 2,6-dibromo-4-(heptafluoro-n-propylthio)phenyl |
| 1129 | 2-fluorophenyl | Me | H | H | H | 2,6-dibromo-4-(heptafluoro-n-propylthio)phenyl |
| 1130 | 3-fluorophenyl | Me | H | H | H | 2,6-dibromo-4-(heptafluoro-n-propylthio)phenyl |
| 1131 | 4-fluorophenyl | Me | H | H | H | 2,6-dibromo-4-(heptafluoro-n-propylthio)phenyl |
| 1132 | 2-chlorophenyl | Me | H | H | H | 2,6-dibromo-4-(heptafluoro-n-propylthio)phenyl |
| 1133 | 4-chlorophenyl | Me | H | H | H | 2,6-dibromo-4-(heptafluoro-n-propylthio)phenyl |
| 1134 | 2-bromophenyl | Me | H | H | H | 2,6-dibromo-4-(heptafluoro-n-propylthio)phenyl |
| 1135 | 2-iodophenyl | Me | H | H | H | 2,6-dibromo-4-(heptafluoro-n-propylthio)phenyl |
| 1136 | 3-cyanophenyl | Me | H | H | H | 2,6-dibromo-4-(heptafluoro-n-propylthio)phenyl |
| 1137 | 4-cyanophenyl | Me | H | H | H | 2,6-dibromo-4-(heptafluoro-n-propylthio)phenyl |
| 1138 | 2-nitrophenyl | Me | H | H | H | 2,6-dibromo-4-(heptafluoro-n-propylthio)phenyl |
| 1139 | 3-nitrophenyl | Me | H | H | H | 2,6-dibromo-4-(heptafluoro-n-propylthio)phenyl |
| 1140 | 4-nitrophenyl | Me | H | H | H | 2,6-dibromo-4-(heptafluoro-n-propylthio)phenyl |
| 1141 | 2-trifluoromethylphenyl | Me | H | H | H | 2,6-dibromo-4-(heptafluoro-n-propylthio)phenyl |
| 1142 | 4-trifluoromethylphenyl | Me | H | H | H | 2,6-dibromo-4-(heptafluoro-n-propylthio)phenyl |
| 1143 | 4-trifluoromethoxyphenyl | Me | H | H | H | 2,6-dibromo-4-(heptafluoro-n-propylthio)phenyl |
| 1144 | 2,3-difluorophenyl | Me | H | H | H | 2,6-dibromo-4-(heptafluoro-n-propylthio)phenyl |
| 1145 | 2,4-difluorophenyl | Me | H | H | H | 2,6-dibromo-4-(heptafluoro-n-propylthio)phenyl |
| 1146 | 2,5-difluorophenyl | Me | H | H | H | 2,6-dibromo-4-(heptafluoro-n-propylthio)phenyl |
| 1147 | 2,6-difluorophenyl | Me | H | H | H | 2,6-dibromo-4-(heptafluoro-n-propylthio)phenyl |
| 1148 | 2,4-dichlorophenyl | Me | H | H | H | 2,6-dibromo-4-(heptafluoro-n-propylthio)phenyl |
| 1149 | 2,6-dichlorophenyl | Me | H | H | H | 2,6-dibromo-4-(heptafluoro-n-propylthio)phenyl |
| 1150 | 3,4-dichlorophenyl | Me | H | H | H | 2,6-dibromo-4-(heptafluoro-n-propylthio)phenyl |
| 1151 | 2-chloro-4-nitrophenyl | Me | H | H | H | 2,6-dibromo-4-(heptafluoro-n-propylthio)phenyl |
| 1152 | 2-chloro-4-fluorophenyl | Me | H | H | H | 2,6-dibromo-4-(heptafluoro-n-propylthio)phenyl |
| 1153 | 2-chloro-6-fluorophenyl | Me | H | H | H | 2,6-dibromo-4-(heptafluoro-n-propylthio)phenyl |
| 1154 | 4-chloro-2-fluorophenyl | Me | H | H | H | 2,6-dibromo-4-(heptafluoro-n-propylthio)phenyl |
| 1155 | 4-chloro-2-nitrophenyl | Me | H | H | H | 2,6-dibromo-4-(heptafluoro-n-propylthio)phenyl |
| 1156 | 2,3,6-trifluorophenyl | Me | H | H | H | 2,6-dibromo-4-(heptafluoro-n-propylthio)phenyl |

TABLE 3-continued

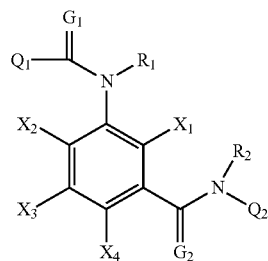

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1157 | pyridin-2-yl | Me | H | H | H | 2,6-dibromo-4-(heptafluoro-n-propylthio)phenyl |
| 1158 | pyridin-3-yl | Me | H | H | H | 2,6-dibromo-4-(heptafluoro-n-propylthio)phenyl |
| 1159 | 2-fluoropyridin-3-yl | Me | H | H | H | 2,6-dibromo-4-(heptafluoro-n-propylthio)phenyl |
| 1160 | 2-chloropyridin-3-yl | Me | H | H | H | 2,6-dibromo-4-(heptafluoro-n-propylthio)phenyl |
| 1161 | 2-chloropyridin-5-yl | Me | H | H | H | 2,6-dibromo-4-(heptafluoro-n-propylthio)phenyl |
| 1162 | 2-methylthiopyridin-3-yl | Me | H | H | H | 2,6-dibromo-4-(heptafluoro-n-propylthio)phenyl |
| 1163 | pyrazin-2-yl | Me | H | H | H | 2,6-dibromo-4-(heptafluoro-n-propylthio)phenyl |
| 1164 | furan-2-yl | Me | H | H | H | 2,6-dibromo-4-(heptafluoro-n-propylthio)phenyl |
| 1165 | thiophen-2-yl | Me | H | H | H | 2,6-dibromo-4-(heptafluoro-n-propylthio)phenyl |
| 1166 | phenyl | Me | H | H | H | 2,6-dibromo-4-(heptafluoro-n-propylsulfinyl)phenyl |
| 1167 | 2-methylphenyl | Me | H | H | H | 2,6-dibromo-4-(heptafluoro-n-propylsulfinyl)phenyl |
| 1168 | 4-methylphenyl | Me | H | H | H | 2,6-dibromo-4-(heptafluoro-n-propylsulfinyl)phenyl |
| 1169 | 2-fluorophenyl | Me | H | H | H | 2,6-dibromo-4-(heptafluoro-n-propylsulfinyl)phenyl |
| 1170 | 3-fluorophenyl | Me | H | H | H | 2,6-dibromo-4-(heptafluoro-n-propylsulfinyl)phenyl |
| 1171 | 4-fluorophenyl | Me | H | H | H | 2,6-dibromo-4-(heptafluoro-n-propylsulfinyl)phenyl |
| 1172 | 2-chlorophenyl | Me | H | H | H | 2,6-dibromo-4-(heptafluoro-n-propylsulfinyl)phenyl |
| 1173 | 4-chlorophenyl | Me | H | H | H | 2,6-dibromo-4-(heptafluoro-n-propylsulfinyl)phenyl |
| 1174 | 2-bromophenyl | Me | H | H | H | 2,6-dibromo-4-(heptafluoro-n-propylsulfinyl)phenyl |
| 1175 | 2-iodophenyl | Me | H | H | H | 2,6-dibromo-4-(heptafluoro-n-propylsulfinyl)phenyl |
| 1176 | 3-cyanophenyl | Me | H | H | H | 2,6-dibromo-4-(heptafluoro-n-propylsulfinyl)phenyl |
| 1177 | 4-cyanophenyl | Me | H | H | H | 2,6-dibromo-4-(heptafluoro-n-propylsulfinyl)phenyl |
| 1178 | 2-nitrophenyl | Me | H | H | H | 2,6-dibromo-4-(heptafluoro-n-propylsulfinyl)phenyl |
| 1179 | 3-nitrophenyl | Me | H | H | H | 2,6-dibromo-4-(heptafluoro-n-propylsulfinyl)phenyl |
| 1180 | 4-nitrophenyl | Me | H | H | H | 2,6-dibromo-4-(heptafluoro-n-propylsulfinyl)phenyl |
| 1181 | 2-trifluoromethylphenyl | Me | H | H | H | 2,6-dibromo-4-(heptafluoro-n-propylsulfinyl)phenyl |
| 1182 | 4-trifluoromethylphenyl | Me | H | H | H | 2,6-dibromo-4-(heptafluoro-n-propylsulfinyl)phenyl |
| 1183 | 4-trilfuoromethoxyphenyl | Me | H | H | H | 2,6-dibromo-4-(heptafluoro-n-propylsulfinyl)phenyl |
| 1184 | 2,3-difluorophenyl | Me | H | H | H | 2,6-dibromo-4-(heptafluoro-n-propylsulfinyl)phenyl |
| 1185 | 2,4-difluorophenyl | Me | H | H | H | 2,6-dibromo-4-(heptafluoro-n-propylsulfinyl)phenyl |
| 1186 | 2,5-difluorophenyl | Me | H | H | H | 2,6-dibromo-4-(heptafluoro-n-propylsulfinyl)phenyl |
| 1187 | 2,6-difluorophenyl | Me | H | H | H | 2,6-dibromo-4-(heptafluoro-n-propylsulfinyl)phenyl |

TABLE 3-continued

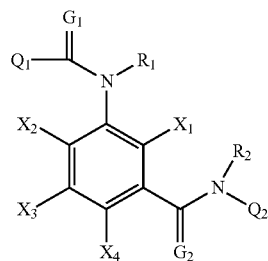

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1188 | 2,4-dichlorophenyl | Me | H | H | H | 2,6-dibromo-4-(heptafluoro-n-propylsulfinyl)phenyl |
| 1189 | 2,6-dichlorophenyl | Me | H | H | H | 2,6-dibromo-4-(heptafluoro-n-propylsulfinyl)phenyl |
| 1190 | 3,4-dichlorophenyl | Me | H | H | H | 2,6-dibromo-4-(heptafluoro-n-propylsulfinyl)phenyl |
| 1191 | 2-chloro-4-nitrophenyl | Me | H | H | H | 2,6-dibromo-4-(heptafluoro-n-propylsulfinyl)phenyl |
| 1192 | 2-chloro-4-fluorophenyl | Me | H | H | H | 2,6-dibromo-4-(heptafluoro-n-propylsulfinyl)phenyl |
| 1193 | 2-chloro-6-fluorophenyl | Me | H | H | H | 2,6-dibromo-4-(heptafluoro-n-propylsulfinyl)phenyl |
| 1194 | 4-chloro-2-fluorophenyl | Me | H | H | H | 2,6-dibromo-4-(heptafluoro-n-propylsulfinyl)phenyl |
| 1195 | 4-chloro-2-nitrophenyl | Me | H | H | H | 2,6-dibromo-4-(heptafluoro-n-propylsulfinyl)phenyl |
| 1196 | 2,3,6-trifluorophenyl | Me | H | H | H | 2,6-dibromo-4-(heptafluoro-n-propylsulfinyl)phenyl |
| 1197 | pyridin-2-yl | Me | H | H | H | 2,6-dibromo-4-(heptafluoro-n-propylsulfinyl)phenyl |
| 1198 | pyridin-3-yl | Me | H | H | H | 2,6-dibromo-4-(heptafluoro-n-propylsulfinyl)phenyl |
| 1199 | 2-fluoropyridin-3-yl | Me | H | H | H | 2,6-dibromo-4-(heptafluoro-n-propylsulfinyl)phenyl |
| 1200 | 2-chloropyridin-3-yl | Me | H | H | H | 2,6-dibromo-4-(heptafluoro-n-propylsulfinyl)phenyl |
| 1201 | 2-chloropyridin-5-yl | Me | H | H | H | 2,6-dibromo-4-(heptafluoro-n-propylsulfinyl)phenyl |
| 1202 | 2-methylthiopyridin-3-yl | Me | H | H | H | 2,6-dibromo-4-(heptafluoro-n-propylsulfinyl)phenyl |
| 1203 | pyrazin-2-yl | Me | H | H | H | 2,6-dibromo-4-(heptafluoro-n-propylsulfinyl)phenyl |
| 1204 | furan-2-yl | Me | H | H | H | 2,6-dibromo-4-(heptafluoro-n-propylsulfinyl)phenyl |
| 1205 | thiophen-2-yl | Me | H | H | H | 2,6-dibromo-4-(heptafluoro-n-propylsulfinyl)phenyl |
| 1206 | 2-fluorophenyl | Et | H | H | H | 2,6-dimethyl-4-(heptafluoroisopropyl)phenyl |
| 1207 | pyridin-3-yl | Et | H | H | H | 2,6-dimethyl-4-(heptafluoroisopropyl)phenyl |
| 1208 | phenyl | Me | H | F | H | 2,6-dimethyl-4-(heptafluoroisopropyl)phenyl |
| 1209 | 2-methylphenyl | Me | H | F | H | 2,6-dimethyl-4-(heptafluoroisopropyl)phenyl |
| 1210 | 3-methylphenyl | Me | H | F | H | 2,6-dimethyl-4-(heptafluoroisopropyl)phenyl |
| 1211 | 4-methylphenyl | Me | H | F | H | 2,6-dimethyl-4-(heptafluoroisopropyl)phenyl |
| 1212 | 2-nitrophenyl | Me | H | F | H | 2,6-dimethyl-4-(heptafluoroisopropyl)phenyl |
| 1213 | 3-nitrophenyl | Me | H | F | H | 2,6-dimethyl-4-(heptafluoroisopropyl)phenyl |
| 1214 | 4-nitrophenyl | Me | H | F | H | 2,6-dimethyl-4-(heptafluoroisopropyl)phenyl |
| 1215 | 2-cyanophenyl | Me | H | F | H | 2,6-dimethyl-4-(heptafluoroisopropyl)phenyl |
| 1216 | 3-cyanophenyl | Me | H | F | H | 2,6-dimethyl-4-(heptafluoroisopropyl)phenyl |
| 1217 | 4-cyanophenyl | Me | H | F | H | 2,6-dimethyl-4-(heptafluoroisopropyl)phenyl |
| 1218 | 2-fluorophenyl | Me | H | F | H | 2,6-dimethyl-4-(heptafluoroisopropyl)phenyl |
| 1219 | 3-fluorophenyl | Me | H | F | H | 2,6-dimethyl-4-(heptafluoroisopropyl)phenyl |
| 1220 | 4-fluorophenyl | Me | H | F | H | 2,6-dimethyl-4-(heptafluoroisopropyl)phenyl |
| 1221 | 2-chlorophenyl | Me | H | F | H | 2,6-dimethyl-4-(heptafluoroisopropyl)phenyl |
| 1222 | 4-chlorophenyl | Me | H | F | H | 2,6-dimethyl-4-(heptafluoroisopropyl)phenyl |
| 1223 | 2-bromophenyl | Me | H | F | H | 2,6-dimethyl-4-(heptafluoroisopropyl)phenyl |
| 1224 | 2-iodophenyl | Me | H | F | H | 2,6-dimethyl-4-(heptafluoroisopropyl)phenyl |
| 1225 | 2-trifluoromethylphenyl | Me | H | F | H | 2,6-dimethyl-4-(heptafluoroisopropyl)phenyl |
| 1226 | 4-trifluoromethylphenyl | Me | H | F | H | 2,6-dimethyl-4-(heptafluoroisopropyl)phenyl |
| 1227 | 4-trifluoromethoxyphenyl | Me | H | F | H | 2,6-dimethyl-4-(heptafluoroisopropyl)phenyl |
| 1228 | 2,3-difluorophenyl | Me | H | F | H | 2,6-dimethyl-4-(heptafluoroisopropyl)phenyl |
| 1229 | 2,4-difluorophenyl | Me | H | F | H | 2,6-dimethyl-4-(heptafluoroisopropyl)phenyl |
| 1230 | 2,5-difluorophenyl | Me | H | F | H | 2,6-dimethyl-4-(heptafluoroisopropyl)phenyl |
| 1231 | 2,6-difluorophenyl | Me | H | F | H | 2,6-dimethyl-4-(heptafluoroisopropyl)phenyl |
| 1232 | 2,4-dichlorophenyl | Me | H | F | H | 2,6-dimethyl-4-(heptafluoroisopropyl)phenyl |

TABLE 3-continued

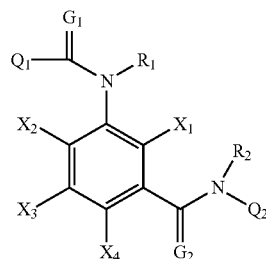

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1233 | 2,6-dichlorophenyl | Me | H | F | H | 2,6-dimethyl-4-(heptafluoroisopropyl)phenyl |
| 1234 | 3,4-dichlorophenyl | Me | H | F | H | 2,6-dimethyl-4-(heptafluoroisopropyl)phenyl |
| 1235 | 2-fluoro-4-nitrophenyl | Me | H | F | H | 2,6-dimethyl-4-(heptafluoroisopropyl)phenyl |
| 1236 | 4-fluoro-2-nitrophenyl | Me | H | F | H | 2,6-dimethyl-4-(heptafluoroisopropyl)phenyl |
| 1237 | 2-chloro-4-fluorophenyl | Me | H | F | H | 2,6-dimethyl-4-(heptafluoroisopropyl)phenyl |
| 1238 | 4-chloro-2-fluorophenyl | Me | H | F | H | 2,6-dimethyl-4-(heptafluoroisopropyl)phenyl |
| 1239 | 2-chloro-6-fluorophenyl | Me | H | F | H | 2,6-dimethyl-4-(heptafluoroisopropyl)phenyl |
| 1240 | 2-chloro-4-nitrophenyl | Me | H | F | H | 2,6-dimethyl-4-(heptafluoroisopropyl)phenyl |
| 1241 | 4-chloro-2-nitrophenyl | Me | H | F | H | 2,6-dimethyl-4-(heptafluoroisopropyl)phenyl |
| 1242 | 2,3,6-trifluorophenyl | Me | H | F | H | 2,6-dimethyl-4-(heptafluoroisopropyl)phenyl |
| 1243 | pyridin-2-yl | Me | H | F | H | 2,6-dimethyl-4-(heptafluoroisopropyl)phenyl |
| 1244 | pyridin-3-yl | Me | H | F | H | 2,6-dimethyl-4-(heptafluoroisopropyl)phenyl |
| 1245 | 2-chloropyridin-3-yl | Me | H | F | H | 2,6-dimethyl-4-(heptafluoroisopropyl)phenyl |
| 1246 | 2-fluoropyridin-3-yl | Me | H | F | H | 2,6-dimethyl-4-(heptafluoroisopropyl)phenyl |
| 1247 | 2-chloropyridin-5-yl | Me | H | F | H | 2,6-dimethyl-4-(heptafluoroisopropyl)phenyl |
| 1248 | 2-methylthiopyridin-3-yl | Me | H | F | H | 2,6-dimethyl-4-(heptafluoroisopropyl)phenyl |
| 1249 | pyrazin-2-yl | Me | H | F | H | 2,6-dimethyl-4-(heptafluoroisopropyl)phenyl |
| 1250 | furan-2-yl | Me | H | F | H | 2,6-dimethyl-4-(heptafluoroisopropyl)phenyl |
| 1251 | furan-3-yl | Me | H | F | H | 2,6-dimethyl-4-(heptafluoroisopropyl)phenyl |
| 1252 | 2-tetrahydrofuranyl | Me | H | F | H | 2,6-dimethyl-4-(heptafluoroisopropyl)phenyl |
| 1253 | benzofuran-2-yl | Me | H | F | H | 2,6-dimethyl-4-(heptafluoroisopropyl)phenyl |
| 1254 | thiophen-2-yl | Me | H | F | H | 2,6-dimethyl-4-(heptafluoroisopropyl)phenyl |
| 1255 | phenyl | Me | H | F | H | 2,6-dimethyl-4-(nonafluoro-2-butyl)phenyl |
| 1256 | 2-methylphenyl | Me | H | F | H | 2,6-dimethyl-4-(nonafluoro-2-butyl)phenyl |
| 1257 | 3-methylphenyl | Me | H | F | H | 2,6-dimethyl-4-(nonafluoro-2-butyl)phenyl |
| 1258 | 4-methylphenyl | Me | H | F | H | 2,6-dimethyl-4-(nonafluoro-2-butyl)phenyl |
| 1259 | 2-nitrophenyl | Me | H | F | H | 2,6-dimethyl-4-(nonafluoro-2-butyl)phenyl |
| 1260 | 2-nitrophenyl | Me | H | F | H | 2,6-dimethyl-4-(nonafluoro-2-butyl)phenyl |
| 1261 | 4-nitrophenyl | Me | H | F | H | 2,6-dimethyl-4-(nonafluoro-2-butyl)phenyl |
| 1262 | 2-cyanophenyl | Me | H | F | H | 2,6-dimethyl-4-(nonafluoro-2-butyl)phenyl |
| 1263 | 3-cyanophenyl | Me | H | F | H | 2,6-dimethyl-4-(nonafluoro-2-butyl)phenyl |
| 1264 | 4-cyanophenyl | Me | H | F | H | 2,6-dimethyl-4-(nonafluoro-2-butyl)phenyl |
| 1265 | 2-fluorophenyl | Me | H | F | H | 2,6-dimethyl-4-(nonafluoro-2-butyl)phenyl |
| 1266 | 3-fluorophenyl | Me | H | F | H | 2,6-dimethyl-4-(nonafluoro-2-butyl)phenyl |
| 1267 | 4-fluorophenyl | Me | H | F | H | 2,6-dimethyl-4-(nonafluoro-2-butyl)phenyl |
| 1268 | 2-chlorophenyl | Me | H | F | H | 2,6-dimethyl-4-(nonafluoro-2-butyl)phenyl |
| 1269 | 4-chlorophenyl | Me | H | F | H | 2,6-dimethyl-4-(nonafluoro-2-butyl)phenyl |
| 1270 | 2-bromophenyl | Me | H | F | H | 2,6-dimethyl-4-(nonafluoro-2-butyl)phenyl |
| 1271 | 2-iodophenyl | Me | H | F | H | 2,6-dimethyl-4-(nonafluoro-2-butyl)phenyl |
| 1272 | 2-trifluoromethylphenyl | Me | H | F | H | 2,6-dimethyl-4-(nonafluoro-2-butyl)phenyl |
| 1273 | 4-trifluoromethylphenyl | Me | H | F | H | 2,6-dimethyl-4-(nonafluoro-2-butyl)phenyl |
| 1274 | 4-trifluoromethoxyphenyl | Me | H | F | H | 2,6-dimethyl-4-(nonafluoro-2-butyl)phenyl |
| 1275 | 2,3-difluorophenyl | Me | H | F | H | 2,6-dimethyl-4-(nonafluoro-2-butyl)phenyl |
| 1276 | 2,4-difluorophenyl | Me | H | F | H | 2,6-dimethyl-4-(nonafluoro-2-butyl)phenyl |
| 1277 | 2,5-difluorophenyl | Me | H | F | H | 2,6-dimethyl-4-(nonafluoro-2-butyl)phenyl |
| 1278 | 2,6-difluorophenyl | Me | H | F | H | 2,6-dimethyl-4-(nonafluoro-2-butyl)phenyl |
| 1279 | 2,4-dichlorophenyl | Me | H | F | H | 2,6-dimethyl-4-(nonafluoro-2-butyl)phenyl |
| 1280 | 2,6-dichlorophenyl | Me | H | F | H | 2,6-dimethyl-4-(nonafluoro-2-butyl)phenyl |
| 1281 | 3,4-dichlorophenyl | Me | H | F | H | 2,6-dimethyl-4-(nonafluoro-2-butyl)phenyl |
| 1282 | 2-fluoro-4-nitrophenyl | Me | H | F | H | 2,6-dimethyl-4-(nonafluoro-2-butyl)phenyl |
| 1283 | 4-fluoro-2-nitrophenyl | Me | H | F | H | 2,6-dimethyl-4-(nonafluoro-2-butyl)phenyl |
| 1284 | 2-chloro-4-fluorophenyl | Me | H | F | H | 2,6-dimethyl-4-(nonafluoro-2-butyl)phenyl |
| 1285 | 4-chloro-2-fluorophenyl | Me | H | F | H | 2,6-dimethyl-4-(nonafluoro-2-butyl)phenyl |
| 1286 | 2-chloro-6-fluorophenyl | Me | H | F | H | 2,6-dimethyl-4-(nonafluoro-2-butyl)phenyl |
| 1287 | 2-chloro-4-nitrophenyl | Me | H | F | H | 2,6-dimethyl-4-(nonafluoro-2-butyl)phenyl |
| 1288 | 4-chloro-2-nitrophenyl | Me | H | F | H | 2,6-dimethyl-4-(nonafluoro-2-butyl)phenyl |
| 1289 | 2,3,6-trifluorophenyl | Me | H | F | H | 2,6-dimethyl-4-(nonafluoro-2-butyl)phenyl |
| 1290 | pyridin-2-yl | Me | H | F | H | 2,6-dimethyl-4-(nonafluoro-2-butyl)phenyl |
| 1291 | pyridin-3-yl | Me | H | F | H | 2,6-dimethyl-4-(nonafluoro-2-butyl)phenyl |
| 1292 | 2-fluoropyridin-3-yl | Me | H | F | H | 2,6-dimethyl-4-(nonafluoro-2-butyl)phenyl |
| 1293 | 2-chloropyridin-3-yl | Me | H | F | H | 2,6-dimethyl-4-(nonafluoro-2-butyl)phenyl |
| 1294 | 2-chloropyridin-5-yl | Me | H | F | H | 2,6-dimethyl-4-(nonafluoro-2-butyl)phenyl |
| 1295 | 2-methylthiopyridin-3-yl | Me | H | F | H | 2,6-dimethyl-4-(nonafluoro-2-butyl)phenyl |

TABLE 3-continued

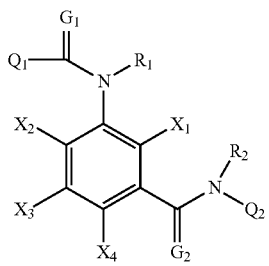

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1296 | pyrazin-2-yl | Me | H | F | H | 2,6-dimethyl-4-(nonafluoro-2-butyl)phenyl |
| 1297 | furan-2-yl | Me | H | F | H | 2,6-dimethyl-4-(nonafluoro-2-butyl)phenyl |
| 1298 | furan-3-yl | Me | H | F | H | 2,6-dimethyl-4-(nonafluoro-2-butyl)phenyl |
| 1299 | 2-tetrahydrofuranyl | Me | H | F | H | 2,6-dimethyl-4-(nonafluoro-2-butyl)phenyl |
| 1300 | benzofuran-2-yl | Me | H | F | H | 2,6-dimethyl-4-(nonafluoro-2-butyl)phenyl |
| 1301 | thiophen-2-yl | Me | H | F | H | 2,6-dimethyl-4-(nonafluoro-2-butyl)phenyl |
| 1302 | phenyl | Me | H | F | H | 2-bromo-4-(heptafluoroisopropyl)-6-(methylsulfonyl)phenyl |
| 1303 | 2-methylphenyl | Me | H | F | H | 2-bromo-4-(heptafluoroisopropyl)-6-(methylsulfonyl)phenyl |
| 1304 | 4-methylphenyl | Me | H | F | H | 2-bromo-4-(heptafluoroisopropyl)-6-(methylsulfonyl)phenyl |
| 1305 | 2-fluorophenyl | Me | H | F | H | 2-bromo-4-(heptafluoroisopropyl)-6-(methylsulfonyl)phenyl |
| 1306 | 3-fluorophenyl | Me | H | F | H | 2-bromo-4-(heptafluoroisopropyl)-6-(methylsulfonyl)phenyl |
| 1307 | 4-fluorophenyl | Me | H | F | H | 2-bromo-4-(heptafluoroisopropyl)-6-(methylsulfonyl)phenyl |
| 1308 | 2-chlorophenyl | Me | H | F | H | 2-bromo-4-(heptafluoroisopropyl)-6-(methylsulfonyl)phenyl |
| 1309 | 4-chlorophenyl | Me | H | F | H | 2-bromo-4-(heptafluoroisopropyl)-6-(methylsulfonyl)phenyl |
| 1310 | 2-bromophenyl | Me | H | F | H | 2-bromo-4-(heptafluoroisopropyl)-6-(methylsulfonyl)phenyl |
| 1311 | 2-iodophenyl | Me | H | F | H | 2-bromo-4-(heptafluoroisopropyl)-6-(methylsulfonyl)phenyl |
| 1312 | 3-cyanophenyl | Me | H | F | H | 2-bromo-4-(heptafluoroisopropyl)-6-(methylsulfonyl)phenyl |
| 1313 | 4-cyanophenyl | Me | H | F | H | 2-bromo-4-(heptafluoroisopropyl)-6-(methylsulfonyl)phenyl |
| 1314 | 2-nitrophenyl | Me | H | F | H | 2-bromo-4-(heptafluoroisopropyl)-6-(methylsulfonyl)phenyl |
| 1315 | 3-nitrophenyl | Me | H | F | H | 2-bromo-4-(heptafluoroisopropyl)-6-(methylsulfonyl)phenyl |
| 1316 | 4-nitrophenyl | Me | H | F | H | 2-bromo-4-(heptafluoroisopropyl)-6-(methylsulfonyl)phenyl |
| 1317 | 2-trifluoromethylphenyl | Me | H | F | H | 2-bromo-4-(heptafluoroisopropyl)-6-(methylsulfonyl)phenyl |
| 1318 | 4-trifluoromethylphenyl | Me | H | F | H | 2-bromo-4-(heptafluoroisopropyl)-6-(methylsulfonyl)phenyl |
| 1319 | 4-trifluoromethoxyphenyl | Me | H | F | H | 2-bromo-4-(heptafluoroisopropyl)-6-(methylsulfonyl)phenyl |
| 1320 | 2,3-difluorophenyl | Me | H | F | H | 2-bromo-4-(heptafluoroisopropyl)-6-(methylsulfonyl)phenyl |
| 1321 | 2,4-difluorophenyl | Me | H | F | H | 2-bromo-4-(heptafluoroisopropyl)-6-(methylsulfonyl)phenyl |
| 1322 | 2,5-difluorophenyl | Me | H | F | H | 2-bromo-4-(heptafluoroisopropyl)-6-(methylsulfonyl)phenyl |
| 1323 | 2,6-difluorophenyl | Me | H | F | H | 2-bromo-4-(heptafluoroisopropyl)-6-(methylsulfonyl)phenyl |
| 1324 | 2,4-dichlorophenyl | Me | H | F | H | 2-bromo-4-(heptafluoroisopropyl)-6-(methylsulfonyl)phenyl |
| 1325 | 2,6-dichlorophenyl | Me | H | F | H | 2-bromo-4-(heptafluoroisopropyl)-6-(methylsulfonyl)phenyl |
| 1326 | 3,4-dichlorophenyl | Me | H | F | H | 2-bromo-4-(heptafluoroisopropyl)-6-(methylsulfonyl)phenyl |
| 1327 | 2-chloro-4-nitrophenyl | Me | H | F | H | 2-bromo-4-(heptafluoroisopropyl)-6-(methylsulfonyl)phenyl |
| 1328 | 2-chloro-4-fluorophenyl | Me | H | F | H | 2-bromo-4-(heptafluoroisopropyl)-6-(methylsulfonyl)phenyl |
| 1329 | 2-chloro-6-fluorophenyl | Me | H | F | H | 2-bromo-4-(heptafluoroisopropyl)-6-(methylsulfonyl)phenyl |

TABLE 3-continued

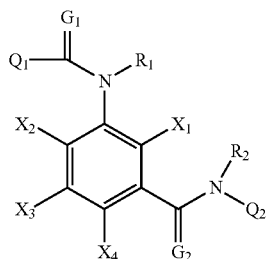

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1330 | 4-chloro-2-fluorophenyl | Me | H | F | H | 2-bromo-4-(heptafluoroisopropyl)-6-(methylsulfonyl)phenyl |
| 1331 | 4-chloro-2-nitrophenyl | Me | H | F | H | 2-bromo-4-(heptafluoroisopropyl)-6-(methylsulfonyl)phenyl |
| 1332 | 2,3,6-trifluorophenyl | Me | H | F | H | 2-bromo-4-(heptafluoroisopropyl)-6-(methylsulfonyl)phenyl |
| 1333 | pyridin-2-yl | Me | H | F | H | 2-bromo-4-(heptafluoroisopropyl)-6-(methylsulfonyl)phenyl |
| 1334 | pyridin-3-yl | Me | H | F | H | 2-bromo-4-(heptafluoroisopropyl)-6-(methylsulfonyl)phenyl |
| 1335 | 2-fluoropyridin-3-yl | Me | H | F | H | 2-bromo-4-(heptafluoroisopropyl)-6-(methylsulfonyl)phenyl |
| 1336 | 2-chloropyridin-3-yl | Me | H | F | H | 2-bromo-4-(heptafluoroisopropyl)-6-(methylsulfonyl)phenyl |
| 1337 | 2-chloropyridin-5-yl | Me | H | F | H | 2-bromo-4-(heptafluoroisopropyl)-6-(methylsulfonyl)phenyl |
| 1338 | 2-methylthiopyridin-3-yl | Me | H | F | H | 2-bromo-4-(heptafluoroisopropyl)-6-(methylsulfonyl)phenyl |
| 1339 | pyrazin-2-yl | Me | H | F | H | 2-bromo-4-(heptafluoroisopropyl)-6-(methylsulfonyl)phenyl |
| 1340 | furan-2-yl | Me | H | F | H | 2-bromo-4-(heptafluoroisopropyl)-6-(methylsulfonyl)phenyl |
| 1341 | thiophen-2-yl | Me | H | F | H | 2-bromo-4-(heptafluoroisopropyl)-6-(methylsulfonyl)phenyl |
| 1342 | phenyl | Me | H | F | H | 2-n-propyl-6-iodo-4-(heptafluoroisopropyl)phenyl |
| 1343 | 2-methylphenyl | Me | H | F | H | 2-n-propyl-6-iodo-4-(heptafluoroisopropyl)phenyl |
| 1344 | 4-methylphenyl | Me | H | F | H | 2-n-propyl-6-iodo-4-(heptafluoroisopropyl)phenyl |
| 1345 | 2-fluorophenyl | Me | H | F | H | 2-n-propyl-6-iodo-4-(heptafluoroisopropyl)phenyl |
| 1346 | 3-fluorophenyl | Me | H | F | H | 2-n-propyl-6-iodo-4-(heptafluoroisopropyl)phenyl |
| 1347 | 4-fluorophenyl | Me | H | F | H | 2-n-propyl-6-iodo-4-(heptafluoroisopropyl)phenyl |
| 1348 | 2-chlorophenyl | Me | H | F | H | 2-n-propyl-6-iodo-4-(heptafluoroisopropyl)phenyl |
| 1349 | 4-chlorophenyl | Me | H | F | H | 2-n-propyl-6-iodo-4-(heptafluoroisopropyl)phenyl |
| 1350 | 2-bromophenyl | Me | H | F | H | 2-n-propyl-6-iodo-4-(heptafluoroisopropyl)phenyl |
| 1351 | 2-iodophenyl | Me | H | F | H | 2-n-propyl-6-iodo-4-(heptafluoroisopropyl)phenyl |
| 1352 | 3-cyanophenyl | Me | H | F | H | 2-n-propyl-6-iodo-4-(heptafluoroisopropyl)phenyl |
| 1353 | 4-cyanophenyl | Me | H | F | H | 2-n-propyl-6-iodo-4-(heptafluoroisopropyl)phenyl |
| 1354 | 2-nitrophenyl | Me | H | F | H | 2-n-propyl-6-iodo-4-(heptafluoroisopropyl)phenyl |
| 1355 | 3-nitrophenyl | Me | H | F | H | 2-n-propyl-6-iodo-4-(heptafluoroisopropyl)phenyl |
| 1356 | 4-nitrophenyl | Me | H | F | H | 2-n-propyl-6-iodo-4-(heptafluoroisopropyl)phenyl |
| 1357 | 2-trifluoromethylphenyl | Me | H | F | H | 2-n-propyl-6-iodo-4-(heptafluoroisopropyl)phenyl |
| 1358 | 4-trifluoromethylphenyl | Me | H | F | H | 2-n-propyl-6-iodo-4-(heptafluoroisopropyl)phenyl |
| 1359 | 4-trifluoromethoxyphenyl | Me | H | F | H | 2-n-propyl-6-iodo-4-(heptafluoroisopropyl)phenyl |
| 1360 | 2,3-difluorophenyl | Me | H | F | H | 2-n-propyl-6-iodo-4-(heptafluoroisopropyl)phenyl |

TABLE 3-continued

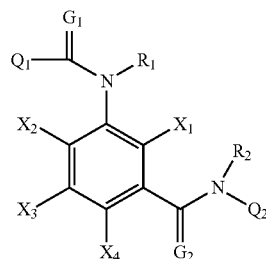

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1361 | 2,4-difluorophenyl | Me | H | F | H | 2-n-propyl-6-iodo-4-(heptafluoroisopropyl)phenyl |
| 1362 | 2,5-difluorophenyl | Me | H | F | H | 2-n-propyl-6-iodo-4-(heptafluoroisopropyl)phenyl |
| 1363 | 2,6-difluorophenyl | Me | H | F | H | 2-n-propyl-6-iodo-4-(heptafluoroisopropyl)phenyl |
| 1364 | 2,4-dichlorophenyl | Me | H | F | H | 2-n-propyl-6-iodo-4-(heptafluoroisopropyl)phenyl |
| 1365 | 2,6-dichlorophenyl | Me | H | F | H | 2-n-propyl-6-iodo-4-(heptafluoroisopropyl)phenyl |
| 1366 | 3,4-dichlorophenyl | Me | H | F | H | 2-n-propyl-6-iodo-4-(heptafluoroisopropyl)phenyl |
| 1367 | 2-chloro-4-nitrophenyl | Me | H | F | H | 2-n-propyl-6-iodo-4-(heptafluoroisopropyl)phenyl |
| 1368 | 2-chloro-4-fluorophenyl | Me | H | F | H | 2-n-propyl-6-iodo-4-(heptafluoroisopropyl)phenyl |
| 1369 | 2-chloro-6-fluorophenyl | Me | H | F | H | 2-n-propyl-6-iodo-4-(heptafluoroisopropyl)phenyl |
| 1370 | 4-chloro-2-fluorophenyl | Me | H | F | H | 2-n-propyl-6-iodo-4-(heptafluoroisopropyl)phenyl |
| 1371 | 4-chloro-2-nitrophenyl | Me | H | F | H | 2-n-propyl-6-iodo-4-(heptafluoroisopropyl)phenyl |
| 1372 | 2,3,6-trifluorophenyl | Me | H | F | H | 2-n-propyl-6-iodo-4-(heptafluoroisopropyl)phenyl |
| 1373 | pyridin-2-yl | Me | H | F | H | 2-n-propyl-6-iodo-4-(heptafluoroisopropyl)phenyl |
| 1374 | pyridin-3-yl | Me | H | F | H | 2-n-propyl-6-iodo-4-(heptafluoroisopropyl)phenyl |
| 1375 | 2-fluoropyridin-3-yl | Me | H | F | H | 2-n-propyl-6-iodo-4-(heptafluoroisopropyl)phenyl |
| 1376 | 2-chloropyridin-3-yl | Me | H | F | H | 2-n-propyl-6-iodo-4-(heptafluoroisopropyl)phenyl |
| 1377 | 2-chloropyridin-5yl | Me | H | F | H | 2-n-propyl-6-iodo-4-(heptafluoroisopropyl)phenyl |
| 1378 | 2-methylthiopyridin-3-yl | Me | H | F | H | 2-n-propyl-6-iodo-4-(heptafluoroisopropyl)phenyl |
| 1379 | pyrazin-2-yl | Me | H | F | H | 2-n-propyl-6-iodo-4-(heptafluoroisopropyl)phenyl |
| 1380 | furan-2-yl | Me | H | F | H | 2-n-propyl-6-iodo-4-(heptafluoroisopropyl)phenyl |
| 1381 | thiophen-2-yl | Me | H | F | H | 2-n-propyl-6-iodo-4-(heptafluoroisopropyl)phenyl |
| 1382 | phenyl | Me | H | F | H | 2,6-dibromo-4-(heptafluoro-n-propylthio)phenyl |
| 1383 | 2-methylphenyl | Me | H | F | H | 2,6-dibromo-4-(heptafluoro-n-propylthio)phenyl |
| 1384 | 4-methylphenyl | Me | H | F | H | 2,6-dibromo-4-(heptafluoro-n-propylthio)phenyl |
| 1385 | 2-fluorophenyl | Me | H | F | H | 2,6-dibromo-4-(heptafluoro-n-propylthio)phenyl |
| 1386 | 3-fluorophenyl | Me | H | F | H | 2,6-dibromo-4-(heptafluoro-n-propylthio)phenyl |
| 1387 | 4-fluorophenyl | Me | H | F | H | 2,6-dibromo-4-(heptafluoro-n-propylthio)phenyl |
| 1388 | 2-chlorophenyl | Me | H | F | H | 2,6-dibromo-4-(heptafluoro-n-propylthio)phenyl |
| 1389 | 4-chlorophenyl | Me | H | F | H | 2,6-dibromo-4-(heptafluoro-n-propylthio)phenyl |
| 1390 | 2-bromophenyl | Me | H | F | H | 2,6-dibromo-4-(heptafluoro-n-propylthio)phenyl |
| 1391 | 2-iodophenyl | Me | H | F | H | 2,6-dibromo-4-(heptafluoro-n-propylthio)phenyl |

TABLE 3-continued

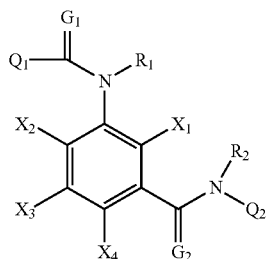

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1392 | 3-cyanophenyl | Me | H | F | H | 2,6-dibromo-4-(heptafluoro-n-propylthio)phenyl |
| 1393 | 4-cyanophenyl | Me | H | F | H | 2,6-dibromo-4-(heptafluoro-n-propylthio)phenyl |
| 1394 | 2-nitrophenyl | Me | H | F | H | 2,6-dibromo-4-(heptafluoro-n-propylthio)phenyl |
| 1395 | 3-nitrophenyl | Me | H | F | H | 2,6-dibromo-4-(heptafluoro-n-propylthio)phenyl |
| 1396 | 4-nitrophenyl | Me | H | F | H | 2,6-dibromo-4-(heptafluoro-n-propylthio)phenyl |
| 1397 | 2-trifluoromethylphenyl | Me | H | F | H | 2,6-dibromo-4-(heptafluoro-n-propylthio)phenyl |
| 1398 | 4-trifluoromethylphenyl | Me | H | F | H | 2,6-dibromo-4-(heptafluoro-n-propylthio)phenyl |
| 1399 | 4-trifluoromethoxyphenyl | Me | H | F | H | 2,6-dibromo-4-(heptafluoro-n-propylthio)phenyl |
| 1400 | 2,3-difluorophenyl | Me | H | F | H | 2,6-dibromo-4-(heptafluoro-n-propylthio)phenyl |
| 1401 | 2,4-difluorophenyl | Me | H | F | H | 2,6-dibromo-4-(heptafluoro-n-propylthio)phenyl |
| 1402 | 2,5-difluorophenyl | Me | H | F | H | 2,6-dibromo-4-(heptafluoro-n-propylthio)phenyl |
| 1403 | 2,6-difluorophenyl | Me | H | F | H | 2,6-dibromo-4-(heptafluoro-n-propylthio)phenyl |
| 1404 | 2,4-dichlorophenyl | Me | H | F | H | 2,6-dibromo-4-(heptafluoro-n-propylthio)phenyl |
| 1405 | 2,6-dichlorophenyl | Me | H | F | H | 2,6-dibromo-4-(heptafluoro-n-propylthio)phenyl |
| 1406 | 3,4-dichlorophenyl | Me | H | F | H | 2,6-dibromo-4-(heptafluoro-n-propylthio)phenyl |
| 1407 | 2-chloro-4-nitrophenyl | Me | H | F | H | 2,6-dibromo-4-(heptafluoro-n-propylthio)phenyl |
| 1408 | 2-chloro-4-fluorophenyl | Me | H | F | H | 2,6-dibromo-4-(heptafluoro-n-propylthio)phenyl |
| 1409 | 2-chloro-6-fluorophenyl | Me | H | F | H | 2,6-dibromo-4-(heptafluoro-n-propylthio)phenyl |
| 1410 | 4-chloro-2-fluorophenyl | Me | H | F | H | 2,6-dibromo-4-(heptafluoro-n-propylthio)phenyl |
| 1411 | 4-chloro-2-nitrophenyl | Me | H | F | H | 2,6-dibromo-4-(heptafluoro-n-propylthio)phenyl |
| 1412 | 2,3,6-trifluorophenyl | Me | H | F | H | 2,6-dibromo-4-(heptafluoro-n-propylthio)phenyl |
| 1413 | pyridin-2-yl | Me | H | F | H | 2,6-dibromo-4-(heptafluoro-n-propylthio)phenyl |
| 1414 | pyridin-3-yl | Me | H | F | H | 2,6-dibromo-4-(heptafluoro-n-propylthio)phenyl |
| 1415 | 2-fluoropyridin-3-yl | Me | H | F | H | 2,6-dibromo-4-(heptafluoro-n-propylthio)phenyl |
| 1416 | 2-chloropyridin-3-yl | Me | H | F | H | 2,6-dibromo-4-(heptafluoro-n-propylthio)phenyl |
| 1417 | 2-chloropyridin-5-yl | Me | H | F | H | 2,6-dibromo-4-(heptafluoro-n-propylthio)phenyl |
| 1418 | 2-methylthiopyridin-3-yl | Me | H | F | H | 2,6-dibromo-4-(heptafluoro-n-propylthio)phenyl |
| 1419 | pyrazin-2-yl | Me | H | F | H | 2,6-dibromo-4-(heptafluoro-n-propylthio)phenyl |
| 1420 | furan-2-yl | Me | H | F | H | 2,6-dibromo-4-(heptafluoro-n-propylthio)phenyl |
| 1421 | thiophen-2-yl | Me | H | F | H | 2,6-dibromo-4-(heptafluoro-n-propylthio)phenyl |
| 1422 | phenyl | Me | H | F | H | 2,6-dibromo-4-(heptafluoro-n-propylsulfinyl)phenyl |

TABLE 3-continued

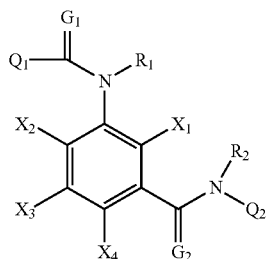

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1423 | 2-methylphenyl | Me | H | F | H | 2,6-dibromo-4-(heptafluoro-n-propylsulfinyl)phenyl |
| 1424 | 4-methylphenyl | Me | H | F | H | 2,6-dibromo-4-(heptafluoro-n-propylsulfinyl)phenyl |
| 1425 | 2-fluorophenyl | Me | H | F | H | 2,6-dibromo-4-(heptafluoro-n-propylsulfinyl)phenyl |
| 1426 | 3-fluorophenyl | Me | H | F | H | 2,6-dibromo-4-(heptafluoro-n-propylsulfinyl)phenyl |
| 1427 | 4-fluorophenyl | Me | H | F | H | 2,6-dibromo-4-(heptafluoro-n-propylsulfinyl)phenyl |
| 1428 | 2-chlorophenyl | Me | H | F | H | 2,6-dibromo-4-(heptafluoro-n-propylsulfinyl)phenyl |
| 1429 | 4-chlorophenyl | Me | H | F | H | 2,6-dibromo-4-(heptafluoro-n-propylsulfinyl)phenyl |
| 1430 | 2-bromophenyl | Me | H | F | H | 2,6-dibromo-4-(heptafluoro-n-propylsulfinyl)phenyl |
| 1431 | 2-iodophenyl | Me | H | F | H | 2,6-dibromo-4-(heptafluoro-n-propylsulfinyl)phenyl |
| 1432 | 3-cyanophenyl | Me | H | F | H | 2,6-dibromo-4-(heptafluoro-n-propylsulfinyl)phenyl |
| 1433 | 4-cyanophenyl | Me | H | F | H | 2,6-dibromo-4-(heptafluoro-n-propylsulfinyl)phenyl |
| 1434 | 2-nitrophenyl | Me | H | F | H | 2,6-dibromo-4-(heptafluoro-n-propylsulfinyl)phenyl |
| 1435 | 3-nitrophenyl | Me | H | F | H | 2,6-dibromo-4-(heptafluoro-n-propylsulfinyl)phenyl |
| 1436 | 4-nitrophenyl | Me | H | F | H | 2,6-dibromo-4-(heptafluoro-n-propylsulfinyl)phenyl |
| 1437 | 2-trifluoromethylphenyl | Me | H | F | H | 2,6-dibromo-4-(heptafluoro-n-propylsulfinyl)phenyl |
| 1438 | 4-trifluoromethylphenyl | Me | H | F | H | 2,6-dibromo-4-(heptafluoro-n-propylsulfinyl)phenyl |
| 1439 | 4-trifluoromethoxyphenyl | Me | H | F | H | 2,6-dibromo-4-(heptafluoro-n-propylsulfinyl)phenyl |
| 1440 | 2,3-difluorophenyl | Me | H | F | H | 2,6-dibromo-4-(heptafluoro-n-propylsulfinyl)phenyl |
| 1441 | 2,4-difluorophneyl | Me | H | F | H | 2,6-dibromo-4-(heptafluoro-n-propylsulfinyl)phenyl |
| 1442 | 2,5-difluorophenyl | Me | H | F | H | 2,6-dibromo-4-(heptafluoro-n-propylsulfinyl)phenyl |
| 1443 | 2,6-difluorophenyl | Me | H | F | H | 2,6-dibromo-4-(heptafluoro-n-propylsulfinyl)phenyl |
| 1444 | 2,4-dichlorophenyl | Me | H | F | H | 2,6-dibromo-4-(heptafluoro-n-propylsulfinyl)phenyl |
| 1445 | 2,6-dichlorophenyl | Me | H | F | H | 2,6-dibromo-4-(heptafluoro-n-propylsulfinyl)phenyl |
| 1446 | 3,4-dichlorophenyl | Me | H | F | H | 2,6-dibromo-4-(heptafluoro-n-propylsulfinyl)phenyl |
| 1447 | 2-chloro-4-nitrophenyl | Me | H | F | H | 2,6-dibromo-4-(heptafluoro-n-propylsulfinyl)phenyl |
| 1448 | 2-chloro-4-fluorophenyl | Me | H | F | H | 2,6-dibromo-4-(heptafluoro-n-propylsulfinyl)phenyl |
| 1449 | 2-chloro-6-fluorophenyl | Me | H | F | H | 2,6-dibromo-4-(heptafluoro-n-propylsulfinyl)phenyl |
| 1450 | 4-chloro-2-fluorophenyl | Me | H | F | H | 2,6-dibromo-4-(heptafluoro-n-propylsulfinyl)phenyl |
| 1451 | 4-chloro-2-nitrophenyl | Me | H | F | H | 2,6-dibromo-4-(heptafluoro-n-propylsulfinyl)phenyl |
| 1452 | 2,3,6-trifluorophenyl | Me | H | F | H | 2,6-dibromo-4-(heptafluoro-n-propylsulfinyl)phenyl |
| 1453 | pyridin-2-yl | Me | H | F | H | 2,6-dibromo-4-(heptafluoro-n-propylsulfinyl)phenyl |

TABLE 3-continued

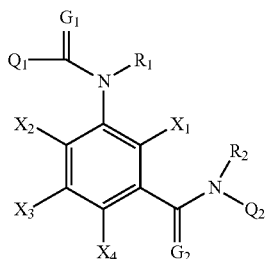

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1454 | pyridin-3-yl | Me | H | F | H | 2,6-dibromo-4-(heptafluoro-n-propylsulfinyl)phenyl |
| 1455 | 2-fluoropyridin-3-yl | Me | H | F | H | 2,6-dibromo-4-(heptafluoro-n-propylsulfinyl)phenyl |
| 1456 | 2-chloropyridin-3-yl | Me | H | F | H | 2,6-dibromo-4-(heptafluoro-n-propylsulfinyl)phenyl |
| 1457 | 2-chloropyridin-5-yl | Me | H | F | H | 2,6-dibromo-4-(heptafluoro-n-propylsulfinyl)phenyl |
| 1458 | 2-methylthiopyridin-3-yl | Me | H | F | H | 2,6-dibromo-4-(heptafluoro-n-propylsulfinyl)phenyl |
| 1459 | pyrazin-2-yl | Me | H | F | H | 2,6-dibromo-4-(heptafluoro-n-propylsulfinyl)phenyl |
| 1460 | furan-2-yl | Me | H | F | H | 2,6-dibromo-4-(heptafluoro-n-propylsulfinyl)phenyl |
| 1461 | thiophen-2-yl | Me | H | F | H | 2,6-dibromo-4-(heptafluoro-n-propylsulfinyl)phenyl |
| 1462 | phenyl | Et | H | F | H | 2,6-dimethyl-4-(heptafluoro isopropyl)phenyl |
| 1463 | phenyl | Me | H | H | F | 2,6-dimethyl-4-(heptafluoro isopropyl)phenyl |
| 1464 | 4-nitrophenyl | Me | H | H | F | 2,6-dimethyl-4-(heptafluoro isopropyl)phenyl |
| 1465 | 4-cyanophenyl | Me | H | H | F | 2,6-dimethyl-4-(heptafluoro isopropyl)phenyl |
| 1466 | phenyl | Me | H | H | F | 2-bromo-4-(heptafluoroisopropyl)-6-(methylsulfonyl)phenyl |
| 1467 | 4-nitrophenyl | Me | H | H | F | 2-bromo-4-(heptafluoroisopropyl)-6-(methylsulfonyl)phenyl |
| 1468 | 4-cyanophenyl | Me | H | H | F | 2-bromo-4-(heptafluoroisopropyl)-6-(methylsulfonyl)phenyl |
| 1469 | phenyl | Me | H | H | F | 2-n-propyl-6-iodo-4-(heptafluoroisopropyl)phenyl |
| 1470 | 4-nitrophenyl | Me | H | H | F | 2-n-propyl-6-iodo-4-(heptafluoroisopropyl)phenyl |
| 1471 | 4-cyanophenyl | Me | H | H | F | 2-n-propyl-6-iodo-4-(heptafluoroisopropyl)phenyl |
| 1472 | phenyl | Me | H | H | F | 2,6-dibromo-4-(heptafluoro-n-propylthio)phenyl |
| 1473 | 4-nitrophenyl | Me | H | H | F | 2,6-dibromo-4-(heptafluoro-n-propylthio)phenyl |
| 1474 | 4-cyanophenyl | Me | H | H | F | 2,6-dibromo-4-(heptafluoro-n-propylthio)phenyl |
| 1475 | phenyl | Me | H | H | F | 2,6-dibromo-4-(heptafluoro-n-propylsulfonyl)phenyl |
| 1476 | 4-nitrophenyl | Me | H | H | F | 2,6-dibromo-4-(heptafluoro-n-propylsulfonyl)phenyl |
| 1477 | 4-cyanophenyl | Me | H | H | F | 2,6-dibromo-4-(heptafluoro-n-propylsulfonyl)phenyl |
| 1478 | phenyl | H | Me | H | H | 2,6-dimethyl-4-(heptafluoro isopropyl)phenyl |
| 1479 | phenyl | H | Me | H | H | 2-bromo-4-(heptafluoro isopropyl)-6-methylphenyl |
| 1480 | phenyl | H | Me | H | H | 2,6-dibromo-4-(heptafluoro-n-propylthio)phenyl |
| 1481 | 2-fluorophendyl | H | Me | H | H | 2,6-dibromo-4-(heptafluoro-n-propylthio)phenyl |
| 1482 | phenyl | H | Et | H | H | 2,6-dimethyl-4-(heptafluoro isopropyl)phenyl |
| 1483 | phenyl | H | i-Pr | H | H | 2,6-dimethyl-4-(heptafluoro isopropyl)phenyl |
| 1484 | phenyl | H | acetyl | H | H | 2,6-dimethyl-4-(heptafluoro isopropyl)phenyl |

TABLE 3-continued

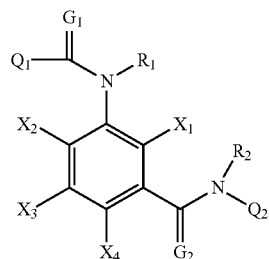

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1485 | phenyl | H | Me | F | H | 2,6-dimethyl-4-(heptafluoro isopropyl)phenyl |
| 1486 | 2-fluorophenyl | H | Me | F | H | 2,6-dimethyl-4-(heptafluoro isopropyl)phenyl |
| 1487 | phenyl | Me | Me | H | H | 2,6-dimethyl-4-(heptafluoro isopropyl)phenyl |
| 1488 | 2-methylphenyl | Me | Me | H | H | 2,6-dimethyl-4-(heptafluoro isopropyl)phenyl |
| 1489 | 4-methylphenyl | Me | Me | H | H | 2,6-dimethyl-4-(heptafluoro isopropyl)phenyl |
| 1490 | 2-fluorophenyl | Me | Me | H | H | 2,6-dimethyl-4-(heptafluoro isopropyl)phenyl |
| 1491 | 3-fluorophenyl | Me | Me | H | H | 2,6-dimethyl-4-(heptafluoro isopropyl)phenyl |
| 1492 | 4-fluorophenyl | Me | Me | H | H | 2,6-dimethyl-4-(heptafluoro isopropyl)phenyl |
| 1493 | 2-chlorophenyl | Me | Me | H | H | 2,6-dimethyl-4-(heptafluoro isopropyl)phenyl |
| 1494 | 4-chlorophenyl | Me | Me | H | H | 2,6-dimethyl-4-(heptafluoro isopropyl)phenyl |
| 1495 | 2-bromophenyl | Me | Me | H | H | 2,6-dimethyl-4-(heptafluoro isopropyl)phenyl |
| 1496 | 2-iodophenyl | Me | Me | H | H | 2,6-dimethyl-4-(heptafluoro isopropyl)phenyl |
| 1497 | 3-cyanophenyl | Me | Me | H | H | 2,6-dimethyl-4-(heptafluoro isopropyl)phenyl |
| 1498 | 4-cyanophenyl | Me | Me | H | H | 2,6-dimethyl-4-(heptafluoro isopropyl)phenyl |
| 1499 | 2-nitrophenyl | Me | Me | H | H | 2,6-dimethyl-4-(heptafluoro isopropyl)phenyl |
| 1500 | 3-nitrophenyl | Me | Me | H | H | 2,6-dimethyl-4-(heptafluoro isopropyl)phenyl |
| 1501 | 4-nitrophenyl | Me | Me | H | H | 2,6-dimethyl-4-(heptafluoro isopropyl)phenyl |
| 1502 | 2-trifluoromethylphenyl | Me | Me | H | H | 2,6-dimethyl-4-(heptafluoro isopropyl)phenyl |
| 1503 | 4-trifluoromethylphenyl | Me | Me | H | H | 2,6-dimethyl-4-(heptafluoro isopropyl)phenyl |
| 1504 | 4-trifluoromethoxyphenyl | Me | Me | H | H | 2,6-dimethyl-4-(heptafluoro isopropyl)phenyl |
| 1505 | 2,3-difluorophenyl | Me | Me | H | H | 2,6-dimethyl-4-(heptafluoro isopropyl)phenyl |
| 1506 | 2,4-difluorophenyl | Me | Me | H | H | 2,6-dimethyl-4-(heptafluoro isopropyl)phenyl |
| 1507 | 2,5-difluorophenyl | Me | Me | H | H | 2,6-dimethyl-4-(heptafluoro isopropyl)phenyl |
| 1508 | 2,6-difluorophenyl | Me | Me | H | H | 2,6-dimethyl-4-(heptafluoro isopropyl)phenyl |
| 1509 | 2,4-dichlorophenyl | Me | Me | H | H | 2,6-dimethyl-4-(heptafluoro isopropyl)phenyl |
| 1510 | 2,6-dichlorophenyl | Me | Me | H | H | 2,6-dimethyl-4-(heptafluoro isopropyl)phenyl |
| 1511 | 3,4-dichlorophenyl | Me | Me | H | H | 2,6-dimethyl-4-(heptafluoro isopropyl)phenyl |
| 1512 | 2-chloro-4-nitrophenyl | Me | Me | H | H | 2,6-dimethyl-4-(heptafluoro isopropyl)phenyl |
| 1513 | 2-chloro-4-fluorophenyl | Me | Me | H | H | 2,6-dimethyl-4-(heptafluoro isopropyl)phenyl |
| 1514 | 2-chloro-6-fluorophenyl | Me | Me | H | H | 2,6-dimethyl-4-(heptafluoro isopropyl)phenyl |
| 1515 | 4-chloro-2-fluorophenyl | Me | Me | H | H | 2,6-dimethyl-4-(heptafluoro isopropyl)phenyl |

TABLE 3-continued

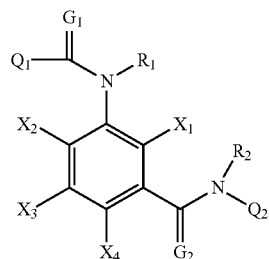

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1516 | 4-chloro-2-nitrophenyl | Me | Me | H | H | 2,6-dimethyl-4-(heptafluoro isopropyl)phenyl |
| 1517 | 2,3,6-trifluorophenyl | Me | Me | H | H | 2,6-dimethyl-4-(heptafluoro isopropyl)phenyl |
| 1518 | pyridin-2-yl | Me | Me | H | H | 2,6-dimethyl-4-(heptafluoro isopropyl)phenyl |
| 1519 | pyridin-3-yl | Me | Me | H | H | 2,6-dimethyl-4-(heptafluoro isopropyl)phenyl |
| 1520 | 2-fluoropyridin-3-yl | Me | Me | H | H | 2,6-dimethyl-4-(heptafluoro isopropyl)phenyl |
| 1521 | 2-chloropyridin-3-yl | Me | Me | H | H | 2,6-dimethyl-4-(heptafluoro isopropyl)phenyl |
| 1522 | 2-chloropyridin-5-yl | Me | Me | H | H | 2,6-dimethyl-4-(heptafluoro isopropyl)phenyl |
| 1523 | 2-methylthiopyridin-3-yl | Me | Me | H | H | 2,6-dimethyl-4-(heptafluoro isopropyl)phenyl |
| 1524 | pyrazin-2-yl | Me | Me | H | H | 2,6-dimethyl-4-(heptafluoro isopropyl)phenyl |
| 1525 | furan-2-yl | Me | Me | H | H | 2,6-dimethyl-4-(heptafluoro isopropyl)phenyl |
| 1526 | thiophen-2-yl | Me | Me | H | H | 2,6-dimethyl-4-(heptafluoro isopropyl)phenyl |
| 1527 | phenyl | Me | Me | H | H | 2-bromo-4-(heptafluoroisopropyl)-6-(methylsulfonyl)phenyl |
| 1528 | 2-methylphenyl | Me | Me | H | H | 2-bromo-4-(heptafluoroisopropyl)-6-(methylsulfonyl)phenyl |
| 1529 | 4-methylphenyl | Me | Me | H | H | 2-bromo-4-(heptafluoroisopropyl)-6-(methylsulfonyl)phenyl |
| 1530 | 2-fluorophenyl | Me | Me | H | H | 2-bromo-4-(heptafluoroisopropyl)-6-(methylsulfonyl)phenyl |
| 1531 | 3-fluorophenyl | Me | Me | H | H | 2-bromo-4-(heptafluoroisopropyl)-6-(methylsulfonyl)phenyl |
| 1532 | 4-fluorophenyl | Me | Me | H | H | 2-bromo-4-(heptafluoroisopropyl)-6-(methylsulfonyl)phenyl |
| 1533 | 2-chlorophenyl | Me | Me | H | H | 2-bromo-4-(heptafluoroisopropyl)-6-(methylsulfonyl)phenyl |
| 1534 | 4-chlorophenyl | Me | Me | H | H | 2-bromo-4-(heptafluoroisopropyl)-6-(methylsulfonyl)phenyl |
| 1535 | 2-bromophenyl | Me | Me | H | H | 2-bromo-4-(heptafluoroisopropyl)-6-(methylsulfonyl)phenyl |
| 1536 | 2-iodophenyl | Me | Me | H | H | 2-bromo-4-(heptafluoroisopropyl)-6-(methylsulfonyl)phenyl |
| 1537 | 3-cyanophenyl | Me | Me | H | H | 2-bromo-4-(heptafluoroisopropyl)-6-(methylsulfonyl)phenyl |
| 1538 | 4-cyanophenyl | Me | Me | H | H | 2-bromo-4-(heptafluoroisopropyl)-6-(methylsulfonyl)phenyl |
| 1539 | 2-nitrophenyl | Me | Me | H | H | 2-bromo-4-(heptafluoroisopropyl)-6-(methylsulfonyl)phenyl |
| 1540 | 3-nitrophenyl | Me | Me | H | H | 2-bromo-4-(heptafluoroisopropyl)-6-(methylsulfonyl)phenyl |
| 1541 | 4-nitrophenyl | Me | Me | H | H | 2-bromo-4-(heptafluoroisopropyl)-6-(methylsulfonyl)phenyl |
| 1542 | 2-trifluoromethylphenyl | Me | Me | H | H | 2-bromo-4-(heptafluoroisopropyl)-6-(methylsulfonyl)phenyl |
| 1543 | 4-trifluoromethylphenyl | Me | Me | H | H | 2-bromo-4-(heptafluoroisopropyl)-6-(methylsulfonyl)phenyl |
| 1544 | 4-trifluoromethoxyphenyl | Me | Me | H | H | 2-bromo-4-(heptafluoroisopropyl)-6-(methylsulfonyl)phenyl |
| 1545 | 2,3-difluorophenyl | Me | Me | H | H | 2-bromo-4-(heptafluoroisopropyl)-6-(methylsulfonyl)phenyl |
| 1546 | 2,4-difluorophenyl | Me | Me | H | H | 2-bromo-4-(heptafluoroisopropyl)-6-(methylsulfonyl)phenyl |

TABLE 3-continued

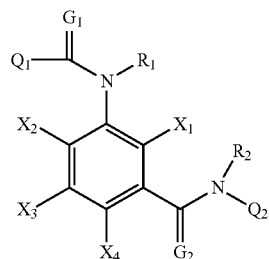

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1547 | 2,5-difluorophenyl | Me | Me | H | H | 2-bromo-4-(heptafluoroisopropyl)-6-(methylsulfonyl)phenyl |
| 1548 | 2,6-difluorophenyl | Me | Me | H | H | 2-bromo-4-(heptafluoroisopropyl)-6-(methylsulfonyl)phenyl |
| 1549 | 2,4-dichlorophenyl | Me | Me | H | H | 2-bromo-4-(heptafluoroisopropyl)-6-(methylsulfonyl)phenyl |
| 1550 | 2,6-dichlorophenyl | Me | Me | H | H | 2-bromo-4-(heptafluoroisopropyl)-6-(methylsulfonyl)phenyl |
| 1551 | 3,4-dichlorophenyl | Me | Me | H | H | 2-bromo-4-(heptafluoroisopropyl)-6-(methylsulfonyl)phenyl |
| 1552 | 2-chloro-4-nitrophenyl | Me | Me | H | H | 2-bromo-4-(heptafluoroisopropyl)-6-(methylsulfonyl)phenyl |
| 1553 | 2-chloro-4-fluorophenyl | Me | Me | H | H | 2-bromo-4-(heptafluoroisopropyl)-6-(methylsulfonyl)phenyl |
| 1554 | 2-chloro-6-fluorophenyl | Me | Me | H | H | 2-bromo-4-(heptafluoroisopropyl)-6-(methylsulfonyl)phenyl |
| 1555 | 4-chloro-2-fluorophenyl | Me | Me | H | H | 2-bromo-4-(heptafluoroisopropyl)-6-(methylsulfonyl)phenyl |
| 1556 | 4-chloro-2-nitrophenyl | Me | Me | H | H | 2-bromo-4-(heptafluoroisopropyl)-6-(methylsulfonyl)phenyl |
| 1557 | 2,3,6-trifluorophenyl | Me | Me | H | H | 2-bromo-4-(heptafluoroisopropyl)-6-(methylsulfonyl)phenyl |
| 1558 | pyridin-2-yl | Me | Me | H | H | 2-bromo-4-(heptafluoroisopropyl)-6-(methylsulfonyl)phenyl |
| 1559 | pyridin-3-yl | Me | Me | H | H | 2-bromo-4-(heptafluoroisopropyl)-6-(methylsulfonyl)phenyl |
| 1560 | 2-fluoropyridin-3-yl | Me | Me | H | H | 2-bromo-4-(heptafluoroisopropyl)-6-(methylsulfonyl)phenyl |
| 1561 | 2-chloropyridin-3-yl | Me | Me | H | H | 2-bromo-4-(heptafluoroisopropyl)-6-(methylsulfonyl)phenyl |
| 1562 | 2-chloropyridin-5-yl | Me | Me | H | H | 2-bromo-4-(heptafluoroisopropyl)-6-(methylsulfonyl)phenyl |
| 1563 | 2-methylthiopyridin-3-yl | Me | Me | H | H | 2-bromo-4-(heptafluoroisopropyl)-6-(methylsulfonyl)phenyl |
| 1564 | pyrazin-2-yl | Me | Me | H | H | 2-bromo-4-(heptafluoroisopropyl)-6-(methylsulfonyl)phenyl |
| 1565 | furan-2-yl | Me | Me | H | H | 2-bromo-4-(heptafluoroisopropyl)-6-(methylsulfonyl)phenyl |
| 1566 | thiophen-2-yl | Me | Me | H | H | 2-bromo-4-(heptafluoroisopropyl)-6-(methylsulfonyl)phenyl |
| 1567 | phenyl | Me | Me | H | H | 2-n-propyl-6-iodo-4-(heptafluoro-isopropyl)phenyl |
| 1568 | 2-methylphenyl | Me | Me | H | H | 2-n-propyl-6-iodo-4-(heptafluoro-isopropyl)phenyl |
| 1569 | 4-methylphenyl | Me | Me | H | H | 2-n-propyl-6-iodo-4-(heptafluoro-isopropyl)phenyl |
| 1570 | 2-fluorophenyl | Me | Me | H | H | 2-n-propyl-6-iodo-4-(heptafluoro-isopropyl)phenyl |
| 1571 | 3-fluorophenyl | Me | Me | H | H | 2-n-propyl-6-iodo-4-(heptafluoro-isopropyl)phenyl |
| 1572 | 4-fluorophenyl | Me | Me | H | H | 2-n-propyl-6-iodo-4-(heptafluoro-isopropyl)phenyl |
| 1573 | 2-chlorophenyl | Me | Me | H | H | 2-n-propyl-6-iodo-4-(heptafluoro-isopropyl)phenyl |
| 1574 | 4-chlorophenyl | Me | Me | H | H | 2-n-propyl-6-iodo-4-(heptafluoro-isopropyl)phenyl |
| 1575 | 2-bromophenyl | Me | Me | H | H | 2-n-propyl-6-iodo-4-(heptafluoro-isopropyl)phenyl |
| 1576 | 2-iodophenyl | Me | Me | H | H | 2-n-propyl-6-iodo-4-(heptafluoro-isopropyl)phenyl |
| 1577 | 3-cyanophenyl | Me | Me | H | H | 2-n-propyl-6-iodo-4-(heptafluoro-isopropyl)phenyl |

TABLE 3-continued

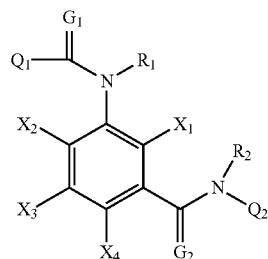

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1578 | 4-cyanophenyl | Me | Me | H | H | 2-n-propyl-6-iodo-4-(heptafluoro-isopropyl)phenyl |
| 1579 | 2-nitrophenyl | Me | Me | H | H | 2-n-propyl-6-iodo-4-(heptafluoro-isopropyl)phenyl |
| 1580 | 3-nitrophenyl | Me | Me | H | H | 2-n-propyl-6-iodo-4-(heptafluoro-isopropyl)phenyl |
| 1581 | 4-nitrophenyl | Me | Me | H | H | 2-n-propyl-6-iodo-4-(heptafluoro-isopropyl)phenyl |
| 1582 | 2-trifluoromethylphenyl | Me | Me | H | H | 2-n-propyl-6-iodo-4-(heptafluoro-isopropyl)phenyl |
| 1583 | 4-trifluoromethylphenyl | Me | Me | H | H | 2-n-propyl-6-iodo-4-(heptafluoro-isopropyl)phenyl |
| 1584 | 4-trifluoromethoxyphenyl | Me | Me | H | H | 2-n-propyl-6-iodo-4-(heptafluoro-isopropyl)phenyl |
| 1585 | 2,3-difluorophenyl | Me | Me | H | H | 2-n-propyl-6-iodo-4-(heptafluoro-isopropyl)phenyl |
| 1586 | 2,4-difluorophenyl | Me | Me | H | H | 2-n-propyl-6-iodo-4-(heptafluoro-isopropyl)phenyl |
| 1587 | 2,5-difluorophenyl | Me | Me | H | H | 2-n-propyl-6-iodo-4-(heptafluoro-isopropyl)phenyl |
| 1588 | 2,6-difluorophenyl | Me | Me | H | H | 2-n-propyl-6-iodo-4-(heptafluoro-isopropyl)phenyl |
| 1589 | 2,4-dichlorophenyl | Me | Me | H | H | 2-n-propyl-6-iodo-4-(heptafluoro-isopropyl)phenyl |
| 1590 | 2,6-dichlorophenyl | Me | Me | H | H | 2-n-propyl-6-iodo-4-(heptafluoro-isopropyl)phenyl |
| 1591 | 3,4-dichlorophenyl | Me | Me | H | H | 2-n-propyl-6-iodo-4-(heptafluoro-isopropyl)phenyl |
| 1592 | 2-chloro-4-nitrophenyl | Me | Me | H | H | 2-n-propyl-6-iodo-4-(heptafluoro-isopropyl)phenyl |
| 1593 | 2-chloro-4-fluorophenyl | Me | Me | H | H | 2-n-propyl-6-iodo-4-(heptafluoro-isopropyl)phenyl |
| 1594 | 2-chloro-6-fluorophenyl | Me | Me | H | H | 2-n-propyl-6-iodo-4-(heptafluoro-isopropyl)phenyl |
| 1595 | 4-chloro-2-fluorophenyl | Me | Me | H | H | 2-n-propyl-6-iodo-4-(heptafluoro-isopropyl)phenyl |
| 1596 | 4-chloro-2-nitrophenyl | Me | Me | H | H | 2-n-propyl-6-iodo-4-(heptafluoro-isopropyl)phenyl |
| 1597 | 2,3,6-trifluorophenyl | Me | Me | H | H | 2-n-propyl-6-iodo-4-(heptafluoro-isopropyl)phenyl |
| 1598 | pyridin-2-yl | Me | Me | H | H | 2-n-propyl-6-iodo-4-(heptafluoro-isopropyl)phenyl |
| 1599 | pyridin-3-yl | Me | Me | H | H | 2-n-propyl-6-iodo-4-(heptafluoro-isopropyl)phenyl |
| 1600 | 2-fluoropyridin-3-yl | Me | Me | H | H | 2-n-propyl-6-iodo-4-(heptafluoro-isopropyl)phenyl |
| 1601 | 2-chloropyridin-3-yl | Me | Me | H | H | 2-n-propyl-6-iodo-4-(heptafluoro-isopropyl)phenyl |
| 1602 | 2-chloropyridin-5-yl | Me | Me | H | H | 2-n-propyl-6-iodo-4-(heptafluoro-isopropyl)phenyl |
| 1603 | 2-methylthiopyridin-3-yl | Me | Me | H | H | 2-n-propyl-6-iodo-4-(heptafluoro-isopropyl)phenyl |
| 1604 | pyrazin-2-yl | Me | Me | H | H | 2-n-propyl-6-iodo-4-(heptafluoro-isopropyl)phenyl |
| 1605 | furan-2-yl | Me | Me | H | H | 2-n-propyl-6-iodo-4-(heptafluoro-isopropyl)phenyl |
| 1606 | thiophen-2-yl | Me | Me | H | H | 2-n-propyl-6-iodo-4-(heptafluoro-isopropyl)phenyl |
| 1607 | phenyl | Me | Me | H | H | 2,6-dibromo-4-(heptafluoro-n-propylthio)phenyl |
| 1608 | 2-methylphenyl | Me | Me | H | H | 2,6-dibromo-4-(heptafluoro-n-propylthio)phenyl |

TABLE 3-continued

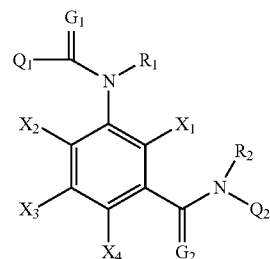

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1609 | 3-methylphenyl | Me | Me | H | H | 2,6-dibromo-4-(heptafluoro-n-propylthio)phenyl |
| 1610 | 4-methylphenyl | Me | Me | H | H | 2,6-dibromo-4-(heptafluoro-n-propylthio)phenyl |
| 1611 | 2-nitrophenyl | Me | Me | H | H | 2,6-dibromo-4-(heptafluoro-n-propylthio)phenyl |
| 1612 | 3-nitrophenyl | Me | Me | H | H | 2,6-dibromo-4-(heptafluoro-n-propylthio)phenyl |
| 1613 | 4-nitrophenyl | Me | Me | H | H | 2,6-dibromo-4-(heptafluoro-n-propylthio)phenyl |
| 1614 | 2-cyanophenyl | Me | Me | H | H | 2,6-dibromo-4-(heptafluoro-n-propylthio)phenyl |
| 1615 | 3-cyanophenyl | Me | Me | H | H | 2,6-dibromo-4-(heptafluoro-n-propylthio)phenyl |
| 1616 | 4-cyanophenyl | Me | Me | H | H | 2,6-dibromo-4-(heptafluoro-n-propylthio)phenyl |
| 1617 | 2-fluorophenyl | Me | Me | H | H | 2,6-dibromo-4-(heptafluoro-n-propylthio)phenyl |
| 1618 | 3-fluorophenyl | Me | Me | H | H | 2,6-dibromo-4-(heptafluoro-n-propylthio)phenyl |
| 1619 | 4-fluorophenyl | Me | Me | H | H | 2,6-dibromo-4-(heptafluoro-n-propylthio)phenyl |
| 1620 | 2-chlorophenyl | Me | Me | H | H | 2,6-dibromo-4-(heptafluoro-n-propylthio)phenyl |
| 1621 | 4-chlorophenyl | Me | Me | H | H | 2,6-dibromo-4-(heptafluoro-n-propylthio)phenyl |
| 1622 | 2-bromophenyl | Me | Me | H | H | 2,6-dibromo-4-(heptafluoro-n-propylthio)phenyl |
| 1623 | 2-iodophenyl | Me | Me | H | H | 2,6-dibromo-4-(heptafluoro-n-propylthio)phenyl |
| 1624 | 2-trifluoromethylphenyl | Me | Me | H | H | 2,6-dibromo-4-(heptafluoro-n-propylthio)phenyl |
| 1625 | 4-trifluoromethylphenyl | Me | Me | H | H | 2,6-dibromo-4-(heptafluoro-n-propylthio)phenyl |
| 1626 | 4-trifluoromethoxyphenyl | Me | Me | H | H | 2,6-dibromo-4-(heptafluoro-n-propylthio)phenyl |
| 1627 | 2,3-difluorophenyl | Me | Me | H | H | 2,6-dibromo-4-(heptafluoro-n-propylthio)phenyl |
| 1628 | 2,4-difluorophenyl | Me | Me | H | H | 2,6-dibromo-4-(heptafluoro-n-propylthio)phenyl |
| 1629 | 2,5-difluorophenyl | Me | Me | H | H | 2,6-dibromo-4-(heptafluoro-n-propylthio)phenyl |
| 1630 | 2,6-difluorophenyl | Me | Me | H | H | 2,6-dibromo-4-(heptafluoro-n-propylthio)phenyl |
| 1631 | 2,4-dichlorophenyl | Me | Me | H | H | 2,6-dibromo-4-(heptafluoro-n-propylthio)phenyl |
| 1632 | 2,6-dichlorophenyl | Me | Me | H | H | 2,6-dibromo-4-(heptafluoro-n-propylthio)phenyl |
| 1633 | 3,4-dichlorophenyl | Me | Me | H | H | 2,6-dibromo-4-(heptafluoro-n-propylthio)phenyl |
| 1634 | 2-fluoro-4-nitrophenyl | Me | Me | H | H | 2,6-dibromo-4-(heptafluoro-n-propylthio)phenyl |
| 1635 | 4-fluoro-2-nitrophenyl | Me | Me | H | H | 2,6-dibromo-4-(heptafluoro-n-propylthio)phenyl |
| 1636 | 2-chloro-4-fluorophenyl | Me | Me | H | H | 2,6-dibromo-4-(heptafluoro-n-propylthio)phenyl |
| 1637 | 4-chloro-2-fluorophenyl | Me | Me | H | H | 2,6-dibromo-4-(heptafluoro-n-propylthio)phenyl |
| 1638 | 2-chloro-6-fluorophenyl | Me | Me | H | H | 2,6-dibromo-4-(heptafluoro-n-propylthio)phenyl |
| 1639 | 2-chloro-4-nitrophenyl | Me | Me | H | H | 2,6-dibromo-4-(heptafluoro-n-propylthio)phenyl |

TABLE 3-continued

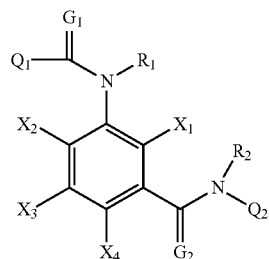

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1640 | 4-chloro-2-nitrophenyl | Me | Me | H | H | 2,6-dibromo-4-(heptafluoro-n-propylthio)phenyl |
| 1641 | 2,3,6-trifluorophenyl | Me | Me | H | H | 2,6-dibromo-4-(heptafluoro-n-propylthio)phenyl |
| 1642 | pyridin-2-yl | Me | Me | H | H | 2,6-dibromo-4-(heptafluoro-n-propylthio)phenyl |
| 1643 | pyridin-3-yl | Me | Me | H | H | 2,6-dibromo-4-(heptafluoro-n-propylthio)phenyl |
| 1644 | 2-fluoropyridin-3-yl | Me | Me | H | H | 2,6-dibromo-4-(heptafluoro-n-propylthio)phenyl |
| 1645 | 2-chloropyridin-3-yl | Me | Me | H | H | 2,6-dibromo-4-(heptafluoro-n-propylthio)phenyl |
| 1646 | 2-chloropyridin-5-yl | Me | Me | H | H | 2,6-dibromo-4-(heptafluoro-n-propylthio)phenyl |
| 1647 | 2-methylthiopyridin-3-yl | Me | Me | H | H | 2,6-dibromo-4-(heptafluoro-n-propylthio)phenyl |
| 1648 | pyrazin-2-yl | Me | Me | H | H | 2,6-dibromo-4-(heptafluoro-n-propylthio)phenyl |
| 1649 | furan-2-yl | Me | Me | H | H | 2,6-dibromo-4-(heptafluoro-n-propylthio)phenyl |
| 1650 | furan-3-yl | Me | Me | H | H | 2,6-dibromo-4-(heptafluoro-n-propylthio)phenyl |
| 1651 | 2-tetrahydrofuranyl | Me | Me | H | H | 2,6-dibromo-4-(heptafluoro-n-propylthio)phenyl |
| 1652 | benzofuran-2-yl | Me | Me | H | H | 2,6-dibromo-4-(heptafluoro-n-propylthio)phenyl |
| 1653 | thiophen-2-yl | Me | Me | H | H | 2,6-dibromo-4-(heptafluoro-n-propylthio)phenyl |
| 1654 | 3,4-dinitrophenyl | Me | Me | H | H | 2,6-dibromo-4-(heptafluoro-n-propylthio)phenyl |
| 1655 | 3-methoxy-4-nitrophenyl | Me | Me | H | H | 2,6-dibromo-4-(heptafluoro-n-propylthio)phenyl |
| 1656 | 2,3,4-trifluorophenyl | Me | Me | H | H | 2,6-dibromo-4-(heptafluoro-n-propylthio)phenyl |
| 1657 | phenyl | Me | Me | H | H | 2,6-dibromo-4-(heptafluoro-n-propylsulfinyl)phenyl |
| 1658 | 2-methylphenyl | Me | Me | H | H | 2,6-dibromo-4-(heptafluoro-n-propylsulfinyl)phenyl |
| 1659 | 4-methylphenyl | Me | Me | H | H | 2,6-dibromo-4-(heptafluoro-n-propylsulfinyl)phenyl |
| 1660 | 2-fluorophenyl | Me | Me | H | H | 2,6-dibromo-4-(heptafluoro-n-propylsulfinyl)phenyl |
| 1661 | 3-fluorophenyl | Me | Me | H | H | 2,6-dibromo-4-(heptafluoro-n-propylsulfinyl)phenyl |
| 1662 | 4-fluorophenyl | Me | Me | H | H | 2,6-dibromo-4-(heptafluoro-n-propylsulfinyl)phenyl |
| 1663 | 2-chlorophenyl | Me | Me | H | H | 2,6-dibromo-4-(heptafluoro-n-propylsulfinyl)phenyl |
| 1664 | 4-chlorophenyl | Me | Me | H | H | 2,6-dibromo-4-(heptafluoro-n-propylsulfinyl)phenyl |
| 1665 | 2-bromophenyl | Me | Me | H | H | 2,6-dibromo-4-(heptafluoro-n-propylsulfinyl)phenyl |
| 1666 | 2-iodophenyl | Me | Me | H | H | 2,6-dibromo-4-(heptafluoro-n-propylsulfinyl)phenyl |
| 1667 | 3-cyanophenyl | Me | Me | H | H | 2,6-dibromo-4-(heptafluoro-n-propylsulfinyl)phenyl |
| 1668 | 4-cyanophenyl | Me | Me | H | H | 2,6-dibromo-4-(heptafluoro-n-propylsulfinyl)phenyl |
| 1669 | 2-nitrophenyl | Me | Me | H | H | 2,6-dibromo-4-(heptafluoro-n-propylsulfinyl)phenyl |
| 1670 | 3-nitrophenyl | Me | Me | H | H | 2,6-dibromo-4-(heptafluoro-n-propylsulfinyl)phenyl |

TABLE 3-continued

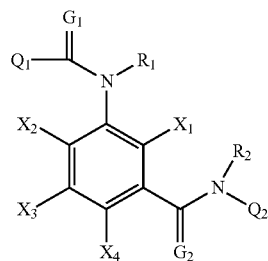

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1671 | 4-nitrophenyl | Me | Me | H | H | 2,6-dibromo-4-(heptafluoro-n-propylsulfinyl)phenyl |
| 1672 | 2-trifluoromethylphenyl | Me | Me | H | H | 2,6-dibromo-4-(heptafluoro-n-propylsulfinyl)phenyl |
| 1673 | 4-trifluoromethylphenyl | Me | Me | H | H | 2,6-dibromo-4-(heptafluoro-n-propylsulfinyl)phenyl |
| 1674 | 4-trifluoromethoxyphenyl | Me | Me | H | H | 2,6-dibromo-4-(heptafluoro-n-propylsulfinyl)phenyl |
| 1675 | 2,3-difluorophenyl | Me | Me | H | H | 2,6-dibromo-4-(heptafluoro-n-propylsulfinyl)phenyl |
| 1676 | 2,4-difluorophenyl | Me | Me | H | H | 2,6-dibromo-4-(heptafluoro-n-propylsulfinyl)phenyl |
| 1677 | 2,5-difluorophenyl | Me | Me | H | H | 2,6-dibromo-4-(heptafluoro-n-propylsulfinyl)phenyl |
| 1678 | 2,6-difluorophenyl | Me | Me | H | H | 2,6-dibromo-4-(heptafluoro-n-propylsulfinyl)phenyl |
| 1679 | 2,4-dichlorophenyl | Me | Me | H | H | 2,6-dibromo-4-(heptafluoro-n-propylsulfinyl)phenyl |
| 1680 | 2,6-dichlorophenyl | Me | Me | H | H | 2,6-dibromo-4-(heptafluoro-n-propylsulfinyl)phenyl |
| 1681 | 3,4-dichlorophenyl | Me | Me | H | H | 2,6-dibromo-4-(heptafluoro-n-propylsulfinyl)phenyl |
| 1682 | 2-chloro-4-nitrophenyl | Me | Me | H | H | 2,6-dibromo-4-(heptafluoro-n-propylsulfinyl)phenyl |
| 1683 | 2-chloro-4-fluorophenyl | Me | Me | H | H | 2,6-dibromo-4-(heptafluoro-n-propylsulfinyl)phenyl |
| 1684 | 2-chloro-6-fluorophenyl | Me | Me | H | H | 2,6-dibromo-4-(heptafluoro-n-propylsulfinyl)phenyl |
| 1685 | 4-chloro-2-fluorophenyl | Me | Me | H | H | 2,6-dibromo-4-(heptafluoro-n-propylsulfinyl)phenyl |
| 1686 | 4-chloro-2-nitrophenyl | Me | Me | H | H | 2,6-dibromo-4-(heptafluoro-n-propylsulfinyl)phenyl |
| 1687 | 2,3,6-trifluorophenyl | Me | Me | H | H | 2,6-dibromo-4-(heptafluoro-n-propylsulfinyl)phenyl |
| 1688 | pyridin-2-yl | Me | Me | H | H | 2,6-dibromo-4-(heptafluoro-n-propylsulfinyl)phenyl |
| 1689 | pyridin-3-yl | Me | Me | H | H | 2,6-dibromo-4-(heptafluoro-n-propylsulfinyl)phenyl |
| 1690 | 2-fluoropyridin-3-yl | Me | Me | H | H | 2,6-dibromo-4-(heptafluoro-n-propylsulfinyl)phenyl |
| 1691 | 2-chloropyridin-3-yl | Me | Me | H | H | 2,6-dibromo-4-(heptafluoro-n-propylsulfinyl)phenyl |
| 1692 | 2-chloropyridin-5-yl | Me | Me | H | H | 2,6-dibromo-4-(heptafluoro-n-propylsulfinyl)phenyl |
| 1693 | 2-methylthiopyridin-3-yl | Me | Me | H | H | 2,6-dibromo-4-(heptafluoro-n-propylsulfinyl)phenyl |
| 1694 | pyrazin-2-yl | Me | Me | H | H | 2,6-dibromo-4-(heptafluoro-n-propylsulfinyl)phenyl |
| 1695 | furan-2-yl | Me | Me | H | H | 2,6-dibromo-4-(heptafluoro-n-propylsulfinyl)phenyl |
| 1696 | thiophen-2-yl | Me | Me | H | H | 2,6-dibromo-4-(heptafluoro-n-propylsulfinyl)phenyl |
| 1697 | phenyl | Me | Me | F | H | 2,6-dimethyl-4-(heptafluoroisopropyl)phenyl |
| 1698 | 2-methylphenyl | Me | Me | F | H | 2,6-dimethyl-4-(heptafluoroisopropyl)phenyl |
| 1699 | 4-methylphenyl | Me | Me | F | H | 2,6-dimethyl-4-(heptafluoroisopropyl)phenyl |
| 1700 | 2-fluorophenyl | Me | Me | F | H | 2,6-dimethyl-4-(heptafluoroisopropyl)phenyl |
| 1701 | 3-fluorophenyl | Me | Me | F | H | 2,6-dimethyl-4-(heptafluoroisopropyl)phenyl |
| 1702 | 4-fluorophenyl | Me | Me | F | H | 2,6-dimethyl-4-(heptafluoroisopropyl)phenyl |
| 1703 | 2-chlorophenyl | Me | Me | F | H | 2,6-dimethyl-4-(heptafluoroisopropyl)phenyl |
| 1704 | 4-chlorophenyl | Me | Me | F | H | 2,6-dimethyl-4-(heptafluoroisopropyl)phenyl |
| 1705 | 2-bromophenyl | Me | Me | F | H | 2,6-dimethyl-4-(heptafluoroisopropyl)phenyl |
| 1706 | 2-iodophenyl | Me | Me | F | H | 2,6-dimethyl-4-(heptafluoroisopropyl)phenyl |
| 1707 | 3-cyanophenyl | Me | Me | F | H | 2,6-dimethyl-4-(heptafluoroisopropyl)phenyl |

TABLE 3-continued

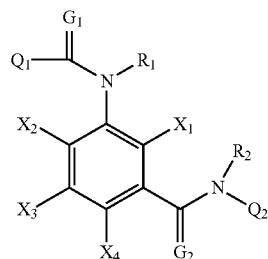

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1708 | 4-cyanophenyl | Me | Me | F | H | 2,6-dimethyl-4-(heptafluoroisopropyl)phenyl |
| 1709 | 2-nitrophenyl | Me | Me | F | H | 2,6-dimethyl-4-(heptafluoroisopropyl)phenyl |
| 1710 | 3-nitrophenyl | Me | Me | F | H | 2,6-dimethyl-4-(heptafluoroisopropyl)phenyl |
| 1711 | 4-nitrophenyl | Me | Me | F | H | 2,6-dimethyl-4-(heptafluoroisopropyl)phenyl |
| 1712 | 2-trifluoromethylphenyl | Me | Me | F | H | 2,6-dimethyl-4-(heptafluoroisopropyl)phenyl |
| 1713 | 4-trifluoromethylphenyl | Me | Me | F | H | 2,6-dimethyl-4-(heptafluoroisopropyl)phenyl |
| 1714 | 4-trifluoromethoxyphenyl | Me | Me | F | H | 2,6-dimethyl-4-(heptafluoroisopropyl)phenyl |
| 1715 | 2,3-difluorophenyl | Me | Me | F | H | 2,6-dimethyl-4-(heptafluoroisopropyl)phenyl |
| 1716 | 2,4-difluorophenyl | Me | Me | F | H | 2,6-dimethyl-4-(heptafluoroisopropyl)phenyl |
| 1717 | 2,5-difluorophenyl | Me | Me | F | H | 2,6-dimethyl-4-(heptafluoroisopropyl)phenyl |
| 1718 | 2,6-difluorophenyl | Me | Me | F | H | 2,6-dimethyl-4-(heptafluoroisopropyl)phenyl |
| 1719 | 2,4-dichlorophenyl | Me | Me | F | H | 2,6-dimethyl-4-(heptafluoroisopropyl)phenyl |
| 1720 | 2,6-dichlorophenyl | Me | Me | F | H | 2,6-dimethyl-4-(heptafluoroisopropyl)phenyl |
| 1721 | 3,4-dichlorophenyl | Me | Me | F | H | 2,6-dimethyl-4-(heptafluoroisopropyl)phenyl |
| 1722 | 2-chloro-4-nitrophenyl | Me | Me | F | H | 2,6-dimethyl-4-(heptafluoroisopropyl)phenyl |
| 1723 | 2-chloro-4-fluorophenyl | Me | Me | F | H | 2,6-dimethyl-4-(heptafluoroisopropyl)phenyl |
| 1724 | 2-chloro-6-fluorophenyl | Me | Me | F | H | 2,6-dimethyl-4-(heptafluoroisopropyl)phenyl |
| 1725 | 4-chloro-2-fluorophenyl | Me | Me | F | H | 2,6-dimethyl-4-(heptafluoroisopropyl)phenyl |
| 1726 | 4-chloro-2-nitrophenyl | Me | Me | F | H | 2,6-dimethyl-4-(heptafluoroisopropyl)phenyl |
| 1727 | 2,3,6-trifluorophenyl | Me | Me | F | H | 2,6-dimethyl-4-(heptafluoroisopropyl)phenyl |
| 1728 | pyridin-2-yl | Me | Me | F | H | 2,6-dimethyl-4-(heptafluoroisopropyl)phenyl |
| 1729 | pyridin-3-yl | Me | Me | F | H | 2,6-dimethyl-4-(heptafluoroisopropyl)phenyl |
| 1730 | 2-fluoropyridin-3-yl | Me | Me | F | H | 2,6-dimethyl-4-(heptafluoroisopropyl)phenyl |
| 1731 | 2-chloropyridin-3-yl | Me | Me | F | H | 2,6-dimethyl-4-(heptafluoroisopropyl)phenyl |
| 1732 | 2-chloropyridin-5-yl | Me | Me | F | H | 2,6-dimethyl-4-(heptafluoroisopropyl)phenyl |
| 1733 | 2-methylthiopyridin-3-yl | Me | Me | F | H | 2,6-dimethyl-4-(heptafluoroisopropyl)phenyl |
| 1734 | pyrazin-2-yl | Me | Me | F | H | 2,6-dimethyl-4-(heptafluoroisopropyl)phenyl |
| 1735 | furan-2-yl | Me | Me | F | H | 2,6-dimethyl-4-(heptafluoroisopropyl)phenyl |
| 1736 | thiophen-2-yl | Me | Me | F | H | 2,6-dimethyl-4-(heptafluoroisopropyl)phenyl |
| 1737 | phenyl | Me | Me | F | H | 2-bromo-4-(heptafluoroisopropyl)-6-(methylsulfonyl)phenyl |
| 1738 | 2-methylphenyl | Me | Me | F | H | 2-bromo-4-(heptafluoroisopropyl)-6-(methylsulfonyl)phenyl |
| 1739 | 4-methylphenyl | Me | Me | F | H | 2-bromo-4-(heptafluoroisopropyl)-6-(methylsulfonyl)phenyl |
| 1740 | 2-fluorophenyl | Me | Me | F | H | 2-bromo-4-(heptafluoroisopropyl)-6-(methylsulfonyl)phenyl |
| 1741 | 3-fluorophenyl | Me | Me | F | H | 2-bromo-4-(heptafluoroisopropyl)-6-(methylsulfonyl)phenyl |
| 1742 | 4-fluorophenyl | Me | Me | F | H | 2-bromo-4-(heptafluoroisopropyl)-6-(methylsulfonyl)phenyl |
| 1743 | 2-chlorophenyl | Me | Me | F | H | 2-bromo-4-(heptafluoroisopropyl)-6-(methylsulfonyl)phenyl |
| 1744 | 4-chlorophenyl | Me | Me | F | H | 2-bromo-4-(heptafluoroisopropyl)-6-(methylsulfonyl)phenyl |
| 1745 | 2-bromophenyl | Me | Me | F | H | 2-bromo-4-(heptafluoroisopropyl)-6-(methylsulfonyl)phenyl |
| 1746 | 2-iodophenyl | Me | Me | F | H | 2-bromo-4-(heptafluoroisopropyl)-6-(methylsulfonyl)phenyl |
| 1747 | 3-cyanophenyl | Me | Me | F | H | 2-bromo-4-(heptafluoroisopropyl)-6-(methylsulfonyl)phenyl |
| 1748 | 4-cyanophenyl | Me | Me | F | H | 2-bromo-4-(heptafluoroisopropyl)-6-(methylsulfonyl)phenyl |
| 1749 | 2-nitrophenyl | Me | Me | F | H | 2-bromo-4-(heptafluoroisopropyl)-6-(methylsulfonyl)phenyl |
| 1750 | 3-nitrophenyl | Me | Me | F | H | 2-bromo-4-(heptafluoroisopropyl)-6-(methylsulfonyl)phenyl |
| 1751 | 4-nitrophenyl | Me | Me | F | H | 2-bromo-4-(heptafluoroisopropyl)-6-(methylsulfonyl)phenyl |
| 1752 | 2-trifluoromethylphenyl | Me | Me | F | H | 2-bromo-4-(heptafluoroisopropyl)-6-(methylsulfonyl)phenyl |
| 1753 | 4-trifluoromethylphenyl | Me | Me | F | H | 2-bromo-4-(heptafluoroisopropyl)-6-(methylsulfonyl)phenyl |

TABLE 3-continued

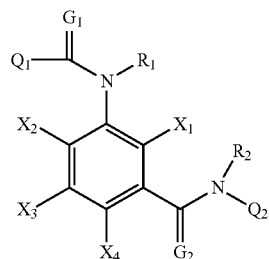

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1754 | 4-trifluoromethoxyphenyl | Me | Me | F | H | 2-bromo-4-(heptafluoroisopropyl)-6-(methylsulfonyl)phenyl |
| 1755 | 2,3-difluorophenyl | Me | Me | F | H | 2-bromo-4-(heptafluoroisopropyl)-6-(methylsulfonyl)phenyl |
| 1756 | 2,4-difluorophenyl | Me | Me | F | H | 2-bromo-4-(heptafluoroisopropyl)-6-(methylsulfonyl)phenyl |
| 1757 | 2,5-difluorophenyl | Me | Me | F | H | 2-bromo-4-(heptafluoroisopropyl)-6-(methylsulfonyl)phenyl |
| 1758 | 2,6-difluorophenyl | Me | Me | F | H | 2-bromo-4-(heptafluoroisopropyl)-6-(methylsulfonyl)phenyl |
| 1759 | 2,4-dichlorophenyl | Me | Me | F | H | 2-bromo-4-(heptafluoroisopropyl)-6-(methylsulfonyl)phenyl |
| 1760 | 2,6-dichlorophenyl | Me | Me | F | H | 2-bromo-4-(heptafluoroisopropyl)-6-(methylsulfonyl)phenyl |
| 1761 | 3,4-dichlorophenyl | Me | Me | F | H | 2-bromo-4-(heptafluoroisopropyl)-6-(methylsulfonyl)phenyl |
| 1762 | 2-chloro-4-nitrophenyl | Me | Me | F | H | 2-bromo-4-(heptafluoroisopropyl)-6-(methylsulfonyl)phenyl |
| 1763 | 2-chloro-4-fluorophenyl | Me | Me | F | H | 2-bromo-4-(heptafluoroisopropyl)-6-(methylsulfonyl)phenyl |
| 1764 | 2-chloro-6-fluorophenyl | Me | Me | F | H | 2-bromo-4-(heptafluoroisopropyl)-6-(methylsulfonyl)phenyl |
| 1765 | 4-chloro-2-fluorophenyl | Me | Me | F | H | 2-bromo-4-(heptafluoroisopropyl)-6-(methylsulfonyl)phenyl |
| 1766 | 4-chloro-2-nitrophenyl | Me | Me | F | H | 2-bromo-4-(heptafluoroisopropyl)-6-(methylsulfonyl)phenyl |
| 1767 | 2,3,6-trifluorophenyl | Me | Me | F | H | 2-bromo-4-(heptafluoroisopropyl)-6-(methylsulfonyl)phenyl |
| 1768 | pyridin-2-yl | Me | Me | F | H | 2-bromo-4-(heptafluoroisopropyl)-6-(methylsulfonyl)phenyl |
| 1769 | pyridin-3-yl | Me | Me | F | H | 2-bromo-4-(heptafluoroisopropyl)-6-(methylsulfonyl)phenyl |
| 1770 | 2-fluoropyridin-3-yl | Me | Me | F | H | 2-bromo-4-(heptafluoroisopropyl)-6-(methylsulfonyl)phenyl |
| 1771 | 2-chloropyridin-3-yl | Me | Me | F | H | 2-bromo-4-(heptafluoroisopropyl)-6-(methylsulfonyl)phenyl |
| 1772 | 2-chloropyridin-5-yl | Me | Me | F | H | 2-bromo-4-(heptafluoroisopropyl)-6-(methylsulfonyl)phenyl |
| 1773 | 2-methylthiopyridin-3-yl | Me | Me | F | H | 2-bromo-4-(heptafluoroisopropyl)-6-(methylsulfonyl)phenyl |
| 1774 | pyrazin-2-yl | Me | Me | F | H | 2-bromo-4-(heptafluoroisopropyl)-6-(methylsulfonyl)phenyl |
| 1775 | furan-2-yl | Me | Me | F | H | 2-bromo-4-(heptafluoroisopropyl)-6-(methylsulfonyl)phenyl |
| 1776 | thiophen-2-yl | Me | Me | F | H | 2-bromo-4-(heptafluoroisopropyl)-6-(methylsulfonyl)phenyl |
| 1777 | phenyl | Me | Me | F | H | 2-n-propyl-6-iodo-4-(heptafluoroisopropyl)phenyl |
| 1778 | 2-methylphenyl | Me | Me | F | H | 2-n-propyl-6-iodo-4-(heptafluoroisopropyl)phenyl |
| 1779 | 4-methylphenyl | Me | Me | F | H | 2-n-propyl-6-iodo-4-(heptafluoroisopropyl)phenyl |
| 1780 | 2-fluorophenyl | Me | Me | F | H | 2-n-propyl-6-iodo-4-(heptafluoroisopropyl)phenyl |
| 1781 | 3-fluorophenyl | Me | Me | F | H | 2-n-propyl-6-iodo-4-(heptafluoroisopropyl)phenyl |
| 1782 | 4-fluorophenyl | Me | Me | F | H | 2-n-propyl-6-iodo-4-(heptafluoroisopropyl)phenyl |
| 1783 | 2-chlorophenyl | Me | Me | F | H | 2-n-propyl-6-iodo-4-(heptafluoroisopropyl)phenyl |
| 1784 | 4-chlorophenyl | Me | Me | F | H | 2-n-propyl-6-iodo-4-(heptafluoroisopropyl)phenyl |

TABLE 3-continued

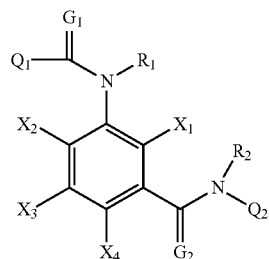

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1785 | 2-bromophenyl | Me | Me | F | H | 2-n-propyl-6-iodo-4-(heptafluoroisopropyl)phenyl |
| 1786 | 2-iodophenyl | Me | Me | F | H | 2-n-propyl-6-iodo-4-(heptafluoroisopropyl)phenyl |
| 1787 | 3-cyanophenyl | Me | Me | F | H | 2-n-propyl-6-iodo-4-(heptafluoroisopropyl)phenyl |
| 1788 | 4-cyanophenyl | Me | Me | F | H | 2-n-propyl-6-iodo-4-(heptafluoroisopropyl)phenyl |
| 1789 | 2-nitrophenyl | Me | Me | F | H | 2-n-propyl-6-iodo-4-(heptafluoroisopropyl)phenyl |
| 1790 | 3-nitrophenyl | Me | Me | F | H | 2-n-propyl-6-iodo-4-(heptafluoroisopropyl)phenyl |
| 1791 | 4-nitrophenyl | Me | Me | F | H | 2-n-propyl-6-iodo-4-(heptafluoroisopropyl)phenyl |
| 1792 | 2-trifluoromethylphenyl | Me | Me | F | H | 2-n-propyl-6-iodo-4-(heptafluoroisopropyl)phenyl |
| 1793 | 4-trifluoromethylphenyl | Me | Me | F | H | 2-n-propyl-6-iodo-4-(heptafluoroisopropyl)phenyl |
| 1794 | 4-trifluoromethoxyphenyl | Me | Me | F | H | 2-n-propyl-6-iodo-4-(heptafluoroisopropyl)phenyl |
| 1795 | 2,3-difluorophenyl | Me | Me | F | H | 2-n-propyl-6-iodo-4-(heptafluoroisopropyl)phenyl |
| 1796 | 2,4-difluorophenyl | Me | Me | F | H | 2-n-propyl-6-iodo-4-(heptafluoroisopropyl)phenyl |
| 1797 | 2,5-difluorophenyl | Me | Me | F | H | 2-n-propyl-6-iodo-4-(heptafluoroisopropyl)phenyl |
| 1798 | 2,6-difluorophenyl | Me | Me | F | H | 2-n-propyl-6-iodo-4-(heptafluoroisopropyl)phenyl |
| 1799 | 2,4-dichlorophenyl | Me | Me | F | H | 2-n-propyl-6-iodo-4-(heptafluoroisopropyl)phenyl |
| 1800 | 2,6-dichlorophenyl | Me | Me | F | H | 2-n-propyl-6-iodo-4-(heptafluoroisopropyl)phenyl |
| 1801 | 3,4-dichlorophenyl | Me | Me | F | H | 2-n-propyl-6-iodo-4-(heptafluoroisopropyl)phenyl |
| 1802 | 2-chloro-4-nitrophenyl | Me | Me | F | H | 2-n-propyl-6-iodo-4-(heptafluoroisopropyl)phenyl |
| 1803 | 2-chloro-4-fluorophenyl | Me | Me | F | H | 2-n-propyl-6-iodo-4-(heptafluoroisopropyl)phenyl |
| 1804 | 2-chloro-6-fluorophenyl | Me | Me | F | H | 2-n-propyl-6-iodo-4-(heptafluoroisopropyl)phenyl |
| 1805 | 4-chloro-2-fluorophenyl | Me | Me | F | H | 2-n-propyl-6-iodo-4-(heptafluoroisopropyl)phenyl |
| 1806 | 4-chloro-2-nitrophenyl | Me | Me | F | H | 2-n-propyl-6-iodo-4-(heptafluoroisopropyl)phenyl |
| 1807 | 2,3,6-trifluorophenyl | Me | Me | F | H | 2-n-propyl-6-iodo-4-(heptafluoroisopropyl)phenyl |
| 1808 | pyridin-2-yl | Me | Me | F | H | 2-n-propyl-6-iodo-4-(heptafluoroisopropyl)phenyl |
| 1809 | pyridin-3-yl | Me | Me | F | H | 2-n-propyl-6-iodo-4-(heptafluoroisopropyl)phenyl |
| 1810 | 2-fluoropyridin-3-yl | Me | Me | F | H | 2-n-propyl-6-iodo-4-(heptafluoroisopropyl)phenyl |
| 1811 | 2-chloropyridin-3-yl | Me | Me | F | H | 2-n-propyl-6-iodo-4-(heptafluoroisopropyl)phenyl |
| 1812 | 2-chloropyridin-5-yl | Me | Me | F | H | 2-n-propyl-6-iodo-4-(heptafluoroisopropyl)phenyl |
| 1813 | 2-methylthiopyridin-3-yl | Me | Me | F | H | 2-n-propyl-6-iodo-4-(heptafluoroisopropyl)phenyl |
| 1814 | pyrazin-2-yl | Me | Me | F | H | 2-n-propyl-6-iodo-4-(heptafluoroisopropyl)phenyl |
| 1815 | furan-2-yl | Me | Me | F | H | 2-n-propyl-6-iodo-4-(heptafluoroisopropyl)phenyl |

TABLE 3-continued

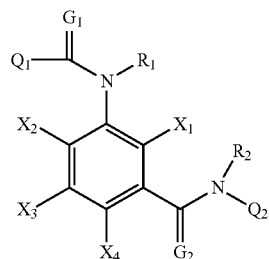

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1816 | thiophen-2-yl | Me | Me | F | H | 2-n-propyl-6-iodo-4-(heptafluoroisopropyl)phenyl |
| 1817 | phenyl | Me | Me | F | H | 2,6-dibromo-4-(heptafluoro-n-propylthio)phenyl |
| 1818 | 2-methylphenyl | Me | Me | F | H | 2,6-dibromo-4-(heptafluoro-n-propylthio)phenyl |
| 1819 | 4-methylphenyl | Me | Me | F | H | 2,6-dibromo-4-(heptafluoro-n-propylthio)phenyl |
| 1820 | 2-fluorophenyl | Me | Me | F | H | 2,6-dibromo-4-(heptafluoro-n-propylthio)phenyl |
| 1821 | 3-fluorophenyl | Me | Me | F | H | 2,6-dibromo-4-(heptafluoro-n-propylthio)phenyl |
| 1822 | 4-fluorophenyl | Me | Me | F | H | 2,6-dibromo-4-(heptafluoro-n-propylthio)phenyl |
| 1823 | 2-chlorophenyl | Me | Me | F | H | 2,6-dibromo-4-(heptafluoro-n-propylthio)phenyl |
| 1824 | 4-chlorophenyl | Me | Me | F | H | 2,6-dibromo-4-(heptafluoro-n-propylthio)phenyl |
| 1825 | 2-bromophenyl | Me | Me | F | H | 2,6-dibromo-4-(heptafluoro-n-propylthio)phenyl |
| 1826 | 2-iodophenyl | Me | Me | F | H | 2,6-dibromo-4-(heptafluoro-n-propylthio)phenyl |
| 1827 | 3-cyanophenyl | Me | Me | F | H | 2,6-dibromo-4-(heptafluoro-n-propylthio)phenyl |
| 1828 | 4-cyanophenyl | Me | Me | F | H | 2,6-dibromo-4-(heptafluoro-n-propylthio)phenyl |
| 1829 | 2-nitrophenyl | Me | Me | F | H | 2,6-dibromo-4-(heptafluoro-n-propylthio)phenyl |
| 1830 | 3-nitrophenyl | Me | Me | F | H | 2,6-dibromo-4-(heptafluoro-n-propylthio)phenyl |
| 1831 | 4-nitrophenyl | Me | Me | F | H | 2,6-dibromo-4-(heptafluoro-n-propylthio)phenyl |
| 1832 | 2-trifluoromethylphenyl | Me | Me | F | H | 2,6-dibromo-4-(heptafluoro-n-propylthio)phenyl |
| 1833 | 4-trifluoromethylphenyl | Me | Me | F | H | 2,6-dibromo-4-(heptafluoro-n-propylthio)phenyl |
| 1834 | 4-trifluoromethoxyphenyl | Me | Me | F | H | 2,6-dibromo-4-(heptafluoro-n-propylthio)phenyl |
| 1835 | 2,3-difluorophenyl | Me | Me | F | H | 2,6-dibromo-4-(heptafluoro-n-propylthio)phenyl |
| 1836 | 2,4-difluorophenyl | Me | Me | F | H | 2,6-dibromo-4-(heptafluoro-n-propylthio)phenyl |
| 1837 | 2,5-difluorophenyl | Me | Me | F | H | 2,6-dibromo-4-(heptafluoro-n-propylthio)phenyl |
| 1838 | 2,6-difluorophenyl | Me | Me | F | H | 2,6-dibromo-4-(heptafluoro-n-propylthio)phenyl |
| 1839 | 2,4-dichlorophenyl | Me | Me | F | H | 2,6-dibromo-4-(heptafluoro-n-propylthio)phenyl |
| 1840 | 2,6-dichlorophenyl | Me | Me | F | H | 2,6-dibromo-4-(heptafluoro-n-propylthio)phenyl |
| 1841 | 3,4-dichlorophenyl | Me | Me | F | H | 2,6-dibromo-4-(heptafluoro-n-propylthio)phenyl |
| 1842 | 2-chloro-4-nitrophenyl | Me | Me | F | H | 2,6-dibromo-4-(heptafluoro-n-propylthio)phenyl |
| 1843 | 2-chloro-4-fluorophenyl | Me | Me | F | H | 2,6-dibromo-4-(heptafluoro-n-propylthio)phenyl |
| 1844 | 2-chloro-6-fluorophenyl | Me | Me | F | H | 2,6-dibromo-4-(heptafluoro-n-propylthio)phenyl |
| 1845 | 4-chloro-2-fluorophenyl | Me | Me | F | H | 2,6-dibromo-4-(heptafluoro-n-propylthio)phenyl |
| 1846 | 4-chloro-2-nitrophenyl | Me | Me | F | H | 2,6-dibromo-4-(heptafluoro-n-propylthio)phenyl |

TABLE 3-continued

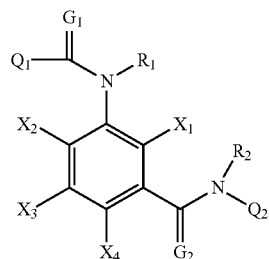

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1847 | 2,3,6-trifluorophenyl | Me | Me | F | H | 2,6-dibromo-4-(heptafluoro-n-propylthio)phenyl |
| 1848 | pyridin-2-yl | Me | Me | F | H | 2,6-dibromo-4-(heptafluoro-n-propylthio)phenyl |
| 1849 | pyridin-3-yl | Me | Me | F | H | 2,6-dibromo-4-(heptafluoro-n-propylthio)phenyl |
| 1850 | 2-fluoropyridin-3-yl | Me | Me | F | H | 2,6-dibromo-4-(heptafluoro-n-propylthio)phenyl |
| 1851 | 2-chloropyridin-3-yl | Me | Me | F | H | 2,6-dibromo-4-(heptafluoro-n-propylthio)phenyl |
| 1852 | 2-chloropyridin-5-yl | Me | Me | F | H | 2,6-dibromo-4-(heptafluoro-n-propylthio)phenyl |
| 1853 | 2-methylthiopyridin-3-yl | Me | Me | F | H | 2,6-dibromo-4-(heptafluoro-n-propylthio)phenyl |
| 1854 | pyrazin-2-yl | Me | Me | F | H | 2,6-dibromo-4-(heptafluoro-n-propylthio)phenyl |
| 1855 | furan-2-yl | Me | Me | F | H | 2,6-dibromo-4-(heptafluoro-n-propylthio)phenyl |
| 1856 | thiophen-2-yl | Me | Me | F | H | 2,6-dibromo-4-(heptafluoro-n-propylthio)phenyl |
| 1857 | phenyl | Me | Me | F | H | 2,6-dibromo-4-(heptafluoro-n-propylsulfinyl)phenyl |
| 1858 | 2-methylphenyl | Me | Me | F | H | 2,6-dibromo-4-(heptafluoro-n-propylsulfinyl)phenyl |
| 1859 | 4-methylphenyl | Me | Me | F | H | 2,6-dibromo-4-(heptafluoro-n-propylsulfinyl)phenyl |
| 1860 | 2-fluorophenyl | Me | Me | F | H | 2,6-dibromo-4-(heptafluoro-n-propylsulfinyl)phenyl |
| 1861 | 3-fluorophenyl | Me | Me | F | H | 2,6-dibromo-4-(heptafluoro-n-propylsulfinyl)phenyl |
| 1862 | 4-fluorophenyl | Me | Me | F | H | 2,6-dibromo-4-(heptafluoro-n-propylsulfinyl)phenyl |
| 1863 | 2-chlorophenyl | Me | Me | F | H | 2,6-dibromo-4-(heptafluoro-n-propylsulfinyl)phenyl |
| 1864 | 4-chlorophenyl | Me | Me | F | H | 2,6-dibromo-4-(heptafluoro-n-propylsulfinyl)phenyl |
| 1865 | 2-bromophenyl | Me | Me | F | H | 2,6-dibromo-4-(heptafluoro-n-propylsulfinyl)phenyl |
| 1866 | 2-iodophenyl | Me | Me | F | H | 2,6-dibromo-4-(heptafluoro-n-propylsulfinyl)phenyl |
| 1867 | 3-cyanophenyl | Me | Me | F | H | 2,6-dibromo-4-(heptafluoro-n-propylsulfinyl)phenyl |
| 1868 | 4-cyanophenyl | Me | Me | F | H | 2,6-dibromo-4-(heptafluoro-n-propylsulfinyl)phenyl |
| 1869 | 2-nitrophenyl | Me | Me | F | H | 2,6-dibromo-4-(heptafluoro-n-propylsulfinyl)phenyl |
| 1870 | 3-nitrophenyl | Me | Me | F | H | 2,6-dibromo-4-(heptafluoro-n-propylsulfinyl)phenyl |
| 1871 | 4-nitrophenyl | Me | Me | F | H | 2,6-dibromo-4-(heptafluoro-n-propylsulfinyl)phenyl |
| 1872 | 2-trifluoromethylphenyl | Me | Me | F | H | 2,6-dibromo-4-(heptafluoro-n-propylsulfinyl)phenyl |
| 1873 | 4-trifluoromethylphenyl | Me | Me | F | H | 2,6-dibromo-4-(heptafluoro-n-propylsulfinyl)phenyl |
| 1874 | 4-trifluoromethoxyphenyl | Me | Me | F | H | 2,6-dibromo-4-(heptafluoro-n-propylsulfinyl)phenyl |
| 1875 | 2,3-difluorophenyl | Me | Me | F | H | 2,6-dibromo-4-(heptafluoro-n-propylsulfinyl)phenyl |
| 1876 | 2,4-difluorophenyl | Me | Me | F | H | 2,6-dibromo-4-(heptafluoro-n-propylsulfinyl)phenyl |
| 1877 | 2,5-difluorophenyl | Me | Me | F | H | 2,6-dibromo-4-(heptafluoro-n-propylsulfinyl)phenyl |

TABLE 3-continued

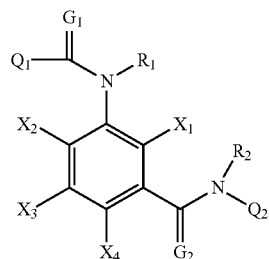

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1878 | 2,6-difluorophenyl | Me | Me | F | H | 2,6-dibromo-4-(heptafluoro-n-propylsulfinyl)phenyl |
| 1879 | 2,4-dichlorophenyl | Me | Me | F | H | 2,6-dibromo-4-(heptafluoro-n-propylsulfinyl)phenyl |
| 1880 | 2,6-dichlorophenyl | Me | Me | F | H | 2,6-dibromo-4-(heptafluoro-n-propylsulfinyl)phenyl |
| 1881 | 3,4-dichlorophenyl | Me | Me | F | H | 2,6-dibromo-4-(heptafluoro-n-propylsulfinyl)phenyl |
| 1882 | 2-chloro-4-nitrophenyl | Me | Me | F | H | 2,6-dibromo-4-(heptafluoro-n-propylsulfinyl)phenyl |
| 1883 | 2-chloro-4-fluorophenyl | Me | Me | F | H | 2,6-dibromo-4-(heptafluoro-n-propylsulfinyl)phenyl |
| 1884 | 2-chloro-6-fluorophenyl | Me | Me | F | H | 2,6-dibromo-4-(heptafluoro-n-propylsulfinyl)phenyl |
| 1885 | 4-chloro-2-fluorophenyl | Me | Me | F | H | 2,6-dibromo-4-(heptafluoro-n-propylsulfinyl)phenyl |
| 1886 | 4-chloro-2-nitrophenyl | Me | Me | F | H | 2,6-dibromo-4-(heptafluoro-n-propylsulfinyl)phenyl |
| 1887 | 2,3,6-trifluorophenyl | Me | Me | F | H | 2,6-dibromo-4-(heptafluoro-n-propylsulfinyl)phenyl |
| 1888 | pyridin-2-yl | Me | Me | F | H | 2,6-dibromo-4-(heptafluoro-n-propylsulfinyl)phenyl |
| 1889 | pyridin-3-yl | Me | Me | F | H | 2,6-dibromo-4-(heptafluoro-n-propylsulfinyl)phenyl |
| 1890 | 2-fluoropyridin-3-yl | Me | Me | F | H | 2,6-dibromo-4-(heptafluoro-n-propylsulfinyl)phenyl |
| 1891 | 2-chloropyridin-3-yl | Me | Me | F | H | 2,6-dibromo-4-(heptafluoro-n-propylsulfinyl)phenyl |
| 1892 | 2-chloropyridin-5-yl | Me | Me | F | H | 2,6-dibromo-4-(heptafluoro-n-propylsulfinyl)phenyl |
| 1893 | 2-methylthiopyridin-3-yl | Me | Me | F | H | 2,6-dibromo-4-(heptafluoro-n-propylsulfinyl)phenyl |
| 1894 | pyrazin-2-yl | Me | Me | F | H | 2,6-dibromo-4-(heptafluoro-n-propylsulfinyl)phenyl |
| 1895 | furan-2-yl | Me | Me | F | H | 2,6-dibromo-4-(heptafluoro-n-propylsulfinyl)phenyl |
| 1896 | thiophen-2-yl | Me | Me | F | H | 2,6-dibromo-4-(heptafluoro-n-propylsulfinyl)phenyl |
| 1897 | 2-fluorophenyl | Me | H | H | H | 2,6-dibromo-4-(pentafluoroethyl)phenyl |
| 1898 | 2-fluorophenyl | Me | H | H | H | 2-bromo-4-heptafluoro isopropyl)-6-methylphenyl |
| 1899 | 2-fluorophenyl | Me | H | H | H | 2-ethyl-4-(heptafluoro isopropyl)-6-methylphenyl |
| 1900 | 2-fluorophenyl | Me | H | H | H | 4-(heptafluoroisopropyl)-2-iodo-6-methylphenyl |
| 1901 | 2-fluorophenyl | Me | H | H | H | 2-chloro-6-ethyl-4-(heptafluoro isopropyl)phenyl |
| 1902 | 2-fluorophenyl | Me | H | H | H | 2-bromo-6-ethyl-4-(heptafluoro isopropyl)phenyl |
| 1903 | 2-fluorophenyl | Me | H | H | H | 2-ethyl-4-(heptafluoro isopropyl)-6-iodophenyl |
| 1904 | 2-fluorophenyl | Me | H | H | H | 4-(heptafluoroisopropyl)-2-isopropyl-6-methylphenyl |
| 1905 | 2-fluorophenyl | Me | H | H | H | 2-bromo-4-(heptafluoro isopropyl)-6-n-propylphenyl |
| 1906 | 2-fluorophenyl | Me | H | H | H | 2-bromo-4-(heptafluoroisopropyl)-6-(trifluoromethylthio)phenyl |
| 1907 | 2-fluorophenyl | Me | H | H | H | 2,6-dibromo-4-(trifluoromethylthio)phenyl |
| 1908 | 2-fluorophenyl | Me | H | H | H | 2,6-dibromo-4-(pentafluoroethylthio)phenyl |
| 1909 | 2-fluorophenyl | Me | H | H | H | 2,6-dibromo-4-(nonafluoro-n-butylthio)phenyl |
| 1910 | 2-fluorophenyl | Me | H | H | H | 2,6-dichloro-4-(heptafluoro-isopropylsulfonyl)phenyl |

TABLE 3-continued

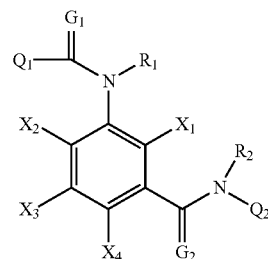

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1911 | 2-fluorophenyl | Me | H | H | H | 2,6-dibromo-4-(heptafluoro-n-propylsulfonyl)phenyl |
| 1912 | 2-fluorophenyl | Me | H | H | H | 2-bromo-6-(heptafluoroisopropyloxy)-4-methylpyridin-3-yl |
| 1913 | 2-fluorophenyl | Me | H | H | H | 2,4-dimethyl-6-(2,2,2-trifluoro-1-trifluoromethylethoxy)pyridin-3-yl |
| 1914 | 2-fluorophenyl | Me | H | H | H | 2-chloro-4-methyl-6-(2,2,2-trifluoro-1-trifluoromethylethoxy)pyridin-3-yl |
| 1915 | 2-fluorophenyl | Me | H | H | H | 2-bromo-4-methyl-6-(2,2,2-trifluoro-1-trifluoromethylethoxy)pyridin-3-yl |
| 1916 | 2-fluorophenyl | Me | H | H | H | 2-iodo-4-methyl-6-(2,2,2-trifluoro-1-trifluoromethylethoxy)pyridin-3-yl |
| 1917 | 2-fluorophenyl | Me | H | F | H | 2,6-dibromo-4-(pentafluoroethyl)phenyl |
| 1918 | 2-fluorophenyl | Me | H | F | H | 2-bromo-4-(heptafluoroisopropyl)-6-methylphenyl |
| 1919 | 2-fluorophenyl | Me | H | F | H | 2-ethyl-4-(heptafluoroisopropyl)-6-methylphenyl |
| 1920 | 2-fluorophenyl | Me | H | F | H | 4-(heptafluoroisopropyl)-2-iodo-6-methylphenyl |
| 1921 | 2-fluorophenyl | Me | H | F | H | 2-chloro-6-ethyl-4-(heptafluoroisopropyl)phenyl |
| 1922 | 2-fluorophenyl | Me | H | F | H | 2-bromo-6-ethyl-4-(heptafluoroisopropyl)phenyl |
| 1923 | 2-fluorophenyl | Me | H | F | H | 2-ethyl-4-(heptafluoroisopropyl)-6-iodophenyl |
| 1924 | 2-fluorophenyl | Me | H | F | H | 4-(heptafluoroisopropyl)-2-isopropyl-6-methylphenyl |
| 1925 | 2-fluorophenyl | Me | H | F | H | 2-bromo-4-(heptafluoroisopropyl)-6-n-propylphenyl |
| 1926 | 2-fluorophenyl | Me | H | F | H | 2-bromo-4-(heptafluoroisopropyl)-6-(trifluoromethylthio)phenyl |
| 1927 | 2-fluorophenyl | Me | H | F | H | 2,6-dibromo-4-(trifluoromethylthio)phenyl |
| 1928 | 2-fluorophenyl | Me | H | F | H | 2,6-dibromo-4-(pentafluoroethylthio)phenyl |
| 1929 | 2-fluorophenyl | Me | H | F | H | 2,6-dibromo-4-(nonafluoro-n-butylthio)phenyl |
| 1930 | 2-fluorophenyl | Me | H | F | H | 2,6-dichloro-4-(heptafluoroisopropylsulfonyl)phenyl |
| 1931 | 2-fluorophenyl | Me | H | F | H | 2,6-dibromo-4-(heptafluoro-n-propylsulfonyl)phenyl |
| 1932 | 2-fluorophenyl | Me | H | F | H | 2-bromo-6-(heptafluoroisopropyloxy)-4-methylpyridin-3-yl |
| 1933 | 2-fluorophenyl | Me | H | F | H | 2,4-dimethyl-6-(2,2,2-trifluoro-1-trifluoromethylethoxy)pyridin-3-yl |
| 1934 | 2-fluorophenyl | Me | H | F | H | 2-chloro-4-methyl-6-(2,2,2-trifluoro-1-trifluoromethylethoxy)pyridin-3-yl |
| 1935 | 2-fluorophenyl | Me | H | F | H | 2-bromo-4-methyl-6-(2,2,2-trifluoro-1-trifluoromethylethoxy)pyridin-3-yl |
| 1936 | 2-fluorophenyl | Me | H | F | H | 2-iodo-4-methyl-6-(2,2,2-trifluoro-1-trifluoromethylethoxy)pyridin-3-yl |
| 1937 | 2-fluorophenyl | Me | Me | H | H | 2,6-dibromo-4-(pentafluoroethyl)phenyl |
| 1938 | 2-fluorophenyl | Me | Me | H | H | 2-bromo-4-(heptafluoroisopropyl)-6-methylphenyl |
| 1939 | 2-fluorophenyl | Me | Me | H | H | 2-ethyl-4-(heptafluoroisopropyl)-6-methylphenyl |
| 1940 | 2-fluorophenyl | Me | Me | H | H | 4-(heptafluoroisopropyl)-2-iodo-6-methylphenyl |
| 1941 | 2-fluorophenyl | Me | Me | H | H | 2-chloro-6-ethyl-4-(heptafluoroisopropyl)phenyl |
| 1942 | 2-fluorophenyl | Me | Me | H | H | 2-bromo-6-ethyl-4-(heptafluoroisopropyl)phenyl |

TABLE 3-continued

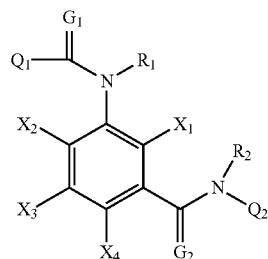

($X_3$, $X_4$ = a hydrogen atom, $G_1$, $G_2$ = an oxygen atom)

| Comp. No. | $Q_1$ | $R_1$ | $R_2$ | $X_1$ | $X_2$ | $Q_2$ |
|---|---|---|---|---|---|---|
| 1943 | 2-fluorophenyl | Me | Me | H | H | 2-ethyl-4-(heptafluoroisopropyl)-6-iodophenyl |
| 1944 | 2-fluorophenyl | Me | Me | H | H | 4-(heptafluoroisopropyl)-2-isopropyl-6-methylphenyl |
| 1945 | 2-fluorophenyl | Me | Me | H | H | 2-bromo-4-(heptafluoroisopropyl)-6-n-propylphenyl |
| 1946 | 2-fluorophenyl | Me | Me | H | H | 2-bromo-4-(heptafluoroisopropyl)-6-(trifluoromethylthio)phenyl |
| 1947 | 2-fluorophenyl | Me | Me | H | H | 2,6-dibromo-4-(trifluoromethylthio)phenyl |
| 1948 | 2-fluorophenyl | Me | Me | H | H | 2,6-dibromo-4-(pentafluoroethylthio)phenyl |
| 1949 | 2-fluorophenyl | Me | Me | H | H | 2,6-dibromo-4-(nonafluoro-n-butylthio)phenyl |
| 1950 | 2-fluorophenyl | Me | Me | H | H | 2,6-dichloro-4-(heptafluoroisopropylsulfonyl)phenyl |
| 1951 | 2-fluorophenyl | Me | Me | H | H | 2,6-dibromo-4-(heptafluoro-n-propylsulfonyl)phenyl |
| 1952 | 2-fluorophenyl | Me | Me | H | H | 2-bromo-6-(heptafluoroisopropyloxy)-4-methylpyridin-3-yl |
| 1953 | 2-fluorophenyl | Me | Me | H | H | 2,4-dimethyl-6-(2,2,2-trifluoro-1-trifluoromethylethoxy)pyridin-3-yl |
| 1954 | 2-fluorophenyl | Me | Me | H | H | 2-chloro-4-methyl-6-(2,2,2-trifluoro-1-trifluoromethylethoxy)pyridin-3-yl |
| 1955 | 2-fluorophenyl | Me | Me | H | H | 2-bromo-4-methyl-6-(2,2,2-trifluoro-1-trifluoromethylethoxy)pyridin-3-yl |
| 1956 | 2-fluorophenyl | Me | Me | H | H | 2-iodo-6-methyl-6-(2,2,2-trifluoro-1-trifluoromethylethoxy)pyridin-3-yl |
| 1957 | 2-fluorophenyl | Me | Me | F | H | 2,6-dibromo-4-(pentafluoroethyl)phenyl |
| 1958 | 2-fluorophenyl | Me | Me | F | H | 2-bromo-4-(heptafluoroisopropyl)-6-methylphenyl |
| 1959 | 2-fluorophenyl | Me | Me | F | H | 2-ethyl-4-(heptafluoroisopropyl)-6-methylphenyl |
| 1960 | 2-fluorophenyl | Me | Me | F | H | 4-(heptafluoroisopropyl)-2-iodo-6-methylphenyl |
| 1961 | 2-fluorophenyl | Me | Me | F | H | 2-chloro-6-ethyl-4-(heptafluoroisopropyl)phenyl |
| 1962 | 2-fluorophenyl | Me | Me | F | H | 2-bromo-6-ethyl-4-(heptafluoroisopropyl)phenyl |
| 1963 | 2-fluorophenyl | Me | Me | F | H | 2-ethyl-4-(heptafluoroisopropyl)-6-iodophenyl |
| 1964 | 2-fluorophenyl | Me | Me | F | H | 4-(heptafluoroisopropyl)-2-isopropyl-6-methylphenyl |
| 1965 | 2-fluorophenyl | Me | Me | F | H | 2-bromo-4-(heptafluoroisopropyl)-6-n-propylphenyl |
| 1966 | 2-fluorophenyl | Me | Me | F | H | 2-bromo-4-(heptafluoroisopropyl)-6-(trifluoromethylthio)phenyl |
| 1967 | 2-fluorophenyl | Me | Me | F | H | 2,6-dibromo-4-(trifluoromethylthio)phenyl |
| 1968 | 2-fluorophenyl | Me | Me | F | H | 2,6-dibromo-4-(pentafluoroethylthio)phenyl |
| 1969 | 2-fluorophenyl | Me | Me | F | H | 2,6-dibromo-4-(nonafluoro-n-butylthio)phenyl |
| 1970 | 2-fluorophenyl | Me | Me | F | H | 2,6-dichloro-4-(heptafluoroisopropylsulfonyl)phenyl |
| 1971 | 2-fluorophenyl | Me | Me | F | H | 2,6-dibromo-4-(heptafluoro-n-propylsulfonyl)phenyl |
| 1972 | 2-fluorophenyl | Me | Me | F | H | 2-bromo-6-(heptafluoroisopropyloxy)-4-methylpyridin-4-yl |
| 1973 | 2-fluorophenyl | Me | Me | F | H | 2,4-dimethyl-6-(2,2,2-trifluoro-1-trifluoromethylethoxy)pyridin-3-yl |
| 1974 | 2-fluorophenyl | Me | Me | F | H | 2-chloro-4-methyl-6-(2,2,2-trifluoro-1-trifluoromethylethoxy)pyridin-3-yl |
| 1975 | 2-fluorophenyl | Me | Me | F | H | 2-bromo-4-methyl-6-(2,2,2-trifluoro-1-trifluoromethylethoxy)pyridin-3-yl |
| 1976 | 2-fluorophenyl | Me | Me | F | H | 2-iodo-4-methyl-6-(2,2,2-trifluoro-1-trifluoromethylethoxy)pyridin-3-yl |

TABLE 4

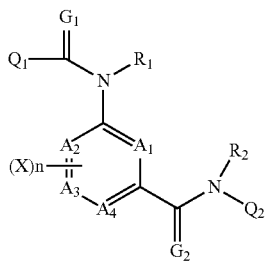

(X, R$_2$ = a hydrogen atom, A$_3$, A$_4$ = a carbon atom, G$_1$, G$_2$ = an oxygen atom, n = 0)

| Comp. No. | Q$_1$ | R$_1$ | A$_1$ | A$_2$ | Q$_2$ |
|---|---|---|---|---|---|
| 2001 | phenyl | H | N | C | 2,6-dimethyl-4-heptafluoroisopropylphenyl |
| 2002 | 2-methylphenyl | H | N | C | 2,6-dimethyl-4-heptafluoroisopropylphenyl |
| 2003 | 4-methylphenyl | H | N | C | 2,6-dimethyl-4-heptafluoroisopropylphenyl |
| 2004 | 2-fluorophenyl | H | N | C | 2,6-dimethyl-4-heptafluoroisopropylphenyl |
| 2005 | 3-fluorophenyl | H | N | C | 2,6-dimethyl-4-heptafluoroisopropylphenyl |
| 2006 | 4-fluorophenyl | H | N | C | 2,6-dimethyl-4-heptafluoroisopropylphenyl |
| 2007 | 2-chlorophenyl | H | N | C | 2,6-dimethyl-4-heptafluoroisopropylphenyl |
| 2008 | 4-chlorophenyl | H | N | C | 2,6-dimethyl-4-heptafluoroisopropylphenyl |
| 2009 | 2-bromophenyl | H | N | C | 2,6-dimethyl-4-heptafluoroisopropylphenyl |
| 2010 | 2-iodophenyl | H | N | C | 2,6-dimethyl-4-heptafluoroisopropylphenyl |
| 2011 | 3-cyanophenyl | H | N | C | 2,6-dimethyl-4-heptafluoroisopropylphenyl |
| 2012 | 4-cyanophenyl | H | N | C | 2,6-dimethyl-4-heptafluoroisopropylphenyl |
| 2013 | 2-nitrophenyl | H | N | C | 2,6-dimethyl-4-heptafluoroisopropylphenyl |
| 2014 | 3-nitrophenyl | H | N | C | 2,6-dimethyl-4-heptafluoroisopropylphenyl |
| 2015 | 4-nitrophenyl | H | N | C | 2,6-dimethyl-4-heptafluoroisopropylphenyl |
| 2016 | 2-trifluoromethylphenyl | H | N | C | 2,6-dimethyl-4-heptafluoroisopropylphenyl |
| 2017 | 4-trifluoromethylphenyl | H | N | C | 2,6-dimethyl-4-heptafluoroisopropylphenyl |
| 2018 | 4-trifluoromethoxyphenyl | H | N | C | 2,6-dimethyl-4-heptafluoroisopropylphenyl |
| 2019 | 2,3-difluorophenyl | H | N | C | 2,6-dimethyl-4-heptafluoroisopropylphenyl |
| 2020 | 2,4-difluorophenyl | H | N | C | 2,6-dimethyl-4-heptafluoroisopropylphenyl |
| 2021 | 2,5-difluorophenyl | H | N | C | 2,6-dimethyl-4-heptafluoroisopropylphenyl |
| 2022 | 2,6-difluorophenyl | H | N | C | 2,6-dimethyl-4-heptafluoroisopropylphenyl |
| 2023 | 2,4-dichlorophenyl | H | N | C | 2,6-dimethyl-4-heptafluoroisopropylphenyl |
| 2024 | 2,6-dichlorophenyl | H | N | C | 2,6-dimethyl-4-heptafluoroisopropylphenyl |
| 2025 | 3,4-dichlorophenyl | H | N | C | 2,6-dimethyl-4-heptafluoroisopropylphenyl |
| 2026 | 2-chloro-4-nitrophenyl | H | N | C | 2,6-dimethyl-4-heptafluoroisopropylphenyl |
| 2027 | 2-chloro-4-fluorophenyl | H | N | C | 2,6-dimethyl-4-heptafluoroisopropylphenyl |
| 2028 | 2-chloro-6-fluorophenyl | H | N | C | 2,6-dimethyl-4-heptafluoroisopropylphenyl |
| 2029 | 4-chloro-2-fluorophenyl | H | N | C | 2,6-dimethyl-4-heptafluoroisopropylphenyl |
| 2030 | 4-chloro-2-nitrophenyl | H | N | C | 2,6-dimethyl-4-heptafluoroisopropylphenyl |
| 2031 | 2,3,6-trifluorophenyl | H | N | C | 2,6-dimethyl-4-heptafluoroisopropylphenyl |
| 2032 | pyridin-2-yl | H | N | C | 2,6-dimethyl-4-heptafluoroisopropylphenyl |
| 2033 | pyridin-3-yl | H | N | C | 2,6-dimethyl-4-heptafluoroisopropylphenyl |
| 2034 | pyridin-4-yl | H | N | C | 2,6-dimethyl-4-heptafluoroisopropylphenyl |
| 2035 | 2-fluoropyridin-3-yl | H | N | C | 2,6-dimethyl-4-heptafluoroisopropylphenyl |
| 2036 | 2-chloropyridin-3-yl | H | N | C | 2,6-dimethyl-4-heptafluoroisopropylphenyl |
| 2037 | 2-chloropyridin-5-yl | H | N | C | 2,6-dimethyl-4-heptafluoroisopropylphenyl |
| 2038 | 2-methylthiopyridin-3-yl | H | N | C | 2,6-dimethyl-4-heptafluoroisopropylphenyl |
| 2039 | pyrazin-2-yl | H | N | C | 2,6-dimethyl-4-heptafluoroisopropylphenyl |
| 2040 | furan-2-yl | H | N | C | 2,6-dimethyl-4-heptafluoroisopropylphenyl |
| 2041 | thiophen-2-yl | H | N | C | 2,6-dimethyl-4-heptafluoroisopropylphenyl |
| 2042 | phenyl | H | N | C | 2,6-dibromo-4-(heptafluoro-n-propylthio)phenyl |
| 2043 | 2-methylphenyl | H | N | C | 2,6-dibromo-4-(heptafluoro-n-propylthio)phenyl |
| 2044 | 4-methylphenyl | H | N | C | 2,6-dibromo-4-(heptafluoro-n-propylthio)phenyl |
| 2045 | 2-fluorophenyl | H | N | C | 2,6-dibromo-4-(heptafluoro-n-propylthio)phenyl |
| 2046 | 3-fluorophenyl | H | N | C | 2,6-dibromo-4-(heptafluoro-n-propylthio)phenyl |
| 2047 | 4-fluorophenyl | H | N | C | 2,6-dibromo-4-(heptafluoro-n-propylthio)phenyl |
| 2048 | 2-chlorophenyl | H | N | C | 2,6-dibromo-4-(heptafluoro-n-propylthio)phenyl |
| 2049 | 4-chlorophenyl | H | N | C | 2,6-dibromo-4-(heptafluoro-n-propylthio)phenyl |
| 2050 | 2-bromophenyl | H | N | C | 2,6-dibromo-4-(heptafluoro-n-propylthio)phenyl |
| 2051 | 2-iodophenyl | H | N | C | 2,6-dibromo-4-(heptafluoro-n-propylthio)phenyl |
| 2052 | 3-cyanophenyl | H | N | C | 2,6-dibromo-4-(heptafluoro-n-propylthio)phenyl |
| 2053 | 4-cyanophenyl | H | N | C | 2,6-dibromo-4-(heptafluoro-n-propylthio)phenyl |
| 2054 | 2-nitrophenyl | H | N | C | 2,6-dibromo-4-(heptafluoro-n-propylthio)phenyl |
| 2055 | 3-nitrophenyl | H | N | C | 2,6-dibromo-4-(heptafluoro-n-propylthio)phenyl |
| 2056 | 4-nitrophenyl | H | N | C | 2,6-dibromo-4-(heptafluoro-n-propylthio)phenyl |
| 2057 | 2-trifluoromethylphenyl | H | N | C | 2,6-dibromo-4-(heptafluoro-n-propylthio)phenyl |

TABLE 4-continued

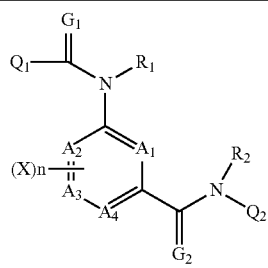

(X, $R_2$ = a hydrogen atom, $A_3$, $A_4$ = a carbon atom, $G_1$, $G_2$ = an oxygen atom, n = 0)

| Comp. No. | $Q_1$ | $R_1$ | $A_1$ | $A_2$ | $Q_2$ |
|---|---|---|---|---|---|
| 2058 | 4-trifluoromethyl-phenyl | H | N | C | 2,6-dibromo-4-(heptafluoro-n-propylthio)phenyl |
| 2059 | 4-trifluoromethoxy-phenyl | H | N | C | 2,6-dibromo-4-(heptafluoro-n-propylthio)phenyl |
| 2060 | 2,3-difluorophenyl | H | N | C | 2,6-dibromo-4-(heptafluoro-n-propylthio)phenyl |
| 2061 | 2,4-difluorophenyl | H | N | C | 2,6-dibromo-4-(heptafluoro-n-propylthio)phenyl |
| 2062 | 2,5-difluorophenyl | H | N | C | 2,6-dibromo-4-(heptafluoro-n-propylthio)phenyl |
| 2063 | 2,6-difluorophenyl | H | N | C | 2,6-dibromo-4-(heptafluoro-n-propylthio)phenyl |
| 2064 | 2,4-dichlorophenyl | H | N | C | 2,6-dibromo-4-(heptafluoro-n-propylthio)phenyl |
| 2065 | 2,6-dichlorophenyl | H | N | C | 2,6-dibromo-4-(heptafluoro-n-propylthio)phenyl |
| 2066 | 3,4-dichlorophenyl | H | N | C | 2,6-dibromo-4-(heptafluoro-n-propylthio)phenyl |
| 2067 | 2-chloro-4-nitro-phenyl | H | N | C | 2,6-dibromo-4-(heptafluoro-n-propylthio)phenyl |
| 2068 | 2-chloro-4-fluoro-phenyl | H | N | C | 2,6-dibromo-4-(heptafluoro-n-propylthio)phenyl |
| 2069 | 2-chloro-6-fluoro-phenyl | H | N | C | 2,6-dibromo-4-(heptafluoro-n-propylthio)phenyl |
| 2070 | 4-chloro-2-fluoro-phenyl | H | N | C | 2,6-dibromo-4-(heptafluoro-n-propylthio)phenyl |
| 2071 | 4-chloro-2-nitro-phenyl | H | N | C | 2,6-dibromo-4-(heptafluoro-n-propylthio)phenyl |
| 2072 | 2,3,6-trifluoro-phenyl | H | N | C | 2,6-dibromo-4-(heptafluoro-n-propylthio)phenyl |
| 2073 | pyridin-2-yl | H | N | C | 2,6-dibromo-4-(heptafluoro-n-propylthio)phenyl |
| 2074 | pyridin-3-yl | H | N | C | 2,6-dibromo-4-(heptafluoro-n-propylthio)phenyl |
| 2075 | 2-fluoropyridin-3-yl | H | N | C | 2,6-dibromo-4-(heptafluoro-n-propylthio)phenyl |
| 2076 | 2-chloropyridin-3-yl | H | N | C | 2,6-dibromo-4-(heptafluoro-n-propylthio)phenyl |
| 2077 | 2-chloropyridin-5-yl | H | N | C | 2,6-dibromo-4-(heptafluoro-n-propylthio)phenyl |
| 2078 | 2-methylthiopyridin-3-yl | H | N | C | 2,6-dibromo-4-(heptafluoro-n-propylthio)phenyl |
| 2079 | pyrazin-2-yl | H | N | C | 2,6-dibromo-4-(heptafluoro-n-propylthio)phenyl |
| 2080 | furan-2-yl | H | N | C | 2,6-dibromo-4-(heptafluoro-n-propylthio)phenyl |
| 2081 | thiophen-2-yl | H | N | C | 2,6-dibromo-4-(heptafluoro-n-propylthio)phenyl |
| 2082 | phenyl | Me | N | C | 2,6-dimethyl-4-heptafluoroisopropylphenyl |
| 2083 | 2-methylphenyl | Me | N | C | 2,6-dimethyl-4-heptafluoroisopropylphenyl |
| 2084 | 4-methylphenyl | Me | N | C | 2,6-dimethyl-4-heptafluoroisopropylphenyl |
| 2085 | 2-fluorophenyl | Me | N | C | 2,6-dimethyl-4-heptafluoroisopropylphenyl |
| 2086 | 3-fluorophenyl | Me | N | C | 2,6-dimethyl-4-heptafluoroisopropylphenyl |
| 2087 | 4-fluorophenyl | Me | N | C | 2,6-dimethyl-4-heptafluoroisopropylphenyl |
| 2088 | 2-chlorophenyl | Me | N | C | 2,6-dimethyl-4-heptafluoroisopropylphenyl |
| 2089 | 4-chlorophenyl | Me | N | C | 2,6-dimethyl-4-heptafluoroisopropylphenyl |
| 2090 | 2-bromophenyl | Me | N | C | 2,6-dimethyl-4-heptafluoroisopropylphenyl |
| 2091 | 2-iodophenyl | Me | N | C | 2,6-dimethyl-4-heptafluoroisopropylphenyl |
| 2092 | 3-cyanophenyl | Me | N | C | 2,6-dimethyl-4-heptafluoroisopropylphenyl |
| 2093 | 4-cyanophenyl | Me | N | C | 2,6-dimethyl-4-heptafluoroisopropylphenyl |
| 2094 | 2-nitrophenyl | Me | N | C | 2,6-dimethyl-4-heptafluoroisopropylphenyl |
| 2095 | 3-nitrophenyl | Me | N | C | 2,6-dimethyl-4-heptafluoroisopropylphenyl |
| 2096 | 4-nitrophenyl | Me | N | C | 2,6-dimethyl-4-heptafluoroisopropylphenyl |
| 2097 | 2-trifluoromethyl-phenyl | Me | N | C | 2,6-dimethyl-4-heptafluoroisopropylphenyl |
| 2098 | 4-trifluoromethyl-phenyl | Me | N | C | 2,6-dimethyl-4-heptafluoroisopropylphenyl |
| 2099 | 4-trifluoromethoxy-phenyl | Me | N | C | 2,6-dimethyl-4-heptafluoroisopropylphenyl |
| 2100 | 2,3-difluorophenyl | Me | N | C | 2,6-dimethyl-4-heptafluoroisopropylphenyl |
| 2101 | 2,4-difluorophenyl | Me | N | C | 2,6-dimethyl-4-heptafluoroisopropylphenyl |
| 2102 | 2,5-difluorophenyl | Me | N | C | 2,6-dimethyl-4-heptafluoroisopropylphenyl |
| 2103 | 2,6-difluorophenyl | Me | N | C | 2,6-dimethyl-4-heptafluoroisopropylphenyl |
| 2104 | 2,4-dichlorophenyl | Me | N | C | 2,6-dimethyl-4-heptafluoroisopropylphenyl |
| 2105 | 2,6-dichlorophenyl | Me | N | C | 2,6-dimethyl-4-heptafluoroisopropylphenyl |
| 2106 | 3,4-dichlorophenyl | Me | N | C | 2,6-dimethyl-4-heptafluoroisopropylphenyl |

TABLE 4-continued

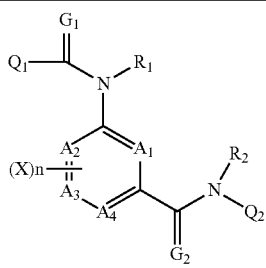

(X, $R_2$ = a hydrogen atom, $A_3$, $A_4$ = a carbon atom, $G_1$, $G_2$ = an oxygen atom, n = 0)

| Comp. No. | $Q_1$ | $R_1$ | $A_1$ | $A_2$ | $Q_2$ |
|---|---|---|---|---|---|
| 2107 | 2-chloro-4-nitro-phenyl | Me | N | C | 2,6-dimethyl-4-heptafluoroisopropylphenyl |
| 2108 | 2-chloro-4-fluoro-phenyl | Me | N | C | 2,6-dimethyl-4-heptafluoroisopropylphenyl |
| 2109 | 2-chloro-6-fluoro-phenyl | Me | N | C | 2,6-dimethyl-4-heptafluoroisopropylphenyl |
| 2110 | 4-chloro-2-fluoro-phenyl | Me | N | C | 2,6-dimethyl-4-heptafluoroisopropylphenyl |
| 2111 | 4-chloro-2-nitro-phenyl | Me | N | C | 2,6-dimethyl-4-heptafluoroisopropylphenyl |
| 2112 | 2,3,6-trifluoro-phenyl | Me | N | C | 2,6-dimethyl-4-heptafluoroisopropylphenyl |
| 2113 | pyridin-2-yl | Me | N | C | 2,6-dimethyl-4-heptafluoroisopropylphenyl |
| 2114 | pyridin-3-yl | Me | N | C | 2,6-dimethyl-4-heptafluoroisopropylphenyl |
| 2115 | 2-fluoropyridin-3-yl | Me | N | C | 2,6-dimethyl-4-heptafluoroisopropylphenyl |
| 2116 | 2-chloropyridin-3-yl | Me | N | C | 2,6-dimethyl-4-heptafluoroisopropylphenyl |
| 2117 | 2-chloropyridin-5-yl | Me | N | C | 2,6-dimethyl-4-heptafluoroisopropylphenyl |
| 2118 | 2-methylthiopyridin-3-yl | Me | N | C | 2,6-dimethyl-4-heptafluoroisopropylphenyl |
| 2119 | pyrazin-2-yl | Me | N | C | 2,6-dimethyl-4-heptafluoroisopropylphenyl |
| 2120 | furan-2-yl | Me | N | C | 2,6-dimethyl-4-heptafluoroisopropylphenyl |
| 2121 | thiophen-2-yl | Me | N | C | 2,6-dimethyl-4-heptafluoroisopropylphenyl |
| 2122 | phenyl | Me | N | C | 2,6-dibromo-4-(heptafluoro-n-propylthio)phenyl |
| 2123 | 2-methylphenyl | Me | N | C | 2,6-dibromo-4-(heptafluoro-n-propylthio)phenyl |
| 2124 | 4-methylphenyl | Me | N | C | 2,6-dibromo-4-(heptafluoro-n-propylthio)phenyl |
| 2125 | 2-fluorophenyl | Me | N | C | 2,6-dibromo-4-(heptafluoro-n-propylthio)phenyl |
| 2126 | 3-fluorophenyl | Me | N | C | 2,6-dibromo-4-(heptafluoro-n-propylthio)phenyl |
| 2127 | 4-fluorophenyl | Me | N | C | 2,6-dibromo-4-(heptafluoro-n-propylthio)phenyl |
| 2128 | 2-chlorophenyl | Me | N | C | 2,6-dibromo-4-(heptafluoro-n-propylthio)phenyl |
| 2129 | 4-chlorophenyl | Me | N | C | 2,6-dibromo-4-(heptafluoro-n-propylthio)phenyl |
| 2130 | 2-bromophenyl | Me | N | C | 2,6-dibromo-4-(heptafluoro-n-propylthio)phenyl |
| 2131 | 2-iodophenyl | Me | N | C | 2,6-dibromo-4-(heptafluoro-n-propylthio)phenyl |
| 2132 | 3-cyanophenyl | Me | N | C | 2,6-dibromo-4-(heptafluoro-n-propylthio)phenyl |
| 2133 | 4-cyanophenyl | Me | N | C | 2,6-dibromo-4-(heptafluoro-n-propylthio)phenyl |
| 2134 | 2-nitrophenyl | Me | N | C | 2,6-dibromo-4-(heptafluoro-n-propylthio)phenyl |
| 2135 | 3-nitrophenyl | Me | N | C | 2,6-dibromo-4-(heptafluoro-n-propylthio)phenyl |
| 2136 | 4-nitrophenyl | Me | N | C | 2,6-dibromo-4-(heptafluoro-n-propylthio)phenyl |
| 2137 | 2-trifluoromethyl-phenyl | Me | N | C | 2,6-dibromo-4-(heptafluoro-n-propylthio)phenyl |
| 2138 | 4-trifluoromethyl-phenyl | Me | N | C | 2,6-dibromo-4-(heptafluoro-n-propylthio)phenyl |
| 2139 | 4-trifluoromethoxy-phenyl | Me | N | C | 2,6-dibromo-4-(heptafluoro-n-propylthio)phenyl |
| 2140 | 2,3-difluorophenyl | Me | N | C | 2,6-dibromo-4-(heptafluoro-n-propylthio)phenyl |
| 2141 | 2,4-difluorophenyl | Me | N | C | 2,6-dibromo-4-(heptafluoro-n-propylthio)phenyl |
| 2142 | 2,5-difluorophenyl | Me | N | C | 2,6-dibromo-4-(heptafluoro-n-propylthio)phenyl |
| 2143 | 2,6-difluorophenyl | Me | N | C | 2,6-dibromo-4-(heptafluoro-n-propylthio)phenyl |
| 2144 | 2,4-dichlorophenyl | Me | N | C | 2,6-dibromo-4-(heptafluoro-n-propylthio)phenyl |
| 2145 | 2,6-dichlorophenyl | Me | N | C | 2,6-dibromo-4-(heptafluoro-n-propylthio)phenyl |
| 2146 | 3,4-dichlorophenyl | Me | N | C | 2,6-dibromo-4-(heptafluoro-n-propylthio)phenyl |
| 2147 | 2-chloro-4-nitro-phenyl | Me | N | C | 2,6-dibromo-4-(heptafluoro-n-propylthio)phenyl |
| 2148 | 2-chloro-4-fluoro-phenyl | Me | N | C | 2,6-dibromo-4-(heptafluoro-n-propylthio)phenyl |
| 2149 | 2-chloro-6-fluoro-phenyl | Me | N | C | 2,6-dibromo-4-(heptafluoro-n-propylthio)phenyl |
| 2150 | 4-chloro-2-fluoro-phenyl | Me | N | C | 2,6-dibromo-4-(heptafluoro-n-propylthio)phenyl |
| 2151 | 4-chloro-2-nitro-phenyl | Me | N | C | 2,6-dibromo-4-(heptafluoro-n-propylthio)phenyl |

TABLE 4-continued

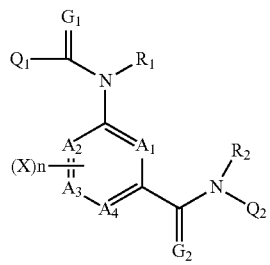

(X, $R_2$ = a hydrogen atom, $A_3$, $A_4$ = a carbon atom, $G_1$, $G_2$ = an oxygen atom, n = 0)

| Comp. No. | $Q_1$ | $R_1$ | $A_1$ | $A_2$ | $Q_2$ |
|---|---|---|---|---|---|
| 2152 | 2,3,6-trifluorophenyl | Me | N | C | 2,6-dibromo-4-(heptafluoro-n-propylthio)phenyl |
| 2153 | pyridin-2-yl | Me | N | C | 2,6-dibromo-4-(heptafluoro-n-propylthio)phenyl |
| 2154 | pyridin-3-yl | Me | N | C | 2,6-dibromo-4-(heptafluoro-n-propylthio)phenyl |
| 2155 | 2-fluoropyridin-3-yl | Me | N | C | 2,6-dibromo-4-(heptafluoro-n-propylthio)phenyl |
| 2156 | 2-chloropyridin-3-yl | Me | N | C | 2,6-dibromo-4-(heptafluoro-n-propylthio)phenyl |
| 2157 | 2-chloropyridin-5-yl | Me | N | C | 2,6-dibromo-4-(heptafluoro-n-propylthio)phenyl |
| 2158 | 2-methylthiopyridin-3-yl | Me | N | C | 2,6-dibromo-4-(heptafluoro-n-propylthio)phenyl |
| 2159 | pyrazin-2-yl | Me | N | C | 2,6-dibromo-4-(heptafluoro-n-propylthio)phenyl |
| 2160 | furan-2-yl | Me | N | C | 2,6-dibromo-4-(heptafluoro-n-propylthio)phenyl |
| 2161 | thiophen-2-yl | Me | N | C | 2,6-dibromo-4-(heptafluoro-n-propylthio)phenyl |
| 2162 | phenyl | H | C | N | 2,6-dimethyl-4-heptafluoroisopropylphenyl |
| 2163 | phenyl | H | C | N-oxide | 2,6-dimethyl-4-heptafluoroisopropylphenyl |
| 2164 | phenyl | H | N-oxide | C | 2,6-dimethyl-4-heptafluoroisopropylphenyl |
| 2165 | 2-fluorophenyl | H | N-oxide | C | 2,6-dimethyl-4-heptafluoroisopropylphenyl |
| 2166 | phenyl | H | N-oxide | C | 2,6-dibromo-4-(heptafluoro-n-propylthio)phenyl |
| 2167 | 2-fluorophenyl | H | N-oxide | C | 2,6-dibromo-4-(heptafluoro-n-propylthio)phenyl |
| 2168 | phenyl | Me | N-oxide | C | 2,6-dimethyl-4-heptafluoroisopropylphenyl |
| 2169 | 2-fluorophenyl | Me | N-oxide | C | 2,6-dimethyl-4-heptafluoroisopropylphenyl |
| 2170 | phenyl | Me | N-oxide | C | 2,6-dibromo-4-(heptafluoro-n-propylthio)phenyl |
| 2171 | 2-fluorophenyl | Me | N-oxide | C | 2,6-dibromo-4-(heptafluoro-n-propylthio)phenyl |

TABLE 5

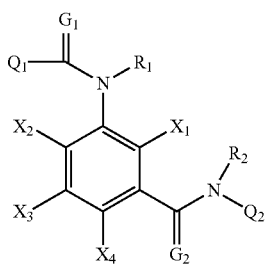

($X_1$, $X_2$, $X_3$, $X_4$, $R_1$, $R_2$ = a hydrogen atom, $Q_1$ = phenyl)

| Comp. No. | $G_1$ | $G_2$ | $Q_2$ |
|---|---|---|---|
| 2201 | O | S | 2,6-dimethyl-4-heptafluoroisopropylphenyl |
| 2202 | S | O | 2,6-dimethyl-4-heptafluoroisopropylphenyl |
| 2203 | S | S | 2,6-dimethyl-4-heptafluoroisopropylphenyl |
| 2204 | O | S | 2,6-dibromo-4-(heptafluoro-n-propylthio)phenyl |
| 2205 | S | O | 2,6-dibromo-4-(heptafluoro-n-propylthio)phenyl |
| 2206 | S | S | 2,6-dibromo-4-(heptafluoro-n-propylthio)phenyl |
| 2207 | O | S | 2,6-dimethyl-4-(nonafluoro-2-butyl)phenyl |
| 2208 | S | O | 2,6-dimethyl-4-(nonafluoro-2-butyl)phenyl |
| 2209 | S | S | 2,6-dimethyl-4-(nonafluoro-2-butyl)phenyl |
| 2210 | O | S | 2-bromo-4-(heptafluoroisopropyl)-6-(methylsulfonyl)phenyl |
| 2211 | S | O | 2-bromo-4-(heptafluoroisopropyl)-6-(methylsulfonyl)phenyl |
| 2212 | S | S | 2-bromo-4-(heptafluoroisopropyl)-6-(methylsulfonyl)phenyl |

TABLE 5-continued

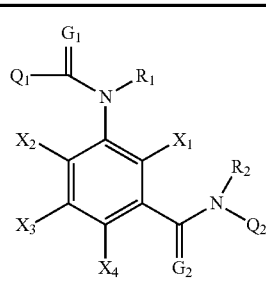

($X_1$, $X_2$, $X_3$, $X_4$, $R_1$, $R_2$ = a hydrogen atom, $Q_1$ = phenyl)

| Comp. No. | $G_1$ | $G_2$ | $Q_2$ |
|---|---|---|---|
| 2213 | O | S | 2-n-propyl-6-iodo-4-(heptafluoroisopropyl)phenyl |
| 2214 | S | O | 2-n-propyl-6-iodo-4-(heptafluoroisopropyl)phenyl |
| 2215 | S | S | 2-n-propyl-6-iodo-4-(heptafluoroisopropyl)phenyl |
| 2216 | O | S | 2,6-dibromo-4-(heptafluoro-n-propylsulfinyl)phenyl |
| 2217 | S | O | 2,6-dibromo-4-(heptafluoro-n-propylsulfinyl)phenyl |
| 2218 | S | S | 2,6-dibromo-4-(heptanuoro-n-propylsulfinyl)phenyl |
| 2219 | O | S | 2,6-dichloro-4-(heptafluoro-n-propylthio)phenyl |
| 2220 | S | O | 2,6-dichloro-4-(heptafluoro-n-propylthio)phenyl |
| 2221 | S | S | 2,6-dichloro-4-(heptafluoro-n-propylthio)phenyl |

TABLE 6

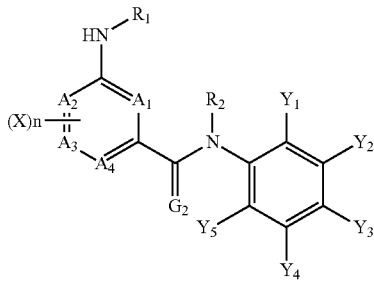

($A_1$, $A_2$, $A_3$, $A_4$ = a carbon atom, X = a hydrogen atom, n = 0, $G_2$ = an oxygen atom)

| Comp. No. | $R_1$ | $R_2$ | $Y_1$ | $Y_2$ | $Y_3$ | $Y_4$ | $Y_5$ |
|---|---|---|---|---|---|---|---|
| I-1 | H | H | Me | H | heptafluoro-n-propyl | H | Me |
| I-2 | H | H | Me | H | heptafluoroisopropyl | H | Me |
| I-3 | H | H | Me | Me | heptafluoroisopropyl | H | Cl |
| I-4 | H | H | Me | I | heptafluoroisopropyl | H | Cl |
| I-5 | H | Me | Me | H | heptafluoroisopropyl | H | Me |
| I-6 | H | i-Pr | Me | H | heptafluoroisopropyl | H | Me |
| I-7 | H | H | Et | H | heptafluoroisopropyl | H | Me |
| I-8 | H | H | Et | H | heptafluoroisopropyl | H | Et |
| I-9 | H | H | Et | H | heptafluoroisopropyl | H | I |
| I-10 | H | H | i-Pr | H | heptafluoroisopropyl | H | Me |
| I-11 | H | H | MeO | H | heptafluoroisopropyl | H | Me |
| I-12 | H | H | Cl | H | heptafluoroisopropyl | H | Et |
| I-13 | H | H | Cl | Me | heptafluoroisopropyl | H | Me |
| I-14 | H | H | Br | H | heptafluoroisopropyl | H | Me |
| I-15 | H | H | Br | H | heptafluoroisopropyl | H | Et |
| I-16 | H | H | Br | H | heptafluoroisopropyl | H | n-Pr |
| I-17 | H | H | Br | H | heptafluoroisopropyl | H | n-Bu |
| I-18 | H | H | Br | Me | heptafluoroisopropyl | H | Me |
| I-19 | H | H | I | H | heptafluoroisopropyl | H | Me |
| I-20 | H | H | I | H | heptafluoroisopropyl | H | n-Pr |
| I-21 | H | H | Me | H | nonafluoto-n-butyl | H | Me |
| I-22 | H | H | Me | H | nonafluoto-2-butyl | H | Me |
| I-23 | H | H | Br | trifluoromethylthio | H | Br |
| I-24 | H | H | Br | trifluoromethylsulfonyl | H | Br |
| I-25 | H | H | Cl | H | heptafluoroisopropylthio | H | Cl |
| I-26 | H | H | Br | H | heptafluoroisopropylthio | H | Br |
| I-27 | H | H | Cl | H | heptafluoro-n-propylthio | H | Cl |
| I-28 | H | H | Br | H | heptafluoro-n-propylthio | H | Br |
| I-29 | H | H | Cl | H | heptafluoroisopropylsulfonyl | H | Cl |
| I-30 | H | H | Br | H | nonafluoto-n-butylthio | H | Br |
| I-31 | H | H | Br | H | pentafluoroethylthio | H | Br |
| I-32 | H | H | Br | H | heptafluoro-n-propylsulfinyl | H | Br |
| I-33 | Me | H | Me | H | heptafluoro-n-propylthio | H | Me |
| I-34 | H | Me | Br | H | heptafluoro-n-propylthio | H | Br |
| I-35 | H | H | Cl | H | heptafluoroisopropyl | H | n-Bu |

TABLE 6-continued

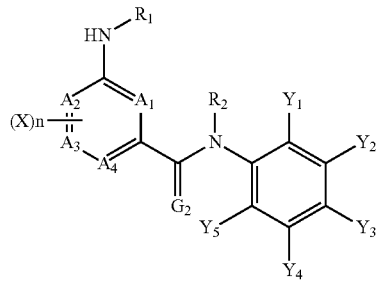

($A_1$, $A_2$, $A_3$, $A_4$ = a carbon atom, X = a hydrogen atom, n = 0, $G_2$ = an oxygen atom)

| Comp. No. | $R_1$ | $R_2$ | $Y_1$ | $Y_2$ | $Y_3$ | $Y_4$ | $Y_5$ |
|---|---|---|---|---|---|---|---|
| I-36 | H | H | I | H | heptafluoroisopropyl | H | n-Bu |
| I-37 | H | H | Br | H | pentafluoroethyl | H | Br |
| I-38 | H | H | Cl | H | heptafluoroisopropyl | H | s-Bu |
| I-39 | H | H | I | H | heptafluoroisopropyl | H | s-Bu |
| I-40 | H | H | Br | H | heptafluoroisopropyl | H | Br |
| I-41 | H | H | Cl | H | pentafluoroethyl | H | Cl |
| I-42 | H | H | Br | H | heptafluoroisopropyl | H | $MeSO_2$ |
| I-43 | Me | H | Br | H | heptafluoroisopropyl | H | $MeSO_2$ |
| I-44 | Me | Me | Br | H | heptafluoroisopropyl | H | $MeSO_2$ |
| I-45 | H | H | Br | H | heptafluoroisopropyl | H | MeSO |
| I-46 | Me | H | Br | H | heptafluoroisopropyl | H | MeSO |
| I-47 | Me | Me | Br | H | heptafluoroisopropyl | H | MeSO |
| I-48 | H | H | Br | H | heptafluoroisopropyl | H | MeS |
| I-49 | Me | H | Br | H | heptafluoroisopropyl | H | MeS |
| I-50 | Me | Me | Br | H | heptafluoroisopropyl | H | MeS |
| I-51 | Me | Me | Me | H | heptafluoroisopropyl | H | Me |
| I-52 | Me | Me | Me | H | nonafluoto-2-butyl | H | Me |
| I-53 | Me | H | I | H | heptafluoroisopropyl | H | n-Pr |
| I-54 | Me | Me | I | H | heptafluoroisopropyl | H | n-Pr |
| I-55 | Me | Me | Br | H | heptafluoro-n-propylthio | H | Br |
| I-56 | Me | H | Br | H | heptafluoro-n-propylthio | H | Br |
| I-57 | H | H | Br | H | heptafluoro-n-propylsulfinyl | H | Br |
| I-58 | Me | H | Br | H | heptafluoro-n-propylsulfinyl | H | Br |
| I-59 | Me | Me | Br | H | heptafluoro-n-propylsulfinyl | H | Br |
| I-60 | H | H | Br | H | heptafluoro-n-propylsulfonyl | H | Br |
| I-61 | Me | H | Br | H | heptafluoro-n-propylsulfonyl | H | Br |
| I-62 | Me | Me | Br | H | heptafluoro-n-propylsulfonyl | H | Br |
| I-63 | Me | Me | Cl | H | heptafluoro-n-propylthio | H | Cl |
| I-64 | Me | H | Cl | H | heptafluoro-n-propylthio | H | Cl |
| I-65 | H | H | Cl | H | heptafluoro-n-propylsulfinyl | H | Cl |
| I-66 | Me | H | Cl | H | heptafluoro-n-propylsulfinyl | H | Cl |
| I-67 | Me | Me | Cl | H | heptafluoro-n-propylsulfinyl | H | Cl |
| I-68 | H | H | Cl | H | heptafluoro-n-propylsulfonyl | H | Cl |
| I-69 | Me | H | Cl | H | heptafluoro-n-propylsulfonyl | H | Cl |
| I-70 | Me | Me | Cl | H | heptafluoro-n-propylsulfonyl | H | Cl |

TABLE 7

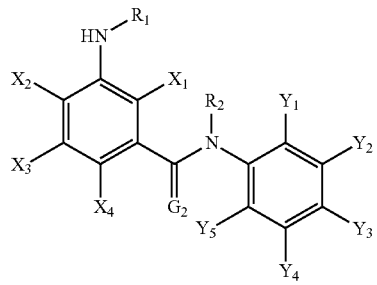

($G_2$ = an oxygen atom, $Y_2$, $Y_4$ = a hydrogen atom)

| Comp. No. | $X_1$ | $X_2$ | $X_3$ | $X_4$ | $R_1$ | $R_2$ | $Y_1$ | $Y_3$ | $Y_5$ |
|---|---|---|---|---|---|---|---|---|---|
| I-81 | Me | H | H | H | H | H | Me | heptafluoroisopropyl | Me |
| I-82 | H | Me | H | H | H | H | Me | heptafluoroisopropyl | Me |
| I-83 | H | H | H | Me | H | H | Me | heptafluoroisopropyl | Me |

TABLE 7-continued

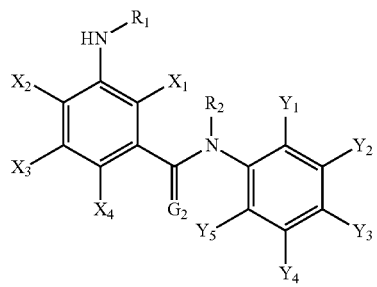

(G$_2$ = an oxygen atom, Y$_2$, Y$_4$ = a hydrogen atom)

| Comp. No. | X$_1$ | X$_2$ | X$_3$ | X$_4$ | R$_1$ | R$_2$ | Y$_1$ | Y$_3$ | Y$_5$ |
|---|---|---|---|---|---|---|---|---|---|
| I-84 | F | H | H | H | H | H | Me | heptafluoroisopropyl | Me |
| I-85 | F | H | H | H | H | H | Me | heptafluoroisopropylthio | Me |
| I-86 | H | F | H | H | H | H | Me | heptafluoroisopropyl | Me |
| I-87 | H | H | H | F | H | H | Me | heptafluoroisopropyl | Me |
| I-88 | Cl | H | H | H | H | H | Me | heptafluoroisopropyl | Me |
| I-89 | H | Cl | H | H | H | H | Me | heptafluoroisopropyl | Me |
| I-90 | H | H | H | Cl | H | H | Me | heptafluoroisopropyl | Me |
| I-91 | Br | H | H | H | H | H | Me | heptafluoroisopropyl | Me |
| I-92 | H | H | H | I | H | H | Me | heptafluoroisopropyl | Me |
| I-93 | H | H | CF$_3$ | H | H | H | Me | heptafluoroisopropyl | Me |
| I-94 | F | H | H | H | H | Me | Me | heptafluoroisopropyl | Me |
| I-95 | F | H | H | H | Me | H | Me | heptafluoroisopropyl | Me |
| I-96 | F | H | H | H | Me | Me | Me | heptafluoroisopropyl | Me |
| I-97 | F | H | H | H | H | Me | Me | nonafluoto-2-butyl | Me |
| I-98 | F | H | H | H | Me | H | Me | nonafluoto-2-butyl | Me |
| I-99 | F | H | H | H | Me | Me | Me | nonafluoto-2-butyl | Me |
| I-100 | F | H | H | H | H | Me | Br | heptafluoro-n-propylthio | Br |
| I-101 | F | H | H | H | Me | H | Br | heptafluoro-n-propylthio | Br |
| I-102 | F | H | H | H | Me | Me | Br | heptafluoro-n-propylthio | Br |
| I-103 | F | H | H | H | H | Me | Br | heptafluoro-n-propylsulfinyl | Br |
| I-104 | F | H | H | H | Me | H | Br | heptafluoro-n-propylsulfinyl | Br |
| I-105 | F | H | H | H | Me | Me | Br | heptafluoro-n-propylsulfinyl | Br |
| I-106 | F | H | H | H | H | Me | n-Pr | heptafluoroisopropyl | I |
| I-107 | F | H | H | H | Me | H | n-Pr | heptafluoroisopropyl | I |
| I-108 | F | H | H | H | Me | Me | n-Pr | heptafluoroisopropyl | I |
| I-109 | F | H | H | H | H | Me | Br | heptafluoroisopropyl | MeSO$_2$ |
| I-110 | F | H | H | H | Me | H | Br | heptafluoroisopropyl | MeSO$_2$ |
| I-111 | F | H | H | H | Me | Me | Br | heptafluoroisopropyl | MeSO$_2$ |
| I-112 | F | H | H | H | H | Me | Br | heptafluoroisopropyl | MeSO |
| I-113 | F | H | H | H | Me | H | Br | heptafluoroisopropyl | MeSO |
| I-114 | F | H | H | H | Me | Me | Br | heptafluoroisopropyl | MeSO |

TABLE 8

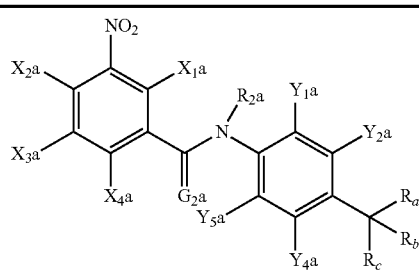

(X$_2$a, X$_3$a, X$_4$a, Y$_2$a, Y$_4$a = a hydrogen atom, Y$_1$a, Y$_5$a = a methyl group, G$_2$a = an oxygen atom)

| Comp. No. | X$_1$a | R$_2$a | R$_a$ | R$_b$ | R$_c$ |
|---|---|---|---|---|---|
| I-121 | H | H | CF$_3$ | F | OH |
| I-122 | H | H | CF$_3$ | F | Cl |
| I-123 | H | H | CF$_3$ | F | Br |
| I-124 | H | H | CF$_3$ | CF$_3$ | OH |
| I-125 | H | H | CF$_3$ | CF$_3$ | Cl |
| I-126 | H | H | CF$_3$ | CF$_3$ | Br |
| I-127 | H | H | CF$_3$ | C$_2$F$_5$ | OH |
| I-128 | H | H | CF$_3$ | C$_2$F$_5$ | Cl |
| I-129 | H | H | CF$_3$ | C$_2$F$_5$ | Br |

TABLE 8-continued

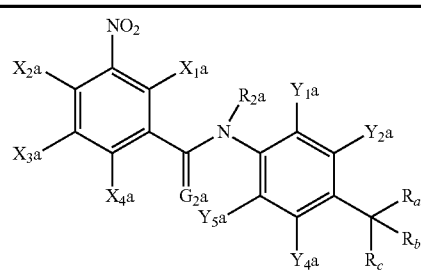

(X$_2$a, X$_3$a, X$_4$a, Y$_2$a, Y$_4$a = a hydrogen atom, Y$_1$a, Y$_5$a = a methyl group, G$_2$a = an oxygen atom)

| Comp. No. | X$_1$a | R$_2$a | R$_a$ | R$_b$ | R$_c$ |
|---|---|---|---|---|---|
| I-130 | F | H | CF$_3$ | F | OH |
| I-131 | F | H | CF$_3$ | F | Cl |
| I-132 | F | H | CF$_3$ | F | Br |
| I-133 | F | H | CF$_3$ | CF$_3$ | OH |
| I-134 | F | H | CF$_3$ | CF$_3$ | Cl |
| I-135 | F | H | CF$_3$ | CF$_3$ | Br |
| I-136 | F | H | CF$_3$ | C$_2$F$_5$ | OH |
| I-137 | F | H | CF$_3$ | C$_2$F$_5$ | Cl |
| I-138 | F | H | CF$_3$ | C$_2$F$_5$ | Br |

TABLE 8-continued

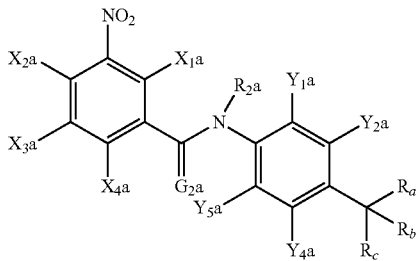

($X_2a$, $X_3a$, $X_4a$, $Y_2a$, $Y_4a$ = a hydrogen atom, $Y_1a$, $Y_5a$ = a methyl group, $G_2a$ = an oxygen atom)

| Comp. No. | $X_1a$ | $R_2a$ | $R_a$ | $R_b$ | $R_c$ |
|---|---|---|---|---|---|
| I-139 | Cl | H | $CF_3$ | F | OH |
| I-140 | Cl | H | $CF_3$ | F | Cl |
| I-141 | Cl | H | $CF_3$ | F | Br |
| I-142 | Cl | H | $CF_3$ | $CF_3$ | OH |
| I-143 | Cl | H | $CF_3$ | $CF_3$ | Cl |
| I-144 | Cl | H | $CF_3$ | $CF_3$ | Br |
| I-145 | Cl | H | $CF_3$ | $C_2F_5$ | OH |
| I-146 | Cl | H | $CF_3$ | $C_2F_5$ | Cl |
| I-147 | Cl | H | $CF_3$ | $C_2F_5$ | Br |
| I-148 | H | Me | $CF_3$ | F | OH |
| I-149 | H | Me | $CF_3$ | F | Cl |
| I-150 | H | Me | $CF_3$ | F | Br |
| I-151 | H | Me | $CF_3$ | $CF_3$ | OH |
| I-152 | H | Me | $CF_3$ | $CF_3$ | Cl |
| I-153 | H | Me | $CF_3$ | $CF_3$ | Br |
| I-154 | H | Me | $CF_3$ | $C_2F_5$ | OH |
| I-155 | H | Me | $CF_3$ | $C_2F_5$ | Cl |
| I-156 | H | Me | $CF_3$ | $C_2F_5$ | Br |
| I-157 | F | Me | $CF_3$ | F | OH |
| I-158 | F | Me | $CF_3$ | F | Cl |
| I-159 | F | Me | $CF_3$ | F | Br |
| I-160 | F | Me | $CF_3$ | $CF_3$ | OH |
| I-161 | F | Me | $CF_3$ | $CF_3$ | Cl |
| I-162 | F | Me | $CF_3$ | $CF_3$ | Br |
| I-163 | F | Me | $CF_3$ | $C_2F_5$ | OH |
| I-164 | F | Me | $CF_3$ | $C_2F_5$ | Cl |
| I-165 | F | Me | $CF_3$ | $C_2F_5$ | Br |
| I-166 | Cl | Me | $CF_3$ | F | OH |
| I-167 | Cl | Me | $CF_3$ | F | Cl |
| I-168 | Cl | Me | $CF_3$ | F | Br |
| I-169 | Cl | Me | $CF_3$ | $CF_3$ | OH |
| I-170 | Cl | Me | $CF_3$ | $CF_3$ | Cl |
| I-171 | Cl | Me | $CF_3$ | $CF_3$ | Br |
| I-172 | Cl | Me | $CF_3$ | $C_2F_5$ | OH |
| I-173 | Cl | Me | $CF_3$ | $C_2F_5$ | Cl |
| I-174 | Cl | Me | $CF_3$ | $C_2F_5$ | Br |

TABLE 9

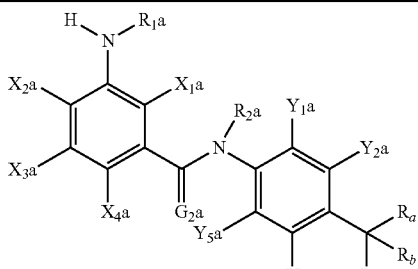

($X_2a$, $X_3a$, $X_4a$, $Y_2a$, $Y_4a$ = a hydrogen atom, $Y_1a$, $Y_5a$ = a methyl group, $G_2a$ = an oxygen atom)

| Comp. No. | $X_1a$ | $R_1a$ | $R_2a$ | $R_a$ | $R_b$ | $R_c$ |
|---|---|---|---|---|---|---|
| I-201 | H | H | H | $CF_3$ | F | OH |
| I-202 | H | H | H | $CF_3$ | F | Cl |
| I-203 | H | H | H | $CF_3$ | F | Br |

TABLE 9-continued

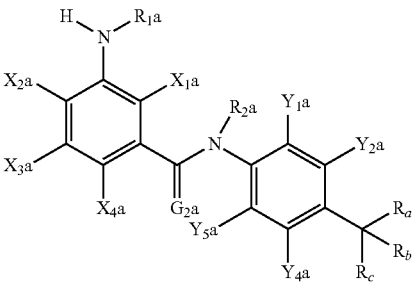

($X_2a$, $X_3a$, $X_4a$, $Y_2a$, $Y_4a$ = a hydrogen atom, $Y_1a$, $Y_5a$ = a methyl group, $G_2a$ = an oxygen atom)

| Comp. No. | $X_1a$ | $R_1a$ | $R_2a$ | $R_a$ | $R_b$ | $R_c$ |
|---|---|---|---|---|---|---|
| I-204 | H | H | H | $CF_3$ | $CF_3$ | OH |
| I-205 | H | H | H | $CF_3$ | $CF_3$ | Cl |
| I-206 | H | H | H | $CF_3$ | $CF_3$ | Br |
| I-207 | H | H | H | $CF_3$ | $C_2F_5$ | OH |
| I-208 | H | H | H | $CF_3$ | $C_2F_5$ | Cl |
| I-209 | H | H | H | $CF_3$ | $C_2F_5$ | Br |
| I-210 | F | H | H | $CF_3$ | F | OH |
| I-211 | F | H | H | $CF_3$ | F | Cl |
| I-212 | F | H | H | $CF_3$ | F | Br |
| I-213 | F | H | H | $CF_3$ | $CF_3$ | OH |
| I-214 | F | H | H | $CF_3$ | $CF_3$ | Cl |
| I-215 | F | H | H | $CF_3$ | $CF_3$ | Br |
| I-216 | F | H | H | $CF_3$ | $C_2F_5$ | OH |
| I-217 | F | H | H | $CF_3$ | $C_2F_5$ | Cl |
| I-218 | F | H | H | $CF_3$ | $C_2F_5$ | Br |
| I-219 | Cl | H | H | $CF_3$ | F | OH |
| I-220 | Cl | H | H | $CF_3$ | F | Cl |
| I-221 | Cl | H | H | $CF_3$ | F | Br |
| I-222 | Cl | H | H | $CF_3$ | $CF_3$ | OH |
| I-223 | Cl | H | H | $CF_3$ | $CF_3$ | Cl |
| I-224 | Cl | H | H | $CF_3$ | $CF_3$ | Br |
| I-225 | Cl | H | H | $CF_3$ | $C_2F_5$ | OH |
| I-226 | Cl | H | H | $CF_3$ | $C_2F_5$ | Cl |
| I-227 | Cl | H | H | $CF_3$ | $C_2F_5$ | Br |
| I-228 | H | H | Me | $CF_3$ | F | OH |
| I-229 | H | H | Me | $CF_3$ | F | Cl |
| I-230 | H | H | Me | $CF_3$ | F | Br |
| I-231 | H | H | Me | $CF_3$ | $CF_3$ | OH |
| I-232 | H | H | Me | $CF_3$ | $CF_3$ | Cl |
| I-233 | H | H | Me | $CF_3$ | $CF_3$ | Br |
| I-234 | H | H | Me | $CF_3$ | $C_2F_5$ | OH |
| I-235 | H | H | Me | $CF_3$ | $C_2F_5$ | Cl |
| I-236 | H | H | Me | $CF_3$ | $C_2F_5$ | Br |
| I-237 | F | H | Me | $CF_3$ | F | OH |
| I-238 | F | H | Me | $CF_3$ | F | Cl |
| I-239 | F | H | Me | $CF_3$ | F | Br |
| I-240 | F | H | Me | $CF_3$ | $CF_3$ | OH |
| I-241 | F | H | Me | $CF_3$ | $CF_3$ | Cl |
| I-242 | F | H | Me | $CF_3$ | $CF_3$ | Br |
| I-243 | F | H | Me | $CF_3$ | $C_2F_5$ | OH |
| I-244 | F | H | Me | $CF_3$ | $C_2F_5$ | Cl |
| I-245 | F | H | Me | $CF_3$ | $C_2F_5$ | Br |
| I-246 | Cl | H | Me | $CF_3$ | F | OH |
| I-247 | Cl | H | Me | $CF_3$ | F | Cl |
| I-248 | Cl | H | Me | $CF_3$ | F | Br |
| I-249 | Cl | H | Me | $CF_3$ | $CF_3$ | OH |
| I-250 | Cl | H | Me | $CF_3$ | $CF_3$ | Cl |
| I-251 | Cl | H | Me | $CF_3$ | $CF_3$ | Br |
| I-252 | Cl | H | Me | $CF_3$ | $C_2F_5$ | OH |
| I-253 | Cl | H | Me | $CF_3$ | $C_2F_5$ | Cl |
| I-254 | Cl | H | Me | $CF_3$ | $C_2F_5$ | Br |
| I-255 | H | Me | H | $CF_3$ | F | OH |
| I-256 | H | Me | H | $CF_3$ | F | Cl |
| I-257 | H | Me | H | $CF_3$ | F | Br |
| I-258 | H | Me | H | $CF_3$ | $CF_3$ | OH |
| I-259 | H | Me | H | $CF_3$ | $CF_3$ | Cl |
| I-260 | H | Me | H | $CF_3$ | $CF_3$ | Br |
| I-261 | H | Me | H | $CF_3$ | $C_2F_5$ | OH |
| I-262 | H | Me | H | $CF_3$ | $C_2F_5$ | Cl |
| I-263 | H | Me | H | $CF_3$ | $C_2F_5$ | Br |
| I-264 | F | Me | H | $CF_3$ | F | OH |
| I-265 | F | Me | H | $CF_3$ | F | Cl |

TABLE 9-continued

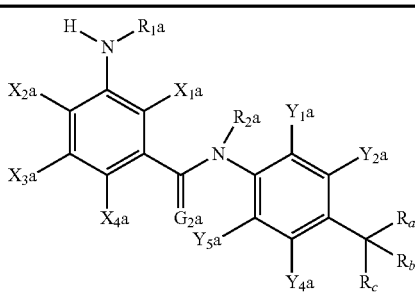

($X_2a$, $X_3a$, $X_4a$, $Y_2a$, $Y_4a$ = a hydrogen atom, $Y_1a$, $Y_5a$ = a methyl group, $G_2a$ = an oxygen atom)

| Comp. No. | $X_1a$ | $R_1a$ | $R_2a$ | $R_a$ | $R_b$ | $R_c$ |
|---|---|---|---|---|---|---|
| I-266 | F | Me | H | $CF_3$ | F | Br |
| I-267 | F | Me | H | $CF_3$ | $CF_3$ | OH |
| I-268 | F | Me | H | $CF_3$ | $CF_3$ | Cl |
| I-269 | F | Me | H | $CF_3$ | $CF_3$ | Br |
| I-270 | F | Me | H | $CF_3$ | $C_2F_5$ | OH |
| I-271 | F | Me | H | $CF_3$ | $C_2F_5$ | Cl |
| I-272 | F | Me | H | $CF_3$ | $C_2F_5$ | Br |
| I-273 | Cl | Me | H | $CF_3$ | F | OH |
| I-274 | Cl | Me | H | $CF_3$ | F | Cl |
| I-275 | Cl | Me | H | $CF_3$ | F | Br |
| I-276 | Cl | Me | H | $CF_3$ | $CF_3$ | OH |
| I-277 | Cl | Me | H | $CF_3$ | $CF_3$ | Cl |
| I-278 | Cl | Me | H | $CF_3$ | $CF_3$ | Br |
| I-279 | Cl | Me | H | $CF_3$ | $C_2F_5$ | OH |
| I-280 | Cl | Me | H | $CF_3$ | $C_2F_5$ | Cl |
| I-281 | Cl | Me | H | $CF_3$ | $C_2F_5$ | Br |
| I-282 | H | Me | Me | $CF_3$ | F | OH |
| I-283 | H | Me | Me | $CF_3$ | F | Cl |
| I-284 | H | Me | Me | $CF_3$ | F | Br |
| I-285 | H | Me | Me | $CF_3$ | $CF_3$ | OH |
| I-286 | H | Me | Me | $CF_3$ | $CF_3$ | Cl |
| I-287 | H | Me | Me | $CF_3$ | $CF_3$ | Br |

TABLE 9-continued

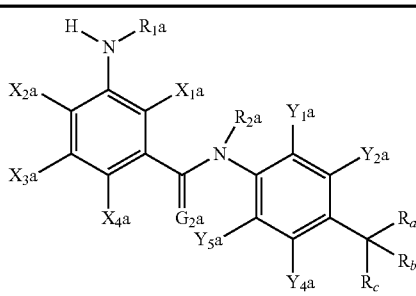

($X_2a$, $X_3a$, $X_4a$, $Y_2a$, $Y_4a$ = a hydrogen atom, $Y_1a$, $Y_5a$ = a methyl group, $G_2a$ = an oxygen atom)

| Comp. No. | $X_1a$ | $R_1a$ | $R_2a$ | $R_a$ | $R_b$ | $R_c$ |
|---|---|---|---|---|---|---|
| I-288 | H | Me | Me | $CF_3$ | $C_2F_5$ | OH |
| I-289 | H | Me | Me | $CF_3$ | $C_2F_5$ | Cl |
| I-290 | H | Me | Me | $CF_3$ | $C_2F_5$ | Br |
| I-291 | F | Me | Me | $CF_3$ | F | OH |
| I-292 | F | Me | Me | $CF_3$ | F | Cl |
| I-293 | F | Me | Me | $CF_3$ | F | Br |
| I-294 | F | Me | Me | $CF_3$ | $CF_3$ | OH |
| I-295 | F | Me | Me | $CF_3$ | $CF_3$ | Cl |
| I-296 | F | Me | Me | $CF_3$ | $CF_3$ | Br |
| I-297 | F | Me | Me | $CF_3$ | $C_2F_5$ | OH |
| I-298 | F | Me | Me | $CF_3$ | $C_2F_5$ | Cl |
| I-299 | F | Me | Me | $CF_3$ | $C_2F_5$ | Br |
| I-300 | Cl | Me | Me | $CF_3$ | F | OH |
| I-301 | Cl | Me | Me | $CF_3$ | F | Cl |
| I-302 | Cl | Me | Me | $CF_3$ | F | Br |
| I-303 | Cl | Me | Me | $CF_3$ | $CF_3$ | OH |
| I-304 | Cl | Me | Me | $CF_3$ | $CF_3$ | Cl |
| I-305 | Cl | Me | Me | $CF_3$ | $CF_3$ | Br |
| I-306 | Cl | Me | Me | $CF_3$ | $C_2F_5$ | OH |
| I-307 | Cl | Me | Me | $CF_3$ | $C_2F_5$ | Cl |
| I-308 | Cl | Me | Me | $CF_3$ | $C_2F_5$ | Br |

TABLE 10

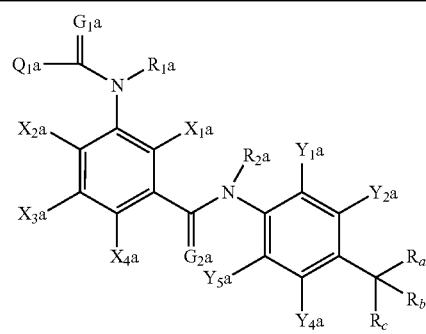

($X_2a$, $X_3a$, $X_4a$, $Y_2a$, $Y_4a$ = a hydrogen atom, $G_1a$, $G_2a$ = an oxygen atom, $R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-351 | phenyl | H | H | H | H | H | $CF_3$ | OH |
| I-352 | 2-methylphenyl | H | H | H | H | H | $CF_3$ | OH |
| I-353 | 3-methylphenyl | H | H | H | H | H | $CF_3$ | OH |
| I-354 | 4-methylphenyl | H | H | H | H | H | $CF_3$ | OH |
| I-355 | 2,3-dimethylphenyl | H | H | H | H | H | $CF_3$ | OH |
| I-356 | 2,4,6-trimethylphenyl | H | H | H | H | H | $CF_3$ | OH |
| I-357 | 4-ethylphenyl | H | H | H | H | H | $CF_3$ | OH |
| I-358 | 2-fluorophenyl | H | H | H | H | H | $CF_3$ | OH |
| I-359 | 3-fluorophenyl | H | H | H | H | H | $CF_3$ | OH |
| I-360 | 4-fluorophenyl | H | H | H | H | H | $CF_3$ | OH |
| I-361 | 2-chlorophenyl | H | H | H | H | H | $CF_3$ | OH |
| I-362 | 3-chlorophenyl | H | H | H | H | H | $CF_3$ | OH |
| I-363 | 4-chlorophenyl | H | H | H | H | H | $CF_3$ | OH |
| I-364 | 2-bromophenyl | H | H | H | H | H | $CF_3$ | OH |
| I-365 | 4-bromophenyl | H | H | H | H | H | $CF_3$ | OH |

TABLE 10-continued

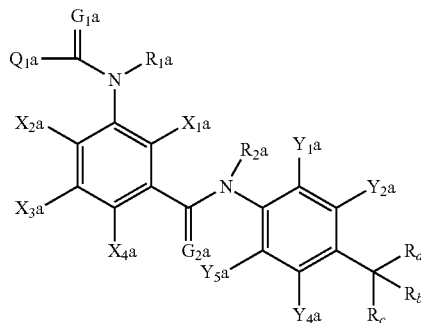

($X_2a$, $X_3a$, $X_4a$, $Y_2a$, $Y_4a$ = a hydrogen atom, $G_1a$, $G_2a$ = an oxygen atom, $R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-366 | 2-iodophenyl | H | H | H | H | H | $CF_3$ | OH |
| I-367 | 3-iodophenyl | H | H | H | H | H | $CF_3$ | OH |
| I-368 | 4-iodophenyl | H | H | H | H | H | $CF_3$ | OH |
| I-369 | 3-cyanophenyl | H | H | H | H | H | $CF_3$ | OH |
| I-370 | 4-cyanophenyl | H | H | H | H | H | $CF_3$ | OH |
| I-371 | 2-nitrophenyl | H | H | H | H | H | $CF_3$ | OH |
| I-372 | 3-nitrophenyl | H | H | H | H | H | $CF_3$ | OH |
| I-373 | 4-nitrophenyl | H | H | H | H | H | $CF_3$ | OH |
| I-374 | 2-trifluoromethylphenyl | H | H | H | H | H | $CF_3$ | OH |
| I-375 | 4-trifluoromethylphenyl | H | H | H | H | H | $CF_3$ | OH |
| I-376 | 4-trifluoromethoxyphenyl | H | H | H | H | H | $CF_3$ | OH |
| I-377 | 2,3-difluorophenyl | H | H | H | H | H | $CF_3$ | OH |
| I-378 | 2,4-difluorophenyl | H | H | H | H | H | $CF_3$ | OH |
| I-379 | 2,5-difluorophenyl | H | H | H | H | H | $CF_3$ | OH |
| I-380 | 2,6-difluorophenyl | H | H | H | H | H | $CF_3$ | OH |
| I-381 | 2,4-dichlorophenyl | H | H | H | H | H | $CF_3$ | OH |
| I-382 | 2,6-dichlorophenyl | H | H | H | H | H | $CF_3$ | OH |
| I-383 | 3,4-dichlorophenyl | H | H | H | H | H | $CF_3$ | OH |
| I-384 | 4-fluoro-3-nitrophenyl | H | H | H | H | H | $CF_3$ | OH |
| I-385 | 5-fluoro-2-nitrophenyl | H | H | H | H | H | $CF_3$ | OH |
| I-386 | 2-chloro-4-nitrophenyl | H | H | H | H | H | $CF_3$ | OH |
| I-387 | 2-chloro-4-fluorophenyl | H | H | H | H | H | $CF_3$ | OH |
| I-388 | 3-chloro-4-fluorophenyl | H | H | H | H | H | $CF_3$ | OH |
| I-389 | 2-chloro-6-fluorophenyl | H | H | H | H | H | $CF_3$ | OH |
| I-390 | 4-chloro-2-fluorophenyl | H | H | H | H | H | $CF_3$ | OH |
| I-391 | 4-chloro-2-nitrophenyl | H | H | H | H | H | $CF_3$ | OH |
| I-392 | 2,3,6-trifluorophenyl | H | H | H | H | H | $CF_3$ | OH |
| I-393 | 2,3,4,5,6-pentafluorophenyl | H | H | H | H | H | $CF_3$ | OH |
| I-394 | pyridin-2-yl | H | H | H | H | H | $CF_3$ | OH |
| I-395 | pyridin-3-yl | H | H | H | H | H | $CF_3$ | OH |
| I-396 | 2-fluoropyridin-3-yl | H | H | H | H | H | $CF_3$ | OH |
| I-397 | 2-chloropyridin-3-yl | H | H | H | H | H | $CF_3$ | OH |
| I-398 | 4-chloropyridin-3-yl | H | H | H | H | H | $CF_3$ | OH |
| I-399 | 2-chloropyridin-5-yl | H | H | H | H | H | $CF_3$ | OH |
| I-400 | 2-methylthiopyridin-3-yl | H | H | H | H | H | $CF_3$ | OH |
| I-401 | 2,6-dichloropyridin-3-yl | H | H | H | H | H | $CF_3$ | OH |
| I-402 | 2,6-dichloropyridin-4-yl | H | H | H | H | H | $CF_3$ | OH |
| I-403 | pyrazin-2-yl | H | H | H | H | H | $CF_3$ | OH |
| I-404 | furan-2-yl | H | H | H | H | H | $CF_3$ | OH |
| I-405 | thiophen-2-yl | H | H | H | H | H | $CF_3$ | OH |
| I-406 | thiophen-3-yl | H | H | H | H | H | $CF_3$ | OH |
| I-407 | 4-methoxyphenyl | H | H | H | H | H | $CF_3$ | OH |
| I-408 | 3,4,5-trimethoxyphenyl | H | H | H | H | H | $CF_3$ | OH |
| I-409 | 3-methoxyphenyl | H | H | H | H | H | $CF_3$ | OH |
| I-410 | 2-methoxyphenyl | H | H | H | H | H | $CF_3$ | OH |
| I-411 | 3,5-dimethoxyphenyl | H | H | H | H | H | $CF_3$ | OH |
| I-412 | 2,6-dimethoxyphenyl | H | H | H | H | H | $CF_3$ | OH |
| I-413 | 4-ethoxyphenyl | H | H | H | H | H | $CF_3$ | OH |
| I-414 | 2-(4-trifluoromethylphenyl)phenyl | H | H | H | H | H | $CF_3$ | OH |
| I-415 | 1-phenyl-5-trifluoromethylpyrazol-4-yl | H | H | H | H | H | $CF_3$ | OH |
| I-416 | 5-methylisoxazol-3-yl | H | H | H | H | H | $CF_3$ | OH |
| I-417 | 4-methyl-1,2,3-thiadiazol-5-yl | H | H | H | H | H | $CF_3$ | OH |
| I-418 | pyrrole-2-yl | H | H | H | H | H | $CF_3$ | OH |
| I-419 | phenyl | H | H | H | H | H | $CF_3$ | Cl |
| I-420 | 2-methylphenyl | H | H | H | H | H | $CF_3$ | Cl |
| I-421 | 4-methylphenyl | H | H | H | H | H | $CF_3$ | Cl |
| I-422 | 2-fluorophenyl | H | H | H | H | H | $CF_3$ | Cl |
| I-423 | 3-fluorophenyl | H | H | H | H | H | $CF_3$ | Cl |
| I-424 | 4-fluorophenyl | H | H | H | H | H | $CF_3$ | Cl |

TABLE 10-continued

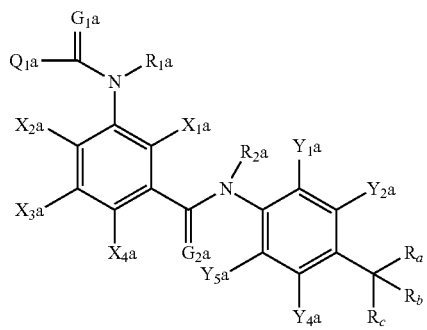

($X_2a$, $X_3a$, $X_4a$, $Y_2a$, $Y_4a$ = a hydrogen atom, $G_1a$, $G_2a$ = an oxygen atom, $R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-425 | 2-chlorophenyl | H | H | H | H | H | $CF_3$ | Cl |
| I-426 | 4-chlorophenyl | H | H | H | H | H | $CF_3$ | Cl |
| I-427 | 2-bromophenyl | H | H | H | H | H | $CF_3$ | Cl |
| I-428 | 2-iodophenyl | H | H | H | H | H | $CF_3$ | Cl |
| I-429 | 3-cyanophenyl | H | H | H | H | H | $CF_3$ | Cl |
| I-430 | 4-cyanophenyl | H | H | H | H | H | $CF_3$ | Cl |
| I-431 | 2-nitrophenyl | H | H | H | H | H | $CF_3$ | Cl |
| I-432 | 3-nitrophenyl | H | H | H | H | H | $CF_3$ | Cl |
| I-433 | 4-nitrophenyl | H | H | H | H | H | $CF_3$ | Cl |
| I-434 | 2-trifluoromethylphenyl | H | H | H | H | H | $CF_3$ | Cl |
| I-435 | 4-trifluoromethylphenyl | H | H | H | H | H | $CF_3$ | Cl |
| I-436 | 4-trifluoromethoxyphenyl | H | H | H | H | H | $CF_3$ | Cl |
| I-437 | 2,3-difluorophenyl | H | H | H | H | H | $CF_3$ | Cl |
| I-438 | 2,4-difluorophenyl | H | H | H | H | H | $CF_3$ | Cl |
| I-439 | 2,5-difluorophenyl | H | H | H | H | H | $CF_3$ | Cl |
| I-440 | 2,6-difluorophenyl | H | H | H | H | H | $CF_3$ | Cl |
| I-441 | 2,4-dichlorophenyl | H | H | H | H | H | $CF_3$ | Cl |
| I-442 | 2,6-dichlorophenyl | H | H | H | H | H | $CF_3$ | Cl |
| I-443 | 3,4-dichlorophenyl | H | H | H | H | H | $CF_3$ | Cl |
| I-444 | 2-chloro-4-nitrophenyl | H | H | H | H | H | $CF_3$ | Cl |
| I-445 | 2-chloro-4-fluorophenyl | H | H | H | H | H | $CF_3$ | Cl |
| I-446 | 2-chloro-6-fluorophenyl | H | H | H | H | H | $CF_3$ | Cl |
| I-447 | 4-chloro-2-fluorophenyl | H | H | H | H | H | $CF_3$ | Cl |
| I-448 | 4-chloro-2-nitrophenyl | H | H | H | H | H | $CF_3$ | Cl |
| I-449 | 2,3,6-trifluorophenyl | H | H | H | H | H | $CF_3$ | Cl |
| I-450 | pyridin-2-yl | H | H | H | H | H | $CF_3$ | Cl |
| I-451 | pyridin-3-yl | H | H | H | H | H | $CF_3$ | Cl |
| I-452 | 2-fluoropyridin-3-yl | H | H | H | H | H | $CF_3$ | Cl |
| I-453 | 2-chloropyridin-3-yl | H | H | H | H | H | $CF_3$ | Cl |
| I-454 | 2-chloropyridin-5-yl | H | H | H | H | H | $CF_3$ | Cl |
| I-455 | 2-methylthiopyridin-3-yl | H | H | H | H | H | $CF_3$ | Cl |
| I-456 | pyrazin-2-yl | H | H | H | H | H | $CF_3$ | Cl |
| I-457 | furan-2-yl | H | H | H | H | H | $CF_3$ | Cl |
| I-458 | thiophen-2-yl | H | H | H | H | H | $CF_3$ | Cl |
| I-459 | phenyl | F | H | H | H | H | $CF_3$ | OH |
| I-460 | 2-methylphenyl | F | H | H | H | H | $CF_3$ | OH |
| I-461 | 4-methylphenyl | F | H | H | H | H | $CF_3$ | OH |
| I-462 | 2-fluorophenyl | F | H | H | H | H | $CF_3$ | OH |
| I-463 | 3-fluorophenyl | F | H | H | H | H | $CF_3$ | OH |
| I-464 | 4-fluorophenyl | F | H | H | H | H | $CF_3$ | OH |
| I-465 | 2-chlorophenyl | F | H | H | H | H | $CF_3$ | OH |
| I-466 | 4-chlorophenyl | F | H | H | H | H | $CF_3$ | OH |
| I-467 | 2-bromophenyl | F | H | H | H | H | $CF_3$ | OH |
| I-468 | 2-iodophenyl | F | H | H | H | H | $CF_3$ | OH |
| I-469 | 3-cyanophenyl | F | H | H | H | H | $CF_3$ | OH |
| I-470 | 4-cyanophenyl | F | H | H | H | H | $CF_3$ | OH |
| I-471 | 2-nitrophenyl | F | H | H | H | H | $CF_3$ | OH |
| I-472 | 3-nitrophenyl | F | H | H | H | H | $CF_3$ | OH |
| I-473 | 4-nitrophenyl | F | H | H | H | H | $CF_3$ | OH |
| I-474 | 2-trifluoromethylphenyl | F | H | H | H | H | $CF_3$ | OH |
| I-475 | 4-trifluoromethylphenyl | F | H | H | H | H | $CF_3$ | OH |
| I-476 | 4-trifluoromethoxyphenyl | F | H | H | H | H | $CF_3$ | OH |
| I-477 | 2,3-difluorophenyl | F | H | H | H | H | $CF_3$ | OH |
| I-478 | 2,4-difluorophenyl | F | H | H | H | H | $CF_3$ | OH |
| I-479 | 2,5-difluorophenyl | F | H | H | H | H | $CF_3$ | OH |
| I-480 | 2,6-difluorophenyl | F | H | H | H | H | $CF_3$ | OH |
| I-481 | 2,4-dichlorophenyl | F | H | H | H | H | $CF_3$ | OH |
| I-482 | 2,6-dichlorophenyl | F | H | H | H | H | $CF_3$ | OH |
| I-483 | 3,4-dichlorophenyl | F | H | H | H | H | $CF_3$ | OH |

TABLE 10-continued

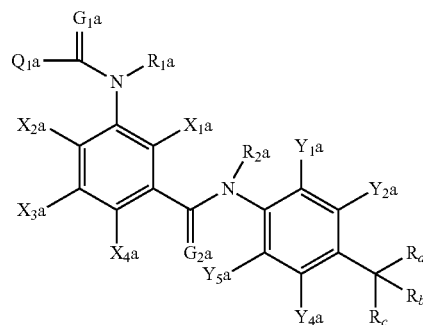

($X_2a$, $X_3a$, $X_4a$, $Y_2a$, $Y_4a$ = a hydrogen atom, $G_1a$, $G_2a$ = an oxygen atom,
$R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-484 | 2-chloro-4-nitrophenyl | F | H | H | H | H | $CF_3$ | OH |
| I-485 | 2-chloro-4-fluorophenyl | F | H | H | H | H | $CF_3$ | OH |
| I-486 | 2-chloro-6-fluorophenyl | F | H | H | H | H | $CF_3$ | OH |
| I-487 | 4-chloro-2-fluorophenyl | F | H | H | H | H | $CF_3$ | OH |
| I-488 | 4-chloro-2-nitrophenyl | F | H | H | H | H | $CF_3$ | OH |
| I-489 | 2,3,6-trifluorophenyl | F | H | H | H | H | $CF_3$ | OH |
| I-490 | pyridin-2-yl | F | H | H | H | H | $CF_3$ | OH |
| I-491 | pyridin-3-yl | F | H | H | H | H | $CF_3$ | OH |
| I-492 | 2-fluoropyridin-3-yl | F | H | H | H | H | $CF_3$ | OH |
| I-493 | 2-chloropyridin-3-yl | F | H | H | H | H | $CF_3$ | OH |
| I-494 | 2-chloropyridin-5-yl | F | H | H | H | H | $CF_3$ | OH |
| I-495 | 2-methylthiopyridin-3-yl | F | H | H | H | H | $CF_3$ | OH |
| I-496 | pyrazin-2-yl | F | H | H | H | H | $CF_3$ | OH |
| I-497 | furan-2-yl | F | H | H | H | H | $CF_3$ | OH |
| I-498 | thiophen-2-yl | F | H | H | H | H | $CF_3$ | OH |
| I-499 | phenyl | F | H | H | H | H | $CF_3$ | Cl |
| I-500 | 2-methylphenyl | F | H | H | H | H | $CF_3$ | Cl |
| I-501 | 4-methylphenyl | F | H | H | H | H | $CF_3$ | Cl |
| I-502 | 2-fluorophenyl | F | H | H | H | H | $CF_3$ | Cl |
| I-503 | 3-fluorophenyl | F | H | H | H | H | $CF_3$ | Cl |
| I-504 | 4-fluorophenyl | F | H | H | H | H | $CF_3$ | Cl |
| I-505 | 2-chlorophenyl | F | H | H | H | H | $CF_3$ | Cl |
| I-506 | 4-chlorophenyl | F | H | H | H | H | $CF_3$ | Cl |
| I-507 | 2-bromophenyl | F | H | H | H | H | $CF_3$ | Cl |
| I-508 | 2-iodophenyl | F | H | H | H | H | $CF_3$ | Cl |
| I-509 | 3-cyanophenyl | F | H | H | H | H | $CF_3$ | Cl |
| I-510 | 4-cyanophenyl | F | H | H | H | H | $CF_3$ | Cl |
| I-511 | 2-nitrophenyl | F | H | H | H | H | $CF_3$ | Cl |
| I-512 | 3-nitrophenyl | F | H | H | H | H | $CF_3$ | Cl |
| I-513 | 4-nitrophenyl | F | H | H | H | H | $CF_3$ | Cl |
| I-514 | 2-trifluoromethylphenyl | F | H | H | H | H | $CF_3$ | Cl |
| I-515 | 4-trifluoromethylphenyl | F | H | H | H | H | $CF_3$ | Cl |
| I-516 | 4-trifluoromethoxyphenyl | F | H | H | H | H | $CF_3$ | Cl |
| I-517 | 2,3-difluorophenyl | F | H | H | H | H | $CF_3$ | Cl |
| I-518 | 2,4-difluorophenyl | F | H | H | H | H | $CF_3$ | Cl |
| I-519 | 2,5-difluorophenyl | F | H | H | H | H | $CF_3$ | Cl |
| I-520 | 2,6-difluorophenyl | F | H | H | H | H | $CF_3$ | Cl |
| I-521 | 2,4-dichlorophenyl | F | H | H | H | H | $CF_3$ | Cl |
| I-522 | 2,6-dichlorophenyl | F | H | H | H | H | $CF_3$ | Cl |
| I-523 | 3,4-dichlorophenyl | F | H | H | H | H | $CF_3$ | Cl |
| I-524 | 2-chloro-4-nitrophenyl | F | H | H | H | H | $CF_3$ | Cl |
| I-525 | 2-chloro-4-fluorophenyl | F | H | H | H | H | $CF_3$ | Cl |
| I-526 | 2-chloro-6-fluorophenyl | F | H | H | H | H | $CF_3$ | Cl |
| I-527 | 4-chloro-2-fluorophenyl | F | H | H | H | H | $CF_3$ | Cl |
| I-528 | 4-chloro-2-nitrophenyl | F | H | H | H | H | $CF_3$ | Cl |
| I-529 | 2,3,6-trifluorophenyl | F | H | H | H | H | $CF_3$ | Cl |
| I-530 | pyridin-2-yl | F | H | H | H | H | $CF_3$ | Cl |
| I-531 | pyridin-3-yl | F | H | H | H | H | $CF_3$ | Cl |
| I-532 | 2-fluoropyridin-3-yl | F | H | H | H | H | $CF_3$ | Cl |
| I-533 | 2-chloropyridin-3-yl | F | H | H | H | H | $CF_3$ | Cl |
| I-534 | 2-chloropyridin-5-yl | F | H | H | H | H | $CF_3$ | Cl |
| I-535 | 2-methylthiopyridin-3-yl | F | H | H | H | H | $CF_3$ | Cl |
| I-536 | pyrazin-2-yl | F | H | H | H | H | $CF_3$ | Cl |
| I-537 | furan-2-yl | F | H | H | H | H | $CF_3$ | Cl |
| I-538 | thiophen-2-yl | F | H | H | H | H | $CF_3$ | Cl |
| I-539 | phenyl | H | Me | H | H | H | $CF_3$ | OH |
| I-540 | 2-methylphenyl | H | Me | H | H | H | $CF_3$ | OH |
| I-541 | 4-methylphenyl | H | Me | H | H | H | $CF_3$ | OH |
| I-542 | 2-fluorophenyl | H | Me | H | H | H | $CF_3$ | OH |

TABLE 10-continued

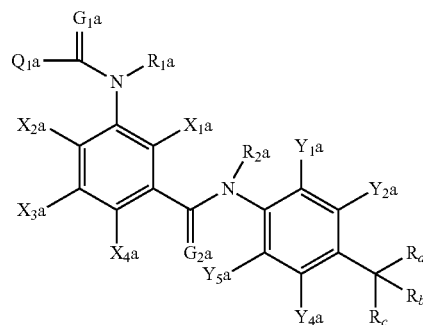

($X_2a$, $X_3a$, $X_4a$, $Y_2a$, $Y_4a$ = a hydrogen atom, $G_1a$, $G_2a$ = an oxygen atom, $R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-543 | 3-fluorophenyl | H | Me | H | H | H | $CF_3$ | OH |
| I-544 | 4-fluorophenyl | H | Me | H | H | H | $CF_3$ | OH |
| I-545 | 2-chlorophenyl | H | Me | H | H | H | $CF_3$ | OH |
| I-546 | 4-chlorophenyl | H | Me | H | H | H | $CF_3$ | OH |
| I-547 | 2-bromophenyl | H | Me | H | H | H | $CF_3$ | OH |
| I-548 | 2-iodophenyl | H | Me | H | H | H | $CF_3$ | OH |
| I-549 | 3-cyanophenyl | H | Me | H | H | H | $CF_3$ | OH |
| I-550 | 4-cyanophenyl | H | Me | H | H | H | $CF_3$ | OH |
| I-551 | 2-nitrophenyl | H | Me | H | H | H | $CF_3$ | OH |
| I-552 | 3-nitrophenyl | H | Me | H | H | H | $CF_3$ | OH |
| I-553 | 4-nitrophenyl | H | Me | H | H | H | $CF_3$ | OH |
| I-554 | 2-trifluoromethylphenyl | H | Me | H | H | H | $CF_3$ | OH |
| I-555 | 4-trifluoromethylphenyl | H | Me | H | H | H | $CF_3$ | OH |
| I-556 | 4-trifluoromethoxyphenyl | H | Me | H | H | H | $CF_3$ | OH |
| I-557 | 2,3-difluorophenyl | H | Me | H | H | H | $CF_3$ | OH |
| I-558 | 2,4-difluorophenyl | H | Me | H | H | H | $CF_3$ | OH |
| I-559 | 2,5-difluorophenyl | H | Me | H | H | H | $CF_3$ | OH |
| I-560 | 2,6-difluorophenyl | H | Me | H | H | H | $CF_3$ | OH |
| I-561 | 2,4-dichlorophenyl | H | Me | H | H | H | $CF_3$ | OH |
| I-562 | 2,6-dichlorophenyl | H | Me | H | H | H | $CF_3$ | OH |
| I-563 | 3,4-dichlorophenyl | H | Me | H | H | H | $CF_3$ | OH |
| I-564 | 2-chloro-4-nitrophenyl | H | Me | H | H | H | $CF_3$ | OH |
| I-565 | 2-chloro-4-fluorophenyl | H | Me | H | H | H | $CF_3$ | OH |
| I-566 | 2-chloro-6-fluorophenyl | H | Me | H | H | H | $CF_3$ | OH |
| I-567 | 4-chloro-2-fluorophenyl | H | Me | H | H | H | $CF_3$ | OH |
| I-568 | 4-chloro-2-nitrophenyl | H | Me | H | H | H | $CF_3$ | OH |
| I-569 | 2,3,6-trifluorophenyl | H | Me | H | H | H | $CF_3$ | OH |
| I-570 | pyridin-2-yl | H | Me | H | H | H | $CF_3$ | OH |
| I-571 | pyridin-3-yl | H | Me | H | H | H | $CF_3$ | OH |
| I-572 | 2-fluoropyridin-3-yl | H | Me | H | H | H | $CF_3$ | OH |
| I-573 | 2-chloropyridin-3-yl | H | Me | H | H | H | $CF_3$ | OH |
| I-574 | 2-chloropyridin-5-yl | H | Me | H | H | H | $CF_3$ | OH |
| I-575 | 2-methylthiopyridin-3-yl | H | Me | H | H | H | $CF_3$ | OH |
| I-576 | pyrazin-2-yl | H | Me | H | H | H | $CF_3$ | OH |
| I-577 | furan-2-yl | H | Me | H | H | H | $CF_3$ | OH |
| I-578 | thiophen-2-yl | H | Me | H | H | H | $CF_3$ | OH |
| I-579 | phenyl | F | Me | H | H | H | $CF_3$ | Cl |
| I-580 | 2-methylphenyl | F | Me | H | H | H | $CF_3$ | Cl |
| I-581 | 4-methylphenyl | F | Me | H | H | H | $CF_3$ | Cl |
| I-582 | 2-fluorophenyl | F | Me | H | H | H | $CF_3$ | Cl |
| I-583 | 3-fluorophenyl | F | Me | H | H | H | $CF_3$ | Cl |
| I-584 | 4-fluorophenyl | F | Me | H | H | H | $CF_3$ | Cl |
| I-585 | 2-chlorophenyl | F | Me | H | H | H | $CF_3$ | Cl |
| I-586 | 4-chlorophenyl | F | Me | H | H | H | $CF_3$ | Cl |
| I-587 | 2-bromophenyl | F | Me | H | H | H | $CF_3$ | Cl |
| I-588 | 2-iodophenyl | F | Me | H | H | H | $CF_3$ | Cl |
| I-589 | 3-cyanophenyl | F | Me | H | H | H | $CF_3$ | Cl |
| I-590 | 4-cyanophenyl | F | Me | H | H | H | $CF_3$ | Cl |
| I-591 | 2-nitrophenyl | F | Me | H | H | H | $CF_3$ | Cl |
| I-592 | 3-nitrophenyl | F | Me | H | H | H | $CF_3$ | Cl |
| I-593 | 4-nitrophenyl | F | Me | H | H | H | $CF_3$ | Cl |
| I-594 | 2-trifluoromethylphenyl | F | Me | H | H | H | $CF_3$ | Cl |
| I-595 | 4-trifluoromethylphenyl | F | Me | H | H | H | $CF_3$ | Cl |
| I-596 | 4-trifluoromethoxyphenyl | F | Me | H | H | H | $CF_3$ | Cl |
| I-597 | 2,3-difluorophenyl | F | Me | H | H | H | $CF_3$ | Cl |
| I-598 | 2,4-difluorophenyl | F | Me | H | H | H | $CF_3$ | Cl |
| I-599 | 2,5-difluorophenyl | F | Me | H | H | H | $CF_3$ | Cl |
| I-600 | 2,6-difluorophenyl | F | Me | H | H | H | $CF_3$ | Cl |
| I-601 | 2,4-dichlorophenyl | F | Me | H | H | H | $CF_3$ | Cl |

TABLE 10-continued

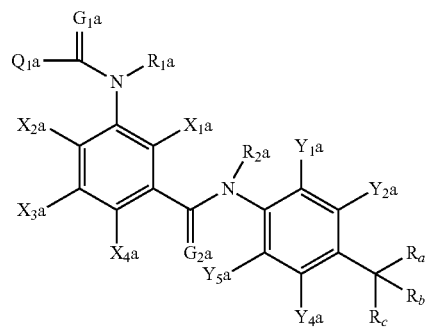

($X_2a$, $X_3a$, $X_4a$, $Y_2a$, $Y_4a$ = a hydrogen atom, $G_1a$, $G_2a$ = an oxygen atom,
$R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-602 | 2,6-dichlorophenyl | F | Me | H | H | H | $CF_3$ | Cl |
| I-603 | 3,4-dichlorophenyl | F | Me | H | H | H | $CF_3$ | Cl |
| I-604 | 2-chloro-4-nitrophenyl | F | Me | H | H | H | $CF_3$ | Cl |
| I-605 | 2-chloro-4-fluorophenyl | F | Me | H | H | H | $CF_3$ | Cl |
| I-606 | 2-chloro-6-fluorophenyl | F | Me | H | H | H | $CF_3$ | Cl |
| I-607 | 4-chloro-2-fluorophenyl | F | Me | H | H | H | $CF_3$ | Cl |
| I-608 | 4-chloro-2-nitrophenyl | F | Me | H | H | H | $CF_3$ | Cl |
| I-609 | 2,3,6-trifluorophenyl | F | Me | H | H | H | $CF_3$ | Cl |
| I-610 | pyridin-2-yl | F | Me | H | H | H | $CF_3$ | Cl |
| I-611 | pyridin-3-yl | F | Me | H | H | H | $CF_3$ | Cl |
| I-612 | 2-fluoropyridin-3-yl | F | Me | H | H | H | $CF_3$ | Cl |
| I-613 | 2-chloropyridin-3-yl | F | Me | H | H | H | $CF_3$ | Cl |
| I-614 | 2-chloropyridin-5-yl | F | Me | H | H | H | $CF_3$ | Cl |
| I-615 | 2-methylthiopyridin-3-yl | F | Me | H | H | H | $CF_3$ | Cl |
| I-616 | pyrazin-2-yl | F | Me | H | H | H | $CF_3$ | Cl |
| I-617 | furan-2-yl | F | Me | H | H | H | $CF_3$ | Cl |
| I-618 | thiophen-2-yl | F | Me | H | H | H | $CF_3$ | Cl |
| I-619 | phenyl | H | Me | Me | H | H | $CF_3$ | OH |
| I-620 | 2-methylphenyl | H | Me | Me | H | H | $CF_3$ | OH |
| I-621 | 4-methylphenyl | H | Me | Me | H | H | $CF_3$ | OH |
| I-622 | 2-fluorophenyl | H | Me | Me | H | H | $CF_3$ | OH |
| I-623 | 3-fluorophenyl | H | Me | Me | H | H | $CF_3$ | OH |
| I-624 | 4-fluorophenyl | H | Me | Me | H | H | $CF_3$ | OH |
| I-625 | 2-chlorophenyl | H | Me | Me | H | H | $CF_3$ | OH |
| I-626 | 4-chlorophenyl | H | Me | Me | H | H | $CF_3$ | OH |
| I-627 | 2-bromophenyl | H | Me | Me | H | H | $CF_3$ | OH |
| I-628 | 2-iodophenyl | H | Me | Me | H | H | $CF_3$ | OH |
| I-629 | 3-cyanophenyl | H | Me | Me | H | H | $CF_3$ | OH |
| I-630 | 4-cyanophenyl | H | Me | Me | H | H | $CF_3$ | OH |
| I-631 | 2-nitrophenyl | H | Me | Me | H | H | $CF_3$ | OH |
| I-632 | 3-nitrophenyl | H | Me | Me | H | H | $CF_3$ | OH |
| I-633 | 4-nitrophenyl | H | Me | Me | H | H | $CF_3$ | OH |
| I-634 | 2-trifluoromethylphenyl | H | Me | Me | H | H | $CF_3$ | OH |
| I-635 | 4-trifluoromethylphenyl | H | Me | Me | H | H | $CF_3$ | OH |
| I-636 | 4-trifluoromethoxyphenyl | H | Me | Me | H | H | $CF_3$ | OH |
| I-637 | 2,3-difluorophenyl | H | Me | Me | H | H | $CF_3$ | OH |
| I-638 | 2,4-difluorophenyl | H | Me | Me | H | H | $CF_3$ | OH |
| I-639 | 2,5-difluorophenyl | H | Me | Me | H | H | $CF_3$ | OH |
| I-640 | 2,6-difluorophenyl | H | Me | Me | H | H | $CF_3$ | OH |
| I-641 | 2,4-dichlorophenyl | H | Me | Me | H | H | $CF_3$ | OH |
| I-642 | 2,6-dichlorophenyl | H | Me | Me | H | H | $CF_3$ | OH |
| I-643 | 3,4-dichlorophenyl | H | Me | Me | H | H | $CF_3$ | OH |
| I-644 | 2-chloro-4-nitrophenyl | H | Me | Me | H | H | $CF_3$ | OH |
| I-645 | 2-chloro-4-fluorophenyl | H | Me | Me | H | H | $CF_3$ | OH |
| I-646 | 2-chloro-6-fluorophenyl | H | Me | Me | H | H | $CF_3$ | OH |
| I-647 | 4-chloro-2-fluorophenyl | H | Me | Me | H | H | $CF_3$ | OH |
| I-648 | 4-chloro-2-nitrophenyl | H | Me | Me | H | H | $CF_3$ | OH |
| I-649 | 2,3,6-trifluorophenyl | H | Me | Me | H | H | $CF_3$ | OH |
| I-650 | pyridin-2-yl | H | Me | Me | H | H | $CF_3$ | OH |
| I-651 | pyridin-3-yl | H | Me | Me | H | H | $CF_3$ | OH |
| I-652 | 2-fluoropyridin-3-yl | H | Me | Me | H | H | $CF_3$ | OH |
| I-653 | 2-chloropyridin-3-yl | H | Me | Me | H | H | $CF_3$ | OH |
| I-654 | 2-chloropyridin-5-yl | H | Me | Me | H | H | $CF_3$ | OH |
| I-655 | 2-methylthiopyridin-3-yl | H | Me | Me | H | H | $CF_3$ | OH |
| I-656 | pyrazin-2-yl | H | Me | Me | H | H | $CF_3$ | OH |
| I-657 | furan-2-yl | H | Me | Me | H | H | $CF_3$ | OH |
| I-658 | thiophen-2-yl | H | Me | Me | H | H | $CF_3$ | OH |
| I-659 | phenyl | F | Me | Me | H | H | $CF_3$ | Cl |
| I-660 | 2-methylphenyl | F | Me | Me | H | H | $CF_3$ | Cl |

TABLE 10-continued

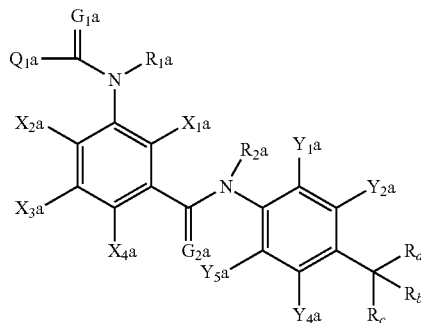

($X_2a$, $X_3a$, $X_4a$, $Y_2a$, $Y_4a$ = a hydrogen atom, $G_1a$, $G_2a$ = an oxygen atom, $R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-661 | 4-methylphenyl | F | Me | Me | H | H | $CF_3$ | Cl |
| I-662 | 2-fluorophenyl | F | Me | Me | H | H | $CF_3$ | Cl |
| I-663 | 3-fluorophenyl | F | Me | Me | H | H | $CF_3$ | Cl |
| I-664 | 4-fluorophenyl | F | Me | Me | H | H | $CF_3$ | Cl |
| I-665 | 2-chlorophenyl | F | Me | Me | H | H | $CF_3$ | Cl |
| I-666 | 4-chlorophenyl | F | Me | Me | H | H | $CF_3$ | Cl |
| I-667 | 2-bromophenyl | F | Me | Me | H | H | $CF_3$ | Cl |
| I-668 | 2-iodophenyl | F | Me | Me | H | H | $CF_3$ | Cl |
| I-669 | 3-cyanophenyl | F | Me | Me | H | H | $CF_3$ | Cl |
| I-670 | 4-cyanophenyl | F | Me | Me | H | H | $CF_3$ | Cl |
| I-671 | 2-nitrophenyl | F | Me | Me | H | H | $CF_3$ | Cl |
| I-672 | 3-nitrophenyl | F | Me | Me | H | H | $CF_3$ | Cl |
| I-673 | 4-nitrophenyl | F | Me | Me | H | H | $CF_3$ | Cl |
| I-674 | 2-trifluoromethylphenyl | F | Me | Me | H | H | $CF_3$ | Cl |
| I-675 | 4-trifluoromethylphenyl | F | Me | Me | H | H | $CF_3$ | Cl |
| I-676 | 4-trifluoromethoxyphenyl | F | Me | Me | H | H | $CF_3$ | Cl |
| I-677 | 2,3-difluorophenyl | F | Me | Me | H | H | $CF_3$ | Cl |
| I-678 | 2,4-difluorophenyl | F | Me | Me | H | H | $CF_3$ | Cl |
| I-679 | 2,5-difluorophenyl | F | Me | Me | H | H | $CF_3$ | Cl |
| I-680 | 2,6-difluorophenyl | F | Me | Me | H | H | $CF_3$ | Cl |
| I-681 | 2,4-dichlorophenyl | F | Me | Me | H | H | $CF_3$ | Cl |
| I-682 | 2,6-dichlorophenyl | F | Me | Me | H | H | $CF_3$ | Cl |
| I-683 | 3,4-dichlorophenyl | F | Me | Me | H | H | $CF_3$ | Cl |
| I-684 | 2-chloro-4-nitrophenyl | F | Me | Me | H | H | $CF_3$ | Cl |
| I-685 | 2-chloro-4-fluorophenyl | F | Me | Me | H | H | $CF_3$ | Cl |
| I-686 | 2-chloro-6-fluorophenyl | F | Me | Me | H | H | $CF_3$ | Cl |
| I-687 | 4-chloro-2-fluorophenyl | F | Me | Me | H | H | $CF_3$ | Cl |
| I-688 | 4-chloro-2-nitrophenyl | F | Me | Me | H | H | $CF_3$ | Cl |
| I-689 | 2,3,6-trifluorophenyl | F | Me | Me | H | H | $CF_3$ | Cl |
| I-690 | pyridin-2-yl | F | Me | Me | H | H | $CF_3$ | Cl |
| I-691 | pyridin-3-yl | F | Me | Me | H | H | $CF_3$ | Cl |
| I-692 | 2-fluoropyridin-3-yl | F | Me | Me | H | H | $CF_3$ | Cl |
| I-693 | 2-chloropyridin-3-yl | F | Me | Me | H | H | $CF_3$ | Cl |
| I-694 | 2-chloropyridin-5-yl | F | Me | Me | H | H | $CF_3$ | Cl |
| I-695 | 2-methylthiopyridin-3-yl | F | Me | Me | H | H | $CF_3$ | Cl |
| I-696 | pyrazin-2-yl | F | Me | Me | H | H | $CF_3$ | Cl |
| I-697 | furan-2-yl | F | Me | Me | H | H | $CF_3$ | Cl |
| I-698 | thiophen-2-yl | F | Me | Me | H | H | $CF_3$ | Cl |
| I-699 | 2-fluorophenyl | H | H | H | $MeSO_2$ | Br | $CF_3$ | OH |
| I-700 | 2-fluorophenyl | H | H | H | $MeSO_2$ | Br | $CF_3$ | Cl |
| I-701 | 2-fluorophenyl | F | H | H | $MeSO_2$ | Br | $CF_3$ | OH |
| I-702 | 2-fluorophenyl | F | H | H | $MeSO_2$ | Br | $CF_3$ | Cl |
| I-703 | 2-fluorophenyl | H | Me | H | $MeSO_2$ | Br | $CF_3$ | OH |
| I-704 | 2-fluorophenyl | H | Me | H | $MeSO_2$ | Br | $CF_3$ | Cl |
| I-705 | 2-fluorophenyl | F | Me | H | $MeSO_2$ | Br | $CF_3$ | OH |
| I-706 | 2-fluorophenyl | F | Me | H | $MeSO_2$ | Br | $CF_3$ | Cl |
| I-707 | 2-fluorophenyl | H | Me | Me | $MeSO_2$ | Br | $CF_3$ | OH |
| I-708 | 2-fluorophenyl | H | Me | Me | $MeSO_2$ | Br | $CF_3$ | Cl |
| I-709 | 2-fluorophenyl | F | Me | Me | $MeSO_2$ | Br | $CF_3$ | OH |
| I-710 | 2-fluorophenyl | F | Me | Me | $MeSO_2$ | Br | $CF_3$ | Cl |
| I-711 | 2-fluorophenyl | H | H | H | n-Pr | I | $CF_3$ | OH |
| I-712 | 2-fluorophenyl | H | H | H | n-Pr | I | $CF_3$ | Cl |
| I-713 | 2-fluorophenyl | F | H | H | n-Pr | I | $CF_3$ | OH |
| I-714 | 2-fluorophenyl | F | H | H | n-Pr | I | $CF_3$ | Cl |
| I-715 | 2-fluorophenyl | H | Me | H | n-Pr | I | $CF_3$ | OH |
| I-716 | 2-fluorophenyl | H | Me | H | n-Pr | I | $CF_3$ | Cl |
| I-717 | 2-fluorophenyl | F | Me | H | n-Pr | I | $CF_3$ | OH |
| I-718 | 2-fluorophenyl | F | Me | H | n-Pr | I | $CF_3$ | Cl |
| I-719 | 2-fluorophenyl | H | Me | Me | n-Pr | I | $CF_3$ | OH |

TABLE 10-continued

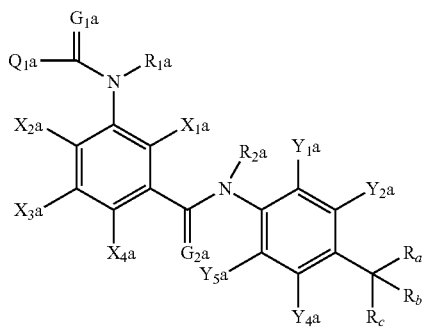

($X_2a$, $X_3a$, $X_4a$, $Y_2a$, $Y_4a$ = a hydrogen atom, $G_1a$, $G_2a$ = an oxygen atom, $R_a$ = a trifluoromethyl group)

| Comp. No. | $Q_1a$ | $X_1a$ | $R_1a$ | $R_2a$ | $Y_1a$ | $Y_5a$ | $R_b$ | $R_c$ |
|---|---|---|---|---|---|---|---|---|
| I-720 | 2-fluorophenyl | H | Me | Me | n-Pr | I | $CF_3$ | Cl |
| I-721 | 2-fluorophenyl | F | Me | Me | n-Pr | I | $CF_3$ | OH |
| I-722 | 2-fluorophenyl | F | Me | Me | n-Pr | I | $CF_3$ | Cl |
| I-723 | 2-fluorophenyl | H | H | H | H | H | $C_2F_5$ | OH |
| I-724 | 2-fluorophenyl | H | H | H | H | H | $C_2F_5$ | Cl |
| I-725 | 2-fluorophenyl | F | H | H | H | H | $C_2F_5$ | OH |
| I-726 | 2-fluorophenyl | F | H | H | H | H | $C_2F_5$ | Cl |
| I-727 | 2-fluorophenyl | H | Me | H | H | H | $C_2F_5$ | OH |
| I-728 | 2-fluorophenyl | H | Me | H | H | H | $C_2F_5$ | Cl |
| I-729 | 2-fluorophenyl | F | Me | H | H | H | $C_2F_5$ | OH |
| I-730 | 2-fluorophenyl | F | Me | H | H | H | $C_2F_5$ | Cl |
| I-731 | 2-fluorophenyl | H | Me | Me | H | H | $C_2F_5$ | OH |
| I-732 | 2-fluorophenyl | H | Me | Me | H | H | $C_2F_5$ | Cl |
| I-733 | 2-fluorophenyl | F | Me | Me | H | H | $C_2F_5$ | OH |
| I-734 | 2-fluorophenyl | F | Me | Me | H | H | $C_2F_5$ | Cl |
| I-35 | 2-fluorophenyl | H | H | H | H | H | $CF_3$ | Br |
| I-736 | 2-fluorophenyl | H | H | H | H | H | $CF_3$ | Br |
| I-737 | 2-fluorophenyl | F | H | H | H | H | $CF_3$ | Br |
| I-738 | 2-fluorophenyl | F | H | H | H | H | $CF_3$ | Br |
| I-739 | 2-fluorophenyl | H | Me | H | H | H | $CF_3$ | Br |
| I-740 | 2-fluorophenyl | H | Me | H | H | H | $CF_3$ | Br |
| I-741 | 2-fluorophenyl | F | Me | H | H | H | $CF_3$ | Br |
| I-742 | 2-fluorophenyl | F | Me | H | H | H | $CF_3$ | Br |
| I-743 | 2-fluorophenyl | H | Me | Me | H | H | $CF_3$ | Br |
| I-744 | 2-fluorophenyl | H | Me | Me | H | H | $CF_3$ | Br |
| I-745 | 2-fluorophenyl | F | Me | Me | H | H | $CF_3$ | Br |
| I-746 | 2-fluorophenyl | F | Me | Me | H | H | $CF_3$ | Br |

Hereinbelow, Table 11 and Table 12 represent the properties of the compounds represented by Formulae (1), (6), (8), (11) and (13). The $^1$H-NMR chemical shift values represented therein are based on tetramethylsilane as the internal standard substance, if not described otherwise.

TABLE 11

| Comp. No. | $^1$H-NMR (DMSO-$d_6$, ppm) |
|---|---|
| 1 | ($CDCl_3$) δ 2.36 (6H, s), 7.36 (2H, s), 7.51-7.65 (5H, m), 7.73 (1H, d, J = 7.8 Hz), 7.86 (1H, d, J = 7.8 Hz), 7.89 (2H, d, J = 7.8 Hz), 8.01 (1H, s), 8.33 (1H, s). |
| 2 | δ 7.52-7.63 (4H, m), 7.77 (1H, d, J = 7.8 Hz), 7.98-8.09 (5H, m), 8.39 (1H, s), 10.48 (1H, s), 10.59 (1H, s). |
| 3 | δ 7.32-7.39 (2H, m), 7.54-7.63 (2H, m), 7.67-7.72 (1H, m), 7.77 (1H, d, J = 7.8 Hz), 7.98 (1H, d, J = 7.8 Hz), 8.03 (2H, s), 8.34 (1H, s), 10.61 (1H, s), 10.65 (1H, s). |
| 4 | δ 7.53-7.63 (4H, m), 7.79 (1H, d, J = 8.3 Hz), 7.99-8.02 (2H, m), 8.08 (1H, dd, J = 2.0, 8.3 Hz), 8.17 (2H, s), 8.39 (1H, d, J = 2.0 Hz), 10.50 (1H, s), 10.63 (1H, s). |
| 5 | δ 7.33-7.40 (2H, m), 7.54-7.63 (2H, m), 7.68-7.72 (1H, m), 7.79 (1H, d, J = 7.8 Hz), 7.99 (1H, d, J = 7.8 Hz), 8.17 (2H, s), 8.35 (1H, s), 10.65 (1H, s), 10.67 (1H, s). |
| 6 | δ 7.52-7.62 (4H, m), 7.75 (1H, d, J = 7.8 Hz), 7.91 (2H, s), 7.97 (2H, d, J = 7.8 Hz), 8.04 (1H, d, J = 7.8 Hz), 8.36 (1H, s), 10.50 (1H, s), 10.61 (1H, s). |
| 7 | δ 7.53-7.64 (4H, m), 7.78 (1H, d, J = 7.8 Hz), 7.99-8.01 (2H, m), 8.06 (2H, s), 8.09 (1H, dd, J = 2.0, 7.8 Hz), 8.39 (1H, s), 10.51 (1H, s), 10.63 (1H, s). |
| 8 | δ 7.33-7.40 (2H, m), 7.55-7.63 (2H, m), 7.68-7.72 (1H, m), 7.78 (1H, d, J = 7.8 Hz), 7.99 (1H, d, J = 7.8 Hz), 8.05 (2H, s), 8.34 (1H, s), 10.65 (1H, s), 10.69 (1H, s). |

TABLE 11-continued

| Comp. No. | |
|---|---|
| 9 | δ 2.29 (6H, s), 7.47 (2H, s), 7.51-7.62 (4H, m), 7.75 (1H, d, J = 7.8 Hz), 7.97-8.00 (2H, m), 8.03-8.06 (1H, m), 8.36 (1H, s), 10.00 (1H, s), 10.45 (1H, s). |
| 10 | δ 2.37 (6H, s), 7.34 (2H, s), 7.46-7.57 (4H, m), 7.75 (1H, d, J = 7.8 Hz), 7.98-8.01 (2H, m), 8.12 (1H, d, J = 7.3 Hz), 8.34 (1H, s), 8.87 (1H, s), 9.66 (1H, s). |
| 11 | (CDCl$_3$) δ 2.35 (6H, s), 2.52 (3H, s), 7.26-7.31 (2H, m), 7.36 (2H, s), 7.37-7.42 (1H, m), 7.49-7.54 (2H, m), 7.68-7.73 (3H, m), 7.79 (1H, d, J = 7.3 Hz), 8.30 (1H, s). |
| 12 | δ 2.30 (6H, s), 2.41 (3H, s), 7.42-7.48 (4H, m), 7.54 (1H, d, J = 7.94 Hz), 7.74-7.82 (3H, m), 8.07 (1H, d, J = 7.94 Hz), 8.35 (1H, s), 9.99 (1H, s), 10.43 (1H, s). |
| 13 | δ 2.30 (6H, s), 2.40 (3H, s), 7.35 (2H, d, J = 8.3 Hz), 7.45 (2H, s), 7.53 (1H, t, J = 7.8 Hz), 7.74 (1H, d, J = 7.81 Hz), 7.92 (2H, d, J = 8.3 Hz), 8.07 (1H, d, J = 7.8 Hz), 8.36 (1H, s), 9.98 (1H, s), 10.39 (1H, s). |
| 14 | δ 1.18 (3H, t, J = 7.6 Hz), 2.30 (6H, s), 2.76 (2H, q, J = 7.6 Hz), 7.30-7.37 (2H, m), 7.42-7.46 (4H, m), 7.52 (1H, t, J = 8.0 Hz), 7.81 (1H, d, J = 8.0 Hz), 7.96 (1H, d, J = 8.0 Hz), 8.35 (1H, s), 9.98 (1H, s), 10.56 (1H, s). |
| 16 | δ 1.22 (3H, t, J = 7.6 Hz), 2.31 (6H, s), 2.69 (2H, q, J = 7.6 Hz), 7.39 (2H, d, J = 8.3 Hz), 7.45 (2H, t, J = 7.9 Hz), 7.53 (2H, d, J = 8.3 Hz), 7.74 (1H, d, J = 7.9 Hz), 7.94 (1H, d, J = 8.3 Hz), 8.07 (1H, d, J = 7.9 Hz), 8.36 (1H, s), 9.99 (1H, s), 10.40 (1H, s). |
| 17 | δ 2.30 (6H, s), 7.33-7.76 (8H, m), 7.97 (1H, d, J = 8.30 Hz), 8.30 (1H, s), 10.01 (1H, s), 10.65 (1H, s). |
| 18 | δ 2.30 (6H, s), 7.45-7.64 (5H, m), 7.76-8.05 (3H, m), 8.06 (1H, d, J = 8.3 Hz), 8.35 (1H, s), 10.00 (1H, s), 10.54 (1H, s). |
| 19 | δ 2.30 (6H, s), 7.37-7.45 (4H, m), 7.54 (1H, t, J = 7.8 Hz), 7.76 (1H, d, J = 7.8 Hz), 8.05-8.11 (3H, m), 8.34 (1H, s), 10.00 (1H, s), 10.49 (1H, s). |
| 20 | (CDCl$_3$) δ 2.35 (6H, s), 7.36 (2H, s), 7.37-7.54 (4H, m), 7.69-7.83 (4H, m), 8.13 (1H, m), 8.33 (1H, s). |
| 22 | δ 2.30 (6H, s), 7.45 (2H, s), 7.56 (1H, dd, J = 7.8, 6.8 Hz), 7.63 (1H, d, J = 8.8 Hz), 7.72 (1H, d, J = 8.8 Hz), 7.77 (1H, d, J = 6.8 Hz), 7.94 (1H, d, J = 8.3 Hz), 8.03 (1H, d, J = 8.8 Hz), 8.17 (1H, d, J = 7.8 Hz), 8.34 (1H, s), 9.99 (1H, s), 10.54 (1H, s). |
| 23 | (CDCl$_3$) δ 2.36 (6H, s), 7.34-7.38 (3H, m), 7.42-7.46 (1H, m), 7.53 (1H, t, J = 7.8 Hz), 7.62 (1H, s), 7.65-7.68 (2H, m), 7.73-7.75 (1H, m), 7.82-7.84 (1H, m), 7.89 (1H, s), 8.32 (1H, s). |
| 26 | (CDCl$_3$) δ 2.36 (6H, s), 7.19 (1H, dt, J = 2.0, 7.8 Hz), 7.36 (2H, s), 7.46 (1H, t, J = 7.8 Hz), 7.52-7.57 (3H, m), 7.66 (1H, s), 7.74 (1H, d, J = 7.8 Hz), 7.85 (1H, d, J = 7.8 Hz), 7.94 (1H, d, J = 7.8 Hz), 8.31 (1H, s) |
| 28 | δ 2.36 (6H, s), 7.33 (2H, s), 7.48 (1H, t, J = 7.8 Hz), 7.75-7.84 (5H, m), 8.14 (1H, d, J = 7.8 Hz), 8.31 (1H, s), 9.20 (1H, s), 10.04 (1H, s). |
| 29 | δ 2.30 (6H, s), 7.45 (2H, s), 7.57 (1H, d, J = 7.8 Hz), 7.75-7.80 (2H, m), 8.06-8.11 (2H, m), 8.29 (1H, d, J = 7.8 Hz), 8.34 (1H, s), 8.46 (1H, s), 10.02 (1H, s), 10.65 (1H, s). |
| 30 | δ 2.30 (6H, s), 7.45 (2H, s), 7.56 (1H, t, J = 7.8 Hz), 7.79 (1H, d, J = 7.8 Hz), 8.04-8.06 (3H, m), 8.16 (2H, d, J = 8.3 Hz), 8.36 (1H, s), 10.02 (1H, s), 10.72 (1H, s). |
| 31 | δ 2.30 (6H, s), 7.45 (2H, s), 7.56 (1H, d, J = 7.8 Hz), 7.76-7.81 (3H, m), 7.88-7.94 (2H, m), 8.17 (1H, d, J = 7.8 Hz), 8.24 (1H, s), 10.02 (1H, s), 10.90 (1H, s). |
| 32 | δ 2.32 (6H, s), 7.46 (2H, s), 7.58 (1H, t, J = 7.8 Hz), 7.80-7.89 (2H, m), 8.11 (1H, d, J = 7.8 Hz), 8.36 (1H, s), 8.44-8.48 (2H, m), 8.86 (1H, s), 10.04 (1H, s), 10.83 (1H, s). |
| 33 | δ 2.31 (6H, s), 7.45 (2H, s), 7.57 (1H, t, J = 8.1 Hz), 7.80 (1H, d, J = 8.1 Hz), 8.08 (1H, d, J = 8.1 Hz), 8.24 (1H, s), 8.36-8.41 (4H, m), 10.01 (1H, s), 10.79 (1H, s). |
| 34 | δ 2.30 (6H, s), 6.39 (2H, s), 6.58-6.62 (1H, m), 6.76 (1H, dd, J = 1.0, 8.3 Hz), 7.19-7.24 (1H, m), 7.45 (2H, s), 7.51 (1H, t, J = 7.8 Hz), 7.66-7.73 (2H, m), 7.94-7.97 (1H, m), 8.30 (1H, d, J = 2.0 Hz), 9.96 (1H, s), 10.20 (1H, s). |
| 35 | δ 2.30 (6H, s), 6.53-6.86 (1H, m), 7.20-7.21 (4H, m), 7.45 (2H, s), 7.52 (1H, t, J = 7.8 Hz), 7.73 (1H, d, J = 7.8 Hz), 8.02 (1H, d, J = 7.8 Hz), 8.35 (1H, s), 9.96 (1H, s), 10.32 (1H, s). |
| 37 | (CDCl$_3$) δ 2.34 (6H, s), 7.35 (2H, s), 7.51 (1H, t, J = 7.8 Hz), 7.62-7.80 (8H, m), 8.25 (1H, s). |
| 39 | δ 2.31 (6H, s), 7.45 (2H, s), 7.57 (1H, t, J = 7.8 Hz), 7.79 (1H, d, J = 7.8 Hz), 7.94 (2H, d, J = 8.3 Hz), 8.07 (1H, d, J = 7.8 Hz), 8.20 (2H, d, J = 8.3 Hz), 8.36 (1H, s), 10.01 (1H, s), 10.70 (1H, s). |
| 40 | δ 2.30 (6H, s), 6.96-7.01 (2H, m), 7.43-7.48 (3H, m), 7.56 (1H, t, J = 8.3 Hz), 7.78 (1H, d, J = 8.3 Hz), 7.97-8.00 (2H, m), 8.29 (1H, s), 10.01 (1H, s), 10.61 (1H, s). |
| 41 | δ 2.30 (6H, s), 3.90 (3H, s), 7.05-7.10 (1H, m), 7.19 (1H, d, J = 8.3 Hz), 7.45 (2H, s), 7.49-7.54 (2H, m), 7.63 (1H, dd, J = 2.0, 7.8 Hz), 7.72 (1H, d, J = 7.8 Hz), 7.96 (1H, d, J = 7.8 Hz), 8.33 (1H, s), 9.98 (1H, s), 10.33 (1H, s). |
| 45 | δ 1.33 (9H, s), 2.31 (6H, s), 7.45 (2H, s), 7.53 (1H, t, J = 7.8 Hz), 7.54 (2H, d, J = 8.3 Hz), 7.74 (1H, d, J = 7.8 Hz), 7.94 (2H, d, J = 8.3 Hz), 8.06 (1H, d, J = 7.8 Hz), 8.36 (1H, s), 9.99 (1H, s), 10.40 (1H, s). |
| 46 | δ 2.30 (6H, s), 2.98 (6H, s), 6.93-6.95 (1H, m), 7.25-7.35 (3H, m), 7.45 (2H, s), 7.53 (1H, t, J = 7.8 Hz), 7.74 (1H, d, J = 7.8 Hz), 8.06 (1H, d, J = 7.8 Hz), 8.35 (1H, s), 9.99 (1H, s), 10.35 (1H, s). |
| 47 | δ 2.30 (6H, s), 3.01 (6H, s), 6.77 (2H, d, J = 9.3 Hz), 7.45 (2H, s), 7.50 (1H, t, J = 7.8 Hz), 7.69 (1H, d, J = 7.8 Hz), 7.91 (2H, d, J = 9.3 Hz), 8.06 (1H, d, J = 7.8 Hz), 8.33 (1H, s), 9.96 (1H, s), 10.09 (1H, s). |
| 48 | δ 2.31 (6H, s), 7.45 (2H, s), 7.53-7.60 (3H, m), 7.77 (1H, d, J = 7.3 Hz), 8.06 (1H, d, J = 8.3 Hz), 8.13 (2H, d, J = 8.3 Hz), 8.35 (1H, s), 10.01 (1H, s), 10.59 (1H, s). |
| 52 | δ 2.21 (3H, s), 2.30 (6H, s), 7.27 (1H, d, J = 8.3 Hz), 7.39-7.44 (1H, m), 7.45 (2H, s), 7.50-7.62 (2H, m), 7.70-7.52 (2H, m), 7.92 (1H, d, J = 7.8 Hz), 8.29 (1H, s), 9.99 (1H, s), 10.57 (1H, s). |
| 54 | δ 2.30 (6H, s), 3.91 (3H, s), 7.45 (2H, s), 7.56 (1H, t, J = 7.8 Hz), 7.78 (1H, d, J = 7.8 Hz), 8.03-8.15 (5H, m), 8.36 (1H, s), 10.01 (1H, s), 10.67 (1H, s). |
| 56 | δ 2.27 (3H, s), 2.30 (6H, s), 7.18-7.22 (1H, m), 7.26-7.30 (2H, m), 7.45 (2H, s), 7.52 (1H, t, J = 7.8 Hz), 7.72 (1H, d, J = 7.8 Hz), 7.95 (1H, d, J = 7.8 Hz), 8.36 (1H, s), 9.98 (1H, s), 10.52 (1H, s). |
| 57 | δ 2.30 (6H, s), 2.33 (3H, s), 2.38 (3H, s), 7.11-7.13 (2H, m), 7.40 (1H, d, J = 7.8 Hz), 7.44 (2H, s), 7.51 (1H, t, J = 7.8 Hz), 7.72 (1H, d, J = 7.8 Hz), 7.95 (1H, d, J = 8.8 Hz), 8.34 (1H, s), 9.98 (1H, s), 10.43 (1H, s). |

TABLE 11-continued

| Comp. No. | |
|---|---|
| 58 | δ 2.30 (12H, s), 7.12 (2H, d, J = 7.8 Hz), 7.23-7.27 (1H, m), 7.45 (2H, s), 7.52 (1H, t, J = 8.3 Hz), 7.75 (1H, d, J = 8.3 Hz), 7.94-7.99 (1H, m), 8.35 (1H, s), 10.00 (1H, s), 10.61 (1H, s). |
| 59 | δ 2.30 (6H, s), 7.34-7.40 (1H, m), 7.45 (2H, s), 7.50-7.58 (2H, m), 7.60-7.68 (1H, m), 7.77 (1H, d, J = 7.8 Hz), 7.96 (1H, d, J = 8.3 Hz), 8.31 (1H, s), 10.02 (1H, s), 10.78 (1H, s). |
| 60 | δ 2.30 (6H, s), 7.22-7.28 (1H, m), 7.42-7.48 (3H, m), 7.53-7.57 (1H, m), 7.75-7.82 (2H, m), 7.96 (1H, d, J = 7.8 Hz), 8.30 (1H, s), 10.01 (1H, s), 10.65 (1H, s). |
| 61 | δ 2.30 (6H, s), 7.45 (2H, s), 7.46-7.49 (2H, m), 7.53-7.59 (2H, m), 7.77 (1H, d, J = 7.8 Hz), 7.96 (1H, d, J = 8.3 Hz), 8.30 (1H, s), 10.02 (1H, broad), 10.72 (1H, broad). |
| 62 | δ 2.30 (6H, s), 7.25-7.30 (2H, m), 7.45 (2H, s), 7.54-7.65 (2H, m), 7.77 (1H, d, J = 7.8 Hz), 7.93 (1H, d, J = 7.8 Hz), 8.29 (1H, s), 10.03 (1H, s), 11.04 (1H, s). |
| 66 | δ 2.30 (6H, s), 7.45 (2H, s), 7.52-7.62 (2H, m), 7.66 (1H, d, J = 8.3 Hz), 7.75-7.80 (2H, m), 7.94 (1H, d, J = 7.8 Hz), 8.30 (1H, s), 10.02 (1H, s), 10.77 (1H, s). |
| 68 | δ 2.30 (6H, s), 7.45 (2H, s), 7.50-7.62 (4H, m), 7.78 (1H, d, J = 7.8 Hz), 7.94 (1H, d, J = 7.8 Hz), 8.28 (1H, s), 10.03 (1H, s), 10.99 (1H, s). |
| 69 | δ 2.30 (6H, s), 7.45 (2H, s), 7.56 (1H, t, J = 7.8 Hz), 7.79 (1H, d, J = 7.8 Hz), 7.85 (1H, d, J = 8.3 Hz), 7.97-8.00 (1H, m), 8.05-8.08 (1H, m), 8.27 (1H, d, J = 2.0 Hz), 8.33 (1H, s), 10.00 (1H, s), 10.61 (1H, s). |
| 70 | δ 2.74 (6H, s), 7.34 (2H, s), 7.52 (1H, t, J = 7.8 Hz), 7.81 (1H, d, J = 7.8 Hz), 7.93 (1H, d, J = 8.3 Hz), 8.13-8.15 (2H, m), 8.58 (1H, d, J = 8.3 Hz), 8.94 (1H, s), 9.27 (1H, s), 10.67 (1H, s). |
| 71 | (CDCl$_3$) δ 1.6-2.4 (6H, broad-s), 6.5-7.7 (3H, broad), 7.8-8.0 (4H, broad), 8.10 (1H, broad-s), 8.28 (1H, d, J = 8.8 Hz). |
| 72 | δ 2.30 (6H, s), 3.78 (6H, s), 6.66-6.75 (2H, m), 7.34-7.50 (4H, m), 7.67 (1H, d, J = 7.8 Hz), 7.91 (1H, d, J = 7.8 Hz), 8.34 (1H, s), 9.98 (1H, s), 10.44 (1H, s). |
| 73 | δ 2.30 (6H, s), 3.83 (6H, s), 6.73 (1H, t, J = 2.4 Hz), 7.15 (2H, d, J = 2.4 Hz), 7.45 (2H, s), 7.54 (1H, t, J = 8.3 Hz), 7.75 (1H, d, J = 8.3 Hz), 8.06 (1H, d, J = 8.3 Hz), 8.33 (1H, s), 9.99 (1H, s), 10.39 (1H, s). |
| 74 | (CDCl$_3$) δ 2.34 (6H, s), 2.68 (3H, s), 7.36 (2H, s), 7.55 (1H, t, J = 7.8 Hz), 7.62 (1H, s), 7.72 (1H, d, J = 7.8 Hz), 7.81 (1H, d, J = 8.3 Hz), 7.88 (1H, s), 7.92 (1H, d, J = 7.8 Hz), 8.05 (1H, d, J = 8.3 Hz), 8.17 (1H, s), 8.26 (1H, s). |
| 75 | δ 2.30 (6H, s), 5.22 (2H, broad-s), 6.67-6.72 (1H, m), 6.78-6.81 (1H, m), 6.97-7.02 (1H, m), 7.45 (2H, s), 7.52 (1H, t, J = 7.8 Hz), 7.72 (1H, d, J = 7.8 Hz), 7.94 (1H, d, J = 7.8 Hz), 8.32 (1H, s), 9.98 (1H, s), 10.46 (1H, s). |
| 77 | δ 2.30 (6H, s), 7.45 (2H, s), 7.58 (1H, t, J = 7.8 Hz), 7.70 (1H, t, J = 8.8 Hz), 7.80 (1H, d, J = 7.8 Hz), 7.99 (1H, d, J = 7.8 Hz), 8.29 (1H, s), 8.45-8.50 (1H, m), 8.57-8.60 (1H, m), 10.03 (1H, s), 10.91 (1H, s). |
| 81 | δ 2.30 (6H, s), 7.56 (1H, t), 7.73-7.80 (6H, m), 7.92 (1H, d, J = 7.81 Hz), 8.22 (1H, s), 10.03 (1H, s), 11.05 (1H, s). |
| 82 | δ 2.30 (6H, s), 7.45 (2H, s), 7.57 (1H, t, J = 7.8 Hz), 7.80 (1H, d, J = 7.8 Hz), 7.92-7.96 (2H, m), 8.29-8.45 (2H, m), 8.45 (1H, m), 10.03 (1H, s), 10.98 (1H, s). |
| 83 | δ 2.28 (6H, s), 7.33-7.38 (1H, m), 7.43 (2H, s), 7.53 (1H, t, J = 7.9 Hz), 7.58 (1H, d, J = 2.4 Hz), 7.61-7.71 (1H, m), 7.75 (1H, d, J = 7.9 Hz), 7.93 (1H, d, J = 7.9 Hz), 8.28 (1H, s), 9.98 (1H, s), 10.71 (1H, s). |
| 84 | δ 2.30 (6H, s), 7.38-7.48 (4H, m), 7.54-7.60 (2H, m), 7.78 (1H, d, J = 7.8 Hz), 7.93 (1H, d, J = 7.8 Hz), 8.28 (1H, s), 10.03 (1H, s), 11.03 (1H, s). |
| 86 | δ 2.30 (6H, s), 7.42-7.47 (3H, m), 7.55 (1H, t, J = 8.0 Hz), 7.64 (1H, d, J = 2.0 Hz), 7.66-7.77 (2H, m), 7.96 (1H, d, J = 8.0 Hz), 8.29 (1H, s), 10.01 (1H, s), 10.69 (1H, s). |
| 87 | δ 2.30 (6H, s), 7.45 (2H, s), 7.56 (1H, t, J = 7.9 Hz), 7.79 (1H, d, J = 7.9 Hz), 7.87 (1H, d, J = 7.9 Hz), 7.92 (1H, dd, J = 8.2, 1.6 Hz), 8.00 (1H, dd, J = 8.2, 1.6 Hz), 8.22 (1H, t, J = 1.6 Hz), 8.29 (1H, d, J = 1.6 Hz), 10.03 (1H, s), 10.94 (1H, s). |
| 88 | (CDCl$_3$) δ 2.37 (6H, s), 4.06 (3H, s), 7.37 (2H, s), 7.44 (1H, d, J = 9.7 Hz), 7.52 (1H, s), 7.58 (1H, t, J = 7.8 Hz), 7.70 (1H, s), 7.74 (1H, d, J = 7.8 Hz), 7.93 (1H, s), 7.95 (1H, s), 8.02 (1H, s), 8.26 (1H, s). |
| 89 | (CDCl$_3$) δ 2.37 (6H, s), 4.22 (3H, s), 7.37 (2H, s), 7.55 (1H, t, J = 7.8 Hz), 7.56 (1H, s), 7.72 (1H, d, J = 7.8 Hz), 7.94-7.97 (2H, m), 8.00 (1H, d, J = 7.8 Hz), 8.28 (1H, s), 8.47 (1H, d, J = 8.8 Hz), 9.83 (1H, s). |
| 91 | δ 2.25 (6H, s), 2.27 (3H, s), 2.29 (6H, s), 6.94 (2H, s), 7.45 (2H, s), 7.51 (1H, t, J = 7.8 Hz), 7.73 (1H, d, J = 7.8 Hz), 7.94 (1H, d, J = 7.8 Hz), 8.34 (1H, s), 9.97 (1H, s), 10.53 (1H, s). |
| 92 | δ 2.33 (6H, s), 7.32-7.40 (1H, m), 7.45 (2H, s), 7.58 (1H, t, J = 8.06 Hz), 7.67-7.75 (1H, m), 7.80 (1H, d, J = 7.81 Hz), 7.92 (1H, d, J = 8.29 Hz), 8.27 (1H, s), 10.04 (1H, s), 11.14 (1H, s). |
| 95 | δ 2.30 (6H, s), 7.45 (2H, s), 7.59 (1H, t, J = 7.8 Hz), 7.83 (1H, d, J = 7.8 Hz), 7.91-7.94 (1H, dd, J = 1.5, 7.8 Hz), 8.25 (1H, d, J = 1.5 Hz), 10.06 (1H, s), 11.27 (1H, s). |
| 96 | δ 2.30 (6H, s), 7.28-7.55 (10H, m), 7.57-7.61 (2H, m), 7.69 (1H, d, J = 7.8 Hz), 7.74 (1H, d, J = 7.8 Hz), 8.13 (1H, s), 9.94 (1H, s), 10.47 (1H, s). |
| 97 | δ 2.32 (6H, s), 7.41-7.57 (6H, m), 7.72-7.82 (3H, m), 7.85-7.88 (2H, m), 8.09-8.13 (3H, m), 8.40 (1H, s), 10.01 (1H, s), 10.53 (1H, s). |
| 98 | δ 2.31 (6H, s), 7.45 (2H, s), 7.54-7.65 (4H, m), 7.76-7.80 (2H, m), 8.01-8.06 (2H, m), 8.10 (1H, d, J = 8.3 Hz), 8.21-8.23 (1H, m), 8.43 (1H, s), 10.01 (1H, s), 10.80 (1H, s). |
| 99 | δ 2.32 (6H, s), 7.46 (2H, s), 7.57 (1H, t, J = 7.8 Hz), 7.61-7.72 (2H, m), 7.78 (1H, d, J = 7.8 Hz), 7.99-8.17 (5H, m), 8.41 (1H, t, J = 2.0 Hz), 8.65 (1H, s), 10.01 (1H, s), 10.66 (1H, s). |
| 100 | δ 2.31 (6H, s), 7.45 (2H, s), 7.55 (1H, t, J = 7.8 Hz), 7.69-7.76 (2H, m), 8.07-8.14 (2H, m), 8.19 (1H, d, J = 7.8 Hz), 8.54 (1H, s), 8.77 (1H, d, J = 4.9 Hz), 9.99 (1H, s), 10.86 (1H, s). |
| 101 | δ 2.30 (6H, s), 7.45 (2H, s), 7.54-7.61 (2H, m), 7.78 (1H, d, J = 8.3 Hz), 8.06 (1H, d, J = 7.3 Hz), 8.32-8.35 (2H, m), 8.77-8.79 (1H, m), 9.14 (1H, d, J = 1.5 Hz), 10.00 (1H, s), 10.66 (1H, s). |

TABLE 11-continued

| Comp. No. | |
|---|---|
| 102 | δ 2.30 (6H, s), 7.45 (2H, s), 7.57 (1H, t, J = 7.8 Hz), 7.80 (1H, d, J = 7.8 Hz), 7.91 (2H, d, J = 5.6 Hz), 8.06 (1H, d, J = 7.8 Hz), 8.35 (1H, s), 8.81 (2H, d, J = 5.6 Hz), 10.01 (1H, s), 10.72 (1H, s). |
| 103 | δ 2.27 (3H, s), 2.30 (6H, s), 7.45 (2H, s), 7.54-8.07 (6H, m), 8.35 (1H, s), 10.02 (1H, s), 10.77 (1H, s). |
| 105 | δ 2.30 (6H, s), 7.45 (2H, s), 7.52-7.58 (2H, m), 7.78 (1H, d, J = 8.30 Hz), 7.97 (1H, d, J = 8.29 Hz), 8.26-8.31 (2H, m), 8.42 (1H, d, J = 4.39 Hz), 10.02 (1H, s), 10.80 (1H, s). |
| 106 | δ 2.30 (6H, s), 7.45 (2H, s), 7.54-7.60 (2H, m), 7.77-7.81 (1H, m), 7.95 (1H, d, J = 7.8 Hz), 8.10-8.13 (1H, m), 8.30 (1H, s), 8.54-8.59 (1H, m), 10.03 (1H, s), 10.88 (1H, s). |
| 108 | δ 2.31 (6H, s), 7.45 (2H, s), 7.56 (1H, t, J = 7.8 Hz), 7.78 (1H, d, J = 7.8 Hz), 7.82 (1H, dd, J = 6.3, 2.4 Hz), 8.11-8.16 (3H, m), 8.47 (1H, s), 10.01 (1H, s), 10.69 (1H, s). |
| 109 | δ 2.31 (6H, s), 7.46 (2H, s), 7.57 (1H, t, J = 8.3 Hz), 7.74 (1H, d, J = 8.3 Hz), 7.80 (1H, d, J = 8.3 Hz), 8.06 (1H, dd, J = 8.3, 1.7 Hz), 8.34 (1H, t, J = 1.7 Hz), 8.40 (1H, dd, J = 8.3, 1.7 Hz), 9.00 (1H, d, J = 1.7 Hz), 10.02 (1H, s), 10.71 (1H, s). |
| 110 | δ 2.31 (6H, s), 7.45 (2H, s), 7.56 (1H, d, J = 8.1 Hz), 7.78 (1H, d, J = 8.1 Hz), 7.86 (1H, d, J = 2.1 Hz), 8.11 (1H, dd, J = 8.1, 2.1 Hz), 8.19 (1H, d, J = 2.1 Hz), 8.53 (1H, t, J = 2.1 Hz), 8.75 (1H, d, J = 5.4 Hz), 10.01 (1H, s), 10.96 (1H, s). |
| 111 | (CDCl$_3$) δ 2.36 (6H, s,), 7.34 (2H, s,), 7.47-8.94 (7H, m,), 9.63 (1H, s,), 10.73 (1H, s,). |
| 113 | (CDCl$_3$) δ 2.36 (6H, s,), 7.34-8.73 (15H, m, Ar,), 10.01 (1H, s,) |
| 114 | δ 2.30 (6H, s), 2.42 (3H, s), 7.25-7.28 (1H, m), 7.44 (2H, s), 7.55 (1H, t, J = 7.8 Hz), 7.77 (1H, d, J = 7.8 Hz), 7.94-7.97 (2H, m), 8.30 (1H, s), 8.61 (1H, dd, J = 4.9, 1.5 Hz), 10.00 (1H, s), 10.67 (1H, s). |
| 115 | δ 2.29 (6H, s), 3.94 (3H, s), 4.06 (3H, s), 6.53 (1H, d, J = 8.3 Hz), 7.44 (2H, s), 7.51 (1H, t, J = 7.9 Hz), 7.72 (1H, d, J = 7.9 Hz), 7.95 (1H, d, J = 7.9 Hz), 8.12 (1H, d, J = 8.3 Hz), 8.28 (1H, s), 9.96 (1H, s), 10.07 (1H, s). |
| 116 | δ 2.29 (6H, s), 7.44 (2H, s), 7.57 (1H, t, J = 7.9 Hz), 7.80 (1H, d, J = 7.9 Hz), 8.05 (1H, d, J = 7.9 Hz), 8.30 (1H, s), 8.67 (1H, d, J = 2.2 Hz), 8.93 (1H, d, J = 2.2 Hz), 10.01 (1H, s), 10.73 (1H, s). |
| 117 | (CDCl$_3$) δ 2.36 (6H, s), 7.37-8.50 (9H, m,), 8.97 (1H, s). |
| 118 | δ 2.28 (6H, s), 7.43 (2H, s), 7.56 (1H, t, J = 8.0 Hz), 7.74-7.79 (2H, m), 7.92 (1H, d, J = 8.0 Hz), 8.20 (1H, d, J = 8.3 Hz), 8.25 (1H, s), 10.01 (1H, s), 10.88 (1H, s). |
| 119 | (CDCl$_3$) δ 2.36 (6H, s), 7.36-8.60 (10H, m,). |
| 120 | δ 2.31 (6H, s), 7.46 (2H, s), 7.57 (1H, t, J = 7.8 Hz), 7.80 (1H, d, J = 7.8 Hz), 8.02 (1H, d, J = 7.8 Hz), 8.08 (2H, d, J = 1.2 Hz), 8.33 (1H, t, J = 2.0 Hz), 8.40 (2H, d, J = 7.3 Hz), 10.02 (1H, s), 10.63 (1H, s). |
| 121 | δ 2.30 (6H, s), 3.89 (3H, s), 6.11 (1H, dd, J = 2.0, 3.9 Hz), 7.03 (1H, t, J = 2.0 Hz), 7.10 (1H, dd, J = 2.0, 3.9 Hz), 7.45 (2H, s), 7.49 (1H, t, J = 7.8 Hz), 7.69 (1H, d, J = 7.8 Hz), 7.99 (1H, d, J = 7.8 Hz), 8.28 (1H, s), 9.95 (2H, s). |
| 122 | δ 2.31 (6H, s), 7.45 (2H, s), 7.57 (1H, t, J = 7.8 Hz), 7.78 (1H, d, J = 7.8 Hz), 8.11 (1H, d, J = 7.8 Hz), 8.53 (1H, s), 8.84 (1H, dd, J = 1.5, 2.4 Hz), 8.95 (1H, d, J = 2.4 Hz), 9.33 (1H, d, J = 1.5 Hz), 10.00 (1H, s), 10.97 (1H, s). |
| 124 | δ 2.28 (6H, s), 7.44 (2H, s), 7.58 (1H, t, J = 7.9 Hz), 7.81 (1H, d, J = 7.9 Hz), 7.92 (1H, d, J = 7.9 Hz), 8.20 (1H, s), 9.43 (1H, s), 9.59 (1H, s), 10.03 (1H, s), 11.06 (1H, s). |
| 125 | δ 2.30 (6H, s), 7.45 (2H, s), 7.50-7.62 (4H, m), 7.78 (1H, d, J = 7.8 Hz), 7.94 (1H, d, J = 7.8 Hz), 8.28 (1H, s), 10.03 (1H, s), 10.99 (1H, s). |
| 126 | δ 2.30 (6H, s), 7.04 (1H, t, J = 1.5 Hz), 7.45 (2H, s), 7.53 (1H, t, J = 8.0 Hz), 7.74-7.82 (2H, m), 8.04 (1H, d, J = 1.5 Hz), 8.25 (1H, d, J = 1.5 Hz), 8.43 (1H, t, J = 1.5 Hz), 9.98 (1H, s), 10.14 (1H, s). |
| 127 | δ 1.86-1.91 (2H, m), 2.00-2.02 (1H, m), 2.19-2.29 (7H, m), 3.81-3.87 (1H, m), 3.98-4.03 (1H, m), 4.40-4.43 (1H, m), 7.44-7.50 (3H, m), 7.77 (1H, d, J = 7.8 Hz), 7.94 (1H, d, J = 7.8 Hz), 8.26 (1H, s), 9.89 (1H, s), 9.94 (1H, s). |
| 128 | (CDCl$_3$) δ 2.02-2.10 (2H, m), 2.28 (6H, m), 3.15-3.22 (1H, m), 3.80-3.98 (4H, m), 7.44 (2H, s), 7.48 (1H, t, J = 7.8 Hz), 7.68 (1H, t, J = 7.8 Hz), 7.87 (1H, d, J = 7.8 Hz), 8.16 (1H, s), 9.96 (1H, s), 10.3 (1H, s). |
| 129 | (CDCl$_3$) δ 2.22 (6H, s), 7.17-7.28 (3H, m), 7.33-7.39 (2H, m), 7.42-7.48 (2H, m), 7.58-7.65 (2H, m), 7.79 (1H, dd, J = 1.5, 8.3 Hz), 7.91 (1H, s), 8.27 (1H, s), 8.51 (1H, s). |
| 130 | (CDCl$_3$) δ 1.48-2.17 (6H, m), 2.34 (6H, s), 3.52-3.60 (1H, m), 3.92 (1H, dd, J = 2.5, 11.2 Hz), 4.11-4.18 (1H, m), 7.35 (2H, s), 7.47 (1H, t, J = 7.8 Hz), 7.60 (1H, broad), 7.69 (1H, d, J = 7.8 Hz), 7.77 (1H, dd, J = 1.0, 7.8 Hz), 8.26 (1H, s), 8.54 (1H, s). |
| 131 | δ 1.97-2.07 (2H, m), 2.15-2.31 (9H, m), 2.97-3.07 (2H, m), 3.99-3.98 (2H, m), 7.46 (2H, s), 7.55 (1H, t, J = 8.0 Hz), 7.65 (1H, d, J = 8.0 Hz), 7.87 (1H, d, J = 8.0 Hz), 8.20 (1H, s), 9.60 (1H, s), 9.91 (1H, s). |
| 132 | (CDCl$_3$) δ 2.35 (6H, s), 7.16 (1H, dd, J = 3.9, 4.9 Hz), 7.36 (2H, s), 7.51 (1H, t, J = 7.8 Hz), 7.59 (1H, dd, J = 1.0, 4.9 Hz), 7.67 (1H, dd, J = 1.0, 3.9 Hz), 7.70-7.74 (2H, m), 7.80-7.83 (1H, m), 7.95 (1H, s), 8.27 (1H, s). |
| 133 | δ 2.30 (6H, s), 7.45 (2H, s), 7.54 (1H, t, J = 8.0 Hz), 7.67 (2H, d, J = 2.4 Hz), 7.75 (1H, d, J = 7.8 Hz), 8.07 (1H, d, J = 7.8 Hz), 8.31 (1H, s), 8.41 (1H, t, J = 2.2 Hz), 9.99 (1H, s), 10.28 (1H, s). |
| 134 | δ 2.30 (6H, s), 2.47 (3H, s), 7.04 (1H, d, J = 4.2 Hz), 7.45 (2H, s), 7.52 (1H, t, J = 7.8 Hz), 7.69 (1H, d, J = 4.2 Hz), 7.74 (1H, d, J = 7.8 Hz), 7.93 (1H, d, J = 7.8 Hz), 8.27 (1H, s), 9.97 (1H, s), 10.17 (1H, s). |
| 135 | δ 2.30 (6H, s), 7.45 (2H, s), 7.56 (1H, t, J = 7.8 Hz), 7.79 (1H, d, J = 7.8 Hz), 8.08 (1H, d, J = 7.8 Hz), 8.30 (1H, s), 8.71 (1H, d, J = 2.0 Hz), 8.74 (1H, d, J = 2.0 Hz), 10.01 (1H, s), 10.54 (1H, s). |
| 136 | δ 2.30 (6H, s), 2.50 (3H, s), 6.94 (1H, d, J = 3.4 Hz), 7.45 (2H, s), 7.52 (1H, t, J = 7.9 Hz), 7.74 (1H, d, J = 7.9 Hz), 7.88 (1H, d, J = 3.4 Hz), 8.02 (1H, d, J = 7.9 Hz), 8.27 (1H, s), 9.97 (1H, s), 10.32 (1H, s). |
| 137 | δ 2.29 (6H, s), 7.22 (1H, d, J = 5.1 Hz), 7.43 (2H, s), 7.53 (1H, t, J = 8.0 Hz), 7.76 (1H, d, J = 8.0 Hz), 7.91-7.93 (2H, m), 8.26 (1H, s), 9.98 (1H, s), 10.42 (1H, s). |
| 138 | δ 2.30 (6H, s), 7.45 (2H, s), 7.57 (1H, t, J = 8.1 Hz), 7.79 (1H, d, J = 8.1 Hz), 8.05 (1H, d, J = 8.1 Hz), 8.52 (1H, s), 9.97 (1H, s), 11.11 (1H, s). |
| 139 | δ 2.30 (6H, s), 7.26 (1H, d, J = 5.4 Hz), 7.45 (2H, s), 7.54 (1H, t, J = 8.0 Hz), 7.77 (1H, d, J = 8.0 Hz), 7.90-7.94 (2H, m), 8.27 (1H, s), 9.99 (1H, s), 10.50 (1H, s). |
| 140 | δ 2.30 (6H, s), 7.39 (1H, d, J = 4.6 Hz), 7.45 (2H, s), 7.54 (1H, t, J = 8.1 Hz), 7.77 (1H, d, J = 8.1 Hz), 7.92 (1H, d, J = 4.6 Hz), 8.02 (1H, d, J = 8.1 Hz), 8.26 (1H, s), 9.99 (1H, s), 10.50 (1H, s). |
| 141 | δ 2.30 (6H, s), 7.29 (1H, d, J = 4.9 Hz), 7.45 (2H, s), 7.55 (1H, t, J = 7.9 Hz), 7.77 (1H, d, J = 7.9 Hz), 7.81 (1H, d, J = 4.9 Hz), 7.92 (1H, d, J = 7.9 Hz), 8.29 (1H, s), 10.00 (1H, s), 10.50 (1H, s). |

TABLE 11-continued

| Comp. No. | |
|---|---|
| 142 | δ 2.27 (6H, s), 7.25-7.52 (10H, m), 7.70-7.73 (1H, m), 7.81-7.20 (1H, m), 8.12 (1H, s), 9.94 (1H, s), 10.27 (1H, s). |
| 143 | δ 2.28 (6H, s), 2.40 (3H, s), 2.45 (3H, s), 6.74 (1H, s), 7.43 (2H, s), 7.49 (1H, t, J = 8.1 Hz), 7.71 (1H, d, J = 8.1 Hz), 7.90 (1H, d, J = 8.1 Hz), 8.24 (1H, s), 9.94 (1H, s), 9.98 (1H, s). |
| 144 | δ 2.31 (6H, s), 7.41-7.59 (5H, m), 7.78 (1H, d, J = 7.8 Hz), 8.00-8.09 (3H, m), 8.34 (1H, d, J = 2.0 Hz), 8.43 (1H, s), 10.02 (1H, s), 10.75 (1H, s). |
| 146 | δ 0.86 (3H, 7.2), 2.30 (6H, s), 4.34 (2H, q, J = 7.2 Hz), 7.45 (2H, s), 7.77-7.79 (3H, m), 7.84 (1H, s), 8.24 (1H, s), 8.37 (1H, s), 10.05 (1H, s), 11.11 (1H, s). |
| 147 | δ 2.30 (6H, s), 3.89 (3H, s), 7.45 (2H, s), 7.52 (1H, t, J = 7.9 Hz), 7.73 (1H, d, J = 7.9 Hz), 7.97 (1H, d, J = 7.9 Hz), 8.23 (1H, s), 8.45 (1H, s), 9.98 (1H, s), 10.08 (1H, s). |
| 148 | δ 2.35 (6H, s), 3.92 (3H, s), 7.26 (1H, s), 7.36 (2H, s), 7.48-7.55 (2H, m),, 7.70 (1H, d, J = 7.7 Hz), 7.83 (1H, d, J = 7.7 Hz), 8.26 (1H, s), 8.47 (1H, s). |
| 149 | δ 2.36 (6H, s), 3.95 (3H, s), 7.26 (1H, s), 7.36 (2H, s), 7.50 (1H, t, J = 7.7 Hz), 7.70 (1H, d, J = 7.7 Hz), 7.83 (1H, d, J = 7.7 Hz), 8.00 (1H, s), 8.26 (1H, s), 8.58 (1H, s). |
| 150 | (CDCl$_3$) δ 2.35 (6H, s), 4.01 (3H, s), 7.36 (2H, s), 7.51 (1H, t, J = 7.8 Hz), 7.68-7.73 (3H, m), 7.92 (1H, s), 8.05 (1H, s), 8.25 (1H, s). |
| 151 | δ 2.29 (6H, s), 4.06 (3H, s), 7.44 (2H, s), 7.53 (1H, t, J = 7.9 Hz), 7.77 (1H, d, J = 7.9 Hz), 7.96 (1H, d, J = 7.9 Hz), 8.11 (1H, s), 8.26 (1H, s), 10.02 (1H, s), 10.58 (1H, s). |
| 152 | δ 2.30 (6H, s), 7.32 (1H, d, J = 2.0 Hz), 7.45 (2H, s), 7.58 (1H, t, J = 7.8 Hz), 7.81 (1H, d, J = 7.8 Hz), 8.04 (1H, d, J = 7.8 Hz), 8.35 (1H, s), 8.84 (1H, d, J = 2.0 Hz), 10.03 (1H, s), 10.97 (1H, s). |
| 153 | δ 2.29 (6H, s), 7.46 (2H, s), 7.64 (1H, t), 7.72 (1H, d, J = 1.0 Hz), 7.81 (1H, s), 7.97 (1H, d, J = 8.0 Hz), 8.17 (1H, s), 8.34 (1H, s), 10.04 (1H, s). |
| 154 | δ 2.29 (6H, s), 2.51 (3H, s), 2.56 (3H, s), 7.46 (2H, s), 7.53 (1H, t, J = 8.03 Hz), 7.75 (1H, d, J = 8.03 Hz), 7.92 (1H, d, J = 8.03 Hz), 8.24 (1H, s), 9.79 (1H, s), 10.30 (1H, s). |
| 155 | δ 1.36 (3H, t, J = 7.3 Hz), 2.30 (6H, s), 2.73 (3H, s), 3.05 (2H, q, J = 7.3 Hz), 7.45 (2H, s), 7.55 (1H, t, J = 8.3 Hz), 7.78 (1H, d, J = 8.3 Hz), 7.98 (1H, d, J = 8.3 Hz), 8.29 (1H, s), 10.01 (1H, s), 10.69 (1H, s). |
| 156 | δ 2.28 (6H, s), 2.57 (3H, s), 7.43 (2H, s), 7.53 (1H, t, J = 7.8 Hz), 7.77 (1H, d, J = 7.8 Hz), 7.91 (1H, d, J = 7.8 Hz), 8.21 (1H, s), 9.98 (1H, s), 10.47 (1H, s). |
| 157 | δ 2.31 (6H, s), 7.45 (2H, s), 7.57 (1H, t, J = 7.8 Hz), 7.79 (1H, d, J = 7.8 Hz), 8.06 (1H, d, J = 7.8 Hz), 8.53 (1H, s), 10.00 (1H, s), 11.12 (1H, s). |
| 158 | δ 2.36 (6H, s), 7.45 (2H, s), 7.57 (1H, t, J = 8.1 Hz), 7.79 (1H, d, J = 8.1 Hz), 8.06 (1H, d, J = 8.1 Hz), 8.53 (1H, s), 10.01 (1H, s), 11.11 (1H, s). |
| 159 | δ 2.30 (6H, s), 7.45 (2H, s), 7.56-7.66 (3H, m), 7.80 (1H, d, J = 8.3 Hz), 7.94-7.98 (2H, m), 8.16-8.20 (1H, m), 8.32 (1H, s), 10.04 (1H, s), 10.79 (1H, s). |
| 160 | δ 2.31 (6H, s), 7.45 (2H, s), 7.53-7.61 (2H, m), 7.78 (1H, d, J = 7.8 Hz), 7.92-7.95 (1H, m), 8.02-8.07 (2H, m), 8.34 (1H, s), 9.99 (1H, s), 10.50 (1H, s). |
| 161 | δ 2.30 (6H, s), 7.37 (1H, t, J = 7.8 Hz), 7.45 (2H, s), 7.57 (1H, t, J = 7.8 Hz), 7.62-7.65 (2H, m), 7.79 (1H, d, J = 7.8 Hz), 7.99 (1H, d, J = 7.8 Hz), 8.30 (1H, s), 10.01 (1H, s), 10.65 (1H, s). |
| 163 | δ 2.38 (3H, s), 7.53-7.63 (4H, m), 7.70 (1H, s), 7.77 (1H, d, J = 7.8 Hz), 7.81 (1H, s), 7.99-8.01 (2H, m), 8.08 (1H, d, J = 7.8 Hz), 8.37 (1H, s), 10.28 (1H, s), 10.50 (1H, s). |
| 164 | (CDCl$_3$) δ 1.20 (3H, t, J = 7.3 Hz), 2.32 (3H, s), 2.67 (2H, q, J = 7.3 Hz), 7.36 (2H, s), 7.46-7.51 (3H, m), 7.55-7.59 (1H, m), 7.67-7.72 (2H, m), 7.85-7.88 (3H, m), 8.15 (1H, s), 8.28 (1H, s). |
| 165 | δ 1.13 (3H, t, J = 7.3 Hz), 2.29 (3H, s), 2.67 (2H, q, J = 7.3 Hz), 7.33-7.41 (3H, m), 7.47 (1H, s), 7.52-7.63 (2H, m), 7.67-7.76 (2H, m), 7.97 (1H, d, J = 7.8 Hz), 8.32 (1H, s), 10.01 (1H, s), 10.65 (1H, s). |
| 166 | δ 2.36 (3H, s), 7.53-7.63 (4H, m), 7.68 (1H, s), 7.79 (1H, d, J = 7.8 Hz), 7.96 (1H, s), 7.99-8.01 (2H, m), 8.08 (1H, dd, J = 1.5, 7.8 Hz), 8.38 (1H, d, J = 1.5 Hz), 10.27 (1H, s), 10.50 (1H, s). |
| 167 | (CDCl$_3$) δ 2.48 (3H, s), 7.05 (1H, s), 7.23 (1H, s), 7.50-7.62 (4H, m), 7.69 (1H, d, J = 7.8 Hz), 7.84 (1H, dd, J = 2.0, 7.8 Hz), 7.89 (2H, d, J = 6.8 Hz), 8.13 (1H, s), 8.16 (1H, d, J = 6.8 Hz), 8.39 (1H, t, J = 1.9 Hz), 8.89 (1H, s). |
| 168 | δ 1.15 (3H, t, J = 7.3 Hz), 2.73 (2H, q, J = 7.3 Hz), 7.50-7.63 (5H, m), 7.71-7.77 (2H, m), 7.94-8.01 (2H, m), 8.08 (1H, d, J = 7.8 Hz), 8.37 (1H, s), 10.28 (1H, s), 10.50 (1H, s). |
| 169 | δ 1.14 (3H, t, J = 7.3 Hz), 2.73 (2H, q, J = 7.3 Hz), 7.52-7.64 (5H, m), 7.76 (1H, d, J = 7.8 Hz), 7.83 (1H, d, J = 2.0 Hz), 7.98-8.01 (2H, m), 8.06-8.09 (1H, m), 8.37 (1H, s), 10.29 (1H, s), 10.48 (1H, s). |
| 170 | δ 1.14 (3H, t, J = 7.3 Hz), 2.72 (2H, q, J = 7.3 Hz), 7.33-7.39 (2H, m), 7.53-7.64 (3H, m), 7.67-7.72 (1H, m), 7.76 (1H, d, J = 7.8 Hz), 7.82 (1H, s), 7.98 (1H, d, J = 8.8 Hz), 8.32 (1H, s), 10.30 (1H, s), 10.65 (1H, s). |
| 171 | δ 1.13 (3H, t, J = 7.3 Hz), 2.71 (2H, q, J = 7.3 Hz), 7.52-7.63 (5H, m), 7.78 (1H, d, J = 7.8 Hz), 7.97-8.01 (3H, m), 8.07-8.09 (1H, m), 8.37 (1H, d, J = 2.0 Hz), 10.28 (1H, s), 10.48 (1H, s). |
| 172 | δ 1.13 (3H, t, J = 7.3 Hz), 2.71 (2H, q, J = 7.3 Hz), 7.33-7.39 (2H, m), 7.54-7.63 (3H, m), 7.67-7.72 (1H, m), 7.78 (1H, d, J = 7.8 Hz), 7.97-8.00 (2H, m), 8.33 (1H, s), 10.30 (1H, s), 10.66 (1H, s). |
| 173 | δ 1.13 (3H, t, J = 7.3 Hz), 2.72 (2H, q, J = 7.3 Hz), 7.57-7.64 (2H, m), 7.83 (1H, d, J = 7.8 Hz), 7.98 (1H, s), 8.10 (1H, d, J = 7.8 Hz), 8.24 (2H, d, J = 8.8 Hz), 8.37 (1H, s), 8.40 (2H, d, J = 8.8 Hz), 10.32 (1H, s), 10.81 (1H, s). |
| 174 | δ 1.13 (3H, t, J = 7.3 Hz), 2.71 (2H, q, J = 7.3 Hz), 7.56-7.63 (2H, m), 7.82 (1H, d, J = 7.8 Hz), 7.98 (1H, s), 8.04-8.10 (3H, m), 8.15 (2H, d, J = 8.3 Hz), 8.36 (1H, s), 10.31 (1H, s), 10.72 (1H, s). |
| 175 | δ 0.85 (3H, t, J = 7.3 Hz), 1.49-1.59 (2H, m), 2.30 (3H, s), 2.65 (2H, t, J = 6.8 Hz), 7.40 (1H, s), 7.47 (1H, s), 7.58 (1H, t, J = 7.8 Hz), 7.79 (1H, d, J = 7.8 Hz), 8.08 (1H, s), 8.22-8.25 (2H, m), 8.36-8.41 (3H, m), 10.03 (1H, s), 10.79 (1H, s). |
| 176 | δ 1.18 (6H, d, J = 6.8 Hz), 2.29 (3H, s), 3.23 (1H, septet, J = 6.8 Hz), 7.41 (1H, s), 7.47 (1H, s), 7.52-7.63 (4H, m), 7.75 (1H, d, J = 7.8 Hz), 7.99-8.01 (2H, m), 8.06-8.09 (1H, m), 8.36 (1H, t, J = 2.0 Hz), 10.00 (1H, s), 10.48 (1H, s). |
| 177 | δ 1.17 (6H, d, J = 6.8 Hz), 2.30 (3H, s), 3.24 (1H, septet, J = 6.8 Hz), 7.28-7.41 (3H, m), 7.47 (1H, s), 7.55-7.63 (2H, m), 7.65-7.78 (2H, m), 7.99 (1H, d, J = 7.8 Hz), 8.33 (1H, s), 10.02 (1H, s), 10.66 (1H, s). |
| 178 | δ 0.85 (3H, t, J = 7.3 Hz), 1.47-1.60 (2H, m), 2.70 (2H, t, J = 7.3 Hz), 7.53-7.63 (5H, m), 7.75 (1H, d, J = 7.8 Hz), 7.83 (1H, d, J = 2.0 Hz), 7.98-8.01 (2H, m), 8.08 (1H, d, J = 7.8 Hz), 8.36 (1H, s), 10.29 (1H, s), 10.49 (1H, s). |

TABLE 11-continued

| Comp. No. | |
|---|---|
| 179 | δ 0.85 (3H, t, J = 7.3 Hz), 1.50-1.60 (2H, m), 2.69 (2H, t, J = 6.8 Hz), 7.29-7.40 (2H, m), 7.53-7.62 (3H, m), 7.67-7.76 (2H, m), 7.83 (1H, d, J = 2.0 Hz), 7.98 (1H, d, J = 7.8 Hz), 8.32 (1H, s), 10.31 (1H, s), 10.66 (1H, s). |
| 180 | δ 0.85 (3H, t, J = 7.3 Hz), 1.50-1.58 (2H, m), 2.70 (2H, t, J = 7.8 Hz), 7.57-7.63 (2H, m), 7.78-7.84 (2H, m), 8.09 (1H, d, J = 7.8 Hz), 8.18-8.24 (2H, m), 8.35-8.41 (3H, m), 10.32 (1H, s), 10.80 (1H, s). |
| 181 | δ 0.85 (3H, t, J = 7.3 Hz), 1.50-1.60 (2H, m), 2.69 (2H, t, J = 7.3 Hz), 7.56-7.62 (2H, m), 7.79 (1H, d, J = 7.8 Hz), 7.83 (1H, d, J = 2.0 Hz), 8.04-8.09 (3H, m), 8.15 (2H, d, J = 8.8 Hz), 8.35 (1H, s), 10.31 (1H, s), 10.72 (1H, s). |
| 182 | δ 0.84 (3H, t, J = 7.3 Hz), 1.49-1.59 (2H, m), 2.68 (2H, t, J = 7.3 Hz), 7.53-7.63 (5H, m), 7.77 (1H, d, J = 7.8 Hz), 7.97-8.01 (3H, m), 8.08 (1H, d, J = 7.8 Hz), 8.37 (1H, s), 10.29 (1H, s), 10.49 (1H, s). |
| 183 | δ 0.84 (3H, t, J = 7.3 Hz), 1.49-1.59 (2H, m), 2.67 (2H, t, J = 7.3 Hz), 7.28-7.40 (2H, m), 7.51-7.63 (3H, m), 7.68-7.72 (1H, m), 7.77 (1H, d, J = 8.3 Hz), 7.97-8.00 (2H, m), 8.33 (1H, s), 10.31 (1H, s), 10.67 (1H, s). |
| 184 | δ 0.84 (3H, t, J = 7.3 Hz), 1.49-1.59 (2H, m), 2.68 (2H, t, J = 6.8 Hz), 7.57-7.62 (2H, m), 7.82 (1H, d, J = 7.8 Hz), 7.98 (1H, d, J = 2.0 Hz), 8.08-8.10 (1H, m), 8.15-8.41 (5H, m), 10.32 (1H, s), 10.80 (1H, s). |
| 185 | δ 0.84 (3H, t, J = 7.3 Hz), 1.49-1.57 (2H, m), 2.68 (2H, broad), 7.56-7.61 (2H, m), 7.81 (1H, d, J = 7.8 Hz), 7.98 (1H, s), 8.05 (2H, d, J = 8.3 Hz), 8.09 (1H, s), 8.15 (2H, d, J = 8.3 Hz), 8.35 (1H, s), 10.31 (1H, s), 10.72 (1H, s). |
| 186 | δ 0.84 (3H, t, J = 7.3 Hz), 1.49-1.57 (2H, m), 2.68 (2H, t, J = 6.8 Hz), 7.56-7.61 (2H, m), 7.80 (1H, d, J = 7.8 Hz), 7.94 (2H, d, J = 8.3 Hz), 7.98 (1H, s), 8.09 (1H, d, J = 7.8 Hz), 8.20 (2H, d, J = 8.3 Hz), 8.36 (1H, s), 10.31 (1H, s), 10.71 (1H, s). |
| 187 | δ 0.83 (3H, t, J = 7.3 Hz), 1.21-1.31 (2H, m), 1.47-1.55 (2H, m), 2.72 (2H, t, J = 7.8 Hz), 7.53-7.63 (5H, m), 7.70-7.75 (2H, m), 7.99-8.01 (2H, m), 8.06-8.09 (1H, m), 8.37 (1H, t, J = 2.0 Hz), 10.27 (1H, s), 10.49 (1H, s). |
| 188 | δ 0.83 (3H, t, J = 7.3 Hz), 1.21-1.31 (2H, m), 1.47-1.55 (2H, m), 2.72 (2H, t, J = 7.8 Hz), 7.33-7.40 (2H, m), 7.53-7.63 (3H, m), 7.67-7.75 (3H, m), 7.98 (1H, d, J = 7.8 Hz), 8.32 (1H, s), 10.29 (1H, s), 10.66 (1H, s). |
| 189 | δ 0.83 (3H, t, J = 7.3 Hz), 1.21-1.31 (2H, m), 1.47-1.55 (2H, m), 2.72 (2H, t, J = 7.3 Hz), 7.52-7.63 (5H, m), 7.75 (1H, d, J = 7.8 Hz), 7.82 (1H, d, J = 1.5 Hz), 7.99-8.01 (2H, m), 8.08 (1H, dd, J = 1.5, 7.8 Hz), 8.37 (1H, t, J = 1.5 Hz), 10.29 (1H, s), 10.49 (1H, s). |
| 190 | δ 0.83 (3H, t, J = 7.3 Hz), 1.21-1.31 (2H, m), 1.47-1.55 (2H, m), 2.71 (2H, t, J = 7.3 Hz), 7.28-7.37 (2H, m), 7.53-7.62 (3H, m), 7.72 (1H, t, J = 7.3 Hz), 7.75 (1H, d, J = 7.8 Hz), 7.82 (1H, s), 7.98 (1H, d, J = 7.8 Hz), 8.62 (1H, s), 10.31 (1H, s), 10.66 (1H, s). |
| 191 | δ 0.82 (3H, t, J = 7.3 Hz), 1.22-1.30 (2H, m), 1.46-1.54 (2H, m), 2.70 (2H, t, J = 7.8 Hz), 7.53-7.63 (5H, m), 7.78 (1H, d, J = 7.8 Hz), 7.93-8.02 (3H, m), 8.07-8.09 (1H, m), 8.37 (1H, s), 10.29 (1H, s), 10.49 (1H, s). |
| 192 | δ 0.83 (3H, t, J = 7.3 Hz), 1.21-1.31 (2H, m), 1.47-1.55 (2H, m), 2.71 (2H, t, J = 7.8 Hz), 7.28-7.40 (2H, m), 7.55-7.65 (3H, m), 7.69-7.73 (1H, m), 7.79 (1H, d, J = 7.8 Hz), 7.98-8.02 (2H, m), 8.35 (1H, s), 10.33 (1H, s), 10.68 (1H, s). |
| 193 | δ 0.75 (3H, t, J = 7.3 Hz), 1.18 (3H, d, J = 6.8 Hz), 1.55-1.60 (2H, m), 3.00-3.05 (1H, m), 7.49-7.67 (5H, m), 7.72-7.77 (2H, m), 7.99-8.02 (2H, m), 8.09 (1H, d, J = 7.8 Hz), 8.36 (1H, s), 10.29 (1H, s), 10.49 (1H, s). |
| 194 | δ 0.75 (3H, t, J = 7.3 Hz), 1.17 (3H, d, J = 6.8 Hz), 1.55-1.60 (2H, m), 2.98-3.04 (1H, m), 7.52-7.63 (5H, m), 7.77 (1H, d, J = 8.3 Hz), 7.84 (1H, s), 7.99-8.10 (3H, m), 8.36 (1H, s), 10.30 (1H, s), 10.49 (1H, s). |
| 195 | δ 0.74 (3H, t, J = 7.3 Hz), 1.17 (3H, d, J = 6.8 Hz), 1.55-1.63 (2H, m), 2.98-3.04 (1H, m), 7.33-7.40 (2H, m), 7.52-7.63 (3H, m), 7.67-7.77 (2H, m), 7.83 (1H, d, J = 1.5 Hz), 7.99 (1H, d, J = 8.3 Hz), 8.32 (1H, s), 10.32 (1H, s), 10.66 (1H, s). |
| 196 | δ 0.74 (3H, t, J = 6.8 Hz), 1.15 (3H, d, J = 6.8 Hz), 1.53-1.64 (2H, m), 2.94-3.04 (1H, m), 7.51-7.63 (5H, m), 7.79 (1H, d, J = 7.3 Hz), 7.98-8.02 (3H, m), 8.09 (1H, dd, J = 1.5, 7.8 Hz), 8.37 (1H, s), 10.30 (1H, s), 10.50 (1H, s). |
| 197 | δ 7.33-7.41 (2H, m), 7.56-7.64 (2H, m), 7.68-7.73 (2H, m), 7.93-8.03 (2H, m), 8.38-8.40 (1H, m), 8.45 (1H, d, J = 2.0 Hz), 10.72 (1H, s), 10.98 (1H, s). |
| 198 | δ 2.50 (3H, s), 7.39 (1H, s), 7.48-7.63 (4H, m), 7.73 (1H, s), 7.77 (1H, d, J = 7.8 Hz), 7.99-8.01 (2H, m), 8.08 (1H, d, J = 7.8 Hz), 8.35 (1H, s), 10.36 (1H, s), 10.50 (1H, s). |
| 199 | δ 2.50 (3H, s), 7.33-7.39 (3H, m), 7.53-7.63 (2H, m), 7.67-7.77 (3H, m), 7.98 (1H, d, J = 7.8 Hz), 8.30 (1H, s), 10.38 (1H, s), 10.67 (1H, s). |
| 200 | δ 2.81 (3H, s), 7.53-7.64 (4H, m), 7.75 (1H, d, J = 8.3 Hz), 7.99-8.01 (2H, m), 8.08-8.11 (2H, m), 8.25 (1H, d, J = 2.0 Hz), 8.40 (1H, t, J = 2.0 Hz), 10.52 (1H, s), 10.61 (1H, s). |
| 201 | δ 3.40 (3H, s), 7.33-7.40 (2H, m), 7.56-7.63 (2H, m), 7.67-7.77 (2H, m), 7.99 (1H, d, J = 8.3 Hz), 8.17 (1H, d, J = 1.5 Hz), 8.35 (1H, s), 8.39 (1H, d, J = 1.5 Hz), 10.63 (1H, s), 10.69 (1H, s). |
| 202 | δ 3.40 (3H, s), 7.57-7.62 (2H, m), 7.79 (1H, d, J = 7.8 Hz), 7.96 (1H, dd, J = 1.5, 8.3 Hz), 8.12 (1H, dd, J = 1.5, 8.3 Hz), 8.17 (1H, d, J = 2.0 Hz), 8.32 (1H, d, J = 2.0 Hz), 8.40 (1H, d, J = 2.0 Hz), 8.54-8.56 (1H, m), 10.65 (1H, s), 10.92 (1H, s). |
| 203 | δ 3.40 (3H, s), 7.53-7.63 (4H, m), 7.78 (1H, d, J = 7.8 Hz), 7.98-8.01 (2H, m), 8.07-8.10 (1H, m), 8.21 (1H, s), 8.39 (1H, s), 8.48 (1H, d, J = 1.5 Hz), 10.51 (1H, s), 10.63 (1H, s). |
| 204 | δ 3.39 (3H, s), 7.33-7.40 (2H, m), 7.56-7.63 (2H, m), 7.68-7.72 (1H, m), 7.78 (1H, d, J = 7.8 Hz), 8.00 (1H, d, J = 7.8 Hz), 8.21 (1H, d, J = 1.5 Hz), 8.35 (1H, s), 8.48 (1H, d, J = 1.5 Hz), 10.66 (1H, s), 10.69 (1H, s). |
| 205 | δ 3.39 (3H, s), 7.36-7.42 (2H, m), 7.58 (1H, t, J = 7.8 Hz), 7.78 (1H, d, J = 7.8 Hz), 8.06-8.10 (3H, m), 8.21 (1H, s), 8.36 (1H, s), 8.48 (1H, s), 10.52 (1H, s), 10.63 (1H, s). |
| 206 | δ 3.39 (3H, s), 7.61 (1H, t, J = 7.8 Hz), 7.82 (1H, d, J = 7.8 Hz), 8.09 (1H, d, J = 7.8 Hz), 8.20-8.24 (3H, m), 8.37-8.41 (3H, m), 8.48 (1H, s), 10.67 (1H, s), 10.83 (1H, s). |
| 207 | δ 3.39 (3H, s), 7.60 (1H, t, J = 7.8 Hz), 7.81 (1H, d, J = 7.8 Hz), 7.97-8.10 (3H, m), 8.14-8.21 (3H, m), 8.37 (1H, t, J = 2.0 Hz), 8.48 (1H, d, J = 2.0 Hz), 10.65 (1H, s), 10.74 (1H, s). |
| 208 | δ 3.39 (3H, s), 7.57-7.62 (2H, m), 7.80 (1H, d, J = 7.8 Hz), 7.96 (1H, dd, J = 1.5, 7.8 Hz), 8.11 (1H, dd, J = 1.5, 7.8 Hz), 8.20 (1H, s), 8.31 (1H, s), 8.51 (1H, s), 8.55 (1H, dd, J = 1.5, 4.9 Hz), 10.68 (1H, s), 10.92 (1H, s). |
| 209 | δ 1.96 (3H, s), 3.84 (2H, broad), 7.53-7.63 (4H, m), 7.73 (1H, d, J = 7.8 Hz), 7.89 (1H, s), 7.99-8.01 (2H, m), 8.07 (1H, dd, J = 1.5, 7.8 Hz), 8.19 (1H, s), 8.33 (1H, t, J = 2.0 Hz), 10.43 (1H, s), 10.49 (1H, s). |
| 210 | δ 7.53-7.64 (4H, m), 7.81 (1H, d, J = 7.8 Hz), 8.00-8.05 (3H, m), 8.11 (1H, d, J = 7.8 Hz), 8.31 (1H, d, J = 1.5 Hz), 8.41 (1H, s), 10.52 (1H, s), 10.93 (1H, s). |

TABLE 11-continued

| Comp. No. | |
|---|---|
| 211 | δ 2.29 (6H, s), 7.47 (2H, s), 7.50-7.62 (4H, m), 7.75 (1H, d, J = 7.8 Hz), 7.97-8.00 (2H, m), 8.05 (1H, dd, J = 1.5, 7.8 Hz), 8.36 (1H, s), 10.01 (1H, s), 10.46 (1H, s). |
| 212 | δ 2.30 (6H, s), 7.45 (2H, s), 7.51-7.63 (4H, m), 7.76 (1H, d, J = 7.8 Hz), 7.98-8.07 (3H, m), 8.37 (1H, d, J = 2.0 Hz), 9.99 (1H, s), 10.48 (1H, s). |
| 255 | δ 7.25-7.29 (2H, m), 7.54-7.65 (2H, m), 7.78 (1H, d, J = 7.8 Hz), 7.92-7.95 (1H, m), 8.03 (2H, s), 8.30 (1H, s), 10.58 (1H, s), 11.05 (1H, s). |
| 256 | δ 7.53-7.63 (4H, m), 7.78 (1H, d, J = 7.3 Hz), 7.99-8.01 (2H, m), 8.06-8.09 (1H, m), 8.17 (2H, s), 8.38 (1H, s), 10.50 (1H, s), 10.55 (1H, s). |
| 257 | δ 7.25-7.29 (2H, m), 7.55-7.63 (2H, m), 7.79 (1H, d, J = 7.3 Hz), 7.94 (1H, d, J = 8.3 Hz), 8.17 (2H, s), 8.30 (1H, s), 10.60 (1H, s), 11.05 (1H, s). |
| 258 | (CDCl$_3$) δ 7.45-7.61 (4H, m), 7.76 (1H, d, J = 7.8 Hz), 7.84-7.91 (3H, m), 7.93 (2H, s), 8.02 (1H, s), 8.08 (1H, d, J = 6.8 Hz), 8.31 (1H, s). |
| 259 | (CDCl$_3$) δ 7.22 (1H, dd, J = 7.8, 12.2 Hz), 7.35 (1H, t, J = 7.8 Hz), 7.52-7.60 (2H, m), 7.77 (1H, d, J = 7.8 Hz), 7.88 (1H, s), 7.92 (1H, s), 7.93 (2H, d), 8.19 (1H, dt, J = 1.9, 7.8 Hz), 8.33 (1H, s), 8.64 (1H, d, J = 15.6 Hz). |
| 260 | (CDCl$_3$) δ 2.31 (6H, s), 7.41 (2H, s), 7.50-7.67 (5H, m), 7.71 (1H, d, J = 7.8 Hz), 7.87-7.90 (3H, m), 8.07 (1H, s), 8.31 (1H, s). |
| 261 | (CDCl$_3$) δ 2.33 (6H, s), 7.20-7.25 (1H, m), 7.35 (1H, t, J = 7.3 Hz), 7.44 (2H, s), 7.52-7.60 (3H, m), 7.73 (1H, d, J = 7.8 Hz), 7.88 (1H, dd, J = 1.0, 7.8 Hz), 8.18 (1H, dt, J = 2.0, 7.8 Hz), 8.33 (1H, s), 8.63 (1H, d, J = 7.3 Hz). |
| 262 | (CDCl$_3$) δ 7.44-7.57 (5H, m), 7.72 (2H, s), 7.78 (1H, d, J = 7.8 Hz), 8.00 (1H, d, J = 6.8 Hz), 8.18 (1H, d, J = 8.3 Hz), 8.34 (1H, t, J = 2.0 Hz), 9.46 (1H, s), 9.83 (1H, s). |
| 263 | (CDCl$_3$) δ 7.47-7.57 (4H, m), 7.78 (1H, d, J = 7.8 Hz), 7.93 (2H, s), 7.99-8.01 (2H, m), 8.18 (1H, d, J = 7.8 Hz), 8.33 (1H, t, J = 2.0 Hz), 9.27 (1H, s), 9.65 (1H, s). |
| 266 | δ 7.20-7.25 (1H, m), 7.35 (1H, t, J = 7.8 Hz), 7.53-7.60 (2H, m), 7.76-7.79 (2H, m), 7.95 (2H, s), 7.96 (1H, s), 8.19 (1H, dt, J = 2.0, 7.8 Hz), 8.32 (1H, s), 8.63 (1H, d, J = 15.7 Hz). |
| 276 | (CDCl$_3$) δ 7.56 (1H, t, J = 7.8 Hz), 7.71 (1H, d, J = 7.8 Hz), 7.75 (1H, d, J = 7.8 Hz), 7.87-7.90 (3H, m), 8.04 (1H, d, J = 7.8 Hz), 8.28 (2H, s), 8.42 (1H, dd, J = 1.0, 7.3 Hz), 8.46 (1H, s), 8.76 (1H, t, J = 2.0 Hz). |
| 284 | (CDCl$_3$) δ 7.03 (2H, t, J = 7.8 Hz), 7.42-7.49 (1H, m), 7.54 (1H, t, J = 7.8 Hz), 7.78 (1H, d, J = 7.8 Hz), 7.81 (1H, s), 7.87-7.92 (2H, m), 7.93 (2H, s), 8.28 (1H, t, J = 2.0 Hz). |
| 285 | δ 6.86 (1H, d, J = 8.8 Hz), 7.24 (1H, t, J = 7.8 Hz), 7.30-7.32 (2H, m), 7.47 (1H, t, J = 7.8 Hz), 7.77 (1H, d, J = 7.8 Hz), 7.93 (2H, s), 8.14 (1H, d, J = 7.3 Hz), 8.31 (1H, s), 9.32 (1H, s), 9.46 (1H, s). |
| 286 | δ 2.17 (3H, s), 7.40 (1H, t, J = 7.8 Hz), 7.49 (1H, t, J = 7.8 Hz), 7.80 (1H, d, J = 7.8 Hz), 7.78 (1H, d, J = 7.8 Hz), 7.94-7.95 (3H, m), 8.06 (1H, s), 8.16 (1H, d, J = 7.8 Hz), 8.31 (1H, s), 9.50 (1H, s), 9.58 (1H, s), 9.79 (1H, s). |
| 287 | δ 3.00 (3H, s), 7.42 (1H, t, J = 7.8 Hz), 7.50 (1H, t, J = 7.8 Hz), 7.48 (1H, s), 7.74 (1H, d, J = 7.8 Hz), 7.79 (1H, d, J = 7.8 Hz), 7.88 (1H, t, J = 2.0 Hz), 7.93 (2H, s), 8.17 (1H, d, J = 7.8 Hz), 8.29 (1H, t, J = 2.0 Hz), 9.37 (1H, s), 9.49 (1H, s), 9.72 (1H, s). |
| 288 | (CDCl$_3$) δ 7.51 (1H, t, J = 7.8 Hz), 7.69 (1H, d, J = 7.8 Hz), 7.86-7.91 (3H, m), 7.95 (2H, s), 8.07 (1H, s), 8.39 (1H, s), 8.53-8.55 (1H, m), 8.90 (1H, s). |
| 289 | (CDCl$_3$) δ 7.54 (1H, t, J = 8.3 Hz), 7.80 (1H, d, J = 7.8 Hz), 7.94 (2H, s), 8.02 (1H, d, J = 8.3 Hz), 8.26-8.27 (2H, m), 8.52 (1H, d, J = 8.3 Hz), 8.74 (1H, s), 8.87 (1H, s), 10.56 (1H, s). |
| 290 | δ 2.68 (3H, s), 7.52 (1H, t, J = 7.8 Hz), 7.81 (1H, d, J = 7.8 Hz), 7.93 (2H, s), 8.03 (2H, s), 8.07 (1H, s), 8.24 (1H, d, J = 7.8 Hz), 8.29 (1H, s), 9.34 (1H, s), 10.13 (1H, s). |
| 291 | (CDCl$_3$) δ 4.17 (2H, s), 6.80-6.84 (1H, m), 6.98 (1H, dd, J = 7.8, 11.2 Hz), 7.33 (1H, dd, J = 2.9, 6.4 Hz), 7.51 (1H, t, J = 7.8 Hz), 7.82 (1H, d, J = 7.8 Hz), 7.94 (2H, s), 8.10 (1H, d, J = 8.2 Hz), 8.22 (1H, s), 9.06 (1H, d, J = 13.2 Hz), 9.48 (1H, s). |
| 292 | (CDCl$_3$) δ 7.44 (1H, dd, J = 8.8, 10.7 Hz), 7.58 (1H, t, J = 7.8 Hz), 7.80 (1H, d, J = 7.8 Hz), 7.85 (1H, s), 7.95 (2H, s), 7.98 (1H, d, J = 7.8 Hz), 8.27 (1H, s), 8.43-8.47 (1H, m), 8.55 (1H, d, J = 14.2 Hz), 9.09 (1H, dd, J = 3.0, 6.4 Hz). |
| 293 | δ 2.97 (3H, s), 7.16 (1H, dd, J = 8.8, 10.8 Hz), 7.49 (1H, t, J = 7.8 Hz), 7.51 (1H, s), 7.83 (1H, d, J = 7.8 Hz), 7.90-7.93 (1H, m), 7.94 (2H, s), 8.10 (1H, d, J = 7.8 Hz), 8.24 (1H, s), 9.15 (1H, d, J = 11.2 Hz), 9.38 (1H, s), 9.58 (1H, s). |
| 294 | (CDCl$_3$) δ 4.22 (3H, s), 7.56 (1H, t, J = 7.8 Hz), 7.75 (1H, t, J = 7.8 Hz), 7.83 (1H, s), 7.94 (1H, s), 7.95 (2H, s), 7.99-8.05 (2H, m), 8.25 (1H, s), 8.47 (1H, d, J = 7.8 Hz), 9.83 (1H, s). |
| 295 | δ 4.06 (3H, s), 7.52 (1H, t, J = 7.3 Hz), 7.73 (1H, d, J = 8.3 Hz), 7.82-7.88 (2H, m), 7.89 (1H, d, J = 8.3 Hz), 7.93 (2H, s), 8.25-8.29 (2H, m), 9.48 (1H, s), 10.23 (1H, s). |
| 296 | (CDCl$_3$) δ 2.16 (3H, s), 7.14 (1H, dd, J = 9.3, 11.2 Hz), 7.52 (1H, t, J = 7.8 Hz), 7.80 (1H, d, J = 7.8 Hz), 7.94 (2H, s), 7.96 (1H, d, J = 2.9 Hz), 8.01 (1H, d, J = 7.8 Hz), 8.13-8.16 (1H, m), 8.27 (1H, s), 8.86 (1H, s), 8.90 (1H, d, J = 14.2 Hz), 9.00 (1H, s). |
| 306 | (CDCl$_3$) δ 7.52-7.58 (2H, m), 7.77 (1H, d, J = 7.8 Hz), 7.90 (1H, s), 7.94 (2H, s), 7.95 (1H, d, J = 7.8 Hz), 8.01-8.03 (1H, m), 8.31 (1H, d, J = 7.8 Hz), 8.47 (1H, s), 8.65 (1H, dd, J = 1.0, 4.9 Hz), 10.25 (1H, s). |
| 307 | (CDCl$_3$) δ 7.57 (1H, t, J = 7.8 Hz), 7.73-7.77 (3H, m), 7.84 (1H, s), 7.89 (2H, s), 8.05 (1H, d, J = 7.8 Hz), 8.26 (1H, s), 8.32 (1H, s), 8.81 (1H, s), 8.83 (1H, s). |
| 309 | (CDCl$_3$) δ 7.44 (1H, dd, J = 4.8, 7.8 Hz), 7.56 (1H, t, J = 7.8 Hz), 7.80 (1H, d, J = 7.8 Hz), 7.86 (1H, s), 7.92 (1H, d, J = 7.3 Hz), 7.95 (2H, s), 8.23 (1H, dd, J = 20., 7.9 Hz), 8.30 (1H, s), 8.41 (1H, s), 8.55 (1H, dd, J = 2.0, 4.5 Hz). |
| 310 | (CDCl$_3$) δ 7.46 (1H, d, J = 8.3 Hz), 7.55 (1H, t, J = 8.3 Hz), 7.74 (1H, d, J = 8.3 Hz), 7.88 (3H, s), 8.03 (1H, d, J = 7.8 Hz), 8.18 (1H, dd, J = 3.0, 8.2 Hz), 8.24 (1H, s), 8.41 (1H, s), 8.90 (1H, d, J = 2.4 Hz). |
| 312 | (CDCl$_3$) δ 7.57 (1H, t, J = 7.8 Hz), 7.70 (2H, s), 7.75 (1H, d, J = 7.8 Hz), 7.83 (1H, s), 7.88 (2H, s), 8.04 (1H, d, J = 7.8 Hz), 8.21 (1H, s), 8.47 (1H, s). |
| 313 | (CDCl$_3$) δ 7.33 (1H, t, J = 7.8 Hz), 7.46 (1H, d, J = 8.3 Hz), 7.60 (1H, s), 7.76 (1H, s), 7.80 (1H, d, J = 7.8 Hz), 7.95 (2H, s), 8.18-8.23 (2H, m), 8.40 (1H, s). |
| 314 | (CDCl$_3$) δ 2.62 (3H, s), 7.29 (1H, s), 7.56 (1H, t, J = 7.8 Hz), 7.77-7.79 (2H, m), 7.91 (1H, s), 7.94 (2H, s), 8.16 (1H, d, J = 7.8 Hz), 8.29 (1H, s), 8.48 (1H, s). |
| 315 | (CDCl$_3$) δ 7.47-7.59 (3H, m), 7.80 (1H, d, J = 7.8 Hz), 7.93 (1H, s), 7.94 (2H, s), 8.26 (1H, s), 8.34 (1H, d, J = 6.5 Hz), 8.47 (1H, t, J = 2.0 Hz), 8.52-8.55 (1H, m), 13.91 (1H, s). |

TABLE 11-continued

| Comp. No. | |
|---|---|
| 316 | (CDCl₃) δ 7.59 (1H, t, J = 7.8 Hz), 7.79 (1H, d, J = 7.8 Hz), 7.84 (1H, s), 7.95 (2H, s), 8.04 (1H, d, J = 7.8 Hz), 8.41 (1H, t, J = 2.0 Hz), 8.63 (1H, t, J = 2.5 Hz), 8.86 (1H, d, J = 2.4 Hz), 9.54 (1H, d, J = 1.5 Hz), 9.87 (1H, s). |
| 317 | (CDCl₃) δ 3.93 (3H, s), 7.53 (1H, t, J = 7.8 Hz), 7.74 (1H, d, J = 7.8 Hz), 7.84 (1H, s), 7.87 (1H, d, J = 7.8 Hz), 7.94 (2H, s), 8.03 (1H, s), 8.26 (1H, t, J = 2.0 Hz), 8.48 (1H, s). |
| 318 | (CDCl₃) δ 4.02 (3H, s), 7.53 (1H, t, J = 7.8 Hz), 7.45 (1H, d, J = 7.8 Hz), 7.80 (1H, d, J = 7.8 Hz), 7.85 (1H, s), 7.89 (1H, s), 7.94 (2H, s), 8.05 (1H, s), 8.24 (1H, s). |
| 319 | (CDCl₃) δ 4.10 (3H, s), 7.53 (1H, t, J = 7.8 Hz), 7.67 (1H, s), 7.76 (1H, d, J = 7.8 Hz), 7.70-7.86 (3H, m), 7.94 (2H, s), 8.21 (1H, s). |
| 320 | (CDCl₃) δ 1.94-2.04 (2H, m), 2.17-2.22 (1H, m), 2.37-2.42 (1H, m), 3.95-4.00 (1H, m), 4.05-4.09 (1H, m), 4.49 (1H, dd, J = 5.9, 8.3 Hz), 7.50 (1H, t, J = 7.8 Hz), 7.72 (1H, d, J = 7.8 Hz), 7.83 (1H, dd, J = 2.0, 7.8 Hz), 7.87 (1H, s), 7.94 (2H, s), 8.23 (1H, t, J = 2.0 Hz), 8.67 (1H, s). |
| 321 | (CDCl₃) δ 7.51-7.53 (3H, m), 7.57 (1H, t, J = 8.3 Hz), 7.76 (1H, d, J = 7.3 Hz), 7.83 (1H, s), 7.95 (2H, s), 8.01-8.07 (3H, m), 8.23 (1H, s), 8.38 (1H, s), 9.51 (1H, s). |
| 327 | (CDCl₃) δ 7.45-7.61 (4H, m), 7.77 (1H, d, J = 7.8 Hz), 7.84-7.91 (3H, m), 7.97-8.18 (4H, m), 8.31 (1H, s). |
| 328 | (CDCl₃) δ 7.24 (1H, d, J = 7.8 Hz), 7.35 (1H, t, J = 7.8 Hz), 7.54-7.60 (2H, m), 7.78 (1H, d, J = 7.8 Hz), 7.89 (1H, s), 7.96 (1H, d, J = 7.8 Hz), 8.15-8.19 (3H, m), 8.33 (1H, s), 8.64 (1H, d, J = 15.6 Hz). |
| 329 | (CDCl₃) δ 7.44-7.57 (4H, m), 7.70 (2H, s), 7.78 (1H, d, J = 7.8 Hz), 8.01 (2H, d, J = 6.8 Hz), 8.17 (1H, dd, J = 1.0, 7.8 Hz), 8.34 (1H, t, J = 2.0 Hz), 9.45 (1H, s), 9.81 (1H, s). |
| 330 | (CDCl₃) δ 7.22 (1H, dd, J = 8.3, 12.2 Hz), 7.34 (1H, t, J = 7.3 Hz), 7.52-7.67 (2H, m), 7.72 (2H, s), 7.76 (1H, d, J = 7.9 Hz), 7.90 (1H, s), 7.92 (1H, s), 8.18 (1H, dt, J = 1.4, 7.8 Hz), 8.33 (1H, t, J = 2.0 Hz), 8.64 (1H, d, J = 16.6 Hz). |
| 331 | (CDCl₃) δ 7.44 (1H, dd, J = 4.4, 7.8 Hz), 7.57 (1H, t, J = 7.8 Hz), 7.73 (2H, s), 7.78 (1H, d, J = 7.8 Hz), 7.84 (1H, s), 7.90 (1H, d, J = 7.8 Hz), 8.23 (1H, dd, J = 2.0, 7.8 Hz), 8.29 (1H, s), 8.41 (1H, s), 8.55 (1H, dd, J = 2.0, 4.9 Hz). |
| 332 | δ 7.43-7.57 (4H, m), 7.79 (1H, d, J = 7.8 Hz), 7.92 (2H, s), 8.00 (2H, d, J = 6.9 Hz), 8.18 (1H, d, J = 8.3 Hz), 8.35 (1H, t, J = 2.0 Hz), 8.59 (1H, s), 9.86 (1H, s). |
| 333 | (CDCl₃) δ 7.30-7.62 (4H, m), 7.75 (1H, d, J = 7.8 Hz), 7.84 (1H, d, J = 7.8 Hz), 7.89-7.92 (3H, m), 7.93 (2H, s), 8.03 (1H, s), 8.31 (1H, s). |
| 334 | (CDCl₃) δ 7.20-7.25 (1H, m), 7.35 (1H, t, J = 6.3 Hz), 7.54-7.58 (2H, m), 7.79 (1H, d, J = 6.3 Hz), 7.90-7.94 (2H, m), 7.95 (2H, s), 8.19 (1H, d, J = 8.3 Hz), 8.33 (1H, t, J = 2.0 Hz), 8.64 (1H, d, J = 16.1 Hz). |
| 335 | (CDCl₃) δ 7.51-7.62 (4H, m), 7.77 (1H, d, J = 7.3 Hz), 7.89-7.93 (3H, m), 8.02 (2H, s), 8.08 (1H, s), 8.26 (1H, s), 8.37 (1H, d, J = 14.6 Hz). |
| 338 | (CDCl₃) δ 7.22 (1H, t, J = 7.8 Hz), 7.36 (1H, t, J = 7.8 Hz), 7.54-7.60 (2H, m), 7.78 (1H, d, J = 7.8 Hz), 7.90 (1H, d, J = 7.8 Hz), 8.03-8.04 (2H, m), 8.19 (1H, t, J = 7.8 Hz), 8.26 (1H, s), 8.41 (1H, s), 8.65 (1H, d, J = 16.6 Hz). |
| 369 | (CDCl₃) δ 7.46 (1H, dd, J = 4.4, 7.8 Hz), 7.59 (1H, t, J = 8.3 Hz), 7.81 (1H, d, J = 8.3 Hz), 7.89-7.92 (1H, m), 8.04 (2H, s), 8.24 (1H, dd, J = 2.0, 7.8 Hz), 8.27 (1H, s), 8.35 (1H, d, J = 13.7 Hz), 8.42 (1H, s), 8.56 (1H, dd, J = 1.4, 4.4 Hz). |
| 375 | δ 7.25 (1H, d, J = 8.3 Hz), 7.27 (1H, d, J = 7.8 Hz), 7.56-7.64 (2H, m), 7.79 (1H, d, J = 7.8 Hz), 7.94 (1H, d, J = 8.3 Hz), 8.32 (1H, s), 8.42 (2H, s), 10.87 (1H, s), 11.05 (1H, s). |
| 376 | δ 7.53-7.64 (4H, m), 7.80 (1H, d, J = 7.8 Hz), 7.99-8.01 (2H, m), 8.09 (1H, dd, J = 1.5, 7.8 Hz), 8.41 (1H, d, J = 1.5 Hz), 8.54 (2H, s), 10.52 (1H, s), 10.83 (1H, s). |
| 377 | δ 7.19-7.30 (2H, m), 7.57-7.66 (2H, m), 7.81 (1H, d, J = 7.8 Hz), 7.95 (1H, dd, J = 1.5, 7.8 Hz), 8.33 (1H, t, J = 1.5 Hz), 8.53 (2H, s), 10.89 (1H, s), 11.08 (1H, s). |
| 378 | (CDCl₃) δ 7.21-7.23 (1H, m), 7.36 (1H, t, J = 6.9 Hz), 7.55-7.59 (2H, m), 7.79 (1H, d, J = 8.3 Hz), 7.84 (1H, d, J = 8.0 Hz), 8.05 (2H, s), 8.17-8.21 (2H, m), 8.43 (1H, t, J = 2.0 Hz), 8.65 (1H, d, J = 6.9 Hz). |
| 379 | (CDCl₃) δ 7.46-7.63 (4H, m), 7.77 (1H, d, J = 7.8 Hz), 7.84-7.91 (3H, m), 8.00 (1H, s), 8.07 (2H, s), 8.14 (1H, s), 8.40 (1H, t, J = 2.0 Hz). |
| 380 | (CDCl₃) δ 7.52-7.63 (4H, m), 7.77 (1H, d, J = 7.8 Hz), 7.89 (1H, s), 7.90 (2H, d, J = 7.8 Hz), 7.99 (1H, s), 8.03 (1H, s), 8.26 (2H, s), 8.39 (1H, t, J = 2.0 Hz). |
| 383 | (CDCl₃) δ 7.21 (1H, d, J = 8.3 Hz), 7.36 (1H, t, J = 7.8 Hz), 7.55-7.61 (2H, m), 7.78 (1H, d, J = 7.8 Hz), 7.90 (1H, d, J = 8.3 Hz), 8.02 (1H, s), 8.19 (1H, dt, J = 1.9, 8.3 Hz), 8.27 (2H, s), 8.41 (1H, s), 8.65 (1H, d, J = 16.6 Hz). |
| 414 | (CDCl₃) δ 7.44 (1H, dd, J = 4.9, 7.8 Hz), 7.59 (1H, t, J = 8.3 Hz), 7.81 (1H, d, J = 7.8 Hz), 7.89 (1H, d, J = 8.3 Hz), 8.04 (1H, s), 8.23 (1H, dd, J = 1.9, 7.8 Hz), 8.27 (2H, s), 8.37 (1H, s), 8.43 (1H, s), 8.55 (1H, dd, J = 1.9, 4.3 Hz). |
| 460 | δ 7.25 (1H, d, J = 8.3 Hz), 7.27 (1H, d, J = 7.8 Hz), 7.56-7.64 (2H, m), 7.79 (1H, d, J = 7.8 Hz), 7.94 (1H, d, J = 8.3 Hz), 8.32 (1H, s), 8.42 (2H, s), 10.87 (1H, s), 11.05 (1H, s). |
| 461 | (CDCl₃) δ 2.47 (3H, s), 7.51-7.62 (5H, m), 7.75 (1H, d, J = 7.8 Hz), 7.89-7.93 (4H, m), 8.00 (1H, broad-s), 8.35 (1H, t, J = 2.0 Hz). |
| 462 | (CDCl₃) δ 2.47 (3H, s), 7.20-7.23 (1H, m), 7.36 (1H, t, J = 7.8 Hz), 7.55-7.60 (3H, m), 7.76 (1H, d, J = 7.8 Hz), 7.89 (1H, s), 7.92 (1H, s), 8.18-8.22 (1H, m), 8.39 (1H, s), 8.62 (1H, broad-s). |
| 463 | (CDCl₃) δ 2.27 (3H, s), 2.41 (3H, s), 6.59 (1H, septet, J = 6.4 Hz), 6.72 (1H, s), 7.49-7.61 (5H, m), 7.70 (1H, d, J = 7.8 Hz), 7.83-7.89 (3H, m), 8.05 (1H, broad-s), 8.33 (1H, t, J = 1.5 Hz). |
| 464 | (CDCl₃) δ 2.38 (3H, s), 6.34 (1H, septet, J = 6.4 Hz), 6.87 (1H, s), 7.50-7.63 (5H, m), 7.72 (1H, d, J = 7.8 Hz), 7.88-7.90 (3H, m), 7.99 (1H, brs), 8.31 (1H, broad-s). |
| 465 | (CDCl₃) δ 2.37 (3H, s), 6.36 (1H, septet, J = 5.9 Hz), 6.87 (1H, s), 7.50-7.61 (4H, m), 7.72-7.73 (2H, m), 7.88-7.90 (3H, m), 8.06 (1H, broad-s), 8.32 (1H, s). |
| 466 | (CDCl₃) δ 2.39 (3H, s), 6.36 (1H, septet, J = 5.9 Hz), 6.89 (1H, s), 7.20-7.25 (1H, m), 7.35 (1H, t, J = 6.8 Hz), 7.52-7.60 (2H, m), 7.70 (1H, broad-s), 7.75 (1H, d, J = 7.8 Hz), 7.89 (1H, d, J = 7.8 Hz), 8.17-8.21 (1H, m), 8.36 (1H, s), 8.64 (1H, broad-d, J = 16.1 Hz). |
| 467 | (CDCl₃) δ 2.53 (3H, s), 6.35 (1H, septet, J = 5.9 Hz), 6.83 (1H, s), 7.49-7.61 (4H, m), 7.66 (1H, s), 7.74 (1H, d, J = 8.3 Hz), 7.88-7.92 (3H, m), 8.32 (1H, broad-s), 8.33 (1H, t, J = 1.9 Hz). |
| 601 | δ 2.34 (6H, s), 7.37 (1H, t, J = 7.8 Hz), 7.45 (2H, s), 7.53-7.65 (4H, m), 7.77-7.82 (1H, m), 8.00-8.02 (2H, m), 10.10 (1H, s), 10.29 (1H, s). |
| 602 | δ 2.36 (6H, s), 2.56 (3H, s), 7.29-7.43 (7H, m), 7.55-7.57 (1H, m), 7.75-7.78 (1H, m), 7.84-7.88 (1H, m), 8.64-8.66 (1H, m). |

TABLE 11-continued

| Comp. No. | |
|---|---|
| 603 | δ 2.37 (6H, s), 2.46 (3H, s), 7.34-7.42 (5H, m), 7.69-7.85 (4H, m), 8.11 (1H, s), 8.59-8.63 (1H, s). |
| 604 | δ 2.38 (6H, s), 2.45 (3H, s), 7.33-7.38 (5H, m), 7.78-7.85 (4H, m), 8.10 (1H, s), 8.61-8.65 (1H, m). |
| 605 | δ 2.34 (6H, s), 7.39 (1H, t, J = 7.4 Hz), 7.44 (2H, s), 7.50-7.54 (1H, m), 7.76-7.80 (2H, m), 7.88 (1H, t, J = 7.4 Hz), 8.12 (1H, t, J = 7.4 Hz), 8.20 (1H, d, J = 1.0 Hz), 10.12 (1H, s), 10.73 (1H, s). |
| 606 | δ 2.35 (6H, s), 7.40 (1H, t, J = 7.8 Hz), 7.45 (2H, s), 7.59-7.62 (1H, m), 7.82-7.90 (2H, m), 8.44-8.50 (2H, m), 8.86 (1H, d, J = 2.0 Hz), 10.12 (1H, s), 10.72 (1H, s). |
| 607 | δ 2.34 (6H, s), 7.40 (1H, t, J = 7.8 Hz), 7.45 (2H, s), 7.57-7.62 (1H, m), 7.81-7.85 (1H, m), 8.22-8.25 (2H, m), 8.39-8.42 (2H, m), 10.12 (1H, s), 10.66 (1H, s). |
| 609 | δ 2.34 (6H, s), 7.39 (1H, t, J = 6.9 Hz), 7.45 (2H, s), 7.58 (1H, t, J = 6.9 Hz), 7.82 (1H, t, J = 6.9 Hz), 8.06 (2H, d, J = 8.8 Hz), 8.15 (2H, d, J = 8.8 Hz), 10.12 (1H, s), 10.58 (1H, s). |
| 610 | δ 2.34 (6H, s), 7.33-7.40 (3H, m), 7.45 (2H, s), 7.52-7.56 (1H, m), 7.59-7.65 (1H, m), 7.72-7.77 (1H, m), 8.00 (1H, t, J = 7.8 Hz), 10.12 (1H, s), 10.35 (1H, s). |
| 611 | δ 2.34 (6H, s), 7.38 (1H, t, J = 7.6 Hz), 7.45-7.65 (5H, m), 7.78-7.83 (2H, m), 7.87 (1H, d, J = 7.6 Hz), 10.10 (1H, s), 10.39 (1H, s). |
| 612 | δ 2.34 (6H, s), 7.35-7.45 (5H, m), 7.55-7.59 (1H, m), 7.77-7.81 (1H, m), 8.07-8.12 (2H, m), 10.09 (1H, s), 10.32 (1H, s). |
| 616 | δ 2.34 (6H, s), 7.22-7.27 (1H, m), 7.38 (1H, t, J = 7.8 Hz), 7.46 (2H, s), 7.50-7.55 (3H, m), 7.95 (1H, d, J = 7.8 Hz), 7.99-8.03 (1H, m), 10.12 (1H, s), 10.50 (1H, s). |
| 618 | δ 2.34 (6H, s), 7.39 (1H, t, J = 7.7 Hz), 7.45 (2H, s), 7.60 (1H, t, J = 7.7 Hz), 7.83 (1H, t, J = 7.7 Hz), 7.95 (2H, d, J = 8.3 Hz), 8.20 (2H, d, J = 8.3 Hz), 10.12 (1H, s), 10.56 (1H, s). |
| 619 | δ 2.34 (6H, s), 7.38 (1H, t, J = 7.4 Hz), 7.45 (2H, s), 7.55-7.60 (3H, m), 7.81 (1H, t, J = 7.4 Hz), 8.14 (2H, d, J = 8.8 Hz), 10.11 (1H, s), 10.40 (1H, s). |
| 620 | δ 2.34 (6H, s), 3.01 (6H, s), 6.77 (2H, d, J = 9.0 Hz), 7.33 (1H, t, J = 7.0 Hz), 7.45 (2H, s), 7.52 (1H, t, J = 7.0 Hz), 7.78 (1H, t, J = 7.0 Hz), 7.90 (2H, d, J = 9.0 Hz), 9.86 (1H, s), 10.07 (1H, s). |
| 624 | δ 2.34 (6H, s), 7.23-7.28 (2H, m), 7.38 (1H, t, J = 7.8 Hz), 7.45 (2H, s), 7.52-7.64 (2H, m), 8.05-8.10 (1H, m), 10.13 (1H, s), 10.88 (1H, s). |
| 628 | δ 2.34 (6H, s), 7.37-7.42 (1H, m), 7.40 (2H, s), 7.55-7.58 (1H, m), 7.95-8.07 (2H, m), 8.21 (1H, dd, J = 8.9, 2.1 Hz), 8.30 (1H, dd, J = 8.9, 2.1 Hz), 10.13 (1H, s), 10.75 (1H, s). |
| 629 | δ 2.34 (6H, s), 7.39 (1H, t, J = 7.4 Hz), 7.45 (2H, s), 7.52 (1H, 7.4), 7.81 (1H, dd, J = 8.3, 2.7 Hz), 7.88 (1H, dd, J = 8.3, 5.6 Hz), 8.10-8.16 (2H, m), 10.13 (1H, s), 10.75 (1H, s). |
| 630 | δ 2.33 (6H, s), 7.34-7.38 (2H, m), 7.43 (2H, s), 7.51-7.54 (1H, m), 7.58-7.60 (1H, m), 7.67-7.71 (1H, m), 8.00-8.04 (1H, m), 10.10 (1H, s), 10.54 (1H, s). |
| 631 | δ 2.34 (6H, s), 7.37 (1H, t, J = 7.9 Hz), 7.45-7.47 (3H, m), 7.52-7.56 (1H, m), 7.65 (1H, dd, J = 10.2, 2.0 Hz), 7.77 (1H, t, J = 7.9 Hz), 7.99-8.02 (1H, m), 10.11 (1H, s), 10.41 (1H, s). |
| 633 | δ 2.34 (6H, s), 7.40 (1H, t, J = 8.1 Hz), 7.45 (2H, s), 7.55 (1H, t, J = 6.5 Hz), 7.92 (1H, d, J = 8.1 Hz), 8.10 (1H, t, J = 6.5 Hz), 8.32 (1H, t, J = 8.1 Hz), 8.43 (1H, s), 10.13 (1H, s), 10.84 (1H, s). |
| 634 | δ 2.34 (6H, s), 7.39 (1H, t, J = 8.0 Hz), 7.45 (2H, s), 7.51-7.55 (1H, m), 7.83 (1H, d, J = 8.0 Hz), 7.99 (1H, dd, J = 7.7, 2.2 Hz), 8.12 (1H, t, J = 7.7 Hz), 8.30 (1H, d, J = 2.2 Hz), 10.13 (1H, s), 10.78 (1H, s). |
| 638 | δ 2.33 (6H, s), 7.37 (1H, t, J = 8.1 Hz), 7.44 (2H, s), 7.50-7.55 (2H, m), 8.03-8.07 (1H, m), 8.26-8.31 (1H, m), 8.41-8.42 (1H, m), 10.10 (1H, s), 10.54 (1H, s). |
| 639 | (CDCl$_3$) δ 2.38 (6H, s), 7.38 (2H, s), 7.41-7.49 (2H, m), 7.80 (1H, broad-d, J = 11.4 Hz), 7.90-7.94 (1H, m), 8.32-8.35 (1H, m), 8.57-8.59 (1H, m), 8.62-8.65 (1H, m), 8.74 (1H, s). |
| 648 | δ 1.80-1.86 (2H, m), 2.05 (3H, s), 2.33-2.38 (8H, m), 3.99 (2H, t, J = 5.1 Hz), 7.29 (1H, t, J = 7.4 Hz), 7.44-7.48 (3H, m), 7.79 (1H, d, J = 7.4 Hz), 9.25 (1H, s), 10.04 (1H, s). |
| 649 | δ 2.29 (6H, s), 7.45 (2H, s), 7.54-7.66 (3H, m), 7.77 (1H, d, J = 8.8 Hz), 7.94 (1H, dd, J = 2.0, 8.1 Hz), 8.00-8.03 (2H, m), 8.19 (1H, d, J = 2.0 Hz), 10.10 (1H, s), 10.29 (1H, s). |
| 650 | δ 2.29 (6H, s), 7.45 (2H, s), 7.48-7.65 (4H, m), 7.93-8.02 (3H, m), 8.23 (1H, dd, J = 2.4, 7.3 Hz), 10.03 (1H, s), 10.32 (1H, s). |
| 651 | δ 2.29 (6H, s), 7.45 (2H, s), 7.54 (1H, dd, J = 8.8, 9.8 Hz), 7.96-8.01 (1H, m), 8.23 (2H, d, J = 8.8 Hz), 8.26 (1H, dd, J = 2.4, 8.8 Hz), 8.40 (2H, d, J = 8.8 Hz), 10.05 (1H, s), 10.70 (1H, s). |
| 652 | δ 2.29 (6H, s), 7.45 (2H, s), 7.51-7.56 (1H, m), 7.96-8.00 (1H, m), 8.06 (2H, d, J = 8.3 Hz), 8.15 (2H, d, J = 8.3 Hz), 8.25 (1H, dd, J = 2.0, 7.3 Hz), 10.05 (1H, s), 10.61 (1H, s). |
| 653 | δ 2.29 (6H, s), 7.33-7.40 (2H, m), 7.45 (2H, s), 7.49-7.54 (1H, m), 7.59-7.65 (1H, m), 7.73-7.77 (1H, m), 7.91-7.95 (1H, m), 8.42 (1H, d, J = 6.3 Hz), 10.05 (1H, s), 10.35 (1H, s). |
| 654 | δ 2.29 (6H, s), 7.37-7.45 (4H, m), 7.51 (1H, dd, J = 8.8, 9.8 Hz), 7.93-7.98 (1H, m), 8.06-8.10 (2H, m), 8.22 (1H, dd, J = 2.0, 7.3 Hz), 10.03 (1H, s), 10.37 (1H, s). |
| 655 | δ 2.29 (6H, s), 7.45 (2H, s), 7.51-7.56 (1H, m), 7.94-8.00 (3H, m), 8.20 (2H, d, J = 8.3 Hz), 8.25 (1H, dd, J = 2.0, 7.3 Hz), 10.05 (1H, s), 10.59 (1H, s). |
| 656 | δ 2.29 (6H, s), 7.23-7.28 (1H, m), 7.42-7.54 (4H, m), 7.80-7.87 (1H, m), 7.91-7.95 (1H, m), 8.41 (1H, d, J = 5.9 Hz), 10.05 (1H, s), 10.36 (1H, s). |
| 657 | δ 2.30 (6H, s), 7.46 (2H, s), 7.50-7.59 (2H, m), 7.92-7.96 (1H, m), 8.10 (1H, dd, J = 2.0, 7.3 Hz), 8.52-8.56 (2H, m), 10.07 (1H, s), 10.73 (1H, s). |
| 658 | δ 2.31 (6H, s), 7.47 (2H, s), 7.55-7.59 (2H, m), 7.62-7.66 (1H, m), 8.01-8.04 (2H, m), 8.09 (1H, s), 8.54 (1H, s), 8.66 (1H, s), 10.27 (1H, s), 10.79 (1H, s). |
| 659 | δ 2.34 (6H, s), 7.40 (1H, t, J = 9.3 Hz), 7.45 (2H, s), 7.53-7.64 (3H, m), 7.97-8.05 (3H, m), 8.14 (1H, dd, J = 2.9, 6.3 Hz), 10.03 (1H, s), 10.48 (1H, s). |
| 660 | δ 2.40 (6H, s), 7.45 (2H, s), 7.54-7.65 (4H, m), 7.97-8.03 (3H, m), 8.09 (1H, d, J = 2.4 Hz), 10.20 (1H, s), 10.56 (1H, s). |
| 661 | δ 2.41 (6H, s), 7.45 (2H, s), 7.54-7.65 (3H, m), 7.72 (1H, d, J = 8.8 Hz), 7.94-7.99 (3H, m), 8.08 (1H, d, J = 2.9 Hz), 10.20 (1H, s), 10.56 (1H, s). |
| 662 | δ 2.44 (6H, s), 7.45 (2H, s), 7.53-7.65 (3H, m), 7.79 (1H, dd, J = 2.4, 8.3 Hz), 7.90-7.98 (3H, m), 8.05 (1H, d, J = 2.4 Hz), 10.15 (1H, s), 10.53 (1H, s). |
| 663 | δ 2.35 (6H, s), 7.32 (1H, t, J = 8.3), 7.46 (2H, s), 7.54-7.77 (4H, m), 8.00 (2H, dd, J = 1.5, J = 8.3), 10.3 (1H, s), 10.6 (1H, s). |
| 664 | (CDCl$_3$) δ 2.53 (6H, s), 7.35 (2H, s), 7.52-7.63 (5H, m), 7.92 (2H, d, J = 8.8 Hz), 8.46 (1H, d, J = 8.8 Hz), 8.57 (1H, s). |
| 665 | δ 2.34 (6H, s), 7.37 (1H, t, J = 7.8 Hz), 7.44 (2H, s), 7.53-7.65 (4H, m), 7.77-7.81 (1H, m), 7.99-8.02 (2H, m), 10.09 (1H, broad), 10.29 (1H, broad). |

TABLE 11-continued

| Comp. No. | |
|---|---|
| 668 | δ 2.34 (6H, s), 7.33-7.40 (3H, m), 7.44 (2H, s), 7.51-7.56 (1H, m), 7.58-7.65 (1H, m), 7.72-7.77 (1H, m), 8.00 (1H, t, J = 8.3 Hz), 10.10 (1H, s), 10.34 (1H, s). |
| 670 | δ 2.28 (6H, s), 7.31-7.44 (5H, m), 7.57 (1H, t, J = 6.3 Hz), 7.79 (1H, t, J = 7.3 Hz), 8.07-8.09 (2H, m), 10.09 (1H, s), 10.32 (1H, s). |
| 676 | δ 7.34 (6H, s), 7.39 (1H, t, J = 7.2 Hz), 7.44 (2H, s), 7.59 (1H, t, J = 7.2 Hz), 7.83 (1H, t, J = 7.2 Hz), 7.99 (2H, d, J = 8.8 Hz), 8.15 (2H, d, J = 8.8 Hz), 10.1 (1H, s), 10.57 (1H, s). |
| 679 | δ 2.35 (6H, s), 7.4 (1H, t, J = 7.3 Hz), 7.44 (2H, s), 7.61 (1H, t, J = 7.3 Hz), 7.84 (1H, t, J = 7.3 Hz), 8.24 (2H, d, J = 8.8 Hz), 8.41 (2H, d, J = 8.8 Hz), 10.11 (1H, s), 10.66 (1H, s). |
| 682 | δ 2.35 (6H, s), 7.38 (1H, t, J = 8.1 Hz), 7.44 (2H, s), 7.49 (1H, d, J = 8.1 Hz), 7.56 (1H, d, J = 8.1 Hz), 8.07 (2H, d, J = 8.8 Hz), 8.14 (2H, d, J = 8.8 Hz), 10.1 (1H, s), 10.43 (1H, s). |
| 686 | δ 2.34 (6H, s), 7.23-7.28 (2H, m), 7.38 (1H, t, J = 7.8 Hz), 7.44 (2H, s), 7.52-7.65 (2H, m), 8.05-8.10 (1H, m), 10.12 (1H, s), 10.88 (1H, s). |
| 699 | δ 2.34 (6H, s), 3.39 (3H, s), 7.39 (1H, t, J = 7.8 Hz), 7.44 (2H, s), 7.49-7.59 (2H, m), 8.08-8.13 (2H, m), 8.55 (1H, dd, J = 4.9, 2.0 Hz), 10.12 (1H, s), 10.73 (1H, s). |
| 708 | (CDCl₃) δ 7.39 (1H, t, J = 7.8 Hz), 7.48-7.64 (3H, m), 7.88-7.96 (4H, m), 8.09-8.13 (2H, m), 8.69 (1H, t, J = 7.8 Hz), 8.75 (1H, d, J = 7.8 Hz). |
| 711 | (CDCl₃) δ 7.22 (1H, d, J = 8.3 Hz), 7.35-7.40 (2H, m), 7.56-7.62 (1H, m), 7.91 (1H, t, J = 7.3 Hz), 7.96 (2H, s), 8.15 (1H, d, J = 13.3 Hz), 8.22 (1H, dt, J = 1.9, 8.3 Hz), 8.73 (1H, dt, J = 1.5, 8.3 Hz), 8.92 (1H, d, J = 17.1 Hz). |
| 719 | (CDCl₃) δ 7.41 (1H, t, J = 8.3 Hz), 7.85 (2H, d, J = 8.3 Hz), 7.92 (1H, d, J = 6.9 Hz), 7.96 (2H, s), 8.03 (2H, d, J = 8.3 Hz), 8.06 (1H, s), 8.10 (1H, s), 8.63 (1H, dt, J = 1.5, 8.3 Hz). |
| 722 | (CDCl₃) δ 7.42 (1H, t, J = 8.3 Hz), 7.93 (1H, d, J = 5.3 Hz), 7.96 (2H, s), 8.06 (1H, d, J = 12.2 Hz), 8.10 (2H, d, J = 8.8 Hz), 8.13 (1H, s), 8.40 (2H, d, J = 8.8 Hz), 8.64 (1H, dt, J = 1.5, 8.3 Hz). |
| 791 | (CDCl₃) δ 2.34 (6H, s), 7.37 (1H, t, J = 7.8 Hz), 7.45 (2H, s), 7.54 (2H, t, J = 7.8 Hz), 7.61 (1H, d, J = 7.8 Hz), 7.80 (1H, d, J = 11.7 Hz), 7.82-7.87 (1H, m), 7.92 (2H, d, J = 7.8 Hz), 8.12 (1H, s), 8.62 (1H, dt, J = 2.0, 7.8 Hz). |
| 831 | (CDCl₃) δ 7.46-7.64 (6H, m), 7.93-7.96 (4H, m), 8.61 (1H, s), 7.75 (1H, dd, J = 1.9, 8.3 Hz). |
| 832 | (CDCl₃) δ 7.24 (1H, d, J = 8.3 Hz), 7.36 (1H, t, J = 8.3 Hz), 7.47 (1H, t, J = 8.3 Hz), 7.55-7.62 (3H, m), 7.96 (2H, s), 8.21 (1H, dt, J = 2.0, 8.3 Hz), 8.77 (1H, dd, J = 2.0, 8.3 Hz), 9.33 (1H, d, J = 16.6 Hz). |
| 833 | (CDCl₃) δ 7.45-7.52 (3H, m), 7.60 (1H, d, J = 8.8 Hz), 7.96 (2H, s), 8.29 (1H, d, J = 7.8 Hz), 8.57 (1H, dd, J = 2.0, 4.4 Hz), 8.72 (1H, d, J = 7.8 Hz), 9.00 (1H, s). |
| 1001 | δ 2.20 (6H, s), 3.45 (3H, s), 7.23-7.30 (5H, m), 7.43-7.45 (4H, m), 7.73-7.76 (2H, m), 9.88 (1H, s). |
| 1013 | δ 2.20 (6H, s), 3.48 (3H, s), 7.39-7.97 (8H, m), 7.43 (2H, s), 9.90 (1H, s). |
| 1016 | δ 2.21 (6H, s), 3.46 (3H, s), 7.40-8.03 (10H, m), 9.91 (1H, s). |
| 1032 | δ 2.08 (3H, s), 2.30 (6H, s), 7.45 (2H, s), 7.47 (1H, d, J = 7.8 Hz), 7.54 (1H, t, J = 7.8 Hz), 7.66 (1H, d, J = 7.8 Hz), 7.75 (1H, d, J = 7.8 Hz), 7.82 (1H, d, J = 7.8 Hz), 8.04 (1H, dd, J = 2.0, 7.8 Hz), 8.13 (1H, s), 8.35 (1H, s), 9.99 (1H, s), 10.16 (1H, s), 10.48 (1H, s). |
| 1043 | (CDCl₃) δ 1.38 (6H, m), 2.37 (6H, s), 3.13 (1H, broad), 3.33 (3H, broad), 3.78 (1H, broad), 3.89 (1H, broad), 7.37 (2H, s), 7.48 (1H, d, J = 7.8 Hz), 7.58 (1H, t, J = 7.8 Hz), 7.77 (1H, s), 7.90 (1H, s), 7.93 (1H, broad). |
| 1089 | (CDCl₃) δ 0.89 (3H, t, J = 7.3 Hz), 1.53-1.62 (2H, m), 2.61 (2H, t, J = 7.3 Hz), 3.50 (3H, broad), 6.80 (1H, broad), 7.03 (1H, broad), 7.22 (1H, broad), 7.34 (3H, broad), 7.47 (1H, s), 7.67-7.76 (3H, broad-m), 7.93 (1H, s). |
| 1091 | (CDCl₃) δ 0.88 (3H, t, J = 7.3 Hz), 1.53-1.63 (2H, m), 2.62 (2H, t, J = 7.8 Hz), 3.52 (3H, s), 6.83-6.89 (2H, m), 7.26-7.32 (3H, m), 7.41 (1H, t, J = 7.8 Hz), 7.48 (1H, s), 7.66 (1H, s), 7.76 (2H, d, J = 8.8 Hz), 7.93 (1H, d, J = 1.5 Hz). |
| 1097 | (CDCl₃) δ 0.90 (3H, t, J = 7.3 Hz), 1.55-1.65 (2H, m), 2.64 (2H, t, J = 7.8 Hz), 3.55 (3H, s), 7.27 (1H, s), 7.40-7.44 (3H, m), 7.49-7.51 (3H, m), 7.59 (1H, s), 7.76 (1H, d, J = 7.8 Hz), 7.95 (1H, s). |
| 1100 | (CDCl₃) δ 0.88 (3H, t, J = 7.3 Hz), 1.54-1.64 (2H, m), 2.63 (2H, t, J = 7.8 Hz), 3.56 (3H, s), 7.29 (1H, s), 7.40-7.50 (4H, m), 7.59 (1H, s), 7.71 (1H, s), 7.76 (1H, d, J = 7.3 Hz), 7.94 (1H, d, J = 1.5 Hz), 8.06 (2H, d, J = 8.8 Hz). |
| 1125 | (CDCl₃) δ 2.25 (6H, s), 3.54 (3H, s), 6.84 (1H, broad-s), 7.00-7.10 (2H, m), 7.20-7.40 (6H, m), 7.50-7.60 (1H, broad), 7.60-7.70 (1H, broad). |
| 1126 | (CDCl₃) δ 3.57 (3H, s), 7.20-7.24 (2H, m), 7.29-7.32 (3H, m), 7.34 (1H, t, J = 7.8 Hz), 7.40-7.44 (2H, m), 7.57 (1H, d, J = 7.8 Hz), 7.86-7.91 (1H, m), 7.92 (2H, s). |
| 1206 | δ 1.17 (3H, broad), 2.22 (6H, s), 3.94 (2H, broad), 7.01-7.08 (2H, m), 7.29-7.43 (6H, m), 7.72-7.77 (2H, m), 9.90 (1H, s). |
| 1207 | δ 1.26 (3H, t, J = 6.8 Hz), 2.04 (6H, s), 4.11 (2H, q, J = 6.8 Hz), 7.16-7.70 (12H, m). |
| 1208 | δ 2.28 (6H, s), 3.36 (3H, s), 7.27-7.32 (6H, m), 7.43 (2H, s), 7.55-7.57 (2H, broad), 9.96 (1H, s). |
| 1209 | δ 2.28 (6H, s), 3.47 (3H, s), 6.98 (1H, broad), 7.11 (2H, broad), 7.19 (1H, broad), 7.37 (1H, broad), 7.44 (2H, s), 7.51 (1H, broad), 7.74 (1H, broad), 9.94 (1H, s). |
| 1210 | δ 2.23 (3H, s), 2.29 (6H, s), 7.07-7.26 (5H, m), 7.44 (2H, s), 7.56-7.77 (2H, m), 9.98 (1H, s). |
| 1211 | δ 2.24 (3H, s), 2.28 (6H, s), 7.08-7.09 (2H, m), 7.22-7.28 (2H, m), 7.44 (2H, s), 7.51-7.58 (3H, m), 9.99 (1H, s). |
| 1212 | δ 2.29 (6H, s), 3.12 (3H, s), 7.17-8.02 (9H, m), 9.95 (1H, s). |
| 1213 | δ 2.26 (6H, s), 3.41 (3H, s), 7.12-8.34 (9H, m), 9.92 (1H, s). |
| 1214 | δ 2.26 (6H, s), 3.40 (3H, s), 7.29 (1H, broad), 7.44 (2H, s), 7.59-7.81 (4H, m), 8.12 (2H, broad), 9.91 (1H, s). |
| 1215 | δ 2.26 (6H, s), 3.40 (3H, s), 7.31-7.39 (7H, m), 7.50-7.56 (1H, m), 7.81-7.83 (1H, m), 9.94 (1H, s). |
| 1216 | δ 2.27 (6H, s), 3.39 (3H, s), 7.31 (1H, m), 7.47 (2H, s), 7.60-7.67 (3H, m), 7.72-7.80 (3H, m), 9.96 (1H, s). |
| 1217 | δ 2.27 (6H, s), 3.37 (3H, s), 7.29 (2H, broad), 7.44-7.48 (3H, m), 7.59-7.64 (2H, m), 7.76 (2H, broad), 9.94 (1H, s). |
| 1218 | δ 2.27 (6H, s), 3.39 (3H, s), 7.03-7.72 (9H, m), 9.94 (1H, s). |
| 1219 | δ 2.28 (6H, s), 3.36 (3H, s), 7.18-8.04 (9H, m), 9.98 (1H, m). |
| 1220 | δ 2.28 (6H, s), 3.34 (3H, s), 7.12-7.56 (9H, m), 9.97 (1H, s). |
| 1229 | δ 2.28 (6H, s), 3.39 (3H, s), 7.02-7.28 (2H, m), 7.35-7.43 (2H, m), 7.55-7.70 (2H, m), 7.93-7.99 (2H, m), 9.95 (1H, m). |

TABLE 11-continued

| Comp. No. | |
|---|---|
| 1235 | δ 2.26 (6H, s), 3.43 (3H, s), 7.27 (1H, t, J = 7.8 Hz), 7.44 (2H, s), 7.58-7.65 (2H, m), 7.71 (1H, t, J = 7.8), 8.00 (1H, dd, J = 8.3, 2.0 Hz), 8.04 (1H, dd, J = 9.3, 2.0 Hz), 9.91 (1H, s). |
| 1236 | δ 2.29 (6H, s), 3.41 (3H, s), 7.44-7.46 (3H, m), 7.59-7.61 (2H, m), 7.72-7.77 (1H, m), 7.88 (1H, d, J = 6.8 Hz), 7.95-7.99 (1H, m), 9.95 (1H, s). |
| 1237 | δ 2.29 (6H, s), 3.40 (3H, s), 7.08-7.91 (8H, m), 9.94 (1H, s). |
| 1238 | δ 2.28 (6H, s), 3.39 (3H, s), 7.21-7.28 (1H, m), 7.34-7.44 (3H, m), 7.54-7.60 (2H, m), 7.79-7.91 (2H, m), 9.95 (1H, m). |
| 1245 | δ 2.28 (6H, s), 3.41 (3H, s), 7.25 (1H, t, J = 7.6 Hz), 7.36 (1H, d, J = 4.7 Hz), 7.44 (2H, s), 7.57-7.64 (2H, m), 7.92 (1H, d, J = 7.6 Hz), 8.32 (1H, dd, J = 4.7, 1.9 Hz), 9.97 (1H, s). |
| 1246 | δ 2.31 (6H, s), 3.60 (3H, s), 7.25-7.31 (2H, m), 7.44 (2H, s), 7.57-7.59 (2H, m), 7.97-8.01 (1H, m), 8.17-8.18 (1H, m), 9.97 (1H, s). |
| 1247 | δ 2.28 (6H, s), 3.39 (3H, s), 7.33 (1H, d, J = 7.6 Hz), 7.44 (2H, s), 7.61-7.69 (3H, m), 7.80 (1H, broad), 8.30 (1H, broad), 10.01 (1H, s). |
| 1255 | δ 2.29 (6H, s), 3.35 (3H, s), 7.19-7.70 (10H, m), 9.98 (1H, s). |
| 1256 | δ 2.28 (6H, s), 2.30 (3H, s), 3.32 (3H, s), 6.98-7.72 (9H, m), 9.93 (1H, s). |
| 1257 | δ 2.23 (3H, s), 2.29 (6H, s), 3.34 (3H, s), 7.07-7.38 (5H, m), 7.53-7.76 (2H, m), 7.43 (2H, s), 9.98 (1H, s). |
| 1258 | δ 2.27 (6H, s), 2.33 (3H, s), 3.31 (3H, s), 6.98-7.51 (9H, s), 9.93 (1H, s). |
| 1259 | δ 2.29 (6H, s), 3.41 (3H, s), 7.18 (1H, J = 7.3 Hz), 7.44 (2H, s), 7.46-7.57 (2H, m), 7.67 (1H, t, J = 7.3 Hz), 7.73-7.82 (2H, m), 8.01 (1H, d, J = 7.8 Hz), 9.95 (1H, s). |
| 1260 | δ 2.26 (6H, s), 3.36 (3H, s), 7.42 (2H, s), 7.59 (1H, broad), 7.7 (1H, broad), 7.82 (1H, t, J = 7.9 Hz), 8.2 (1H, broad), 8.34-8.37 (1H, m), 8.48 (1H, dd, J = 7.9, 1.7 Hz), 8.62 (1H, t, J = 2.0 Hz), 9.92 (1H, s). |
| 1261 | δ 2.27 (6H, s), 3.37 (3H, s), 7.43 (2H, s), 7.59-7.65 (2H, m), 8.11 (1H, broad), 8.18 (2H, d, J = 8.8 Hz), 8.29 (2H, d, J = 8.8 Hz), 9.91 (1H, s). |
| 1262 | δ 2.33 (6H, s), 3.35 (3H, s), 7.30-7.83 (9H, m), 9.93 (1H, s). |
| 1263 | δ 2.27 (6H, s), 3.37 (3H, s), 7.18-7.80 (9H, m), 9.96 (1H, s). |
| 1264 | δ 2.27 (6H, s), 3.35 (3H, s), 7.43 (2H, s), 7.48 (1H, broad), 7.58 (1H, broad), 7.75 (1H, broad), 7.99 (2H, d, J = 8.5 Hz), 8.08 (2H, d, J = 8.5 Hz), 9.95 (1H, s). |
| 1265 | δ 2.27 (6H, s), 3.36 (3H, s), 7.03-7.73 (9H, m), 9.93 (1H, s). |
| 1266 | δ 2.28 (6H, s), 3.35 (2H, s), 7.18-7.61 (9H, m), 9.99 (1H, s). |
| 1267 | δ 2.28 (6H, s), 3.39 (3H, s), 7.11-7.18 (3H, m), 7.26-7.30 (1H, t, J = 7.8 Hz), 7.40-7.47 (3H, m), 7.58 (2H, t, J = 7.6 Hz), 9.96 (1H, s). |
| 1274 | δ 2.27 (6H, s), 3.37 (3H, s), 7.29 (3H, broad), 7.41-7.47 (4H, m), 7.59-7.61 (2H, m), 9.95 (1H, s). |
| 1293 | δ 2.28 (6H, s), 3.41 (3H, s), 7.25 (1H, t, J = 7.6 Hz), 7.35 (1H, dd, J = 7.3, 4.9 Hz), 7.43 (2H, s), 7.57-7.63 (2H, m), 7.91 (1H, d, J = 7.6 Hz), 8.32 (1H, dd, J = 4.9, 2.0 Hz), 9.96 (1H, s). |
| 1294 | δ 2.28 (6H, s), 3.39 (3H, s), 7.31-7.35 (1H, m), 7.42 (2H, s), 7.43-7.48 (1H, m), 7.61-7.75 (2H, m), 7.80 (1H, s), 8.32 (1H, broad), 10.01 (1H, s). |
| 1463 | δ 2.25 (6H, s), 3.38 (3H, s), 7.27-7.41 (6H, m), 7.45 (2H, s), 7.90 (1H, broad), 8.05 (1H, d, J = 6.8 Hz), 9.96 (1H, s). |
| 1464 | δ 2.23 (6H, s), 3.42 (3H, s), 7.41 (1H, broad), 7.45 (2H, s), 7.60 (2H, broad), 7.90 (1H, broad), 8.08-8.13 (3H, broad), 9.93 (1H, s). |
| 1465 | δ 2.25 (6H, s), 3.40 (3H, s), 7.39-7.42 (1H, m), 7.45 (2H, s), 7.50 (1H, broad), 7.78 (1H, broad), 7.91 (1H, broad), 7.97-8.10 (3H, m), 9.94 (1H, s). |
| 1478 | δ 2.29 (6H, s), 3.24 (3H, s), 6.84 (1H, d, J = 7.8 Hz), 7.12 (1H, t, J = 7.8 Hz), 7.33 (2H, s), 7.50-7.64 (4H, m), 7.85-7.88 (2H, m), 7.98-8.03 (1H, m), 10.22 (1H, s). |
| 1479 | δ 2.41 (3H, s), 3.25 (3H, s), 6.95 (1H, dd, J = 1.5, 7.8 Hz), 7.16 (1H, t, J = 7.8 Hz), 7.50-7.64 (4H, m), 7.68 (1H, s), 7.86-7.88 (2H, m), 7.93 (1H, t, J = 1.5 Hz), 7.98-8.00 (1H, m), 10.24 (1H, s). |
| 1480 | (CDCl$_3$) δ 3.34 (3H, s), 7.13-7.19 (2H, m), 7.49-7.58 (3H, m), 7.70-7.73 (2H, m), 7.78-7.91 (4H, m), 8.12 (1H, s). |
| 1481 | (CDCl$_3$) δ 3.35 (3H, s), 7.15-7.20 (3H, m), 7.32 (1H, t, J = 7.8 Hz), 7.51-7.55 (1H, m), 7.71 (1H, d, J = 2.9 Hz), 7.72 (1H, d, J = 2.0 Hz), 7.80 (2H, s), 8.14 (1H, dt, J = 2.0, 7.8 Hz), 8.37 (1H, d, J = 16.1 Hz). |
| 1482 | δ 1.18 (3H, t, J = 7.3 Hz), 2.30 (6H, s), 3.76 (2H, q, J = 7.3 Hz), 6.81 (1H, d, J = 7.8 Hz), 7.11 (1H, t, J = 7.8 Hz), 7.33 (2H, s), 7.50-7.62 (4H, m), 7.84-7.88 (2H, m), 7.95-8.00 (1H, m), 10.20 (1H, s). |
| 1483 | δ 1.44 (6H, d, J = 6.3 Hz), 2.07 (6H, s), 5.35 (1H, septet, J = 6.3 Hz), 6.84 (1H, d, J = 7.8 Hz), 7.21 (1H, t, J = 7.8 Hz), 7.21 (2H, s), 7.50-7.61 (3H, m), 7.75 (1H, dd, J = 1.5, 7.8 Hz), 7.86-7.89 (3H, m), 10.29 (1H, s). |
| 1484 | δ 2.18 (3H, s), 2.32 (6H, s), 7.37-7.59 (11H, m), 10.42 (1H, s). |
| 1485 | δ 2.34 (3H, s), 2.35 (6H, s), 7.34-8.02 (10H, m), 10.33 (1H, s). |
| 1486 | δ 2.33 (3H, s), 2.36 (6H, s), 7.29-8.12 (9H, m), 10.37 (1H, s). |
| 1487 | δ 2.20 (6H, s), 3.08 (3H, s), 3.20 (3H, s), 6.93-7.39 (10H, m), 7.45-7.51 (1H, m). |
| 1607 | (CDCl$_3$) δ 3.31 (3H, s), 3.35 (3H, s), 6.81 (1H, dt, J = 6.8, 1.0 Hz), 6.94 (1H, t, J = 7.8 Hz), 7.10-7.24 (5H, m), 7.35-7.40 (1H, m), 7.41 (1H, s), 7.78 (2H, s). |
| 1617 | (CDCl$_3$) δ 3.30 (3H, s), 3.33 (3H, s), 6.76-7.00 (4H, m), 7.19-7.23 (3H, m), 7.37 (1H, s), 7.77 (2H, s). |
| 1645 | (CDCl$_3$) δ 3.30 (3H, s), 3.36 (3H, s), 6.96-7.06 (3H, m), 7.12-7.16 (1H, m), 7.39-7.42 (2H, m), 7.95 (2H, s), 8.24 (1H, s). |
| 1654 | (CDCl$_3$) δ 3.30 (3H, s), 3.42 (3H, s), 7.01 (1H, d, J = 7.3 Hz), 7.10 (1H, t, J = 7.8 Hz), 7.16 (1H, dd, J = 1.4, 7.8 Hz), 7.41 (1H, t, J = 1.4 Hz), 7.54 (1H, dd, J = 1.9 Hz), 7.56 (1H, d, J = 1.9 Hz), 7.80 (1H, s), 7.81 (2H, s). |
| 1655 | (CDCl$_3$) δ 3.29 (3H, s), 3.38 (3H, s), 3.78 (3H, s), 6.73 (1H, d, J = 8.3 Hz), 6.96 (1H, d, J = 8.3 Hz), 7.04 (1H, t, J = 7.8 Hz), 7.08 (1H, d, J = 1.5 Hz), 7.14 (1H, d, J = 7.8 Hz), 7.40 (1H, s), 7.54 (1H, d, J = 8.3 Hz), 7.81 (2H, s). |
| 1697 | δ 2.23 (6H, s), 3.32 (3H, s), 3.39 (3H, s), 7.15-7.43 (10H, m). |
| 2001 | (CDCl$_3$) δ 2.36 (6H, s), 7.36 (2H, s), 7.53-7.57 (2H, m), 7.61-7.65 (1H, m), 7.95-8.03 (3H, m), 8.08 (1H, dd, J = 7.3, 1.0 Hz), 8.52 (1H, broad-s), 8.62 (1H, dd, J = 8.3, 1.0 Hz), 9.19 (1H, broad-s). |
| 2004 | δ 2.30 (6H, s), 7.37-7.43 (2H, m), 7.46 (2H, s), 7.65 (1H, d, J = 8.1 Hz), 7.83 (1H, dd, J = 7.5, 5.6 Hz), 7.88 (1H, d, J = 7.5 Hz), 8.13 (1H, t, J = 8.1 Hz), 8.40 (1H, d, J = 8.1 Hz), 10.08 (1H, s), 10.62 (1H, s). |

TABLE 11-continued

| Comp. No. | |
|---|---|
| 2032 | δ 2.30 (6H, s), 7.46 (2H, s), 7.75-7.78 (1H, m), 7.91 (1H, dd, J = 7.3, 1.0 Hz), 8.13-8.18 (2H, m), 8.27 (1H, d, J = 8.0 Hz), 8.56 (1H, d, J = 8.0 Hz), 8.77 (1H, d, J = 1.0 Hz), 10.62 (1H, s), 10.75 (1H, s). |
| 2033 | δ 2.27 (6H, s), 6.16 (2H, s), 6.71 (1H, d, J = 7.6 Hz), 7.01 (2H, d, J = 1.0 Hz), 7.24 (1H, d, J = 6.9 Hz), 7.42 (2H, s), 7.59 (1H, dd, J = 7.6, 6.9 Hz), 7.65 (1H, s), 9.94 (1H, s). |
| 2034 | δ 2.32 (6H, s), 7.47 (2H, s), 7.90-7.93 (3H, m), 8.15 (1H, t, J = 8.0 Hz), 8.37 (1H, d, J = 8.0 Hz), 8.83 (2H, dd, J = 4.6, 1.7 Hz), 10.12 (1H, s), 10.92 (1H, s). |
| 2035 | δ 2.30 (6H, s), 7.46 (2H, s), 7.55-7.56 (1H, m), 7.89 (1H, d, J = 7.4 Hz), 8.14 (1H, t, J = 7.8 Hz), 8.34-8.41 (2H, m), 8.45 (1H, dd, J = 5.4, 1.2 Hz), 10.03 (1H, s), 10.90 (1H, s). |
| 2036 | δ 2.29 (6H, s), 7.45 (2H, s), 7.59 (1H, t, J = 6.3 Hz), 7.88 (1H, d, J = 6.3 Hz), 8.12-8.16 (2H, m), 8.39 (1H, m), 8.55 (1H, m), 9.93 (1H, s), 11.25 (1H, s). |
| 2037 | δ 2.32 (6H, s), 7.47 (2H, s), 7.67 (1H, d, J = 7.6 Hz), 7.75 (1H, d, J = 8.3 Hz), 7.90 (1H, d, J = 7.6 Hz), 8.14 (1H, t, J = 7.6 Hz), 8.29 (1H, dd, J = 8.3 Hz, 2.0 Hz), 8.89 (1H, d, J = 2.0 Hz), 10.07 (1H, s), 10.97 (1H, s). |
| 2082 | δ 2.20 (6H, s), 3.58 (3H, s), 7.29-7.39 (5H, m), 7.43 (2H, s), 7.50 (1H, d, J = 7.4 Hz), 7.83 (1H, t, J = 7.4 Hz), 7.94 (1H, t, J = 7.4 Hz), 9.91 (1H, s). |
| 2085 | δ 2.22 (6H, s), 3.57 (3H, s), 7.12 (1H, t, J = 9.2 Hz), 7.20 (1H, t, J = 7.3 Hz), 7.28-7.30 (1H, m), 7.44 (2H, s), 7.55 (1H, t, J = 7.2 Hz), 7.63 (1H, broad), 7.87 (1H, d, J = 7.2 Hz), 7.98 (1H, t, J = 7.2 Hz), 9.90 (1H, s). |
| 2093 | δ 2.14 (6H, s), 3.57 (3H, s), 7.42 (2H, s), 7.66-7.87 (3H, m), 7.96-8.09 (4H, m), 9.77 (1H, s). |
| 2116 | δ 2.23 (6H, s), 3.55 (3H, s), 7.45 (3H, s), 7.89-9.91 (2H, m), 8.03-8.10 (3H, m), 9.82 (1H, s). |
| 2117 | δ 2.13 (6H, s), 3.58 (3H, s), 7.42 (2H, s), 7.46 (1H, d, J = 8.2 Hz), 7.72-7.75 (2H, m), 7.90 (1H, d, J = 8.2 Hz), 8.08 (1H, t, J = 8.2 Hz), 8.35 (1H, d, J = 2.0 Hz), 9.83 (1H, s). |
| 2162 | (CDCl₃) δ 2.38 (6H, s), 7.38 (2H, s), 7.53-7.57 (2H, m), 7.62 (1H, d, J = 7.8 Hz), 7.68 (1H, dd, J = 4.9, 1.5 Hz), 7.85 (1H, broad-s), 7.95 (2H, d, J = 7.8 Hz), 8.52 (1H, d, J = 4.9 Hz), 8.22 (1H, broad-s), 8.88 (1H, s). |
| 2163 | (CDCl₃) δ 2.36 (6H, s), 7.38 (2H, s), 7.55-7.59 (2H, m), 7.64-7.72 (2H, m), 7.75 (1H, broad-s), 8.01 (2H, d, J = 7.3 Hz), 8.41 (1H, d, J = 6.8 Hz), 9.14 (1H, d, J = 2.4 Hz), 10.9 (1H, broad-s). |
| 2164 | (CDCl₃) δ 2.34 (6H, s), 7.47 (2H, s), 7.62-7.65 (2H, m), 7.70-7.81 (2H, m), 8.04-8.04 (3H, m), 8.64 (1H, dd, J = 8.3, 1.5 Hz), 10.9 (1H, broad-s), 12.3 (1H, broad-s). |
| 2165 | δ 2.35 (6H, s), 7.29-8.03 (10H, m), 8.75 (1H, d, J = 2.0 Hz). |
| 2168 | δ 2.25 (6H, s), 3.32 (3H, s), 7.26 (1H, d, J = 7.7 Hz), 7.38 (1H, d, J = 7.7 Hz), 7.44 (2H, s), 7.55 (1H, t, J = 7.7 Hz), 7.90 (3H, m), 8.11 (2H, m), 12.40 (1H, s). |
| 2201 | (CDCl₃) δ 2.38 (6H, s), 7.25-8.00 (11H, m), 8.34 (1H, s), 8.85 (1H, broad.). |
| 2202 | (CDCl₃) δ 2.36 (6H, s), 7.37 (2H, s), 7.47-7.61 (5H, m), 7.85-8.03 (4H, m), 8.57 (1H, s), 9.18 (1H, s). |
| 2203 | (CDCl₃) δ 2.38 (6H, s), 7.41 (2H, s), 7.45-7.55 (4H, m), 7.90-7.96 (4H, m), 8.57 (1H, broad), 8.74 (1H, broad), 9.18 (1H, broad). |

¹H-NMR (CDCl₃, ppm)

| | |
|---|---|
| I-1 | δ 2.34 (6H, s), 3.87 (2H, broad-s), 6.86-6.89 (1H, m), 7.21-7.30 (3H, m), 7.33 (2H, s), 7.39 (1H, s) |
| I-2 | δ 2.34 (6H, s), 3.87 (2H, broad), 6.86-6.89 (1H, m), 7.20-7.35 (6H, m) |
| I-4 | δ 2.60 (3H, s), 3.92 (2H, broad-s), 6.89-6.92 (1H, m), 7.24-7.32 (3H, m), 7.46 (1H, s), 7.76 (1H, broad-s) |
| I-5 | δ 2.27 (6H, s), 3.31 (3H, s), 6.40-6.43 (1H, m), 6.54-6.58 (1H, m), 6.71 (1H, t, J = 2.0 Hz), 6.76-6.86 (1H, m), 7.22 (2H, s) |
| I-6 | δ 1.45 (6H, d, J = 6.3 Hz), 2.07 (6H, s), 3.53 (2H, broad), 5.37 (1H, septet, J = 6.3 Hz), 6.56-6.63 (3H, m), 6.96 (1H, t, J = 7.8 Hz), 7.16 (2H, s) |
| I-7 | δ 1.17 (3H, t, J = 7.6 Hz), 2.28 (3H, s), 2.65 (2H, q, J = 7.6 Hz), 3.85 (2H, broad-s), 6.82-6.85 (1H, m), 7.21-7.23 (3H, m), 7.34 (2H, s), 7.64 (1H, s) |
| I-8 | δ 1.22 (6H, t, J = 7.6 Hz), 2.69 (4H, q, J = 7.6 Hz), 3.86 (2H, broad-s), 6.86-6.89 (1H, m), 7.15-7.36 (4H, m), 7.38 (2H, s) |
| I-9 | δ 1.23 (3H, t, J = 7.3 Hz), 2.76 (2H, q, J = 7.3 Hz), 3.88 (2H, broad-s), 6.88-6.91 (1H, m), 7.26-7.32 (3H, m), 7.50 (1H, s), 7.53 (1H, s), 7.95 (1H, d, J = 1.5 Hz) |
| I-10 | δ 1.22 (6H, d, J = 6.8 Hz), 2.32 (3H, s), 3.17 (1H, septet, J = 6.8 Hz), 3.87 (2H, broad-s), 6.85-6.93 (1H, m), 7.20-7.29 (3H, m), 7.35 (1H, s), 7.40-7.45 (2H, m). |
| I-11 | δ 2.35 (3H, s), 3.85 (5H, s), 6.85-6.89 (1H, m), 6.95 (1H, s), 7.13 (1H, s), 7.23-7.30 (3H, m), 7.62 (1H, s) |
| I-12 | δ 1.25 (3H, t, J = 7.6 Hz), 2.76 (2H, q, J = 7.6 Hz), 3.88 (2H, broad-s), 6.87-6.91 (1H, m), 7.24-7.31 (3H, m), 7.47 (1H, s), 7.55 (1H, s), 7.57 (1H, s) |
| I-13 | δ 2.35 (3H, s), 2.57 (3H, d, J = 6.8 Hz), 3.88 (2H, broad-s), 6.88-6.91 (1H, m), 7.25-7.34 (4H, m), 7.67 (1H, s) |
| I-14 | δ 2.41 (3H, s), 3.88 (2H, broad-s), 6.87-6.91 (1H, m), 7.25-7.31 (3H, m), 7.47 (1H, s), 7.65 (1H, s), 7.72 (1H, s) |
| I-15 | δ 1.23 (3H, t, J = 7.3 Hz), 2.74 (2H, q, J = 7.3 Hz), 3.87 (2H, broad-s), 6.86-6.91 (1H, m), 7.25-7.31 (3H, m), 7.50 (1H, s), 7.59 (1H, s), 7.73 (1H, d, J = 1.5 Hz) |
| I-16 | (DMSO-d₆) δ 0.84 (3H, t, J = 7.3 Hz), 1.48-1.58 (2H, m), 2.66 (2H, t, J = 7.3 Hz), 5.36 (2H, broad-s), 6.77 (1H, dd, J = 1.0 Hz, 7.8 Hz), 7.10-7.19 (3H, m), 7.59 (1H, s), 7.80 (1H, s), 10.03 (1H, s) |
| I-17 | δ 0.90 (3H, t, J = 7.3 Hz), 1.25-1.37 (2H, m), 1.55-1.63 (2H, m), 2.72 (2H, t, J = 7.8 Hz), 3.89 (2H, broad), 6.87-6.91 (1H, m), 7.24-7.31 (3H, m), 7.48 (1H, s), 7.55 (1H, s), 7.73 (1H, d, J = 1.5 Hz) |
| I-18 | δ 2.39 (3H, s), 2.66 (3H, d, J = 6.9 Hz), 7.43 (1H, s), 7.75-7.79 (2H, m), 8.33 (1H, d, J = 8.3 Hz), 8.48 (1H, d, J = 8.3 Hz), 8.80 (1H, s) |
| I-19 | δ 2.41 (3H, s), 3.88 (2H, s), 6.86-6.91 (1H, m), 7.28-7.32 (3H, m), 7.49 (1H, s), 7.58 (1H, s), 7.93 (1H, d, J = 1.2 Hz) |
| I-20 | δ 0.91 (3H, t, J = 7.3 Hz), 1.58-1.67 (2H, m), 2.69 (2H, t, J = 7.8 Hz), 3.88 (2H, broad-s), 6.87-6.90 (1H, m), 7.26-7.31 (3H, m), 7.50 (1H, s), 7.54 (1H, s), 7.95 (1H, d, J = 2.0 Hz) |
| I-21 | δ 2.33 (6H, s), 3.87 (2H, broad-s), 6.86-6.89 (1H, m), 7.21-7.29 (3H, m), 7.34 (2H, s), 7.52 (1H, s) |
| I-22 | δ 2.32 (6H, s), 3.86 (2H, broad-s), 6.85-6.88 (1H, m), 7.20-7.28 (3H, m), 7.33 (2H, s), 7.60 (1H, s) |
| I-23 | δ 3.99 (2H, broad-s), 6.85-6.88 (1H, m), 7.23-7.34 (3H, m), 7.91 (2H, s), 8.69 (1H, s) |
| I-24 | (DMSO-d₆) δ 5.39 (2H, broad-s), 6.77-6.80 (1H, m), 7.12-7.19 (3H, m), 8.49 (2H, s), 10.53 (1H, s) |

TABLE 11-continued

| Comp. No. | |
|---|---|
| I-26 | δ 3.88 (2H, s), 6.90 (1H, d, J = 6.8 Hz), 7.23-7.32 (3H, m), 7.60 (1H, s), 7.92 (2H, s) |
| I-27 | δ 3.89 (2H, broad-s), 6.90 (1H, dt, J = 2.5 Hz, 6.3 Hz), 7.25-7.32 (3H, m), 7.59 (1H, s), 7.72 (2H, s) |
| I-28 | δ 3.89 (2H, broad-s), 6.90 (1H, dt, J = 2.5 Hz, 6.4 Hz), 7.28-7.30 (3H, m), 7.60 (1H, s), 7.93 (2H, s) |
| I-29 | δ 3.92 (2H, s), 6.92 (1H, dt, J = 1.5 Hz, 7.3 Hz), 7.23-7.30 (3H, m), 7.79 (1H, s), 8.04 (2H, s) |
| I-30 | δ 3.89 (2H, broad-s), 6.90 (1H, dd, J = 2.4 Hz, 4.9 Hz), 7.23-7.32 (3H, m), 7.61 (1H, s), 7.93 (2H, s) |
| I-31 | δ 3.88 (2H, broad-s), 6.90 (1H, d, J = 6.3 Hz), 7.23-7.32 (3H, m), 7.62 (1H, s), 7.92 (2H, s) |
| I-32 | δ 6.90-6.94 (1H, m), 7.28-7.33 (3H, m), 7.73 (1H, s), 8.02 (1H, s), 8.25 (1H, s) |
| I-33 | δ 2.31 (6H, s), 2.90 (3H, s), 6.81 (1H, dd, J = 1.9 Hz, 7.8 Hz), 7.15-7.18 (2H, m), 7.30 (1H, t, J = 7.8 Hz), 7.42 (1H, s), 7.52 (2H, s) |
| I-35 | δ 0.89 (3H, t, J = 7.3 Hz), 1.23-1.37 (2H, m), 1.54-1.62 (2H, m), 2.70 (2H, t, J = 7.8 Hz), 3.88 (2H, broad), 6.86-6.90 (1H, m), 7.22-7.30 (3H, m), 7.44 (1H, s), 7.56-7.59 (2H, m). |
| I-36 | (DMSO-d$_6$) δ 0.82 (3H, t, J = 7.3 Hz), 1.19-1.29 (2H, m), 1.44-1.52 (2H, m), 2.66 (2H, t, J = 7.8 Hz), 5.36 (2H, broad-s), 6.75-6.81 (1H, m), 7.12-7.19 (3H, m), 7.58 (1H, s), 7.95 (1H, d, J = 1.5 Hz), 10.02 (1H, s). |
| I-37 | (DMSO-d$_6$) δ 5.37 (2H, s), 6.76-6.80 (1H, m), 7.13-7.19 (3H, m), 8.13 (2H, s), 10.35 (1H, s). |
| I-38 | δ 0.79 (3H, t, J = 7.3 Hz), 1.23 (3H, d, J = 6.8 Hz), 1.53-1.63 (2H, m), 2.90-2.99 (1H, m), 3.87 (2H, broad-s), 6.85-6.89 (1H, m), 7.25-7.29 (3H, m), 7.44 (1H, s), 7.55-7.57 (2H, m). |
| I-39 | δ 0.79 (3H, t, J = 7.3 Hz), 1.21 (3H, d, J = 6.8 Hz), 1.50-1.61 (2H, m), 2.91-3.00 (1H, m), 3.88 (2H, broad-s), 6.86-6.91 (1H, m), 7.26-7.31 (3H, m), 7.51 (2H, s), 7.94 (1H, d, J = 2.0 Hz). |
| I-40 | (DMSO-d$_6$) δ 5.39 (2H, broad-s), 6.77-6.80 (1H, m), 7.13-7.20 (3H, m), 8.02 (2H, s), 10.35 (1H, s). |
| I-41 | (DMSO-d$_6$) δ 5.38 (2H, broad-s), 6.75-6.80 (1H, m), 7.12-7.19 (3H, m), 8.01 (2H, s), 10.34 (1H, s). |
| I-42 | (DMSO-d$_6$) δ 3.34 (3H, s), 5.40 (2H, broad-s), 6.80 (1H, d, J = 7.8 Hz), 7.14-7.21 (3H, m), 8.19 (1H, s), 8.45 (1H, s), 10.36 (1H, s). |
| I-48 | (DMSO-d$_6$) δ 2.48 (3H, s), 5.36 (2H, broad-s), 6.77 (1H, d, J = 7.3 Hz), 7.11-7.18 (3H, m), 7.36 (1H, s), 7.70 (1H, s), 10.09 (1H, s). |
| I-53 | δ 0.91 (3H, t, J = 7.3 Hz), 1.57-1.66 (2H, m), 2.69 (2H, t, J = 7.8 Hz), 2.88 (3H, s), 3.97 (1H, s), 6.80 (1H, dd, J = 2.4, 7.8 Hz), 7.19-7.32 (3H, m), 7.49 (1H, s), 7.60 (1H, s), 7.94 (1H, d, J = 2.0 Hz). |
| I-55 | δ 2.73 (3H, s), 3.32 (3H, s), 6.54 (1H, d, J = 8.3 Hz), 6.73 (1H, s), 6.74 (1H, d, J = 8.3 Hz), 6.96 (1H, t, J = 8.3 Hz), 7.77 (2H, s). |
| I-56 | δ 2.91 (3H, s), 6.82-6.85 (1H, m), 7.21-7.23 (2H, m), 7.32 (1H, t, J = 7.8 Hz), 7.64 (1H, s), 7.93 (2H, s) |
| I-83 | δ 2.38 (6H, s), 2.42 (3H, s), 3.70 (2H, broad), 6.72 (1H, dd, J = 2.4 Hz, 8.1 Hz), 6.89 (1H, d, J = 2.4 Hz), 7.05 (1H, s), 7.07 (1H, d, J = 8.1 Hz), 7.36 (2H, s) |
| I-84 | δ 2.37 (6H, s), 3.90 (2H, broad-s), 6.96-7.01 (1H, m), 7.10 (1H, t, J = 7.8 Hz), 7.36 (2H, s), 7.43-7.47 (1H, m), 7.86 (1H, d, J = 13.2 Hz) |
| I-85 | δ 2.33 (6H, s), 6.99 (1H, dt, J = 1.5 Hz, 7.8 Hz), 7.10 (1H, t, J = 7.8 Hz), 7.43 (2H, s), 7.46 (1H, d, J = 7.8 Hz), 7.84 (1H, d, J = 13.2 Hz) |
| I-86 | δ 2.33 (6H, s), 3.93 (2H, s), 7.05-7.14 (1H, m), 7.17-7.21 (1H, m), 7.31 (1H, s), 7.35 (2H, s), 7.37-7.40 (1H, m) |
| I-87 | δ 2.35 (6H, s), 3.74 (2H, broad-s), 6.77-6.83 (1H, m), 7.01 (1H, dd, J = 8.8 Hz, 11.7 Hz), 7.35 (2H, s), 7.42 (1H, dd, J = 2.9 Hz, 6.6 Hz), 8.01 (1H, dd, J = 15.6 Hz) |
| I-88 | δ 2.40 (6H, s), 4.27 (2H, broad-s), 6.88 (1H, dd, J = 1.5 Hz, 7.8 Hz), 7.03 (1H, dd, J = 1.5 Hz, 7.8 Hz), 7.16 (1H, t, J = 7.8 Hz), 7.29 (1H, s), 7.36 (2H, s) |
| I-89 | δ 2.33 (6H, s), 4.27 (2H, broad-s), 7.15 (1H, d, J = 8.1 Hz), 7.35-7.38 (5H, m) |
| I-90 | δ 2.39 (6H, s), 3.85 (2H, broad-s), 6.72 (1H, dd, J = 2.7 Hz, 8.5 Hz), 7.15 (1H, d, J = 2.7 Hz), 7.22 (1H, d, J = 8.5 Hz), 7.36 (2H, s), 7.66 (1H, s) |
| I-91 | δ 2.43 (6H, s), 4.34 (2H, broad), 6.86 (1H, dd, J = 1.5 Hz, 8.3 Hz), 6.96 (1H, dd, J = 1.5 Hz, 8.3 Hz), 7.13 (1H, s), 7.19 (1H, t, J = 8.3 Hz), 7.36 (2H, s) |
| I-92 | δ 2.44 (6H, s), 3.86 (2H, broad-s), 6.52 (1H, dd, J = 2.9 Hz, 8.5 Hz), 6.91 (1H, d, J = 2.9 Hz), 7.12 (1H, s), 7.35 (2H, s), 7.62 (1H, d, J = 8.5 Hz) |
| I-93 | δ 2.27 (6H, s), 4.09 (2H, broad-s), 7.08 (1H, s), 7.33 (2H, s), 7.37 (1H, s), 7.43 (1H, s), 7.83 (1H, s) |
| I-94 | (DMSO-d$_6$) δ 2.29 (3H, s), 2.33 (6H, s), 5.43 (2H, s), 6.57-6.59 (1H, m), 6.85-6.90 (1H, m), 7.01 (1H, t, J = 7.8 Hz), 7.49 (2H, s). |
| I-95 | (DMSO-d$_6$) δ 2.32 (6H, s), 2.76 (3H, d, J = 4.9 Hz), 5.84 (1H, broad), 6.77-6.81 (2H, m), 7.10 (1H, t, J = 7.8 Hz), 7.43 (2H, s), 9.90 (1H, s). |
| I-96 | (DMSO-d$_6$) δ 2.33 (6H, s), 2.76 (3H, d, J = 4.9 Hz), 4.55 (3H, s), 6.58-6.62 (1H, m), 6.70-6.78 (1H, m), 7.13 (1H, t, J = 7.8 Hz), 7.31 (1H, s), 7.50 (2H, s). |
| I-98 | (DMSO-d$_6$) δ 2.32 (6H, s), 2.77 (3H, d, J = 4.9 Hz), 5.82 (1H, broad), 6.79 (1H, t, J = 7.8 Hz), 7.08-7.21 (2H, m), 7.42 (2H, s), 9.88 (1H, s). |
| I-124 | (DMSO-d$_6$) δ 2.26 (6H, s), 7.46 (2H, s), 7.88 (1H, t, J = 7.8 Hz), 8.43-8.48 (2H, m), 8.73 (1H, s), 8.81 (1H, s), 10.27 (1H, s). |
| I-125 | δ 2.16 (6H, s), 7.23 (1H, s), 7.53 (2H, s), 7.73 (1H, t, J = 7.8 Hz), 8.45 (1H, d, J = 7.8 Hz), 8.55 (1H, d, J = 7.8 Hz), 9.05 (1H, t, J = 2.0 Hz). |
| I-204 | (DMSO-d$_6$) δ 2.35 (6H, s), 4.31 (2H, broad), 6.84-6.87 (1H, m), 7.21-7.25 (1H, m), 7.29-7.31 (2H, m), 7.47-7.49 (2H, m), 7.83 (1H, s), 8.94 (1H, s). |
| I-351 | (DMSO-d$_6$) δ 2.26 (6H, s), 7.44 (2H, s), 7.51-7.63 (4H, m), 7.74 (1H, d, J = 7.8 Hz), 7.98-8.07 (3H, m), 8.35 (1H, s), 8.71 (1H, s), 9.90 (1H, s), 10.47 (1H, s). |
| I-358 | (DMSO-d$_6$) δ 2.34 (6H, s), 7.21 (1H, dd, J = 8.2, 11.2 Hz), 7.32 (1H, t, J = 7.8 Hz), 7.49-7.56 (4H, m), 7.78 (1H, d, J = 7.8 Hz), 8.04-8.08 (1H, m), 8.23 (1H, s), 8.71 (1H, s), 9.08 (1H, d, J = 11.2 Hz). |
| I-419 | (DMSO-d$_6$) δ 2.34 (6H, s), 7.49-7.63 (6H, m), 7.76 (1H, d, J = 7.8 Hz), 7.99-8.08 (3H, m), 8.37 (1H, s), 9.99 (1H, s), 10.48 (1H, s). |

TABLE 12

| Comp. No. | LC-MS Molecular Ion Peak |
|---|---|
| I-384 | 573.80 |
| I-385 | 573.73 |
| I-401 | 579.67 |
| I-406 | 516.73 |
| I-414 | 654.73 |
| I-418 | 499.87 |

The insecticide containing the compound represented by Formula (1) of the invention as an active ingredient is suitable for controlling various pests which give damage to paddy rices, fruit trees, vegetables, other crops and flowers and ornamental plants in agricultural, horticultural or stored grain products, or sanitary pests, or for controlling and it may include vermin such as eelworm, for example, those having strong insecticidal effect against Lepidoptera such as cotton caterpillar (Diaphania indica), oriental tea tortrix (Homona magnanima), cabbage webworm (Hellulla undalis), summer fruit tortrix (Adoxophyes orana fasciata), smaller tea tortrix (Adoxophyes sp.), apple tortrix (Archips fuscocupreanus), peach fruit moth (Carposina niponensis), Manchurian fruit moth (Grapholita inopinata), oriental fruit moth (Grapholita molesta), soybean pod borer (Leguminivora glycinivorella), mulberry leafroller (Olethreutes mori), citrus leafminer (Phyllocnistis citrella), persimmon fruit moth (Stathmopoda masinissa), tea leafroller (Caloptilia theivora), (Caloptilia zachrysa), apple leafminer (Phyllonorycter ringoniella), pear barkminer (Spulerrina astaurota), small citrus dog (Papilio xuthus), common cabbage worm (Pieris rapae crucivora), tobacco budworm (Heliothis armigera), codling moth (Cydia pomonella), diamondback moth (Plutella xylostella), apple fruit moth (Argyresthia conjugella), peach fruit moth (Carposina niponensis), rice stem borer (Chilo suppressalis), rice leafroller (Cnaphalocrocis medinalis), tobacco moth (Ephestia elutella), mulberry pyralid (Glyphodes pyloalis), paddy borer (Scirpophaga incertulas), rice skipper (Parnara guttata), rice armyworm (Pseudaletia separata), pink borer (Sesamia inferens), cabbage armyworm (Mamestra brassicae), common cutworm (Spodoptera litura), beet armyworm (Spodoptera exigua), black cutworm (Agrotis ipsilon), turnip moth (Agrotis segetum), beet semi-looper (Autographa nigrisigna), cabbage looper (Trichoplusia ni); Hemiptera such as aster leafhopper (Macrosteles fascifrons), green rice leafhopper (Nephotettix cincticeps), brown rice planthopper (Nilaparvata lugens), small brown planthopper (Laodelphax striatellus), whitebacked rice planthopper (Sogatella furcifera), citrus psylla (Diaphorina citri), grape whitefly (Aleurolobus taonabae), silverleaf whitefly (Bermisia argentifolii), sweetpotato whitefly (Bemisia tabaci), greenhouse whitefly (Trialeurodes vaporariorum), turnip aphid (Lipaphis erysimi), cotton aphid (Aphis gossypii), apple aphid (Aphis Citricola), green peach aphid (Myzus persicae), Indian wax scale (Ceroplastes ceriferus), Comstock mealybug (Pseudococcus Comstocki), Japanease mealybug (Planococcus kraunhiae), cottony citrus scale (Pulvinaria aurantii), camphor scale (Pseudaonidia duplex), san Jose scale (Comstockaspis perniciosa), arrowhead scale (Unaspis yanonensis), brownwinged green bug (Plautia Stali), brown marmorated stink bug (Halyomorpha mista); Coleoptera such as soybean beetle (Anomala rufocuprea), Japanese beetle (Popillia japonica), cigarette beetle (Lasioderma serricorne), powderpost beetle (Lyctusbrunneus), twenty-eight-spotted ladybird (Epilachna vigintioctopunctata), adzuki bean weevil (Callosobruchus chinensis), vegetable weevil (Listroderes costirostris), maize weevil (Sitophilus zeamais), boll weevil (Anthonomus grandis), rice water weevil (Lissorhoptrus oryzophilus), cucurbit leaf beetle (Aulacophora femoralis), rice leaf beetle (Oulema oryzae), striped flea beetle (Phyllotreta striolata), pine shoot beetle (Tomicus piniperda), Colorado potato beetle (Leptinotarsa decemlineata), Mexican bean beetle (Epilachna varivestis), corn rootworm (Diabrotica sp.), yellowspotted longicorn beetle (Psacothea hilaris), whitespotted longicorn beetle (Anoplophora malasiaca); Diptera such as melon fly (Dacus (Bactrocera) dorsalis), rice leafminer (Agromyza oryzae), onion maggot (Delia antiqua), seedcorn maggot (Delia platura), soybean pod gall midge (Asphondylia sp.), house fly (Musca domestica), garden pea leafminer (Chromatomyia horticola), legume leafminer (Liriomyza trifolii), bryony leafminer (Liriomyza bryoniae), common house mosquito (Culex pipiens); Nematoda such as coffee root-lesion nematode (Pratylenchus coffeae), root-lesion nematode (Pratylenchus sp.), potato cyst nematode (Globodera rostochiensis), root-knot nematode (Meloidogyne sp.), citrus nematode (Tylemchulus semipenetrans), nematode (Aphelenchus avenae), chrysanthemum foliar nematode (Aphelenchoides ritzemabosi); Thysanoptera such as melon thrips (Thrips palmi), western flower thrips (Frankliniella occidentalis), yellow tea thrips (Scirtothrips dorsalis), honeysuckle thrips (Thrips flavus), onion thrips (Thrips tabaci); Orthoptera such as German cockroach (Blattella germanica), American cockroach (Periplaneta americana), rice grasshopper (Oxya yezoensis) and the like.

The insecticides containing the compound represented by Formula (1) of the invention as an active ingredient have notable insecticidal effect against the above-described pests that damage various lowland crops, upland crops, fruit trees, vegetables, other crops and horticultural products. Thus, the insecticidal effect of the invention can be obtained by treating the paddy field water, plant stems and leaves, or soil of the crops of lowland, upland, fruit trees, vegetables, other crops, and flowers and ornamental plants, during the seasons expected of the appearance of such pests, or before or at the point of pest appearance.

The insecticides of the invention are in general used in appropriate formulation forms according to the use, prepared by conventional methods for preparation of agricultural and horticultural chemicals. That is, the compounds represented by Formula (1) may be used in suitable formulations, such as a suspension, an emulsion, a liquid formulation, a water-dispersible powder, a granule, a dust formulation, tablets and the like, prepared by blending the compounds with suitable inert carriers, or with auxiliary agents if necessary, in appropriate proportions, followed by dissolution, separation, suspension, mixing, impregnation, adsorption or adhesion of the ingredients.

The inert carrier that can be used in the invention may be solids or liquids and include, in particular, soybean powders, grain powders, wood powders, bark powders, coarse powders, tobacco powders, walnut shell powders, brans, cellulose powders, residues from plant extraction, synthetic polymers such as pulverized synthetic resins, clays (for example, kaolin, bentonite, acidic white clay), talc (for examples, talc, pyrophyllite, etc.), silica (for examples, diatomite, sand, mica, white carbon (hydrous silica powders, hydrous silica powders called synthetic high dispersity silicic acids, there are also products containing calcium silicate as main component)), activated carbon, sulfur powder, pumice, calcined diatomaceous powders, pulverized bricks, fly ash, sand, inorganic mineral powders such as calcium carbonate and calcium phosphate, chemical fertilizers such as ammonium sulfate, ammonium phosphate, ammonium nitrate, urea and ammonium chloride, a compost and the like, which are used alone or as mixtures of two or more.

Materials that can be used as the inert carrier for liquids are selected from those having the function as solvent, as well as those capable of dispersing the active ingredient compound under an aid of an auxiliary agent even if the inert carrier has not the function as solvent, and they can be exemplified by, for example, the carriers listed below: water, alcohols (e.g., methanol, ethanol, isopropanol, butanol, ethylene glycol, etc.), ketones (e.g., acetone, methyl ethyl ketone, methyl isobutyl ketone, diisobutylketone, cyclohexanone, etc.), ethers (e.g., diethyl ether, dioxane, cellosolve, diisopropyl ether, tetrahydrofuran, etc.), aliphatic hydrocarbons (e.g., kerosene, mineral oil, etc.), aromatic hydrocarbons (e.g., benzene, toluene, xylene, solvent naphtha, alkyl naphthalene, etc.), halogenated hydrocarbons (e.g., dichloromethane, chloroform, tetrachlorocarbon, chlorobenzene, etc.), esters (e.g., ethyl acetate, butyl acetate, ethyl propionate, diisobutyl phthalate, dibutyl phthalate, dioctyl phthalate, etc.), amides (e.g., dimethyl formamide, diethyl formamide, dimethyl acetamide, etc.), and nitriles (e.g., acetonitrile, etc.), which are used alone or as mixtures of two or more.

The auxiliary agent may include the following representative auxiliary agents, which are used alone or in combination of two or more of them depending on the purpose; however, it is also possible not to use any auxiliary agent.

For the purpose of emulsification, dispersion, solubilization and/or wetting of the active ingredient compound, surfactants can be used, for example, polyoxyethylene alkyl ethers, polyoxyethylene alkyl aryl ethers, polyoxyethylene higher fatty acid esters, polyoxyethylene resin acid esters, polyoxyethylene sorbitan monolaurate, polyoxyethylene sorbitan monooleates, alkyl aryl sulfonate, naphthalene sulfonate, lignin sulfonate, higher alcohol sulfonate esters and the like.

For the purpose of dispersion stabilization, adhesion and/or binding of the active ingredient compound, the following auxiliary agent can be use, for example, casein, gelatin, starch, methyl cellulose, carboxymethyl cellulose, gum Arabic, polyvinyl alcohol, pine root oil, corn oil, bentonite, xanthan gum, lignin sulfonate salts and the like.

For the purpose of improving the flowability of solid products, the auxiliary agents can be used, for example, wax, stearic acid salts, phosphoric alkyl esters and the like. An auxiliary agent such as a naphthalene sulfonate condensation product, or a condensed phosphate salt can be used as a suspending agent in suspensions. An antifoaming agent such as silicone oils can be also used as an auxiliary agent.

In addition, the compound represented by Formula (1) of the invention is stable against light, heat, oxidation and the like, but if desired, more stable compositions may obtained by adding a stabilizer. The stabilizer may include, for example, antioxidants or UV absorbents, phenol derivatives such as BHT (2,6-di-t-butyl-4-methyl phenol), BHA (butyl hydroxy anisole), bisphenol derivatives, and aryl amines such as phenyl-α-naphthyl amine, phenyl-β-naphthyl amine, condensation product of phenetidine and acetone, or benzophenone compounds.

The effective amount of the compound represented by Formula (1) of the invention is typically 0.5 to 20% by weight in a dust formulation, 5 to 50% by weight in an emulsion, 10 to 90% by weight in a water-dispersible powder, 0.1 to 20% by weight in a granule, and 10 to 90% by weight in a flowable formulation. Meanwhile, the amount of carrier in the respective formulations is typically 60 to 99% by weight in a dust formulation, 40 to 95% by weight in an emulsion, 10 to 90% by weight in a water-dispersible powder, 80 to 99% by weight in a granule, and 10 to 90% by weight in a flowable formulation. The amount of such auxiliary agent is typically 0.1 to 20% by weight in a dust formulation, 1 to 20% by weight in an emulsion, 0.1 to 20% by weight in a water-dispersible powder, 0.1 to 20% by weight in a granule, and 0.1 to 20% by weight in a flowable formulation.

In order to control various pests, an amount effective for blight control can be applied, just as it is, or as an adequate dilution with water, or as a suspension, to the crops expected of the appearance of the corresponding pests or to the places where such occurrence is not preferable. The amount of use depends on various factors such as, for example, the purpose, the pest to be controlled, the state of plant growth, trend of pest appearance, climate, environmental conditions, formulation, method of use, place of use, timing of use and the like, but it is preferable to use the active ingredient in the concentration of 0.0001 to 5000 ppm, and preferably 0.01 to 1000 ppm. The dose that can be used in approximately 10 a is generally in the range of 1 to 300 g of the active ingredient.

The insecticide of the invention containing the compound represented by Formula (1) as an active ingredient may be used alone in control of various pests in agricultural, horticultural and stored grain products, which damage the rice plants, fruit trees, vegetables, other crops and flowers, or sanitary pests or eelworms, and further in order to obtain superior control effect with respect to various pests which occur at the same time, it may be used in combination with at least one other insecticide and/or fungicide.

Examples of other insecticides which can be combined with the compound represented by Formula (1) of the invention may include, for example, pyrethroid insecticides such as allethrin, tetramethrin, resmethrin, phenothrin, furamethrin, permethrin, cypermethrin, deltamethrin, cyhalothrin, cyfluthrin, fenpropathrin, tralomethrin, cyclopropthrin, flucythrinate, fluvalinate, acrinathrin, tefluthrin, bifenthrin, empenthrin, beta-cyfluthrin, zeta-cypermethrin, fenvalerate and the like, and various isomers thereof; or Dalmatian pyrethrum extract; organophosphate insecticides such as DDVP, cyanophos, fenthion, fenitrothion, tetrachlorvinphos, dimethylvinphos, propaphos, methylparathion, temephos, phoxim, acephate, isofenphos, salithion, DEP, EPN, ethion, mecarbam, pyridafenthion, diazinon, pirimiphos-methyl, etrimfos, isoxathion, quinalphos, chlorpyrifos-methyl, chlorpyrifos, phosalone, phosmet, methidathion, oxydeprofos, vamidothion, malathion, phenthoate, dimethoate, formothion, thiometon, disulfoton, phorate, terbufos, profenofos, prothiofos, sulprofos, pyraclofos, monocrotofos, naled, fosthiazate, cadusafos; carbamate insecticides such as NAC, MTMC, MIPC, BPMC, XMC, PHC, MPMC, ethiofencarb, bendiocarb, pirimicarb, carbosulfan, benfuracarb, methomyl, oxamyl, aldicarb; arylpropylether insecticides such as etofenprox, halfenprox; silylether compounds such as silafluofen; insecticidal natural products such as nicotine-sulfate, polynactins, abamectin, milbemectin, BT; insecticides such as cartap, thiocyclam, bensultap, diflubenzuron, chlorfluazuron, teflubenzuron, triflumuron, flufenoxuron, flucycloxuron, hexaflumuron, fluazuron, imidacloprid, nitenpyram, acetamiprid, dinotefuran, pymetrozine, fipronil, buprofezin, fenoxycarb, pyriproxyfen, methoprene, hydroprene, kinoprene, endosulfan, diafenthiuron, triazamate, tebufenozide, benzoepin; acaricides such as dicofol, chlorobenzilate, phenisobromolate, tetradifon, CPCBS, BPPS, chinomethionate, amitraz, benzomate, hexythiazox, fenbutatin oxide, cyhexatin, dienochlor, clofentezine, pyridaben, fenpyroximate, fenazaquin, tebufenpyrad; novaluron, noviflumuron, emamectin benzoate, clothianidin, thiacloprid, thiamethoxam, flupyrazofos, acequinocyl, bifenazate, chromafenozide, etoxazole, fluacrypyrim, flufenzine, halofenozide, indoxacarb, methoxyfenozide, spirodiclofen, tolfenpyrad, gamma-cyhalothrin, ethiprole, amidoflumet, bistrifluron, flonicamid, flubrocythrinate, flufenerim, pyridalyl, pyrimidifen, spinosad, or spiromesifen.

Examples of the fungicides which can be combined with the compound represented by Formula (1) of the invention may include, for example, azole fungicides such as triadimefon, hexaconazole, propiconazole, ipconazole, prochloraz, triflumizole; pyrimidine fungicides such as pyrifenox, fenarimol; anilinopyrimidine fungicides such as mepanipyrim, cyprodinil; acylalanine fungicides such as metalaxyl, oxadixyl, benalaxyl; benzimidazole fungicides such as thiophanate-methyl, benomyl; dithiocarbamate fungicides such as mancozeb, propineb, zineb, metiram; organochlorine fungicides such as tetrachloroisophthalonitrile; carboxamide fungicides such as carpropamid, ethaboxam; morpholine fungicides such as dimethomorph; strobilurin fungicides such as azoxystrobin, kresoxim-methyl, metominostrobin, orysastrobin, fluoxastrobin, trifloxystrobin, dimoxystrobin, pyraclostrobin, picoxystrobin; dicarboximide fungicides such as iprodione, procymidone; soil-applied fungicides such as flusulfamide, dazomet, methyl isothiocyanate, chloropicrin; copper fungicides such as basic copper chloride, basic copper sulfate, copper nonylphenol sulfonate, oxine-copper; inorganic fungicides such as sulfur, zinc sulfate; organophosphate fungicides such as edifenphos, tolclofos-methyl, fosetyl; melanin biosynthesis inhibitors such as phthalide, tricyclazole, pyroquilon, diclocymet; antibiotics such as kasugamycin, validamycin, polyoxins; fungicidal natural products such as rape seed oil; fungicides such as benthiavalicarb-isopropyl, iprovalicarb, cyflufenamid, fenhexamid, quinoxyfen, spiroxamine, diflumetorim, metrafenone, picobenzamid, proquinazid, silthiofam, oxpoconazole, famoxadone, cyazofamid, fenamidone, furametpyr, zoxamide, boscalid, tiadinil, simeconazole, chlorothalonil, cymoxanil, captan, dithianon, fluazinam, folpet, dichlofluanid, (RS)—N-[2-(1,3-dimethylbutyl)thiophen-3-yl]-1-methyl-3-trifluoro methyl-1H-pyrazole-4-carboxamide (penthiopyrad: ISO proposed), oxycarboxin, mepronil, flutolanil, triforine, oxolinic acid, probenazole, acibenzolar-S-methyl, isoprothiolane, ferimzone, diclomezine, pencycuron, fluoroimide, chinomethionate, iminoctadine-triacetate, iminoctadine-albesilate and the like.

When the compound represented by Formula (1) of the invention is used in combination with at least one other insecticide and/or fungicide, a mixed composition of the compound represented by Formula (1) and other insecticide and/or fungicide may be used, or the compound represented by Formula (1) and other insecticide/fungicide may be mixed and used at the time of apply.

In addition to the above-mentioned insecticides and fungicides, the compound represented by Formula (1) can be mixed with plant protecting agents such as a herbicide, a fertilizer, a soil reformer, a plant growth controlling agent and a material, in order to form multi-purpose compositions of high efficacy, which are expected to provide an additive effect or a synergistic effect.

The following Examples illustrate representative Examples of the invention, but they are not intended to limit the invention.

Example 1-1

Preparation of N-(2,6-dimethyl-4-heptafluoroisopropyl)phenyl 3-nitrobenzamide

To a solution prepared by adding 20.0 g of 2,6-dimethyl-4-heptafluoroisopropylaniline and 11.0 g of pyridine to 100 ml of tetrahydrofuran at room temperature with stirring, 13.0 g of 3-nitrobenzoyl chloride dissolved in 20 ml of tetrahydrofuran was gradually added dropwise thereto. After the reaction solution was stirred at room temperature for 10 hours, ethyl acetate and water were added thereto. Phase separation was carried out, and then the organic layer was separated and dried over anhydrous magnesium sulfate. This solution was filtered, the filtrate was collected, and the solvent was distilled off under reduced pressure. Thus obtained residue was washed with a solvent mixture of hexane-diisopropyl ether to give 26.0 g (yield 85%) of the title compound as a white solid.

$^1$H-NMR (CDCl$_3$, ppm) δ 2.33 (6H, s), 7.37 (2H, s), 7.68 (1H, s), 7.72 (1H, t, J=8.1 Hz), 8.28 (1H, d, J=8.1 Hz), 8.44 (1H, dd, J=1.2, 8.1 Hz), 8.75 (1H, t, J=1.2 Hz).

Example 1-2

Preparation of N-(2,6-dimethyl-4-heptafluoroisopropyl)phenyl 3-aminobenzamide (Compound No. I-2)

To a solution prepared by adding 0.90 g of N-(2,6-dimethyl-4-heptafluoroisopropyl)phenyl 3-nitrobenzamide and 1.56 g of anhydrous tin(II) chloride to 25 ml of ethanol at room temperature with stirring, 2 ml of concentrated hydrochloric acid was added and the mixture was stirred at 60° C. for one hour. After brought back to room temperature, the reaction solution was poured onto water, and neutralization was carried out using potassium carbonate. Ethyl acetate was added, the insolubles were filtered off, and then the organic layer was separated and dried over anhydrous magnesium sulfate. This solution was filtered, the filtrate was collected, and the solvent was distilled off under reduced pressure. Thus obtained residue was washed with hexane to give 0.44 g (yield 53%) of the title compound as a white solid.

$^1$H-NMR (CDCl$_3$, ppm) δ 2.34 (6H, s), 3.87 (2H, broad), 6.86-6.89 (1H, m), 7.20-7.35 (6H, m)

Example 1-3

Preparation of N-(2,6-dimethyl-4-heptafluoroisopropyl)phenyl 3-(benzoylamino)benzamide (Compound No. 10)

To a solution prepared by adding 0.25 g of N-(2,6-dimethyl-4-heptafluoroisopropyl)phenyl 3-aminobenzamide and 0.06 g of pyridine to 5 ml of tetrahydrofuran at room temperature with stirring, 0.09 g of benzoyl chloride dissolved in 1 ml of tetrahydrofuran was added dropwise. After stirring at room temperature for 1 hour, ethyl acetate and 1N hydrochloric acid were added to the reaction solution, and the organic layer was separated. The organic layer was washed once with saturated aqueous sodium hydrogen carbonate solution and dried over anhydrous magnesium sulfate. This solution was filtered, the filtrate was collected, and the solvent was distilled off under reduced pressure. Thus obtained solid was washed with diisopropyl ether to give 0.29 g (yield 92%) of the title compound as a white solid.

$^1$H-NMR (DMSO-d$_6$, ppm) δ 2.37 (6H, s), 7.34 (2H, s), 7.46-7.57 (4H, m), 7.75 (1H, d, J=7.8 Hz), 7.98-8.01 (2H, m), 8.12 (1H, d, J=7.3 Hz), 8.34 (1H, s), 8.87 (1H, s), 9.66 (1H, s).

Example 2-1

Preparation of N-(2,6-dimethyl-4-heptafluoroisopropyl)phenyl-N-methyl 3-nitrobenzamide To a suspension of 0.18 g of 60% sodium hydride in 15 ml of tetrahydrofuran, 2.0 g of N-(2,6-dimethyl-4-heptafluoroisopropyl)phenyl 3-nitrobenzamide dissolved in 5 ml of tetrahydrofuran was added dropwise at room temperature. After the mixture was stirred at room temperature for 30 minutes, 0.65 g of methyl iodide dissolved in 5 ml of tetrahydrofuran was added dropwise. Then, after raising temperature to 50° C. and stirred for 4 hours, the reaction solution was returned to room temperature, and ethyl acetate and water were added. The organic layer was separated, washed once with water and dried over anhydrous magnesium sulfate, and the solvent was distilled off under reduced pressure. Thus obtained residue was purified by silica gel column chromatography (eluent: hexane:ethyl acetate=6:1) to give 1.73 g (yield 84%) of the title compound as a white solid.

$^1$H-NMR (CDCl$_3$, ppm) δ 2.31 (6H, s), 3.38 (3H, s), 7.27 (2H, s), 7.37 (1H, t, J=7.8 Hz), 7.62-7.65 (1H, m), 8.05 (1H, t, J=2.0 Hz), 8.11-8.14 (1H, m).

Example 2-2

Preparation of N-(2,6-dimethyl-4-heptafluoroisopropyl)phenyl-N-methyl 3-aminobenzamide (Compound No. I-5)

A solution prepared by adding 1.50 g of N-(2,6-dimethyl-4-heptafluoroisopropyl)phenyl-N-methyl 3-nitrobenzamide and 0.15 g of 10% palladium-carbon to 20 ml of methanol, was stirred under a hydrogen atmosphere at atmospheric pressure for 2 hours. After the catalyst was filtered off, the solvent was distilled off under reduced pressure. Then, thus obtained solid was washed with hexane to give 1.24 g of the title compound (yield 88%) as a white solid.

$^1$H-NMR (CDCl$_3$, ppm) δ 2.27 (6H, s), 3.31 (3H, s), 3.80 (2H, broad), 6.40-6.43 (1H, m), 6.54-6.58 (1H, m), 6.71 (1H, t, J=2.0 Hz), 6.76-6.86 (1H, m), 7.22 (2H, s).

Example 2-3

Preparation of N-(2,6-dimethyl-4-heptafluoroisopropyl)phenyl-N-methyl 3-(benzoylamino)benzamide (Compound No. 1478)

The title compound was prepared as a white solid according to the conditions described in Example 1-3.

$^1$H-NMR (DMSO-d$_6$, ppm) δ 2.29 (6H, s), 3.24 (3H, s), 6.84 (1H, d, J=7.8 Hz), 7.12 (1H, t, J=7.8 Hz), 7.33 (2H, s), 7.50-7.64 (4H, m), 7.85-7.88 (2H, m), 7.98-8.03 (1H, m), 10.22 (1H, s).

Example 3

Preparation of N-(2,6-dimethyl-4-heptafluoroisopropyl)phenyl 3-[(2-chloropyridin-3-yl)carbonylamino]benzamide (Compound No. 106)

To a solution prepared by adding 0.6 g of N-(2,6-dimethyl-4-heptafluoroisopropyl)phenyl 3-aminobenzamide and 0.4 g of pyridine to 10 ml of tetrahydrofuran, 0.35 g of 2-chloronicotinoyl chloride hydrochloride was added and the mixture was stirred at room temperature for 4 hours. Ethyl acetate was added, the mixture was twice washed with saturated sodium hydrogen carbonate solution, and the solvent was distilled off under reduced pressure. Thus obtained solid was washed with a solvent mixture of hexane-diisopropyl ether and dried to give 0.64 g (yield 75%) of the title compound as a white solid.

$^1$H-NMR (DMSO-d$_6$, ppm) δ 2.30 (6H, s), 7.45 (2H, s), 7.54-7.60 (2H, m), 7.77-7.80 (1H, m), 7.95 (1H, d, J=7.8 Hz), 8.10-8.12 (1H, m), 8.30 (1H, s), 8.54-8.59 (1H, m), 10.03 (1H, s), 10.88 (1H, s).

Example 4

Preparation of N-(2,6-dimethyl-4-heptafluoroisopropyl)phenyl 3-[(pyridin-3-yl)carbonylamino]benzamide (Compound No. 101)

A solution prepared by adding 99 mg of nicotinic acid and 153 mg of 1,1'-oxalyl diimidazole to 10 ml of acetonitrile was stirred at room temperature for 15 minutes and again at 40° C. for 40 minutes. After returning back to room temperature, 300 mg of N-(2,6-dimethyl-4-heptafluoroisopropyl)phenyl 3-aminobenzamide was added, and the mixture was stirred at 60° C. for 5 hours. Then, the solvent was distilled off under reduced pressure, and to the residue obtained therefrom, ethyl acetate was added. The organic layer was twice washed with saturated sodium hydrogen carbonate solution, and the solvent was again distilled off under reduced pressure. Thus obtained residue was purified by silica gel column chromatography (eluent: hexane:ethyl acetate=1:3) to give 70 mg (yield 18%) of the title compound as a white solid.

$^1$H-NMR (DMSO-d$_6$, ppm) δ 2.30 (6H, s), 7.45 (2H, s), 7.54-7.61 (2H, m), 7.78 (1H, d, J=8.3 Hz), 8.06 (1H, d, J=7.3 Hz), 8.32-8.35 (2H, m), 8.77-8.79 (1H, m), 9.15 (1H, d, J=1.5 Hz), 10.00 (1H, s), 10.66 (1H, s).

Example 5-1

Preparation of N-methyl-2-bromo-4-heptafluoroisopropyl-6-methylaniline

To a solution prepared by adding 1.0 g of N-methyl-4-heptafluoroisopropyl-2-methylaniline to 5 ml of N,N-dimethyl formamide, 0.8 g of N-bromosuccinimide dissolved in 3 ml of N,N-dimethyl formamide was added dropwise. After the mixture was stirred at room temperature for 5 hours, ethyl acetate and water were added, and the organic layer was separated. The organic layer was twice washed with water and dried over anhydrous magnesium sulfate, and the solvent was distilled off under reduced pressure. Thus obtained residue was purified by silica gel column chromatography (eluent: hexane:ethyl acetate=9:1) to give 0.86 g (yield 68%) of the title compound as a red oil.

$^1$H-NMR (CDCl$_3$, ppm) δ 2.41 (3H, s), 2.93 (3H, s), 3.90 (1H, broad), 7.23 (1H, s), 7.54 (1H, s).

Example 5-2

Preparation of N-(2-bromo-4-heptafluoroisopropyl-6-methyl)phenyl-N-methyl 3-(benzoylamino)benzamide (Compound No. 1479)

The title compound was prepared as a white solid from N-methyl-2-bromo-4-heptafluoroisopropyl-6-methylaniline according to the conditions described in Examples 1-2 and 1-3.
$^1$H-NMR (DMSO-d$_6$, ppm) δ 2.41 (3H, s), 3.25 (3H, s), 6.95 (1H, dd, J=1.5, 7.8 Hz), 7.16 (1H, t, J=7.8 Hz), 7.50-7.64 (4H, m), 7.68 (1H, s), 7.86-7.88 (2H, m), 7.93 (1H, t, J=1.5 Hz), 7.98-8.00 (1H, m), 10.24 (1H, s).

Example 6

Preparation of N-(2,6-dimethyl-4-heptafluoroisopropyl)phenyl-N-methyl 3-(N-methylbenzoylamino)benzamide (Compound No. 1487)

To a suspension of 40 mg of 60% sodium hydride in 10 ml of tetrahydrofuran, 0.3 g of N-(2,6-dimethyl-4-heptafluoroisopropyl)phenyl-N-methyl 3-(benzoylamino)benzamide dissolved in 5 ml of tetrahydrofuran was added dropwise at room temperature. After the mixture was stirred at room temperature for 1 hour, 0.16 g of methyl iodide dissolved in 5 ml of tetrahydrofuran was added dropwise. Then, after returning to a temperature to 50° C. and stirred for 4 hours, the reaction solution was returned to room temperature, and ethyl acetate and water were added to the reaction solution. The organic layer was separated, washed once with water and dried over anhydrous magnesium sulfate, and the solvent was distilled off under reduced pressure. Thus obtained residue was washed with diisopropyl ether to give 1.73 g (yield 84%) of the title compound as a white solid.
$^1$H-NMR (DMSO-d$_6$, ppm) δ 2.20 (6H, s), 3.08 (3H, s), 3.20 (3H, s), 6.93-7.39 (10H, m), 7.45-7.51 (1H, m).

Example 7-1

Preparation of N-(2,6-dimethyl-4-heptafluoroisopropyl)phenyl 3-aminobenzthioamide 0.35 g of N-(2,6-dimethyl-4-heptafluoroisopropyl)phenyl 3-aminobenzamide and 0.19 g of Lawesson's reagent was added to 10 ml of toluene, and the mixture was heated with stirring at reflux temperature for 6 hours. The reaction solution was concentrated under reduced pressure, the solvent was distilled off, and thus obtained residue was purified by silica gel column chromatography (eluent: hexane:ethyl acetate=3:1) to give 0.07 g (yield 20%) of the title compound.
$^1$H-NMR (CDCl$_3$, ppm) δ 2.36 (6H, s), 3.87 (2H, broad-s), 6.84-6.87 (1H, m), 7.18-7.24 (2H, m), 7.33 (1H, s), 7.39 (2H, s), 8.56 (1H, broad-s).

Example 7-2

Preparation of N-(2,6-dimethyl-4-heptafluoroisopropyl)phenyl 3-(benzoylamino)benzthioamide (Compound No. 2201)

The title compound was prepared from N-(2,6-dimethyl-4-heptafluoroisopropyl)phenyl 3-aminobenzthioamide according to the conditions described in Example 1-3.
$^1$H-NMR (CDCl$_3$, ppm) δ 2.38 (6H, s), 7.25-8.00 (11H, m), 8.34 (1H, s), 8.85 (1H, broad.).

Example 8

Preparation of N-(2,6-dimethyl-4-heptafluoroisopropyl)phenyl 3-(phenylthiocarbonylamino)benzamide (Compound No. 2202) and N-(2,6-dimethyl-4-heptafluoroisopropyl)phenyl 3-(phenylthiocarbonylamino)benzthioamide (Compound No. 2203)

A solution of 0.37 g of N-(2,6-dimethyl-4-heptafluoroisopropyl)phenyl 3-(benzoylamino)benzamide and 0.30 g of Lawesson's reagent in 10 ml of toluene was stirred at 70° C. for 6 hours. The reaction solution was concentrated under reduced pressure, and thus obtained residue was purified by silica gel column chromatography (eluent: hexane:ethyl acetate=3:1) to give 0.18 g (yield 47%) of N-(2,6-dimethyl-4-heptafluoroisopropyl)phenyl 3-(phenylthiocarbonylamino)benzamide and 0.05 g (yield 13%) of N-(2,6-dimethyl-4-heptafluoroisopropyl)phenyl 3-(phenylthiocarbonylamino)benzthioamide.
Characterization of Compound No. 2202
$^1$H-NMR (CDCl$_3$, ppm) δ 2.36 (6H, s), 7.37 (2H, s), 7.47-7.61 (5H, m), 7.85-8.03 (4H, m), 8.57 (1H, s), 9.18 (1H, s).
Characterization of Compound No. 2203
$^1$H-NMR (CDCl$_3$, ppm) δ 2.38 (6H, s), 7.41 (2H, s), 7.45-7.55 (4H, m), 7.90-7.96 (4H, m), 8.57 (1H, broad), 8.74 (1H, broad), 9.18 (1H, broad).

Example 9-1

Preparation of N-benzyl-N-(2,6-dimethyl-4-heptrafluoroisopropyl)phenyl 3-nitrobenzamide The title compound was prepared from N-(2,6-dimethyl-4-heptafluoroisopropyl)phenyl 3-nitrobenzamide and benzyl bromide according to the process described in Example 6.

Example 9-2

Preparation of N-benzyl-N-(2,6-dimethyl-4-heptafluoroisopropyl)phenyl 3-(2-fluorobenzoylamino)benzamide The title compound was prepared from N-benzyl-N-(2,6-dimethyl-4-heptafluoroisopropyl)phenyl 3-nitrobenzamide and 2-fluorobenzoyl chloride according to the processes described in Examples 1-2 and 1-3.

Example 9-3

Preparation of N-benzyl-N-(2,6-dimethyl-4-heptafluoroisopropyl)phenyl 3-[N-ethyl-N-(2-fluorobenzoyl)amino]benzamide The title compound was prepared from N-benzyl-N-(2,6-dimethyl-4-heptafluoroisopropyl)phenyl 3-(2-fluorobenzoylamino)benzamide and ethyl iodide according to the process described in Example 6.

Example 9-4

Preparation of N-(2,6-dimethyl-4-heptafluoroisopropyl)phenyl 3-[N-ethyl-N-(2-fluorobenzoyl)amino]benzamide (Compound No. 1206)

A solution of 1.07 g of N-benzyl-N-(2,6-dimethyl-4-heptafluoroisopropyl)phenyl 3-[N-ethyl-N-(2-fluorobenzoyl)amino]benzamide and 0.15 g of 10% palladium-carbon in 10 ml of methanol was stirred at 45° C. for 6 hours under a hydrogen atmosphere. The catalyst was filtered off, and the solvent was distilled off under reduced pressure. Then, thus obtained residue was purified by silica gel (Fuji Silysia Chemical Ltd., NH silica) column chromatography (eluent: hexane:ethyl acetate=1:1) to give 0.30 g (yield 32%) of the title compound as a white solid.

$^1$H-NMR (DMSO-d$_6$, ppm) δ 1.17 (3H, broad), 2.22 (6H, s), 3.99 (2H, broad), 7.01-7.08 (2H, m), 7.29-7.43 (6H, m), 7.72-7.77 (2H, m), 9.90 (1H, s).

Example 10-1

Preparation of N-(2,6-dimethyl-4-heptafluoroisopropyl)phenyl 2-fluoro-3-nitrobenzamide 2.35 g of N-(2,6-dimethyl-4-heptafluoroisopropyl)phenyl 2-chloro-3-nitrobenzamide prepared according to the process described in Example 1-1 and 0.87 g of potassium fluoride (spray-dried product) were added to 25 ml of N,N-dimethyl formamide dried by molecular sieves, and the mixture was heated with stirring at 150° C. for 3 hours. After the reaction solution was brought back to room temperature, ethyl acetate and water were added thereto, and phase separation was carried out. The organic layer was separated, washed twice with water and dried over anhydrous magnesium sulfate. This solution was filtered, the filtrate was collected, and the solvent was distilled off under reduced pressure. Thus obtained residue was purified by silica gel chromatography (eluent: hexane:ethyl acetate=4:1) to give 1.02 g (yield 45%) of the title compound as a solid.

$^1$H-NMR (CDCl$_3$, ppm) δ 2.37 (6H, s), 7.39 (2H, s), 7.48-7.53 (1H, m), 7.87 (1H, d, J=11.5 Hz), 8.23-8.28 (1H, m), 8.42-8.46 (1H, m).

Example 10-2

Preparation of N-(2,6-dimethyl-4-heptafluoroisopropyl)phenyl 3-(benzoylamino)-2-fluorobenzamide (Compound No. 601)

The title compound was prepared according to the processes described in Examples 1-2 and 1-3.

$^1$H-NMR (DMSO-d$_6$, ppm) δ 2.34 (6H, s), 7.37 (1H, t, J=7.8 Hz), 7.45 (2H, s), 7.53-7.65 (4H, m), 7.77-7.82 (1H, m), 8.00-8.02 (2H, m), 10.10 (1H, s), 10.29 (1H, s).

Example 11-1

Preparation of N-(2,6-dimethyl-4-heptafluoroisopropyl)phenyl 4-fluoro-3-nitrobenzamide 5.22 g of 4-fluoro-3-nitrobenzoic acid and 0.1 g of N,N-dimethyl formamide were introduced to 30 ml of toluene, and 3.7 g of thionyl chloride was added. The reaction mixture was stirred at 80° C. for 1 hour and again for 2 hours under reflux conditions. After cooling to room temperature, the solvent was distilled off under reduced pressure, thus obtained residue was dissolved in 10 ml of tetrahydrofuran, and this solution was added dropwise to a mixed solution of 8.1 g of 2,6-dimethyl-4-heptafluoroisopropylaniline, 4.4 g of pyridine and 20 ml of tetrahydrofuran. After the mixture was stirred for 2 hours, ethyl acetate was introduced, and the organic layer was washed with water and saturated sodium hydrogen carbonate solution sequentially. The organic layer was dried over anhydrous magnesium sulfate, the solvent was distilled off under reduced pressure, and thus obtained residue was purified by silica gel column chromatography (eluent: hexane:ethyl acetate=4:1) to give 5.9 g (yield 46%) of the title compound as a white solid.

$^1$H-NMR (CDCl$_3$, ppm) δ 2.11 (6H, s), 7.26-7.31 (3H, m), 8.12-8.15 (1H, m), 8.60-8.62 (1H, m), 8.70 (1H, s).

Example 11-2

Preparation of N-(2,6-dimethyl-4-heptafluoroisopropyl)phenyl 3-amino-4-fluorobenzamide The title compound was prepared according to the conditions described in Example 1-2. The compound was obtained as a white solid.

$^1$H-NMR (DMSO-d$_6$, ppm) δ 2.26 (6H, s), 5.42 (2H, broad-s), 7.10-7.19 (2H, m), 7.37 (1H, dd, J=2.0, 8.8 Hz), 7.42 (2H, s), 9.78 (1H, s).

Example 11-3

Preparation of N-(2,6-dimethyl-4-heptafluoroisopropyl)phenyl 4-fluoro-3-(methylamino)benzamide 18 ml of 98% sulfuric acid was cooled to a temperature of 0° C. to 5° C. and stirred, and 2.50 g of N-(2,6-dimethyl-4-heptafluoroisopropyl)phenyl 3-amino-4-fluorobenzamide was added thereto. After the reaction mixture was stirred for 15 minutes, 18 ml of an aqueous solution of 37% formaldehyde was added dropwise, and the mixture was stirred at 0° C. for 1 hour and for further 3 hours at room temperature. To the reaction solution cooled again to 0° C., 28% ammonia solution in water was added to neutralize the solution, ethyl acetate was added, and the organic layer was separated. The organic layer was dried over anhydrous magnesium sulfate, the solvent was distilled off under reduced pressure, and thus obtained residue was purified by silica gel column chromatography (eluent: hexane:ethyl acetate=4:1) to give 1.74 g (yield 67%) of the title compound in an amorphous form.

$^1$H-NMR (CDCl$_3$, ppm) δ 2.32 (6H, s), 2.94 (3H, d, J=4.9 Hz), 4.14 (1H, broad), 7.03 (1H, dd, J=8.3, 11.2 Hz), 7.10-7.13 (1H, m), 7.24 (1H, s), 7.34 (2H, s), 7.42 (1H, s).

The following compounds were prepared according to the process described in Example 11-3:

N-(2,6-dimethyl-4-heptafluoroisopropyl)phenyl 2-fluoro-3-(methylamino)benzamide $^1$H-NMR (DMSO-d$_6$) δ 2.32 (6H, s), 2.76 (3H, d, J=4.9 Hz), 5.84 (1H, broad), 6.77-6.81 (2H, m), 7.10 (1H, t, J=7.8 Hz), 7.43 (2H, s), 9.90 (1H, s).

N-[2,6-dimethyl-4-(nonafluoro-2-butyl)]phenyl 2-fluoro-3-(methylamino)benzamide $^1$H-NMR (DMSO-d$_6$) δ 2.32 (6H, s), 2.77 (3H, d, J=4.9 Hz), 5.82 (1H, broad), 6.79 (1H, t, J=7.8 Hz), 7.08-7.21 (2H, m), 7.42 (2H, s), 9.88 (1H, s).

N-(2,6-dimethyl-4-heptafluoroisopropyl)phenyl-N-methyl 2-fluoro-3-(methylamino)benzamide $^1$H-NMR (DMSO-d$_6$) δ 2.33 (6H, s), 2.76 (3H, d, J=4.9 Hz), 4.55 (3H, s), 6.58-6.62 (1H, m), 6.70-6.78 (1H, m), 7.13 (1H, t, J=7.8 Hz), 7.31 (1H, s), 7.50 (2H, s).

Example 11-4

Preparation of N-(2,6-dimethyl-4-heptafluoroisopropyl)phenyl 4-fluoro-3-[N-methyl-N-(4-nitrobenzoyl)amino]benzamide (Compound No. 1464)

The title compound was obtained as a white solid using 4-nitrobenzoyl chloride according to the conditions described in Example 1-3.

$^1$H-NMR (DMSO-$d_6$, ppm) δ 2.23 (6H, s), 3.42 (3H, s), 7.41 (1H, broad), 7.45 (2H, s), 7.60 (2H, broad), 7.90 (1H, broad), 8.08-8.13 (3H, broad), 9.93 (1H, s).

Example 12-1

Preparation of N-(2,6-dimethyl-4-heptafluoroisopropyl)phenyl 6-chloropyridine-2-carboxamide A mixture of 2.2 g of 6-chloropyridine-2-carboxylic acid and 0.1 g of N,N-dimethyl formamide was introduced to 10 ml of toluene, and then 2.0 g of thionyl chloride was added thereto. After stirred at 80° C. for 1 hour, the reaction mixture was stirred for another 2 hours under reflux conditions. The mixture was cooled to room temperature, the solvent was distilled off under reduced pressure, and thus obtained residue was added dropwise to a mixed solution of 3.67 g of 2,6-dimethyl-4-heptafluoroisopropylaniline, 1.22 g of pyridine and 20 ml of tetrahydrofuran. After the mixture was stirred at room temperature for 2 hours, ethyl acetate was added thereto, and the organic layer was washed with water and saturated aqueous sodium hydrogen carbonate solution sequentially. The organic layer was dried over anhydrous magnesium sulfate, the solvent was distilled off under reduced pressure, and thus obtained residue was washed with cooled hexane at 5° C. to give 4.42 g (yield 77%) of the title compound as a white solid.

$^1$H-NMR (CDCl$_3$, ppm) δ 2.36 (6H, s), 7.36 (2H, s), 7.56 (1H, dd, J=1.0, 8.1 Hz), 7.88 (1H, dd, J=7.6, 8.1 Hz), 8.23 (1H, dd, J=1.0, 7.6 Hz), 9.27 (1H, broad-s).

Example 12-2

Preparation of N-(2,6-dimethyl-4-heptafluoroisopropyl)phenyl 6-aminopyridin-2-carboxamide A mixture of 3.08 g of N-(2,6-dimethyl-4-heptafluoroisopropyl)phenyl 6-chloropyridin-2-carboxamide, 30 ml of 28% ammonia solution in water, 0.20 g of copper sulfate and 70 ml of methanol was introduced into a 200 ml autoclave and was heated with stirring at 150° C. for 2 hours. After the mixture was cooled to room temperature, ammonia was distilled off at 60° C. and atmospheric pressure, and methanol was distilled off under reduced pressure. Ethyl acetate and water were added to the reaction solution, phase separation was carried out, and the organic layer was separated and dried over anhydrous sodium sulfate. This solution was filtered, the filtrate was collected, and the solvent was distilled under reduced pressure. Thus obtained residue was purified by silica gel column chromatography (eluent: hexane:ethyl acetate=3:2 to 2:3) to give 2.90 g (yield 98%) of the title compound as an oil.

$^1$H-NMR (CDCl$_3$, ppm) δ 2.35 (6H, s), 4.57 (2H, broad-s), 6.69-6.74 (1H, m), 7.34 (2H, s), 7.62-7.66 (2H, m), 9.39 (1H, broad-s).

Example 12-3

Preparation of N-(2,6-dimethyl-4-heptafluoroisopropyl)phenyl 6-(benzoylamino)pyridin-2-carboxamide (Compound No. 2001)

A mixture of 0.16 g of N-(2,6-dimethyl-4-heptafluoroisopropyl)phenyl 6-aminopyridin-2-carboxamide and 62 mg of pyridine was introduced to 3 ml of tetrahydrofuran, 63 mg of benzoyl chloride was added, and the mixture was stirred at room temperature for 3 hours. Ethyl acetate was introduced, and the organic layer was washed with water and then with saturated aqueous sodium hydrogen carbonate solution. The organic layer was dried over anhydrous magnesium sulfate, and the solvent was distilled off under reduced pressure, and thus obtained residue was purified by silica gel column chromatography (eluent: hexane:ethyl acetate=6:4) to give 0.13 g (yield 65%) of the title compound as a white solid.

$^1$H-NMR (CDCl$_3$, ppm) δ 2.36 (6H, s), 7.36 (2H, s), 7.53-7.57 (2H, m), 7.61-7.65 (1H, m), 7.95-8.03 (3H, m), 8.08 (1H, dd, J=1.0, 7.3 Hz), 8.52 (1H, broad-s), 8.62 (1H, dd, J=1.0, 8.3 Hz), 9.19 (1H, broad-s).

Example 12-4

Preparation of N-(2,6-dimethyl-4-heptafluoroisopropyl)phenyl 6-(benzoylamino)-1-oxopyridin-2-carboxamide (Compound No. 2164)

A mixture of 65 mg of N-(2,6-dimethyl-4-heptafluoroisopropyl)phenyl 6-(benzoylamino)pyridin-2-carboxamide and 0.11 g of m-chloroperbenzoic acid was introduced to 5 ml of benzene, and the mixture was stirred at 80° C. for 4 hours. The mixture was cooled to room temperature, and the organic layer was washed with water and saturated aqueous sodium hydrogen carbonate solution sequentially and dried over anhydrous magnesium sulfate. The solvent was distilled off under reduced pressure, and thus obtained residue was purified by silica gel column chromatography (eluent: hexane:ethyl acetate=4:1) to give 52 mg (yield 52%) of the title compound as a white solid.

$^1$H-NMR (CDCl$_3$, ppm) δ 2.34 (6H, s), 7.47 (2H, s), 7.62-7.65 (2H, m), 7.70-7.81 (2H, m), 8.00-8.04 (3H, m), 8.64 (1H, dd, J=1.5, 8.3 Hz), 10.90 (1H, broad-s), 12.30 (1H, broad-s).

Example 13-1

Preparation of 2,6-dibromo-4-heptafluoroisopropylaniline

To a solution prepared by adding 2.0 g of 4-heptafluoroisopropylaniline in 5 ml of N,N-dimethyl formamide, 2.73 g of N-bromosuccinimide dissolved in 10 ml of N,N-dimethyl formamide was introduced at 5° C. After the reaction solution was returned to room temperature and stirred for 2 hours, ethyl acetate and water were added thereto, and the organic layer was separated and washed once with water. The solvent was distilled off under reduced pressure, and thus obtained residue was purified by silica gel column chromatography (eluent: hexane:ethyl acetate=20:1) to give 2.20 g (yield 69%) of the title compound as an orange oil.

$^1$H-NMR (CDCl$_3$, ppm) δ 4.89 (2H, broad-s), 7.59 (2H, s).

Example 13-2

Preparation of
N-(2,6-dibromo-4-heptafluoroisopropyl)phenyl
3-nitrobenzamide

A mixed solution of 2.20 g of 2,6-dibromo-4-heptafluoroisopropylaniline, 1.46 g of 3-nitrobenzoyl chloride and 10 ml of pyridine was stirred at 70° C. for 20 hours. After the solution was returned to room temperature, ethyl acetate and 1N hydrochloric acid were added, and the organic layer was separated and washed with a saturated aqueous sodium hydrogen carbonate solution. The solvent was distilled off under reduced pressure, and thus obtained residue was dissolved in a solvent mixture of 8 ml of tetrahydrofuran and 2 ml of methanol. Then, the solution was cooled to 5° C., 0.30 g of sodium hydroxide was added, the solution was stirred for 2 hours, and ethyl acetate and water were added to the reaction solution. The organic layer was separated, washed with saturated brine and dried over anhydrous magnesium sulfate. The solvent was distilled off under reduced pressure, and thus obtained residue was washed with hexane to give 2.19 g (yield 73%) of the title compound as a pale brown solid.

$^1$H-NMR (DMSO-$d_6$, ppm) δ 7.92 (1H, t, J=7.8 Hz), 8.08 (2H, s), 8.45 (1H, d, J=7.8 Hz), 8.53 (1H, dd, J=1.5, 7.8 Hz), 8.85 (1H, d, J=1.5 Hz), 11.08 (1H, s).

Example 13-3

Preparation of
N-(2,6-dibromo-4-heptafluoroisopropyl)phenyl
3-aminobenzamide

The title product was obtained as a white solid according to the conditions described in Example 1-2.

$^1$H-NMR (DMSO-$d_6$, ppm) δ 5.39 (2H, broad-s), 6.77-6.80 (1H, m), 7.13-7.20 (3H, m), 8.02 (2H, s), 10.35 (1H, s).

Example 13-4

Preparation of N-(2,6-dibromo-4-heptafluoroisopropyl)phenyl 3-(2-fluorobenzoyl)aminobenzamide (Compound No. 8)

The title compound was obtained as a white solid using 2-fluorobenzoyl chloride according to the conditions described in Example 1-3.

$^1$H-NMR (DMSO-$d_6$, ppm) δ 7.33-7.40 (2H, m), 7.55-7.63 (2H, m), 7.68-7.72 (1H, m), 7.78 (1H, d, J=7.8 Hz), 7.99 (1H, d, J=7.8 Hz), 8.05 (2H, s), 8.34 (1H, s), 10.65 (1H, s), 10.69 (1H, s).

Example 14-1

Preparation of 4-(heptafluoro-n-propylthio)aniline

To 20 ml of an acetonitrile solution of 1.25 g of 4-aminothiophenol and 1.11 g of triethylamine, 5.91 g of 1-iodoheptafluoro-n-propane was added, and the mixture was stirred at room temperature for 3 hours. The mixture was diluted with ether, washed with an aqueous solution of 1N sodium hydroxide and purified by silica gel column chromatography (eluent: hexane:ethyl acetate=4:1) to give 1.85 g (yield 63%) of the title compound.

$^1$H-NMR (CDCl$_3$, ppm) δ 3.95 (2H, s), 6.66 (2H, d, J=8.8 Hz), 7.40 (2H, d, J=8.8 Hz).

Example 14-2

Preparation of
2,6-dibromo-4-(heptafluoro-n-propylthio)aniline

To a solution prepared by adding 0.77 g of 4-(heptafluoro-n-propylthio)aniline in 15 ml of N,N-dimethyl formamide, 0.98 g of N-bromosuccinimide was introduced. After the mixture was stirred at 60° C. for 2 hours, ether and water were added, and the organic layer was separated. The organic layer was twice washed with water and dried over anhydrous magnesium sulfate, and the solvent was distilled off under reduced pressure. Thus obtained residue was purified by silica gel column chromatography (eluent: hexane:ethyl acetate=9:1) to give 1.19 g (yield 100%) of the title compound as a red oil.

$^1$H-NMR (CDCl$_3$, ppm) δ 4.98 (2H, broad-s), 7.66 (2H, s).

Example 14-3

Preparation of
N-(2,6-dibromo-4-heptafluoro-n-propylthio)phenyl
3-nitrobenzamide To a solution prepared by adding 1.08 g of 2,6-dibromo-4-(heptafluoro-n-propylthio)aniline and 0.4 g of pyridine to 20 ml of tetrahydrofuran with stirring at room temperature, 0.55 g of 3-nitrobenzoyl chloride dissolved in 20 ml of tetrahydrofuran was gradually introduced dropwise. After the mixture was stirred at room temperature for 10 hours, ethyl acetate and water were added to the reaction solution. The organic layer was separated and dried over anhydrous magnesium sulfate. This solution was filtered, the filtrate was collected, and the solvent was distilled off under reduced pressure. Thus obtained residue was purified by silica gel column chromatography (eluent: hexane:ethyl acetate=4:1) to give 0.86 g (yield 48%) of the title compound as a white solid.

$^1$H-NMR (CDCl$_3$, ppm) δ 7.73 (1H, s, J=7.8 Hz), 7.77 (1H, t, J=7.8 Hz), 7.96 (2H, s), 8.31 (1H, s), 8.47-8.50 (1H, m), 8.79 (1H, t, J=2.0 Hz).

Example 14-4

Preparation of N-{2,6-dibromo-4-(heptafluoro-n-propylthio)}phenyl 3-aminobenzamide (Compound No. I-28)

To a solution prepared by adding 0.97 g of N-{2,6-dibromo-4-(heptafluoro-n-propylthio)phenyl 3-nitrobenzamide and 0.95 g of anhydrous tin(II) chloride to 20 ml of ethanol with stirring at room temperature, 2 ml of concentrated hydrochloric acid was added, and the mixture was heated with stirring at 60° C. for 1 hour. After the mixture was returned to room temperature, the reaction solution was poured onto water, and neutralization was carried out using potassium carbonate. Ethyl acetate was added, the insolubles were filtered off, and the organic layer was separated and dried over anhydrous magnesium sulfate. This solution was filtered, the filtrate was collected, and the solvent was distilled off under reduced pressure. Thus obtained residue was washed with hexane to give 0.75 g (yield 81%) of the title compound as a white solid.

$^1$H-NMR (CDCl$_3$, ppm) δ 3.89 (2H, broad-s), 6.90 (1H, dt, J=2.5, 6.4 Hz), 7.28-7.30 (3H, m), 7.60 (1H, s), 7.93 (2H, s).

Example 14-5

Preparation of N-(2,6-dibromo-4-heptafluoro-n-propylthio)phenyl 3-(benzoylamino)benzamide (Compound No. 263)

To a solution prepared by adding 0.10 g of N-(2,6-dibromo-4-heptafluoro-n-propylthio)phenyl 3-aminobenzamide and 0.02 g of pyridine to 5 ml of tetrahydrofuran with stirring at room temperature, 0.03 g of benzoyl chloride dissolved in 1 ml of tetrahydrofuran was introduced. After the mixture was stirred at room temperature for 1 hour, ethyl acetate and 1N hydrochloric acid were added, and the organic layer was separated. The organic layer was washed once with saturated aqueous sodium hydrogen carbonate solution and dried over anhydrous magnesium sulfate. This solution was filtered, the filtrate was collected, and the solvent was distilled off under reduced pressure. Thus obtained residue was purified by silica gel column chromatography (eluent: hexane:ethyl acetate=3:1) to give 0.10 g (yield 67%) of the title compound as a white solid.
$^1$H-NMR (DMSO-d$_6$, ppm) δ 7.47-7.57 (4H, m), 7.78 (1H, d, J=7.8 Hz), 7.93 (2H, s), 7.99-8.01 (2H, m), 8.18 (1H, d, J=7.8 Hz), 8.33 (1H, t, J=2.0 Hz), 9.27 (1H, s), 9.65 (1H, s).

Example 14-6

Preparation of N-(2,6-dibromo-4-heptafluoro-n-propylthio)phenyl 3-[(2-chloropyridin-3-yl)carbonylamino]benzamide (Compound No. 309)

To a solution prepared by adding 0.15 g of N-(2,6-dibromo-4-heptafluoro-n-propylthio)phenyl 3-aminobenzamide and 0.03 g of pyridine to 5 ml of tetrahydrofuran, 0.05 g of 2-chloronicotinoyl chloride hydrochloride was added, and the mixture was stirred at room temperature for 4 hours. Ethyl acetate was added, the mixture was twice washed with saturated sodium hydrogen carbonate solution, and the solvent was distilled off under reduced pressure. Thus obtained solid was purified by silica gel column chromatography (eluent: hexane:ethyl acetate=3:1) to give 0.17 g (yield 92%) of the title compound in an amorphous form.
$^1$H-NMR (CDCl$_3$, ppm) δ 7.44 (1H, dd, J=4.8, 7.8 Hz), 7.56 (1H, t, J=7.8 Hz), 7.80 (1H, d, J=7.8 Hz), 7.86 (1H, s), 7.92 (1H, d, J=7.8 Hz), 7.95 (2H, s), 8.23 (1H, dd, J=2.0, 7.8 Hz), 8.30 (1H, s), 8.41 (1H, s), 8.55 (1H, dd, J=2.0, 4.8 Hz).

Example 14-7

Preparation of N-(2,6-dibromo-4-heptafluoro-n-propylsulfinyl)phenyl 3-nitrobenzamide To a solution prepared by adding 0.5 g of N-(2,6-dibromo-4-heptafluoro-n-propylthio)phenyl 3-nitrobenzamide to 15 ml of chloroform and stirring at room temperature, 0.5 g of m-chloroperbenzoic acid was introduced. The mixture was stirred at room temperature for 2 days, and after addition of an aqueous solution of sodium sulfite, the mixture was stirred again. Phase separation was carried out, an obtained organic layer was washed with an aqueous solution of sodium hydroxide and saturated brine, and the solvent was distilled off under reduced pressure. Thus obtained solid was purified by silica gel column chromatography (eluent: hexane:ethyl acetate=4:1) to give 0.36 g (yield 70%) of the title compound as a white solid.
$^1$H-NMR (CDCl$_3$, ppm) δ 7.76-7.82 (2H, m), 8.06 (1H, s), 8.29 (1H, s), 8.33-8.35 (1H, m), 8.49-8.53 (1H, m), 8.81 (1H, s).

Example 14-8

Preparation of N-(2,6-dibromo-4-heptafluoro-n-propylsulfinyl)phenyl 3-aminobenzamide (Compound No. I-57)

The title compound was obtained using N-(2,6-dibromo-4-heptafluoro-n-propylsulfinyl)phenyl 3-nitrobenzamide according to the conditions described in Example 1-2.
$^1$H-NMR (CDCl$_3$, ppm) δ 6.90-6.94 (1H, m), 7.28-7.33 (3H, m), 7.73 (1H, s), 8.02 (1H, s), 8.25 (1H, s).

Example 14-9

Preparation of N-(2,6-dibromo-4-heptafluoro-n-propylsulfinyl)phenyl 3-(benzoylamino)benzamide (Compound No. 335)

The title compound was obtained using N-(2,6-dibromo-4-heptafluoro-n-propylsulfinyl)phenyl 3-aminobenzamide according to the conditions described in Example 1-3.
$^1$H-NMR (CDCl$_3$, ppm) δ 7.45-7.61 (4H, m), 7.77-7.79 (1H, m), 7.87-7.91 (3H, m), 8.01 (1H, s), 8.07-8.10 (1H, m), 8.15 (1H, s), 8.25 (1H, s), 8.38 (1H, s).

Example 14-10

Preparation of 2,6-dimethyl-4-(heptafluoro-n-propylthio)aniline

A mixture of 3.0 g (1.3 mmol) of 2,6-dibromo-4-heptafluoro-n-propylthioaniline, 3.0 g (21.9 mmol) of potassium carbonate, 0.75 g (0.65 mmol) of tetrakis(triphenylphosphine)palladium and 0.17 g (1.3 mmol) of trimethylboroxine was added to 20 ml of DMF, and this was stirred at 135° C. for 6 hours. The reaction solution was returned to room temperature, the insolubles were removed by celite filtration, and filtrate was concentrated under reduced pressure. Thus obtained residue was purified by silica gel column chromatography (eluent: hexane:ethyl acetate=12:1 to 4:1) to give 1.17 g (yield 55%) of the title compound as an oil.
$^1$H-NMR (CDCl$_3$, ppm) δ 2.17 (6H, s), 3.86 (2H, broad-s), 7.22 (2H, s).

Example 15

Preparation of N-(2,6-dimethyl-4-heptafluoroisopropyl)phenyl 3-(methylamino)benzamide A mixture of 20.0 g of N-(2,6-dimethyl-4-heptafluoroisopropyl)phenyl 3-aminobenzamide, 4.40 g of an aqueous solution of 37% formaldehyde, 2.0 g of 10% palladium-carbon and 200 ml of ethyl acetate was stirred under a hydrogen atmosphere at room temperature and ambient pressure. The insolubles in the reaction solution were separated by filtration, and the filtered residue was washed with ethyl acetated. The filtrate was collected, the solvent was distilled off under reduced pressure, and thus obtained residue was washed with diisopropyl ether to give 13.5 g (yield 65%) of the title compound as a white solid.

$^1$H-NMR (CDCl$_3$, ppm) δ 2.35 (6H, s), 2.91 (3H, s), 6.82 (1H, d, J=7.3 Hz), 7.18-7.52 (7H, m).

Example 16-1

Preparation of 3-(benzoylamino)benzoic Acid

To a solution of 1.37 g of 3-aminobenzoic acid and 0.4 g of sodium hydroxide in 50 ml of water, 1.41 g of benzoyl chloride and a solution containing 0.4 g of sodium hydroxide in 5 ml of water were simultaneously added dropwise, in an ice bath, and the mixture was stirred at room temperature for 6 hours. The reaction solution was adjusted to pH 1 by addition of 1N hydrochloric acid, and thus obtained solid was collected by filtration to give 1.92 g (yield 80%) of the title compound as a white solid.

$^1$H-NMR (CDCl$_3$, ppm) δ 7.40-7.56 (5H, m), 7.78 (1H, d, J=7.8 Hz), 8.00 (2H, d, J=8.3 Hz), 8.15 (1H, d, J=7.8 Hz), 8.35 (1H, t, J=2.0 Hz), 9.89 (1H, s).

Example 16-2

Preparation of 3-(benzoylamino)benzoyl Chloride

To a suspension of 1.5 g of 3-(benzoylamino)benzoic acid in 10 ml of toluene, 2 ml of thionyl chloride was added, and the mixture was stirred under reflux conditions for 2 hours. After the mixture was returned to room temperature, the solvent was distilled off under reduced pressure to give 1.53 g (yield 95%) of the title compound as a white solid.

$^1$H-NMR (CDCl$_3$, ppm) δ 7.51-7.62 (4H, m), 7.90 (2H, d, J=7.3 Hz), 7.93 (1H, s), 7.97 (1H, s), 8.15 (1H, dt, J=1.0, 5.9 Hz), 8.28 (1H, t, J=2.0 Hz).

Using readily available benzoic acids, the following compounds can be prepared according to the processes described in Examples 16-1 and 16-2:
3-[(2-fluorobenzoyl)amino]benzoyl chloride
3-[(3-fluorobenzoyl)amino]benzoyl chloride
3-[(4-fluorobenzoyl)amino]benzoyl chloride
3-[(2-chlorobenzoyl)amino]benzoyl chloride
3-[(3-chlorobenzoyl)amino]benzoyl chloride
3-[(4-chlorobenzoyl)amino]benzoyl chloride
3-[(3-cyanobenzoyl)amino]benzoyl chloride
3-[(4-cyanobenzoyl)amino]benzoyl chloride
3-[(2-methyl benzoyl)amino]benzoyl chloride
3-[(3-methyl benzoyl)amino]benzoyl chloride
3-[(4-methyl benzoyl)amino]benzoyl chloride
3-[(2-nitro benzoyl)amino]benzoyl chloride
3-[(3-nitrobenzoyl)amino]benzoyl chloride
3-[(4-nitrobenzoyl)amino]benzoyl chloride
3-[(2-trifluoromethyl benzoyl)amino]benzoyl chloride
3-[(3-trifluoromethyl benzoyl)amino]benzoyl chloride
3-[(4-trifluoromethyl benzoyl)amino]benzoyl chloride
3-[(2-trifluoromethoxy benzoyl)amino]benzoyl chloride
3-[(3-trifluoromethoxy benzoyl)amino]benzoyl chloride
3-[(4-trifluoromethoxy benzoyl)amino]benzoyl chloride
3-[(2,3-difluorobenzoyl)amino]benzoyl chloride
3-[(2,4-difluorobenzoyl)amino]benzoyl chloride
3-[(2,5-difluorobenzoyl)amino]benzoyl chloride
3-[(2,6-difluorobenzoyl)amino]benzoyl chloride
3-[(3,4-difluorobenzoyl)amino]benzoyl chloride
3-[(pyridin-3-yl)carbonylamino]benzoyl chloride
3-[(2-fluoropyridin-3-yl)carbonylamino]benzoyl chloride
3-[(2-chloropyridin-3-yl)carbonylamino]benzoyl chloride
3-[(2,4-dichlorobenzoyl)amino]benzoyl chloride
3-[(2,6-dichlorobenzoyl)amino]benzoyl chloride
3-[(3,4-dichlorobenzoyl)amino]benzoyl chloride
3-[(2-chloro-4-fluorobenzoyl)amino]benzoyl chloride
3-[(4-chloro-2-fluorobenzoyl)amino]benzoyl chloride
3-[(2-chloro-6-fluorobenzoyl)amino]benzoyl chloride
3-[(2,3,6-trifluorobenzoyl)amino]benzoyl chloride Example 16-3

Preparation of N-(2,6-dimethyl-4-heptafluoro-n-propylthio)phenyl 3-(benzoylamino)benzamide (Compound No. 260)

To a solution prepared by adding 0.1 g of 2,6-dimethyl-4-(heptafluoro-n-propylthio)aniline and 0.03 g of pyridine to 5 ml of tetrahydrofuran and stirring at room temperature, 0.09 g of 3-(benzoylamino)benzoyl chloride dissolved in 1 ml of tetrahydrofuran was introduced. After the mixture was stirred at room temperature for 1 hour, ethyl acetate and 1N hydrochloric acid were added, and the organic layer was separated. The organic layer was washed once with a saturated aqueous sodium hydrogen carbonate solution and dried over anhydrous magnesium sulfate. This solution was filtered, the filtrate was collected, and the solvent was distilled off under reduced pressure. Thus obtained residue was purified by silica gel column chromatography (eluent: hexane:ethyl acetate=3:1) to give 0.10 g (yield 53%) of the title compound as a white solid.

$^1$H-NMR (DMSO-d$_6$, ppm) δ 2.31 (6H, s), 7.41 (2H, s), 7.50-7.67 (5H, m), 7.71 (1H, d, J=7.8 Hz), 7.87-7.90 (3H, m), 8.07 (1H, s), 8.31 (1H, s).

Example 17-1

Preparation of 2,6-dimethyl-4-[1-hydroxy-2,2,2-trifluoro-1-(trifluoromethyl)ethyl]aniline At room temperature, 24.4 g of 2,6-dimethylaniline and 50.0 g of hexafluoroacetone hydrate were mixed, and 0.5 g of p-toluenesulfonic acid monohydrate was added. The reaction solution was stirred and heated to 100° C. After the loss of the starting material was confirmed through TLC, ethyl acetate and an aqueous solution of 1N sodium hydroxide were added to the reaction solution, and phase separation was carried out. The organic layer was dried over anhydrous magnesium sulfate and filtered. The filtrate was concentrated under reduced pressure, and the residue was washed by addition of hexane. The suspension was filtered, and thus obtained filtered residue was dried under reduced pressure at room temperature to give 24.3 g (yield 69%) of the title compound as a powder form.

$^1$H-NMR (CDCl$_3$, ppm) δ 2.20 (6H, s), 3.26 (1H, broad-s), 3.76 (2H, broad-s), 7.25 (2H, s).

Example 17-2

Preparation of N-[2,6-dimethyl-4-{1-hydroxy-2,2,2-trifluoro-1-(trifluoromethyl)ethyl}phenyl]3-nitrobenzamide (Compound No. I-124)

At room temperature, 5.0 g of 2,6-dimethyl-4-[1-hydroxy-2,2,2-trifluoro-1-(trifluoromethyl)ethyl]aniline, 3.9 g of 3-nitrobenzoyl chloride and 2.1 g of pyridine were introduced to 50 ml of tetrahydrofuran in a reactor, and the mixture was stirred at room temperature. After the loss of the starting material was confirmed through TLC, a saturated sodium hydrogen carbonate solution was added to the reaction solution and the solution was stirred for a while. Subsequently, ethyl acetate and water were added to the reaction solution, and phase separation was carried out. The separated organic layer was dried over anhydrous magnesium sulfate and filtered. The filtrate was concentrated under reduced pressure and dried, and thus obtained residue was grinded to give 7.5 g (yield 95%) of the title compound as a powder form.

$^1$H-NMR (DMSO-$d_6$, ppm) δ 2.26 (6H, s), 7.46 (2H, s), 7.88 (1H, t, J=7.8 Hz), 8.43-8.48 (2H, m), 8.73 (1H, s), 8.81 (1H, s), 10.27 (1H, s).

Example 17-3

Preparation of N-[2,6-dimethyl-4-{1-hydroxy-2,2,2-trifluoro-1-(trifluoromethyl)ethyl}phenyl]3-aminobenzamide (Compound No. I-204)

A solution prepared by adding 8.0 g of N-[2,6-dimethyl-4-{1-hydroxy-2,2,2-trifluoro-1-(trifluoromethyl)ethyl}phenyl]3-aminobenzamide and 0.8 g of 10% palladium-carbon to 50 ml of methanol, was stirred at room temperature under a hydrogen atmosphere. After the loss of the starting material was confirmed through TLC, the reaction solution filtered, and thus obtained filtrate was concentrated under reduced pressure. Thus obtained residue was purified by silica gel chromatography (eluent: hexane:ethyl acetate=3:1) to give 6.3 g (yield 85%) of the title compound as a powder form.

$^1$H-NMR (DMSO-$d_6$, ppm) δ 2.35 (6H, s), 4.31 (2H, broad), 6.84-6.87 (1H, m), 7.21-7.25 (1H, m), 7.29-7.31 (2H, m), 7.47-7.49 (2H, m), 7.83 (1H, s), 8.94 (1H, s).

Example 17-4

Preparation of N-[2,6-dimethyl-4-{1-hydroxy-2,2,2-trifluoro-1-(trifluoromethyl)ethyl}phenyl]3-(benzoylamino)benzamide (Compound No. I-351)

At room temperature, 6.0 g of N-[2,6-dimethyl-4-{1-hydroxy-2,2,2-trifluoro-1-(trifluoromethyl)ethyl}phenyl]3-aminobenzamide, 2.5 g of benzoyl chloride and 1.8 g of pyridine were introduced to 50 ml of tetrahydrofuran. After the loss of the starting material was confirmed through TLC, the reaction solution was filtered, and thus obtained filtrate was concentrated under reduce pressure. Thus obtained residue was purified by silica gel chromatography (eluent: hexane:ethyl acetate=3:1) to give 6.3 g (yield 85%) of the title compound as a powder form.

$^1$H-NMR (DMSO-$d_6$, ppm) δ 2.26 (6H, s), 7.44 (2H, s), 7.51-7.63 (4H, m), 7.74 (1H, d, J=7.8 Hz), 7.98-8.07 (3H, m), 8.35 (1H, s), 8.71 (1H, s), 9.90 (1H, s), 10.47 (1H, s).

Using 2-fluorobenzoyl chloride instead of benzoyl chloride, N-[2,6-dimethyl-4-{1-hydroxy-2,2,2-trifluoro-1-(trifluoromethyl)ethyl}phenyl]3-[(2-fluorobenzoyl)amino]benzamide (Compound No. I-358) was prepared according to Example 17-4.

$^1$H-NMR (DMSO-$d_6$, ppm) δ 2.34 (6H, s), 7.21 (1H, dd, J=8.2, 11.2 Hz), 7.32 (1H, t, J=7.8 Hz), 7.49-7.56 (4H, m), 7.78 (1H, d, J=7.8 Hz), 8.04-8.08 (2H, m), 8.23 (1H, s), 8.71 (1H, s), 9.08 (1H, d, J=11.2 Hz).

Example 17-5

Preparation of N-[2,6-dimethyl-4-{1-chloro-2,2,2-trifluoro-1-(trifluoromethyl)ethyl}phenyl]3-(benzoylamino)benzamide (Compound No. I-419)

At room temperature, 8.0 g of N-[2,6-dimethyl-4-{1-hydroxy-2,2,2-trifluoro-1-(trifluoromethyl)ethyl}phenyl]3-(benzoylamino)benzamide and 1.0 g of pyridine were introduced to 40 ml of thionyl chloride. Then, the temperature was elevated, and the mixture was stirred under reflux conditions. After the loss of the starting material was confirmed through TLC, the reaction solution was cooled and was concentrated under reduce pressure. Thus obtained residue was purified by silica gel chromatography (eluent: hexane:ethyl acetate=3:1) to give 6.2 g (yield 75%) of the title compound as a powder form.

$^1$H-NMR (DMSO-$d_6$, ppm) δ 2.34 (6H, s), 7.49-7.63 (6H, m), 7.76 (1H, d, J=7.8 Hz), 7.99-8.08 (3H, m), 8.37 (1H, s), 9.99 (1H, s), 10.48 (1H, s).

Example 17-6

Preparation of N-(2,6-dimethyl-4-heptafluoroisopropyl)phenyl 3-(benzoylamino)benzamide (Compound No. 10)

At room temperature, 300 mg of N-[2,6-dimethyl-4-{1-chloro-2,2,2-trifluoro-1-(trifluoromethyl)ethyl}phenyl]3-(benzoylamino)benzamide and 165 mg of potassium fluoride were introduced to 20 ml of N,N-dimethyl formamide. Then, the temperature was elevated to 120° C., and the mixture was stirred for 4 hours. The reaction solution was cooled to room temperature, ethyl acetate and water were added, and the organic layer was separated. The organic layer was dried over anhydrous magnesium sulfate and filtered, and the filtrate was concentrated under reduce pressure. Thus obtained residue was washed by addition of diisopropyl ether. The suspension was filtered, and thus obtained filtered residue was dried under reduced pressure at room temperature to give 250 mg (yield 85%) of the title compound as a powder form.

The characterization is described in Example 1-3.

Example 17-7

N-[2,6-dimethyl-4-{1-hydroxy-2,2,2-trifluoro-1-(trifluoromethyl)ethyl}phenyl]3-(benzoylamino)benzamide (Compound No. I-351)

At room temperature, 2.0 g of 2,6-dimethyl-4-[1-hydroxy-2,2,2-trifluoro-1-(trifluoromethyl)ethyl]aniline, 2.7 g of 3-(benzoylamino)benzoyl chloride and 1.2 g of pyridine were introduced to 50 ml of tetrahydrofuran, and the mixture was stirred at room temperature. After the loss of the starting material was confirmed through TLC, a saturated aqueous sodium hydrogen carbonate solution was added to the reaction solution and the solution was stirred for a while. Subsequently, ethyl acetate and water were added to the reaction solution, and phase separation was carried out. The separated organic layer was dried over anhydrous magnesium sulfate and filtered. The filtrate was concentrated under reduced pressure and dried, and thus obtained residue was grinded to give 3.4 g (yield 95%) of the title compound as a powder form.

The characterization is described in Example 17-4.

Example 17-8

Preparation of N-(2,6-dimethyl-4-heptafluoroisopropyl)phenyl 3-(benzoylamino)benzamide (Compound No. 10)

At room temperature, 300 mg of N-[2,6-dimethyl-4-{1-hydroxy-2,2,2-trifluoro-1-(trifluoromethyl)ethyl}phenyl]3-(benzoylamino)benzamide was introduced to 20 ml of methylene chloride. Then, 480 mg of 2,2-difluoro-1,3-dimethyl-2-imidazolidinone was added dropwise, and the mixture was stirred at room temperature for 8 hours. Water was added to the reaction solution, and the organic layer was separated. The organic layer was dried over anhydrous magnesium sulfate and filtered, and thus obtained filtrate was concentrated under reduce pressure and dried. Thus obtained solid was grinded to give 180 mg (yield 60%) of the title compound as a powder form.

The characterization is described in Example 1-3.

Example 18-1

Preparation of 4-methyl-5-nitro-2-(2,2,2-trifluoro-1-trifluoromethylethoxy)pyridine After 1.33 g of 60% sodium hydride was introduced to 15 ml of tetrahydrofuran and cooled to 5° C., 5.84 g of 1,1,1,3,3,3-hexafluoro-2-propanol was added dropwise. The mixture was stirred at 5° C. for 30 minutes, and then 3.0 g of 2-chloro-4-methyl-5-nitropyridine dissolved in 10 ml of tetrahydrofuran was added dropwise, this being stirred at room temperature for 3 hours. After being left at room temperature for 3 days, ethyl acetate and water were added thereto, and the organic layer was separated and washed with saturated brine. The organic layer was dried over anhydrous magnesium sulfate, and the solvent was distilled off under reduced pressure. Thus obtained residue was purified by silica gel column chromatography (eluent: hexane:ethyl acetate=10:1) to give 4.5 g (yield 80%) of the title compound as a yellow oil.

$^1$H-NMR (CDCl$_3$, ppm) δ 2.69 (3H, s), 6.54 (1H, septet, J=6.8 Hz), 6.95 (1H, s), 8.90 (1H, s).

Example 18-2

Preparation of 5-amino-4-methyl-2-(2,2,2-trifluoro-1-trifluoromethylethoxy)pyridine The title compound was prepared using 4-methyl-5-nitro-2-(2,2,2-trifluoro-1-trifluoromethylethoxy)pyridine according to the conditions described in Example 1-2.

$^1$H-NMR (CDCl$_3$, ppm) δ 2.04 (3H, s), 3.49 (2H, broad-s), 6.40 (1H, septet, J=6.3 Hz), 6.69 (1H, s), 7.54 (1H, s).

Example 18-3

Preparation of 3-amino-2-chloro-4-methyl-6-(2,2,2-trifluoro-1-trifluoromethylethoxy)pyridine 1.0 g of 5-amino-4-methyl-2-(2,2,2-trifluoro-1-trifluoromethylethoxy)pyridine was introduced to 10 ml of N,N-dimethyl formamide, and 0.56 g of N-chlorosuccinimide was added at room temperature. The temperature was elevated to 60° C., and the mixture was stirred for 1 hour and poured into water. The mixture was extracted with ethyl acetate and dried over anhydrous magnesium sulfate. The solvent was distilled off under reduced pressure, and thus obtained residue was purified by silica gel column chromatography (eluent: hexane:ethyl acetate=10:1) to give 0.50 g (yield 44%) of the title compound as a brown oil.

$^1$H-NMR (CDCl$_3$, ppm) δ 2.23 (3H, s), 3.82 (2H, broad-s), 6.24 (1H, septet, J=6.3 Hz), 6.67 (1H, s).

Example 18-4

Preparation of N-[2-chloro-4-methyl-6-(2,2,2-trifluoro-1-trifluoromethylethoxy)pyridin-3-yl]3-(benzoylamino)benzamide (Compound No. 464)

The title compound was prepared using 5-amino-4-methyl-2-(2,2,2-trifluoro-1-trifluoromethylethoxy)pyridine according to the conditions described in Example 1.

$^1$H-NMR (CDCl$_3$, ppm) δ 2.38 (3H, s), 6.34 (1H, septet, J=6.3 Hz), 6.87 (1H, s), 7.50-7.63 (5H, m), 7.72 (1H, d, J=7.8 Hz), 7.88-7.90 (3H, m), 7.99 (1H, broad-s), 8.31 (1H, broad-s).

Preparation examples containing the compound represented by Formula (1) of the invention as an active ingredient are presented in the following, but the invention is not intended to be limited thereto. Additionally, in the formulations, the unit expressed in parts mean parts by weight.

Preparation Example 1

An emulsion was obtained by homogeneously mixing, with stirring, 20 parts of the compound represented by Formula (1) of the invention, 10 parts of Sol Pol 355S (Toho Chemical Industry Co., LTD, a surfactant) and 70 parts of xylene.

Preparation Example 2

A water-dispersible powder was obtained by homogeneously mixing, with stirring, 10 parts of the compound represented by Formula (1) of the invention, 2 parts of sodium alkylnaphthalenesulfonate, 1 part of sodium ligninsulfonate, 5 parts of white carbon and 82 parts of diatomite.

Preparation Example 31

A dust formulation was obtained by homogeneously mixing, with grinding, a homogeneous mixture of 0.3 part of the compound represented by Formula (1) of the invention and 0.3 part of white carbon with 99.2 parts of clay and 0.2 part of Driless A (Sankyo Co., Ltd).

Preparation Example 4

A granule was obtained by homogeneously mixing, with grinding, 2 parts of the compound represented by Formula (1) of the invention, 2 parts of white carbon, 2 parts of sodium ligninsulfonate and 94 parts of bentonite, kneading with water, and by granulating and drying.

Preparation Example 5

A flowable formulation was prepared by sufficiently stirring and mixing 20 parts of the compound represented by Formula (1) of the invention and 5 parts of a 20% aqueous solution of polyvinyl alcohol, adding 75 parts of a 0.8% aqueous solution of xanthan gum, and stirring and mixing them again.

Furthermore, in order to confirm the excellent insecticidal activity of the compound represented by Formula (1) of the invention, Experimental Examples will be presented below, which are not intended to limit the invention anyway.

Experimental Example 1

Insecticidal Testing Against Common Cutworm (*Spodoptera litura*)

Cabbage leaves were immersed in a liquid comprising the testing compound to a predetermined concentration for 30 seconds and air-dried. They were placed in a 7-cm polyethylene cup, and the second-stage larvae of common cutworm were left therein. The cup was placed in a constant-temperature room at 25° C., and the survival rate was investigated after 3 days. The test was carried out with two groups of 5 larvae per group. As a result, Compound No. (to be described later)
2, 3, 4, 5, 6, 7, 8, 9, 10, 11, 12, 13, 14, 16, 17, 18, 19, 20, 21, 22, 23, 25, 26, 27, 28, 29, 30, 31, 32, 33, 37, 39, 42, 43, 46, 48, 56, 57, 58, 59, 60, 61, 62, 66, 68, 69, 70, 71, 73, 74, 75, 81, 82, 83, 84, 85, 86, 87, 89, 92, 96, 99, 100, 101, 105, 106, 109, 114, 117, 122, 124, 125, 126, 127, 129, 130, 132, 136, 140, 150, 160, 163, 164, 165, 166, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 204, 207, 208, 210, 212, 256, 257, 258, 259, 260, 261, 262, 263, 266, 276, 284, 288, 309, 310, 327, 328, 329, 330, 331, 332, 333, 334, 335, 338, 369, 375, 376, 377, 378, 379, 380, 383, 414, 460, 461, 462, 463, 464, 465, 466, 467, 601, 602, 603, 604, 605, 606, 607, 609, 610, 611, 612, 616, 618, 619, 624, 628, 629, 630, 631, 633, 634, 638, 639, 649, 650, 651, 652, 653, 654, 655, 656, 657, 658, 661, 665, 668, 670, 676, 679, 682, 686, 699, 708, 711, 719, 722, 791, 1001, 1016, 1043, 1089, 1091, 1097, 1100, 1125, 1126, 1206, 1207, 1208, 1209, 1210, 1211, 1212, 1213, 1214, 1216, 1217, 1218, 1219, 1220, 1229, 1235, 1236, 1237, 1238, 1245, 1246, 1247, 1255, 1256, 1257, 1258, 1259, 1260, 1261, 1262, 1263, 1264, 1265, 1266, 1267, 1274, 1293, 1294, 1463, 1464, 1465, 1478, 1479, 1480, 1481, 1482, 1483, 1484, 1485, 1486, 1487, 1607, 1617, 1645, 1697, 2001, 2004, 2034, 2035, 2036, 2037, 2082, 2085, 2093, 2116, 2117, 2164, 2168, 2201, 2202, 2203
exhibited an pesticidal rate of 70% or more at a concentration of 100 ppm.

Experimental Example 2

Insecticidal Testing Against Diamondback Moth (*Plutella xylostella*)

Cabbage leaves were immersed in a liquid comprising the testing compound to a predetermined concentration for 30 seconds and air-dried. They were placed in a 7-cm polyethylene cup, and the second-stage larvae of diamondback moth were left therein. The cup was placed in a constant-temperature room at 25° C., and the survival rate was investigated after 3 days. The test was carried out with two groups of 5 larvae per group. As a result, Compound No. (to be described later)
2, 3, 4, 5, 6, 7, 8, 9, 10, 11, 12, 13, 17, 18, 19, 20, 21, 22, 23, 25, 26, 27, 29, 30, 31, 32, 33, 37, 39, 43, 47, 56, 58, 59, 60, 61, 62, 66, 68, 69, 70, 82, 83, 84, 85, 86, 87, 89, 92, 100, 101, 105, 106, 109, 114, 118, 122, 124, 127, 130, 132, 135, 147, 150, 154, 160, 163, 164, 165, 166, 168, 169, 170, 171, 172, 173, 174, 175, 176, 177, 178, 179, 180, 181, 182, 183, 184, 185, 186, 194, 196, 197, 198, 199, 200, 201, 202, 203, 204, 206, 207, 208, 209, 210, 212, 256, 258, 259, 260, 261, 262, 263, 266, 284, 309, 310, 314, 318, 327, 328, 329, 330, 331, 332, 333, 334, 335, 338, 369, 375, 376, 377, 378, 379, 383, 414, 460, 461, 462, 463, 464, 465, 466, 467, 601, 602, 603, 604, 605, 606, 607, 609, 610, 611, 612, 616, 618, 619, 620, 624, 628, 629, 630, 631, 633, 634, 638, 639, 650, 651, 652, 653, 654, 655, 656, 657, 665, 668, 670, 676, 679, 682, 686, 699, 708, 711, 719, 722, 791, 1001, 1016, 1043, 1089, 1091, 1097, 1100, 1125, 1126, 1206, 1207, 1208, 1209, 1210, 1211, 1212, 1213, 1214, 1215, 1216, 1217, 1218, 1219, 1220, 1229, 1235, 1236, 1237, 1238, 1245, 1246, 1247, 1255, 1256, 1257, 1258, 1259, 1260, 1261, 1262, 1263, 1264, 1265, 1266, 1267, 1274, 1293, 1294, 1463, 1464, 1465, 1478, 1479, 1480, 1481, 1482, 1484, 1485, 1486, 1487, 1607, 1617, 1645, 1697, 2001, 2034, 2037, 2082, 2085, 2093, 2116, 2117, 2164, 2168, 2201, 2202, 2203
exhibited an pesticidal rate of 70% or more at a concentration of 100 ppm.

Experimental Example 3

Insecticidal Testing Against Small Brown Planthopper (*Laodelphax striatellus*)

An additional test was carried out with 10 small brown planthoppers by preparing an acetone solution of the testing compound diluted to a predetermined concentration, and spraying the solution on rice paddies and air drying them. The medicament was all used as received. The paddies were placed in a constant-temperature room at 25° C., and the survival rate was investigated after 6 days. The test was carried out by means of one group of 10 pests. As a result, Compound No. (to be described later)
7, 8, 17, 25, 31, 62, 101, 105, 106, 122, 130, 164, 165, 166, 169, 170, 171, 172, 173, 174, 175, 178, 179, 180, 181, 182, 183, 184, 185, 197, 199, 201, 202, 206, 207, 208, 210, 369, 601, 604, 607, 609, 610, 611, 612, 618, 619, 620, 624, 628, 630, 633, 639, 650, 651, 652, 654, 655, 657, 665, 668, 686, 1043, 1089, 1091, 1097, 1100, 1207, 1208, 1209, 1210, 1211, 1212, 1213, 1214, 1216, 1217, 1218, 1219, 1220, 1229, 1235, 1236, 1237, 1238, 1245, 1246, 1247, 1255, 1259, 1260, 1262, 1263, 1264, 1265, 1266, 1293, 1463, 1464, 1465, 1487, 1607, 1645, 1697, 2034, 2035, 2082, 2085, 2093, 2116, 2117, 2203
exhibited an pesticidal rate of 70% or more at a concentration of 1000 ppm.

Comparative Experimental Example 1

Pesticidal testing using
N-(4-heptafluoroisopropyl-2-methyl)phenyl
3-(2-iodobenzoylamino)benzamide (Compound A) and
N-(2,6-dimethyl-4-trifluoromethyl)phenyl
3-(benzoylamino)benzamide (Compound B)
Additional tests were carried out using said Compound A and Compound B following the procedures of Experimental Examples 1 and 2, but insecticidal activity was not observed under the same conditions.

The invention claimed is:
1. A compound represented by Formula (4):

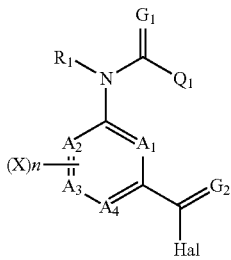

(4)

wherein (a) in the case of $R_1$ represents a hydrogen atom;
$A_1$, $A_2$, $A_3$ and $A_4$ represent a carbon atom;
$G_1$ and $G_2$ each represent an oxygen atom or a sulfur atom;
X represents a hydrogen atom;
n represents 4;
$Q_1$ represents a substituted phenyl group having one or more substituents, which may be identical or different, selected from a halogen atom, a C1-C4 alkyl group, a C1-C4 haloalkyl group, a cyano group and a nitro group; a pyridyl group; or a substituted pyridyl group having one or more substituents, which may be identical or different, selected from a halogen atom;
(b) in the case of $R_1$ represents a C1-C4 alkyl group or a C1-C4 alkylcarbonyl group;
$A_1$, $A_2$, $A_3$ and $A_4$ each represent a carbon atom, a nitrogen atom or an oxidized nitrogen atom;
$G_1$ and $G_2$ each represent an oxygen atom or a sulfur atom;
X, which may be identical or different each other, represents a hydrogen atom, a halogen atom, an optionally substituted C1-C3 alkyl group or a trifluoromethyl group;
n represents an integer of 0 to 4;
$Q_1$ represents a phenyl group; a substituted phenyl group having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group and a phenyl group; a heterocyclic group (the heterocyclic group herein represents a pyridyl group, a pyridin-N-oxide group, a pyrimidinyl group, a pyridazyl group, a pyrazyl group, a furyl group, a thienyl group, an oxazolyl group, an isoxazolyl group, an oxadiazolyl group, a thiazolyl group, an isothiazolyl group, an imidazolyl group, a triazolyl group, a pyrrolyl group, a pyrazolyl group or a tetrazolyl group); or a substituted heterocyclic group (which means the same as those described above) having one or more substituents, which may be identical or different, selected from a halogen atom, a C1-C4 alkyl group, a C1-C4 haloalkyl group, a C2-C4 alkenyl group, a C2-C4 haloalkenyl group, a C2-C4 alkynyl group, a C2-C4 haloalkynyl group, a C3-C6 cycloalkyl group, a C3-C6 halocycloalkyl group, a C1-C3 alkoxy group, a C1-C3 haloalkoxy group, a C1-C3 alkylthio group, a C1-C3 haloalkylthio group, a C1-C3 alkylsulfinyl group, a C1-C3 haloalkylsulfinyl group, a C1-C3 alkylsulfonyl group, a C1-C3 haloalkylsulfonyl group, a C1-C4 alkylamino group, a di-C1-C4-alkylamino group, a cyano group, a nitro group, a hydroxyl group, a C1-C4 alkylcarbonyl group, a C1-C4 alkylcarbonyloxy group, a C1-C4 alkoxycarbonyl group, an acetylamino group or a phenyl group; and
Hal represents a chlorine atom or a bromine atom; and excluding the following compounds;

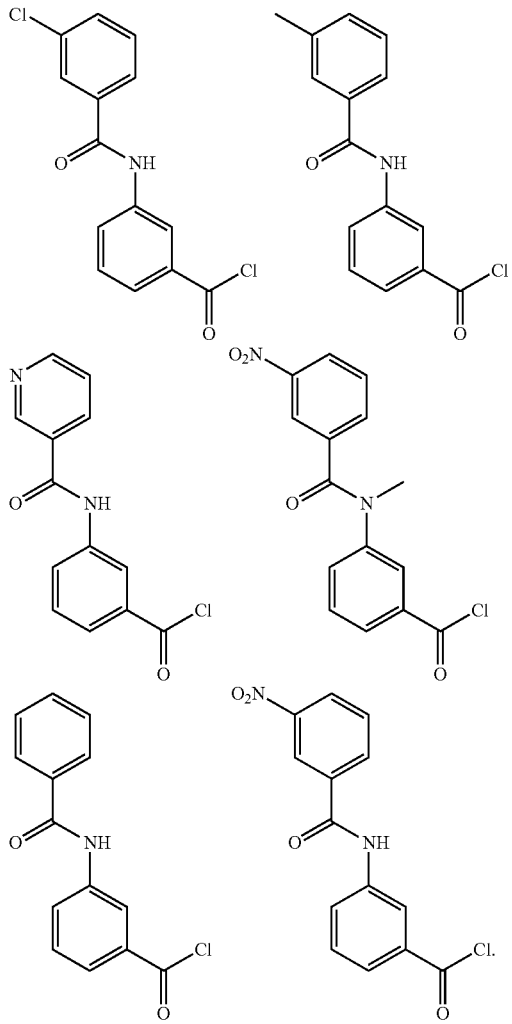

* * * * *